US009598393B2

(12) United States Patent
Demangel et al.

(10) Patent No.: US 9,598,393 B2
(45) Date of Patent: Mar. 21, 2017

(54) STRUCTURAL VARIANTS OF MYCOLACTONES FOR USE IN MODULATING INFLAMMATION, IMMUNITY AND PAIN

(71) Applicant: INSTITUT PASTEUR, Paris (FR)

(72) Inventors: Caroline Demangel, Paris (FR); Nicolas Blanchard, Niffer (FR); Georges Bismuth, Paris (FR); Jacques Eustache, Fermanville (FR); Virginie Casarotto, Rixheim (FR); Anne-Caroline Chany, Oxford (GB); Laure Guenin-Mace, Paris (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 14/358,501

(22) PCT Filed: Nov. 16, 2012

(86) PCT No.: PCT/IB2012/056506
§ 371 (c)(1),
(2) Date: May 15, 2014

(87) PCT Pub. No.: WO2013/072896
PCT Pub. Date: May 23, 2013

(65) Prior Publication Data
US 2014/0329771 A1 Nov. 6, 2014

(30) Foreign Application Priority Data
Nov. 18, 2011 (EP) ..................................... 11306521

(51) Int. Cl.
| | |
|---|---|
| C07D 313/00 | (2006.01) |
| A61K 31/335 | (2006.01) |
| C07C 69/76 | (2006.01) |
| C07D 521/00 | (2006.01) |
| C07C 69/732 | (2006.01) |
| C07C 43/15 | (2006.01) |
| C07C 59/135 | (2006.01) |
| C07F 5/02 | (2006.01) |

(52) U.S. Cl.
CPC .......... *C07D 313/00* (2013.01); *A61K 31/335* (2013.01); *C07C 43/15* (2013.01); *C07C 59/135* (2013.01); *C07C 69/732* (2013.01); *C07C 69/76* (2013.01); *C07D 521/00* (2013.01); *C07F 5/022* (2013.01); *C07C 2101/10* (2013.01); *C07C 2101/14* (2013.01)

(58) Field of Classification Search
CPC ............................. C07D 313/00; A61K 31/335
See application file for complete search history.

(56) References Cited

PUBLICATIONS

Tsubushi et al. (CAPLUS Abstract of: JP 04356512 (1992)).*
Zhu et al. (Tuberculosis, vol. 88, Supplement 1, Aug. 2008, pp. S49-S63).*
Stadler et al. (CAPLUS Abstract of: Advanced Functional Materials (2008), 18(7), 1119-1130).*
Aubry et al., "Synthesis and Structure of Mycolactone E Isolated from Frog *Mycobacterium*," Organic Letters, 2008, vol. 10, No. 23, pp. 5385-5388.
Benowitz et al., "Stereochemistry of the Core Structure of the Mycolactones," J. Am. Chem. Soc., 2001, vol. 123, pp. 5128-5129.
Coutanceau et al., "Selective Suppression of Dendritic Cell Functions by *Mycobacterium ulcerans* Toxin Mycolactone," Journal of Experimental Medicine, Jun. 2007, vol. 204, No. 6, pp. 1395-1403.
En et al., "Mycolactone Is Responsible for the Painlessness of *Mycobacterium ulcerans* Infection (Buruli Ulcer) in a Murine Study," Infection and Immunity, May 2008, vol. 76, No. 5, pp. 2002-2007.
Gersbach et al., "A Ring-Closing Metathesis (RCM)-Based Approach to Mycolactones A/B," Chem. Eur. J., 2011, vol. 17, pp. 13017-13031.
International Search Report for International Application No. PCT/IB2012/056506 dated Mar. 3, 2013.
Spangenberg et al., "Synthesis and Structure Assignment of the Minor Metabolite Arising From the Frog Pathogen *Mycobacterium liflandii*," Tetrahedron Letters, 2010, vol. 51, pp. 1782-1785.
"Methanol: Systemic Agent"; Centers for Disease Control and Prevention; [online] Retrieved on Jun. 3, 2016 from the Internet: <URL: http://www.cdc.gov/niosh/ershdb/emergencyresponsecard_29750029.html> 16 pages.
"Methanol"; Wikipedia, the free encyclopedia; [online] Retrieved on Jun. 3, 2016 from the Internet: <URL: https://en.wikipedia.org/wiki/Methanol>; 14 pages.

* cited by examiner

*Primary Examiner* — Robert Havlin
(74) *Attorney, Agent, or Firm* — Foley & Lardner LLP

(57) ABSTRACT

The present invention is related to variants of mycolactones of formula (I), processes for the preparation thereof, pharmaceutical compositions thereof and their use in modulating inflammation, immunity and pain. Y—O—W (I), wherein Y and W are as defined in claim 1.

11 Claims, 5 Drawing Sheets

Figure 1:
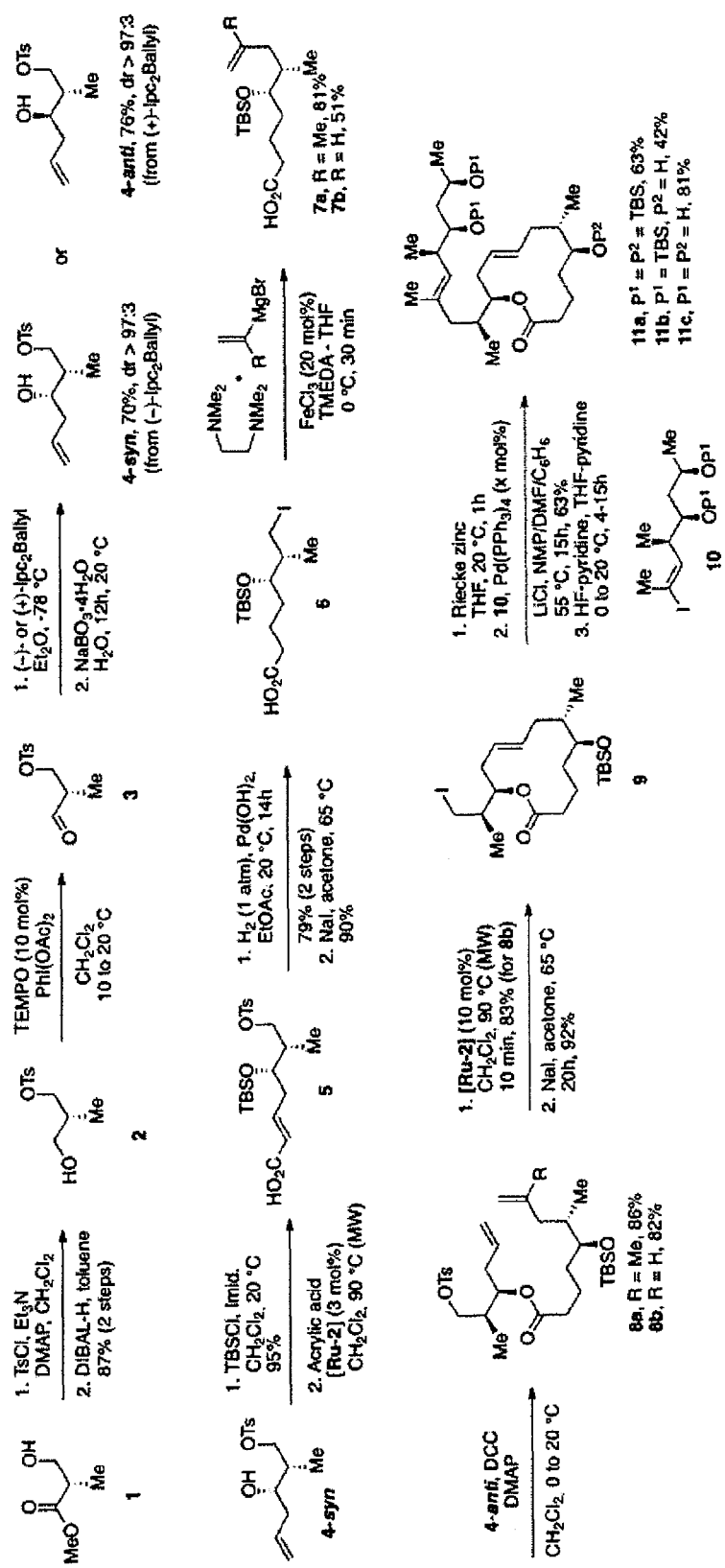

STRUCTURAL VARIANTS OF MYCOLACTONES FOR USE IN MODULATING INFLAMMATION, IMMUNITY AND PAIN

The present invention is related to variants of mycolactones, processes for the preparation thereof, pharmaceutical compositions thereof and their use in modulating inflammation, immunity and pain.

Mycolactones are a group of polyketide-derived 12-membered macrolides that are produced by different strains of *Mycobacterium ulcerans* (Mu), and that are causally involved in Buruli ulcer (BU).

Buruli ulcer is a devastating necrotizing skin disease present in more than thirty countries in the world, located mainly in West and Central Africa but also in Australia and now Japan.[1] In addition, it has been recently proposed that other genetically related mycolactone-producing mycobacteria (MPM) such as *M. shinshuense, M. pseudoshottsii, M. marinum* (except *M. marinum* strain M) and *M. liflandii* that are pathogenic agents for human, frogs and fishes should be now reclassified as *M. ulcerans* strains, thus highlighting the worldwide distribution and broad host range of this mycobacterial species.[2]

To date no efficient global treatment of Buruli ulcer has been developed; the use of a combination of streptomycin and rifampicin recommended by the World Health Organization is effective in early and limited infections[3] but still needs to be combined with wide surgical excision in severe cases.[4]

So far, seven different mycolactones, namely mycolactones A/B, C, D, E, and F/dia-F (Scheme 1), have been isolated from different strains of *Mycobacterium ulcerans*, including *Mycobacterium marinum* and *Mycobacterium liflandii*. Structurally, all known mycolactones are based on a common macrolide core to which two side chains are attached via a C—C and an ester bond (Scheme 1). Structural variations between individual mycolactones have only been found in the polyunsaturated fatty acid side chain C1'-C16', whereas the C1-C11 macrolactone ring and the C—C linked C12-C20 side chain are fully conserved.

Scheme 1: The family of naturally-occuring mycolactones

Importantly, mycolactones A/B represent a rapidly equilibrating mixture of Z-$\Delta^{4',5'}$ (mycolactone A) and E-$\Delta^{4',5'}$ (mycolactone B) geometric isomers; this mixture is isolated as such from bacterial cultures.

Mycolactones are cytotoxic at micromolar concentrations on mammalian cells (reviewed in Hong et al., 2008)[5]. Interestingly, at non-cytotoxic doses they display potent immunomodulatory properties on most subsets of immune cells (reviewed in Demangel et al., Nature Rev Microbial, 2009)[6], making them potentially useful immunosuppressors. In particular, it has been shown that mycolactone A/B blocks the release of inflammatory TNF by macrophages (Coutanceau et al., Cell Microbial, 2005)[7a], inhibits the production of chemotactic signals by dendritic cells (Coutanceau et al., JEM, 2007)[7b] and severely impairs T cell trafficking in vivo (Guenin-Macé et al., PNAS, 2011) [7c], all mechanisms being essential for the development of inflammatory diseases.

It now has been discovered new structural variants of mycolactones A to F, which are of interest for treating inflammation, immune-mediated diseases and/or pain. Advantageously, these variants may display an immunosuppressive effect similar to that of mycolactone but with a lower cytotoxicity.

Thus, the present invention in one aspect is directed to various novel structural variants of mycolactone of formula (I):
  (I)
and its stereoisomeric forms, mixtures of stereoisomeric forms n is 0 or 1;

m is 0, 1 or 2;

o is 0, 1 or 2;

provided that m+n+o=3;

p is 0 or 1;

q is 0 or 1;

r is 1 or 2;

Y is selected from $C_2$-$C_6$ alkenyl, $C_3$-$C_{10}$ cycloalkyl, $C_3$-$C_{10}$ cycloalkenyl, ($C_1$-$C_6$)alkoxy($C_1$-$C_6$)alkyl, ($C_1$-$C_6$)alkoxy($C_6$-$C_{10}$)aryl, and Z;

Z is:

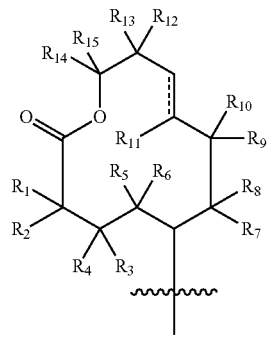
(Z)

$R^1$ to $R^{10}$ and $R^{12}$, $R^{13}$ are each independently selected from H and $C_1$-$C_6$ alkyl;

$R^{11}$ is selected from H, $C_1$-$C_6$ alkyl, $C_3$-$C_{10}$ cycloalkyl, $CF_3$, and halogen;

----- is a single bond (C—C) or a double bond (C=C);

$R^{14}$, $R^{15}$ are each independently selected from H, $C_1$-$C_6$ alkyl, and $C_3$-$C_{10}$ cycloalkyl, or one of $R^{14}$, $R^{15}$ is L and the other is H;

L is $L_1$, $L_2$, or $L_3$:

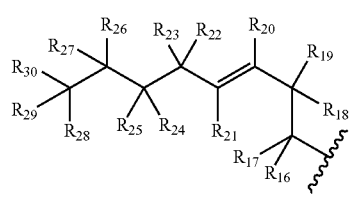
($L_1$)

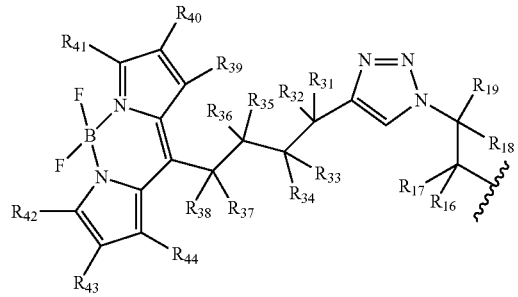
($L_2$)

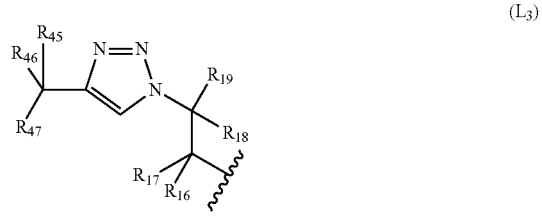
($L_3$)

$R^{16}$, $R^{17}$, $R^{18}$, $R^{19}$, $R^{20}$, $R^{21}$, $R^{22}$, $R^{23}$, $R^{26}$, $R^{27}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, and $R^{46}$ are each independently selected from H and $C_1$-$C_6$ alkyl;

$R^{24}$, $R^{25}$, $R^{28}$, $R^{29}$ and $R^{47}$ are each independently selected from H, halogen, hydroxyl, and ($C_1$-$C_6$)alkoxy;

With the provision that when X is $X_a$, and one of $R^{14}$, $R^{15}$ is $L_1$, then $R^{11}$ cannot be $CH_3$;

With the provision that when X is $X_b$ with n=1 and o=2, and one of $R^{14}$, $R^{15}$ is $L_1$, then $R^{11}$ cannot be $CH_3$; and With the provision that when W is H, and $R^{11}$ is H, then one of $R^{14}$, $R^{15}$ cannot be $C_1$-$C_6$ alkyl, With the provision that when Y is selected from $C_2$-$C_6$ alkenyl, $C_3$-$C_{10}$ cycloalkyl, $C_3$-$C_{10}$ cycloalkenyl, ($C_1$-$C_6$)alkoxy($C_1$-$C_6$)alkyl, ($C_1$-$C_6$)alkoxy($C_6$-$C_{10}$)aryl, then W is —C(=O)—X;

With the exclusion of the compounds wherein:

Y is Z; W is H; ----- is C=C; $R^{11}$ is $CH_3$; $R^7$ is $CH_3$; $R^{15}$ is $L_1$ with $R^{16}$, $R^{20}$, $R^{22}$ and $R^{30}$ are $CH_3$; $R^{24}$ and $R^{28}$ are OH; and the other radicals $R^i$ are H;

Y is Z; W is H; ----- is C=C; $R^{11}$ is $CH_3$; $R^{15}$ is isopropyl; $R^7$ is $CH_3$; and the other radicals $R^i$ are H;

and the stereoisomeric forms, or mixtures of stereoisomeric forms thereof.

In a particular aspect of the invention, there are included compounds of formula (I), wherein:

$$Y—O—W \quad (I)$$

Wherein:

W is H or C(=O)—X;

X is $X_a$, $X_b$ or $X_c$:

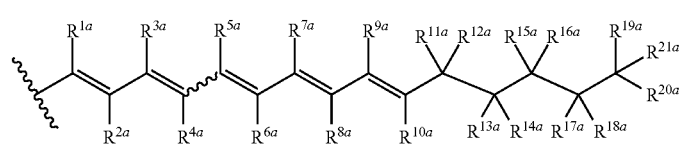
($X_a$)

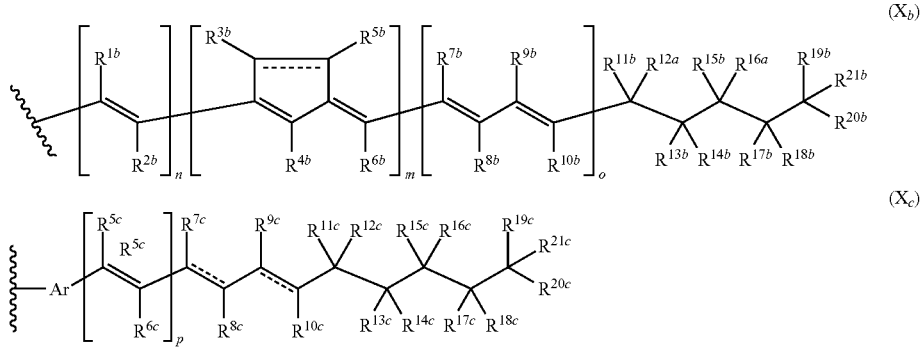

$R^{1a}$ to $R^{10a}$, $R^{1b}$ to $R^{10b}$, $R^{5c}$ to $R^{10c}$, and $R^{21a}$, $R^{21b}$, $R^{21c}$ are each independently selected from H and $C_1$-$C_6$ alkyl;

$R^{11a}$ to $R^{20a}$, $R^{11b}$ to $R^{20b}$, $R^{11c}$ to $R^{20c}$ are each independently selected from H, halogen, notably fluorine, hydroxy, and $C_1$-$C_6$ alkoxy;

Ar is a phenylene group or a 5 membered heteroarylene group, said phenylene and heteroarylene groups being optionally substituted with one to four groups selected from $C_1$-$C_6$ alkyl;

n is 0 or 1;

m is 0, 1 or 2;

o is 0, 1 or 2;

provided that m+n+o=3;

p is 0 or 1;

Y is selected from $C_2$-$C_6$ alkenyl, $C_3$-$C_{10}$ cycloalkyl, $C_3$-$C_{10}$ cycloalkenyl, $(C_1$-$C_6)$alkoxy$(C_1$-$C_6)$alkyl, $(C_1$-$C_6)$alkoxy$(C_6$-$C_{10})$aryl, or Z;

Z is:

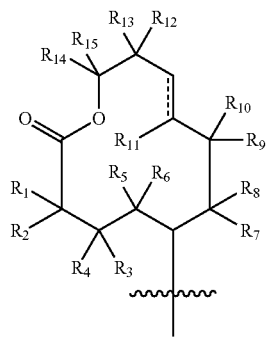

$R^1$ to $R^{10}$ and $R^{12}$, $R^{13}$ are each independently selected from H or $C_1$-$C_6$ alkyl;

$R^{11}$ is selected from H, $C_1$-$C_6$ alkyl, $C_3$-$C_{10}$ cycloalkyl, $CF_3$, and halogen;

----- is a single bond (C—C) or a double bond (C=C);

$R^{14}$, $R^{15}$ are each independently selected from H, $C_1$-$C_6$ alkyl, and $C_3$-$C_{10}$ cycloalkyl, or
one of $R^{14}$, $R^{15}$ is L and the other is H;
L is $L_1$ or $L_2$:

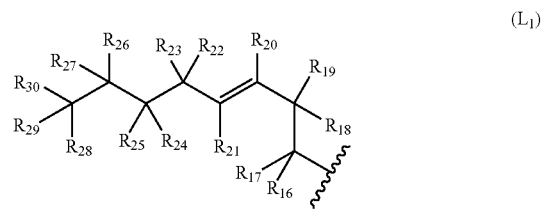

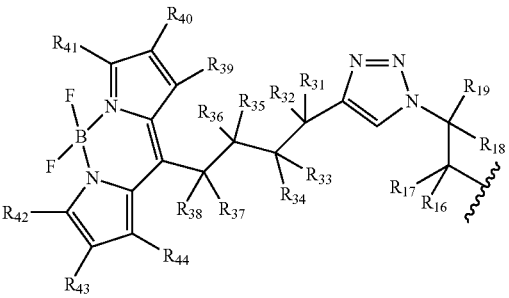

$R_{16}$, $R_{17}$, $R_{18}$, $R_{19}$, $R_{20}$, $R_{21}$, $R_{22}$, $R_{23}$, $R_{26}$, $R_{27}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, and $R_{44}$ are each independently selected from H and $C_1$-$C_6$ alkyl;

$R_{24}$, $R_{25}$, $R_{28}$ and $R_{29}$ are each independently selected from H, halogen, hydroxyl or $(C_1$-$C_6)$alkoxy;

With the provision that when X is $X_a$, and one of $R^{14}$, $R^{15}$ is $L_1$, then $R^{11}$ cannot be $CH_3$; and With the provision that when W is H, and $R^{11}$ is H, then one of $R^{14}$, $R^{15}$ cannot be $C_1$-$C_6$ alkyl;

and the stereoisomeric forms, or mixtures of stereoisomeric forms thereof.

In a particular aspect of the present invention, there are included compounds of formula (I) wherein W is —C(=O)—X.

In a particular aspect of the present invention, there are included compounds of formula (I) wherein $R^{11a}$ to $R^{20a}$, $R^{11b}$ to $R^{20b}$, $R^{11c}$ to $R^{20c}$ are each independently selected from H, and hydroxyl.

In another aspect of the present invention, there are included compounds of formula (I) wherein $R^{1a}$ to $R^{10a}$, $R^{1b}$ to $R^{10b}$, $R^{5c}$ to $R^{10c}$, and $R^{21a}$, $R^{21b}$, $R^{21c}$ are each independently selected from H and $CH_3$.

In additional aspects of the present invention, there are included compounds of formula (I) wherein X is selected from:

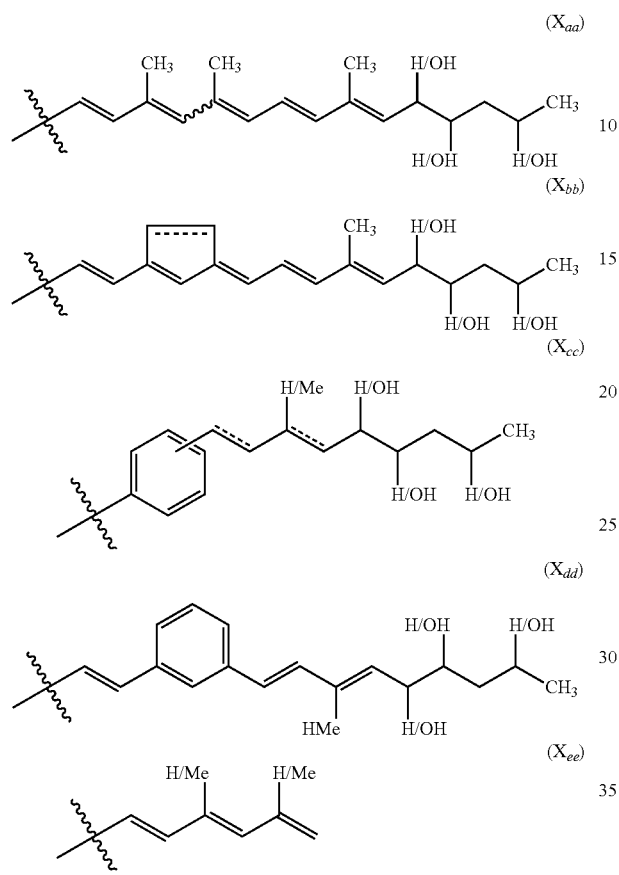

In certain aspects of the present invention, there are included compounds of formula (I) wherein Y is $C_3$-$C_{10}$ cycloalkyl, notably $C_5$-$C_7$ cycloalkyl, or Z.

In further aspects of the present invention, there are included compounds of formula (I), wherein Z is

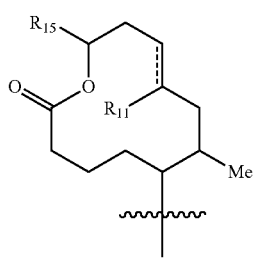

Wherein
$R^{15}$ is $C_1$-$C_6$ alkyl, or L;
$R^{11}$ is H or $CH_3$,
With the provision that when X is $X_a$, and $R^{15}$ is $L_1$, then $R^{11}$ cannot be $CH_3$.

In a further aspect of the present invention, there are included compounds of formula (I) wherein when X is $X_a$, and one of $R^{14}$, $R^{15}$ is $L_1$, then $R^{11}$ cannot be $C_1$-$C_6$ alkyl and may be selected from H, $C_3$-$C_{10}$ cycloalkyl, $CF_3$, and halogen. In a particular embodiment, when X is $X_a$, and one of $R^{14}$, $R^{15}$ is $L_1$, then $R^{11}$ is H.

In a particular aspect of the present invention, there are included compounds of formula (I) wherein $R^{15}$ is isopropyl or $L_1$, notably $L_{1a}$:

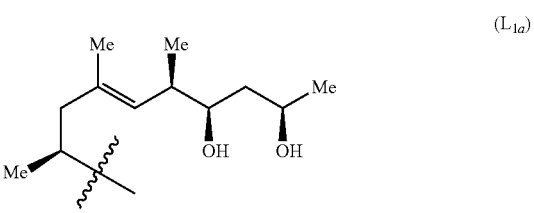 [SMILES: *[C@@H](C)C/C(C)=C/[C@@H](C)[C@H](O)C[C@@H](C)O]

In another aspect of the present invention, there are included compounds of formula (I) selected from:

cycloalkyl(2E,4E,6E,8E,10E)-12,13,15-trihydroxy-4,6,10-trimethylhexadeca-2,4,6,8,10-pentaenoate

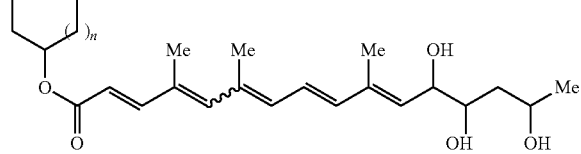

cycloalkenyl(2E)-3-[(3E)-3-[(2E,4E)-6,7,9-trihydroxy-4-methyldeca-2,4-dien-1-ylidene]cyclopent-1-en-1-yl]prop-2-enoate

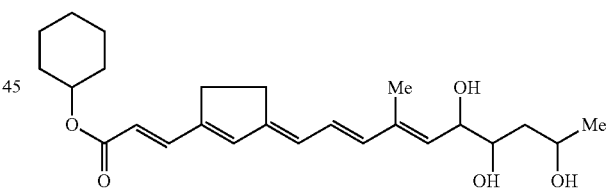

cycloalkenyl 3-[(1E,3E)-5,6,8-trihydroxy-3-methylnona-1,3-dien-1-yl]benzoate

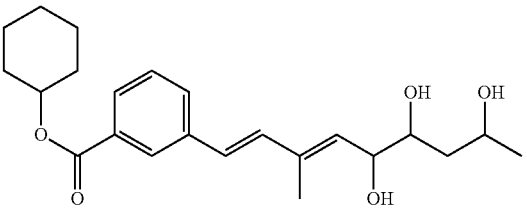 [SMILES: CC(/C=C/c1cccc(C(=O)OC2CCCCC2)c1)=C\C(O)C(O)CC(C)O]

(9E)-7-methyl-2-oxo-12-(propan-2-yl)-1-oxacyclododec-9-en-6-yl(2E,4E,6E,8E,10E)-12,13,15-trihydroxy-4,6,10-trimethylhexadeca-2,4,6,8,10-pentaenoate

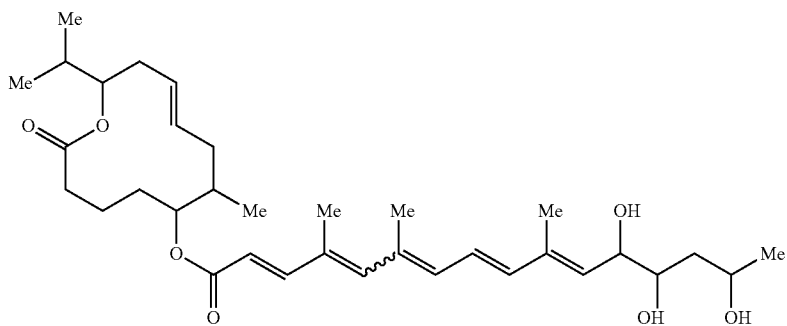 [SMILES: CC(=C/C=C/C(C)=C/C(O)C(O)CC(C)O)C=C(C)/C=C/C(=O)OC1CCCC(=O)OC(C(C)C)C/C=C/CC1C]
(9E)-7-methyl-2-oxo-12-(propan-2-yl)-1-oxacyclododec-9-en-6-yl(2E)-3-[(3E)-3-[(2E,4E)-6,7,9-trihydroxy-4-methyldeca-2,4-dien-1-ylidene]cyclopent-1-en-1-yl]prop-2-enoate
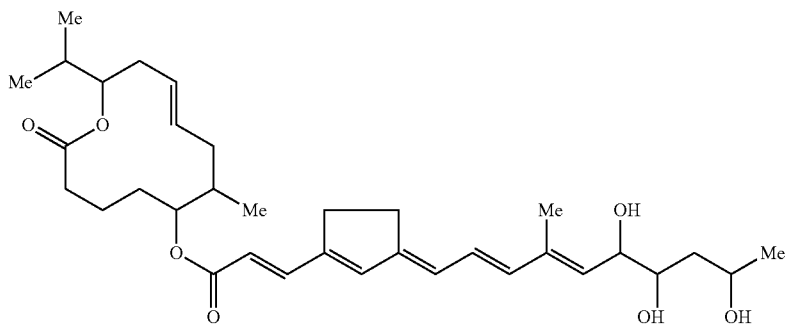 [SMILES: CC(/C=C/C=C1C=C(/C=C/C(=O)OC2CCCC(=O)OC(C(C)C)C/C=C/CC2C)CC/1)=C\C(O)C(O)CC(C)O]
(9E)-7-methyl-2-oxo-12-(propan-2-yl)-1-oxacyclododec-9-en-6-yl 3-[(1E,3E)-5,6,8-trihydroxy-3-methylnona-1,3-dien-1-yl]benzoate;
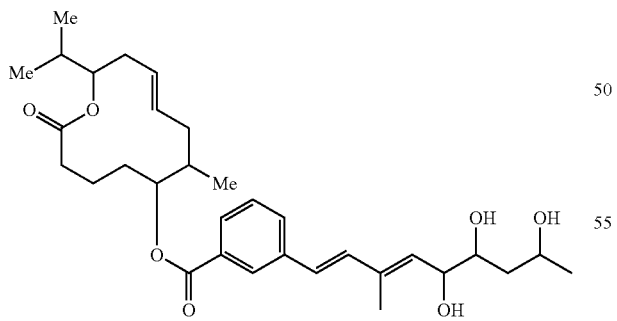
(9E)-12-[(4E)-7,9-dihydroxy-4,6-dimethyldec-4-en-2-yl]-7-methyl-2-oxo-1-oxacyclododec-9-en-6-yl(2E,4E,6E,8E,10E)-12,13,15-trihydroxy-4,6,10-trimethylhexadeca-2,4,6,8,10-pentaenoate:

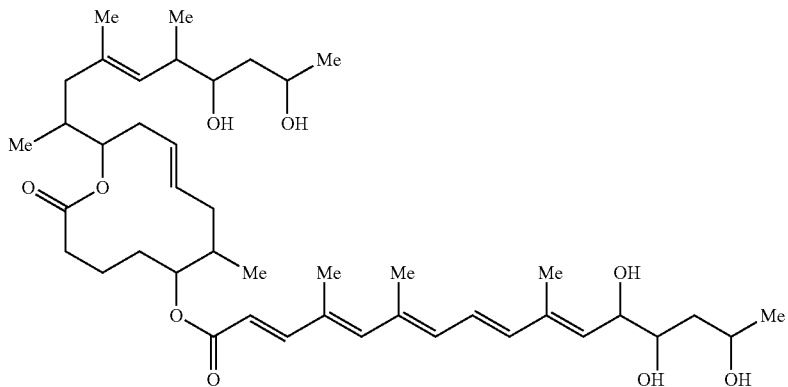 [SMILES: CC(=C\C=C\C(C)=C\C(O)C(O)CC(C)O)/C=C(C)/C=C/C(=O)OC1CCCC(=O)OC(C(C)C/C(C)=C/C(C)C(O)CC(C)O)C/C=C/CC1C]

(9E)-12-[(4E)-7,9-dihydroxy-4,6-dimethyldec-4-en-2-yl]-7-methyl-2-oxo-1-oxacyclododec-9-en-6-yl 3-[(1E,3E)-6,8-dihydroxy-3-methylnona-1,3-dien-1-yl]benzoate:

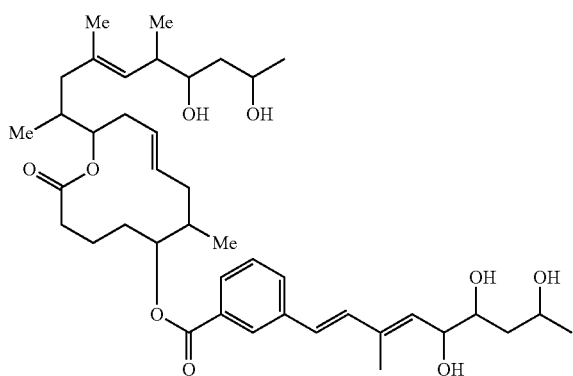 [SMILES: CC(/C=C/c1cccc(C(=O)OC2CCCC(=O)OC(C(C)C/C(C)=C/C(C)C(O)CC(C)O)C/C=C/CC2C)c1)=C\C(O)C(O)CC(C)O]

(9E)-12-[(4E)-7,9-dihydroxy-4,6-dimethyldec-4-en-2-yl]-7-methyl-2-oxo-1-oxacyclododec-9-en-6-yl(2E)-3-[(3E)-3-[(2E,4E)-7,9-dihydroxy-4-methyldeca-2,4-dien-1-ylidene]cyclopent-1-en-1-yl]prop-2-enoate:

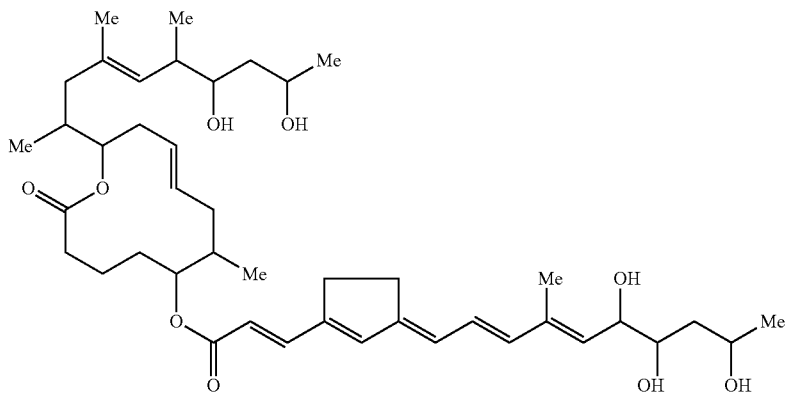 [SMILES: CC(/C=C/C=C1C=C(/C=C/C(=O)OC2CCCC(=O)OC(C(C)C/C(C)=C/C(C)C(O)CC(C)O)C/C=C/CC2C)CC/1)=C\C(O)C(O)CC(C)O]

20

(6S,7S,9E,12R)-12-[(2S,4E,6R,7R,9R)-7,9-dihydroxy-4,6-dimethyldec-4-en-2-yl]-7-methyl-2-oxo-1-oxacyclododec-9-en-6-yl(2E,4E,6E,8E,10E,12S,13S,15S)-12,13,15-trihydroxy-4,6,10-trimethylhexadeca-2,4,6,8,10-pentaenoate (compound 20a);

(6S,7S,9E,12R)-12-[(2S,4E,6R,7R,9R)-7,9-dihydroxy-4,6-dimethyldec-4-en-2-yl]-7-methyl-2-oxo-1-oxacyclododec-9-en-6-yl(2E,4E,6E,8E,10E,12S,13S,15R)-12,13,15-trihydroxy-4,6,10-trimethylhexadeca-2,4,6,8,10-pentaenoate (compound 20b);

(6S,7S,9E,12R)-12-[(2 S,4E,6R,7R,9R)-7,9-dihydroxy-4,6-dimethyldec-4-en-2-yl]-7-methyl-2-oxo-1-oxacyclododec-9-en-6-yl(2E,4E,6E,8E,10E,12R,13R,15R)-12,13,15-trihydroxy-4,6,10-trimethylhexadeca-2,4,6,8,10-pentaenoate (compound 20c);

(6S,7S,9E,12R)-12-[(2S,4E,6R,7R,9R)-7,9-dihydroxy-4,6-dimethyldec-4-en-2-yl]-7-methyl-2-oxo-1-oxacyclododec-9-en-6-yl(2E,4E,6E,8E,10E,13R,15R)-13,15-dihydroxy-4,6,10-trimethylhexadeca-2,4,6,8,10-pentaenoate (compound 20d);

(6 S,7 S,9E,12R)-12-[(2S,4E,6R,7R,9R)-7,9-dihydroxy-4,6-dimethyldec-4-en-2-yl]-6-hydroxy-7-methyl-1-oxacyclododec-9-en-2-one (compound 11c);

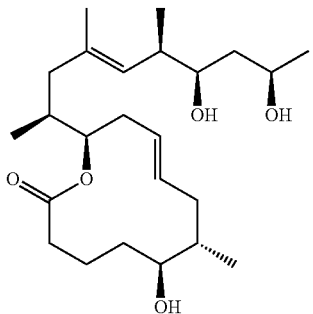

(6S,7S,9E,12R)-7-methyl-2-oxo-12-(propan-2-yl)-1-oxacyclododec-9-en-6-yl(2E,4E,6E,8E,10E,12S,13S,15S)-12,13,15-trihydroxy-4,6,10-trimethylhexadeca-2,4,6,8,10-pentaenoate (compound 22);

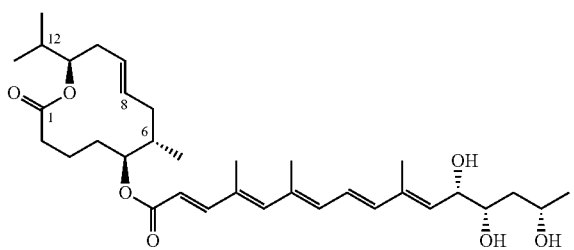

2,2-difluoro-4,6,10,12-tetramethyl-8-(4-{1-[(2S)-2-[(2R,4E,7S,8S)-7-methyl-12-oxo-8-{[(2E,4E,6E,8E,10E,12S,13S,15S)-12,13,15-trihydroxy-4,6,10-trimethylhexadeca-2,4,6,8,10-pentaenoyl]oxy}-1-oxacyclododec-4-en-2-yl]propyl]-1H-1,2,3-triazol-4-yl}butyl)-1λ$^5$,3-diaza-2λ$^4$-boratricyclo[7.3.0.0$^{3,7}$]dodeca-1(12),4,6,8,10-pentaen-1-ylium (compound 28);

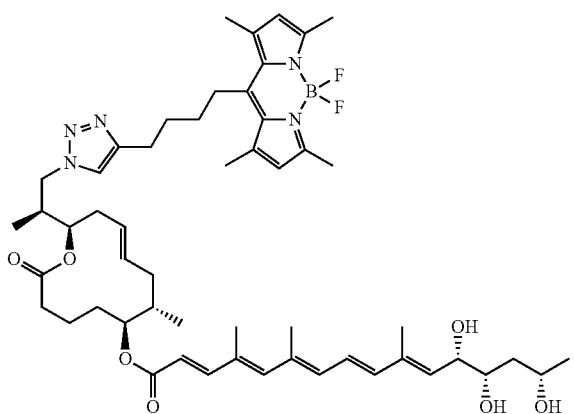

2,2-difluoro-8-(4-{1-[(2S)-2-[(2R,4E,7S,8S)-8-hydroxy-7-methyl-12-oxo-1-oxacyclododec-4-en-2-yl]propyl]-1H-1,2,3-triazol-4-yl}butyl)-4,6,10,12-tetramethyl-1λ$^5$,3-diaza-2λ$^4$-boratricyclo[7.3.0.0$^{3,7}$]dodeca-1(12),4,6,8,10-pentaen-1-ylium (Compound 29):

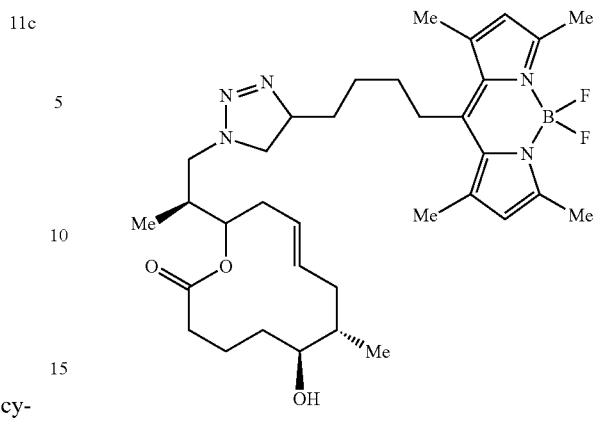

(6S,7S,9E,12R)-7-methyl-2-oxo-12-(propan-2-yl)-1-oxacyclododec-9-en-6-yl(2E,4E,6E,8E,10E,12S,13S,15R)-12,13,15-trihydroxy-4,6,10-trimethylhexadeca-2,4,6,8,10-pentaenoate (compound 22b);

(6S,7S,9E,12R)-7-methyl-2-oxo-12-(propan-2-yl)-1-oxacyclododec-9-en-6-yl(2E,4E,6E,8E,10E,12R,13R,15R)-12,13,15-trihydroxy-4,6,10-trimethylhexadeca-2,4,6,8,10-pentaenoate (compound 22c);

(6S,7S,9E,12R)-7-methyl-2-oxo-12-(propan-2-yl)-1-oxacyclododec-9-en-6-yl(2E,4E,6E,8E,10E,13S,15S)-13,15-dihydroxy-4,6,10-trimethylhexadeca-2,4,6,8,10-pentaenoate (compound 22d);

(6S,7 S,9E,12R)-7-methyl-2-oxo-12-(propan-2-yl)-1-oxacyclododec-9-en-6-yl(2E,4E,6E,8E,10E,13S)-13-hydroxy-4,6,10-trimethylhexadeca-2,4,6,8,10-pentaenoate (compound 22e);

(6S,7S,9E,12R)-7-methyl-2-oxo-12-(propan-2-yl)-1-oxacyclododec-9-en-6-yl 3-[(1E,3E,5S,6S,8S)-5,6,8-trihydroxy-3-methylnona-1,3-dien-1-yl]benzoate (compound 22f);

(6S,7S,9E,12R)-7-methyl-2-oxo-12-(propan-2-yl)-1-oxacyclododec-9-en-6-yl(2E,4E,6E,8E,10E,12S,13 S)-12,13-dihydroxy-4,6,10-trimethylhexadeca-2,4,6,8,10-pentaenoate (compound 22g);

(6S,7S,9E,12R)-7-methyl-2-oxo-12-(propan-2-yl)-1-oxacyclododec-9-en-6-yl(2E,4E,6E,8E,10E,12R,13R)-12,13-dihydroxy-4,6,10-trimethylhexadeca-2,4,6,8,10-pentaenoate (compound 22h);

(6S,7S,9E,12R)-7-methyl-2-oxo-12-(propan-2-yl)-1-oxacyclododec-9-en-6-yl(2E,4E,6E,8E,10E,12S)-12-hydroxy-4,6,10-trimethylhexadeca-2,4,6,8,10-pentaenoate (compound 22i);

(6S,7S,9E,12R)-7-methyl-2-oxo-12-(propan-2-yl)-1-oxacyclododec-9-en-6-yl(2E,4E,6E,8E,10E,15S)-15-dihydroxy-4,6,10-trimethylhexadeca-2,4,6,8,10-pentaenoate (compound 22j);

(6S,7S,9E,12R)-7-methyl-2-oxo-12-(propan-2-yl)-1-oxacyclododec-9-en-6-yl 3-[(1E,3E,5E,7S,8S,10S)-7,8,10-trihydroxy-5-methylundeca-1,3,5-trien-1-yl]benzoate (compound 22k);

(6S,7S,9E,12R)-7-methyl-2-oxo-12-(propan-2-yl)-1-oxacyclododec-9-en-6-yl(2E)-3-{3-[(1E,3E,5S,6S,8S)-5,6,8-trihydroxy-3-methylnona-1,3-dien-1-yl]phenyl}prop-2-enoate (compound 22l);

(6S,7S,9E,12R)-7-methyl-2-oxo-12-(propan-2-yl)-1-oxacyclododec-9-en-6-yl(2E,4E)-4,6-dimethylhepta-2,4,6-trienoate (compound 22m);

(6S,7S,9E,12R)-7-methyl-2-oxo-12-(propan-2-yl)-1-oxacyclododec-9-en-6-yl(2E,4E,6E,8E,10E,12R,13S,15S)-12, 13,15-trihydroxy-4,6,10-trimethylhexadeca-2,4,6,8,10-pentaenoate (compound 22n);

(6 S,7S,9E,12R)-7-methyl-2-oxo-12-(propan-2-yl)-1-oxacyclododec-9-en-6-yl(2E,4E,6E,8E,10E,12S,13R,15S)-12,13,15-trihydroxy-4,6,10-trimethylhexadeca-2,4,6,8,10-pentaenoate (compound 22o);

(2E,8E,10E,12S,13S)-((6S,7S,12R,E)-12-((2S,6R,7R,9R,E)-7,9-dihydroxy-4,6-dimethyldec-4-en-2-yl)-7-methyl-2-oxooxacyclodec-9-en-6-yl) 12,13-dihydroxy-4,6,10-trimethylhexadeca-2,4,6,8,10-pentaenoate (Compound 20e)

(6S,7S,12R)-7-methyl-2-oxo-12-(propan-2-yl)-1-oxacyclododecan-6-yl(2E,4E,6E,8E,10E,12S,13S,15S)-12,13,15-trihydroxy-4,6,10-trimethylhexadeca-2,4,6,8,10-pentaenoate (compound C-004);

Cyclohexyl(2E,4E,6E,8E,10E,12S,13S,15S)-12,13,15-trihydroxy-4,6,10-trimethylhexadeca-2,4,6,8,10-pentaenoate (compound C-002);

(6 S,7S,9E,12R)-12-[(2S)-1-(4-pentyl-1H-1,2,3-triazol-1-yl)propan-2-yl]-7-methyl-2-oxo-1-oxacyclododec-9-en-6-yl(2E,4E,6E,8E,10E,12S,13R,15S)-12,13,15-trihydroxy-4,6,10-trimethylhexadeca-2,4,6,8,10-pentaenoate (compound 28b);

(6S,7S,9E,12R)-12-[(2S)-1-{4-[(1S)-1-hydroxyethyl]-1H-1,2,3-triazol-1-yl}propan-2-yl]-7-methyl-2-oxo-1-oxacyclododec-9-en-6-yl(2E,4E,6E,8E,10E,12S,13R,15S)-12,13,15-trihydroxy-4,6,10-trimethylhexadeca-2,4,6,8,10-pentaenoate (compound 28c);

In another object, the present invention relates to a pharmaceutical composition comprising a compound of formula (I) as defined above, in admixture with one or more pharmaceutically acceptable excipients.

In a further object, the present invention relates to a compound of formula (I) as defined above for use in the treatment of inflammation and/or as an immunosuppressing agent.

In another object, the present invention relates to a compound of formula (A) for use in the treatment of pain:

$$Y—O—W \tag{A}$$

Wherein:

W is H or —C(=O)—X;

X is $X_a$, $X_b$, $X_c$, $X_d$ or $X_e$:

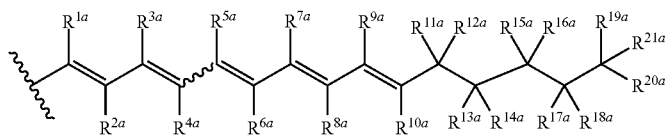

(X$_a$)

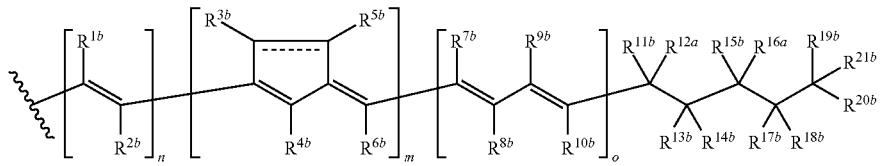

(X$_b$)

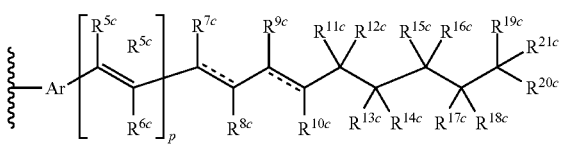

(X$_c$)

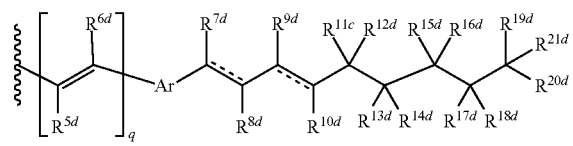

(X$_d$)

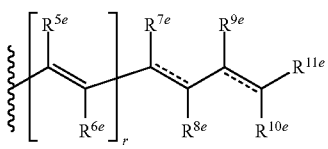

(X$_e$)

$R^{1a}$ to $R^{10a}$, $R^{1b}$ to $R^{10b}$, $R^{5c}$ to $R^{10c}$, $R^{5d}$ to $R^{10d}$, $R^{5e}$ to $R^{10e}$ and $R^{21a}$, $R^{21b}$, $R^{21c}$, $R^{21d}$ and $R^{11e}$ are each independently selected from H and $C_1$-$C_6$ alkyl;

$R^{11a}$ to $R^{20a}$, $R^{11b}$ to $R^{20b}$, $R^{11c}$ to $R^{20c}$, $R^{11d}$ to $R^{21d}$ are each independently selected from H, halogen, notably fluorine, hydroxy, and $C_1$-$C_6$ alkoxy;

Ar is a phenylene group or a 5 membered heteroarylene group, said phenylene and heterorylene groups being optionally substituted with one to four groups selected from $C_1$-$C_6$ alkyl;

n is 0 or 1;

m is 0, 1 or 2;

o is 0, 1 ort;

provided that m+n+o=3;

p is 0 or 1;

q is 0 or 1;

r is 1 or 2;

Y is selected from $C_2$-$C_6$ alkenyl, $C_3$-$C_{10}$ cycloalkyl, $C_3$-$C_{10}$ cycloalkenyl, ($C_1$-$C_6$)alkoxy($C_1$-$C_6$)alkyl, ($C_1$-$C_6$) alkoxy($C_6$-$C_{10}$)aryl, and Z;

Z is:

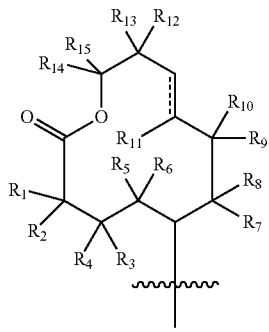

(Z)

$R^1$ to $R^{10}$ and $R^{12}$, $R^{13}$ are each independently selected from H and $C_1$-$C_6$ alkyl;

$R^{11}$ is selected from H, $C_1$-$C_6$ alkyl, $C_3$-$C_{10}$ cycloalkyl, $CF_3$, and halogen;

===== is a single bond (C—C) or a double bond (C=C);

$R^{14}$, $R^{15}$ are each independently selected from H, $C_1$-$C_6$ alkyl, and $C_3$-$C_{10}$ cycloalkyl, or one of $R^{14}$, $R^{15}$ is L and the other is H;

L is $L_1$, $L_2$, or $L_3$:

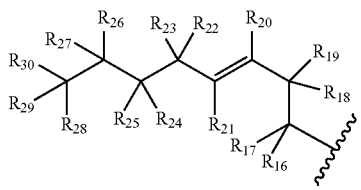

(L₁)

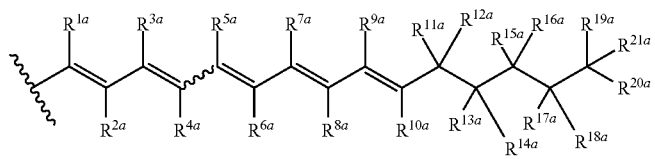

(L₂)

(L₃)

$R^{16}$, $R^{17}$, $R^{18}$, $R^{19}$, $R^{20}$, $R^{21}$, $R^{22}$, $R^{23}$, $R^{26}$, $R^{27}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, and $R^{46}$ are each independently selected from H and $C_1$-$C_6$ alkyl;

$R^{24}$, $R^{25}$, $R^{28}$, $R^{29}$ and $R^{47}$ are each independently selected from H, halogen, hydroxyl, and $(C_1$-$C_6)$alkoxy;

With the provision that when W is H, and $R^{11}$ is H, then one of $R^{14}$, $R^{15}$ cannot be $C_1$-$C_6$ alkyl;

With the provision that when Y is selected from $C_2$-$C_6$ alkenyl, $C_3$-$C_{10}$ cycloalkyl, $C_3$-$C_{10}$ cycloalkenyl, $(C_1$-$C_6)$ alkoxy$(C_1$-$C_6)$alkyl, $(C_1$-$C_6)$alkoxy$(C_6$-$C_{10})$aryl, then W is —C(=O)—X;

and the stereoisomeric forms, or mixtures of stereoisomeric forms thereof.

In a particular aspect, there is included the compounds of formula (A):

$$Y\text{—}O\text{—}W \quad (A)$$

Wherein:

W is H or C(=O)—X;

X is $X_a$, $X_b$ or $X_c$:

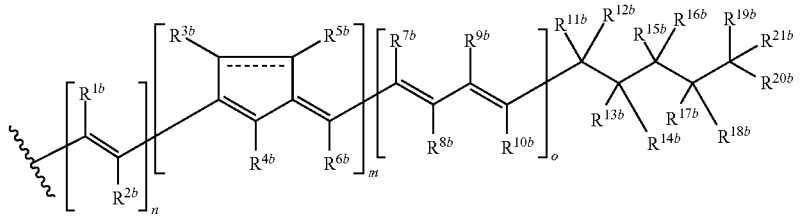

(Xₐ)

(X_b)

-continued (X_c)

[structure with Ar, R^{5c}, R^{6c}, R^{7c}, R^{8c}, R^{9c}, R^{10c}, R^{11c}, R^{12c}, R^{13c}, R^{14c}, R^{15c}, R^{16c}, R^{17c}, R^{18c}, R^{19c}, R^{20c}, R^{21c}]

$R^{1a}$ to $R^{10a}$, $R^{1b}$ to $R^{10b}$, $R^{5c}$ to $R^{10c}$, and $R^{21a}$, $R^{21b}$, $R^{21c}$ are each independently selected from H and $C_1$-$C_6$ alkyl;

$R^{11a}$ to $R^{20a}$, $R^{11b}$ to $R^{20b}$, $R^{11c}$ to $R^{20c}$ are each independently selected from H, halogen, notably fluorine, hydroxy, and $C_1$-$C_6$ alkoxy;

Ar is a phenylene group or a 5 membered heteroarylene group, said phenylene and heteroarylene groups being optionally substituted with one to four groups selected from $C_1$-$C_6$ alkyl;

n is 0 or 1;
m is 0, 1 ort;
o is 0, 1 or 2;
provided that m+n+o=3;
p is 0 or 1;
Y is selected from $C_2$-$C_6$ alkenyl, $C_3$-$C_{10}$ cycloalkyl, $C_3$-$C_{10}$ cycloalkenyl, $(C_1$-$C_6)$alkoxy$(C_1$-$C_6)$alkyl, $(C_1$-$C_6)$alkoxy$(C_6$-$C_{10})$aryl, or Z;
Z is:

(Z)

[structure with R_1 through R_{15}]

$R^1$ to $R^{10}$ and $R^{12}$, $R^{13}$ are each independently selected from H or $C_1$-$C_6$ alkyl;

$R^{11}$ is selected from H, $C_1$-$C_6$ alkyl, $C_3$-$C_{10}$ cycloalkyl, $CF_3$, and halogen;

===== is a single bond (C—C) or a double bond (C=C);

$R^{14}$, $R^{15}$ are each independently selected from H, $C_1$-$C_6$ alkyl, and $C_3$-$C_{10}$ cycloalkyl, or
one of $R^{14}$, $R^{15}$ is L and the other is H;
L is $L_1$ or $L_2$:

(L_1)

[structure with R_{16} through R_{30}]

(L_2)

[structure with BODIPY-like moiety and R_{16}–R_{44}]

$R^{16}$, $R^{17}$, $R^{18}$, $R^{19}$, $R^{20}$, $R^{21}$, $R^{22}$, $R^{23}$, $R^{26}$, $R^{27}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$ and $R^{44}$ are each independently selected from H and $C_1$-$C_6$ alkyl;

$R^{24}$, $R^{25}$, $R^{28}$ and $R^{29}$ are each independently selected from H, halogen, hydroxyl or $(C_1$-$C_6)$alkoxy;

With the provision that when W is H, and $R^{11}$ is H, then one of $R^{14}$, $R^{15}$ cannot be $C_1$-$C_6$ alkyl;

and the stereoisomeric forms, or mixtures of stereoisomeric forms thereof.

In a particular aspect of the present invention, there are included compounds of formula (I) for use in the treatment of pain.

In a particular aspect, the compounds of formulae (A) and/or (I) for use in the treatment of inflammation and/or pain, are used at non-cytotoxic or non-cytopathic doses, notably at doses which do not cause any neuronal toxicity.

Methods for determining cytotoxicity or cytopathicity of a compound are known in the art and in particular described in the examples below.

As used herein, a neuronal toxicity means a toxicity which leads to a neuronal death or to a regression of its extremities, for example its dendritic or axonal extremities.

In a further aspect, the compounds of formulae (A) and/or (I), notably mycolactone A/B, are used at a dose inferior or equal to 2.5 mg per kg of body weight of the individual to be treated (mg/kg), notably at a dose inferior or equal to 1 mg/kg.

According to yet another object, the present invention relates to a method of treatment of inflammation, said method comprising administering a therapeutically effective amount of a compound of formula (I) to a patient in need thereof.

According to a further object, the present invention relates to a method of treatment of pain, said method comprising administering a therapeutically effective amount of a compound of formula (A) to a patient in need thereof.

According to a still further object, the present invention relates to a method of preparation of compounds of formula (I).

The compounds can be synthesized, for example, in a number of ways well known to those skilled in the art, or by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations*, Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Additionally, the process of the invention may lead to several regioisomers which are all encompassed by the present invention. Regioisomers are generally isolated by chromatography.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 3$^{rd}$ ed., John Wiley and Sons, 1999; J. F. W. McOmie in *Protective Groups in Organic Chemistry*, Plenum Press, 1973.

The compound prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

According to a first aspect, the present invention provides a method of preparation of compounds of formula (I) as defined above, said method comprising the steps of:

i) Coupling a compound of formula (II) with a compound of formula (III) according to an esterification reaction,

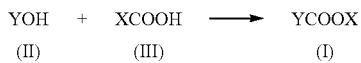

Wherein X and Y are as defined in formula (I) hereinabove, the functional groups optionally present in X and Y groups being protected by protecting groups when appropriate;

ii) Removing, when present, said protecting groups in the obtained protected compound of formula (I); and optionally iii) Recovering the obtained compound of formula (I).

In an additional aspect, the compound of formula (II) has the formula (IIa) and is prepared from a compound of formula (IVa) and a compound of formula (IVb):

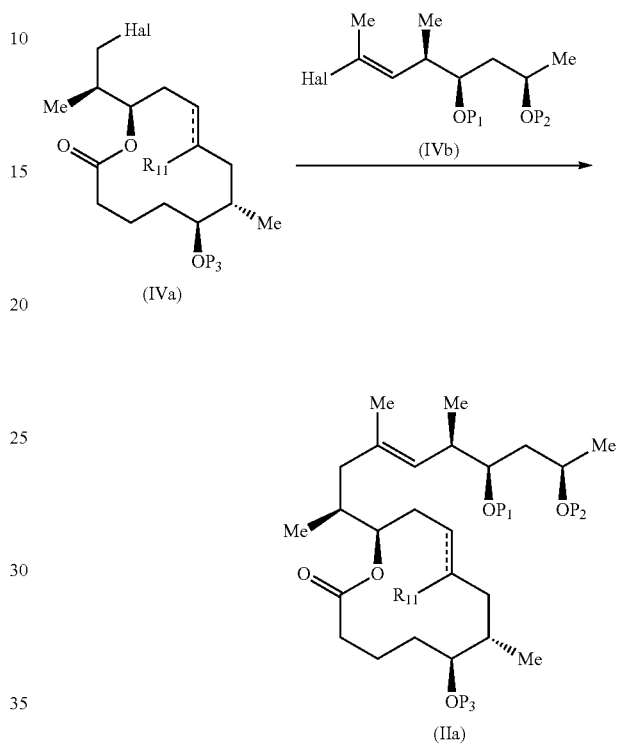

Wherein $P_1$, $P_2$ and $P_3$ are protecting groups and Hal is halogen, notably I.

$P_1$, $P_2$ and/or $P_3$ form preferably a silyl ether group with the oxygen to which they are attached and are notably selected from a trimethylsilyl (TMS), or a tert-butyldimethylsilyl (TBDMS) protecting group.

The conversion of the compound of formula (IVa) into (IIa) may be performed according to the following steps:

Converting the halomacrolactone (IVa) into the corresponding organozinc derivative by treatment with Riecke zinc;

Coupling the obtained organozinc derivative with the vinylhalogen (IVb) according to a Negishi coupling, notably carried out in the presence of Pd(PPh$_3$)$_4$, LiCl, NMP/DMF/C$_6$H$_6$; and optionally Removing the hydroxyl protecting groups $P_1$, $P_2$ and/or $P_3$ in the presence of HF. Pyridine.

For more information regarding the above Negishi coupling, reference could be made to the publications of Kishi et al.[22] and Burkart et al.[23].

In an additional aspect of the present invention, the compound of formula (IVa) is prepared from a compound of formula (V):

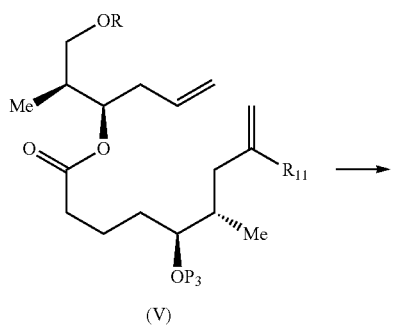

(V)

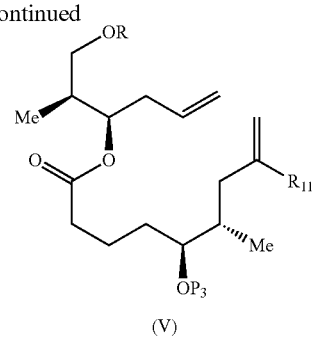

(V)

This reaction may be carried out using Steglich conditions, notably in the presence of N,N'-dicyclohexylcarbodiimide (DCC) and of dimethylaminopyridine (DMAP).

In a further aspect, the compound of formula (VII) is prepared from a compound of formula (VIII):

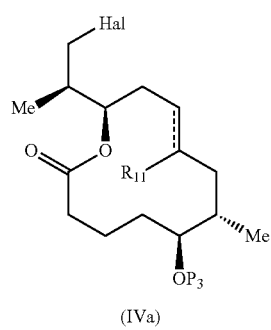

(IVa)

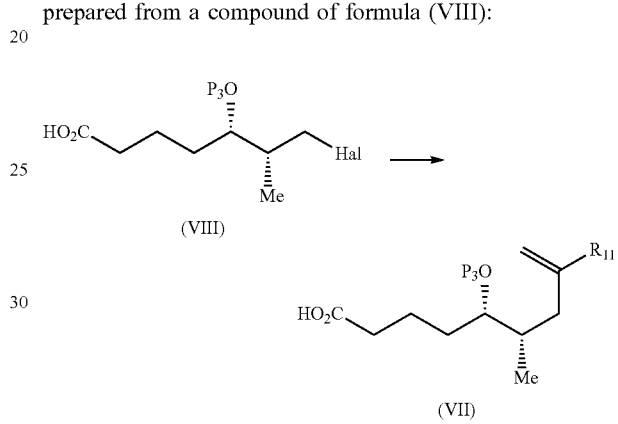

(VIII)

(VII)

Wherein R is Ms ($CH_3SO_2$) or Ts (pMe($C_6H_4$)$SO_2$).

The conversion of (V) in (IVa) may be carried according to the following steps:
  Performing a ring-closing metathesis (RCM) in the presence of a ruthenium carbene catalyst; and
  Substituting the OR leaving group by an halogen atom (Hal) according to a Finkelstein reaction.

The ruthenium carbene catalyst may be selected from Grubbs catalyst, notably of second generation.

In another aspect of the present invention, the compound of formula (V) is prepared by coupling a compound of formula (VI) with a compound of formula (VII) according to an esterification reaction:

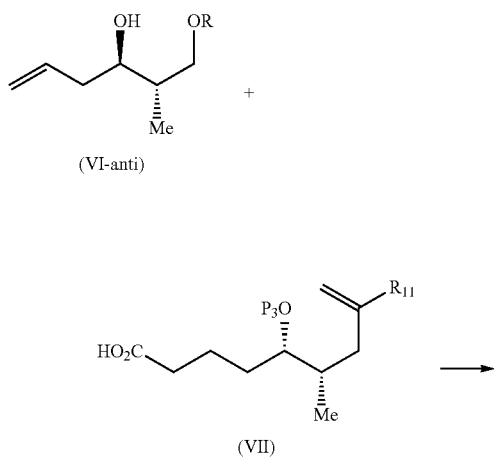

(VI-anti)

(VII)

Wherein Hal is an halogen atom, preferably I.

This reaction may be carried out according to the iron-catalyzed alkenylation reaction developed by Cossy[8], in the presence of $Me_2N(CH_2)_2NMe_2$ (TMEDA), $H_2C{=}CR^{11}MgBr$, $FeCl_3$ in THF.

In an additional embodiment, the compound of formula (VIII) is prepared from a compound of formula (IX)

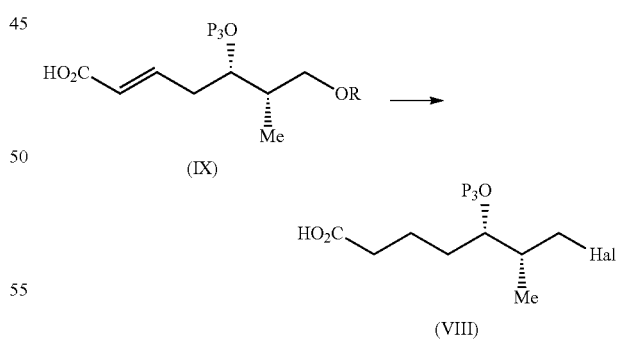

(IX)

(VIII)

Wherein R is Ms or Ts.

This conversion may be performed according to the following steps:
  Hydrogenating the double bound of (IX), for example in the presence of $H_2$, Pd(OH)$_2$;
  Substituting the OR leaving group by an halogen atom, for example in the presence of NaI.

In a further aspect, the compound of formula (IX) is prepared from a compound of formula (VI-syn):

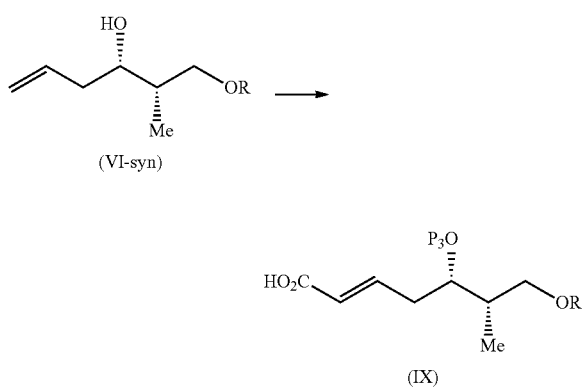

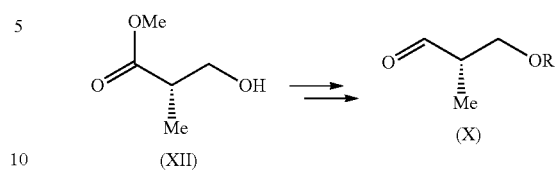

In another aspect, the compound of formula (X) is prepared from a compound of formula (XII):

In a further aspect, the compound of formula (III) has the formula (IIIc) which is prepared from a compound of formula (XIII) and (XIV):

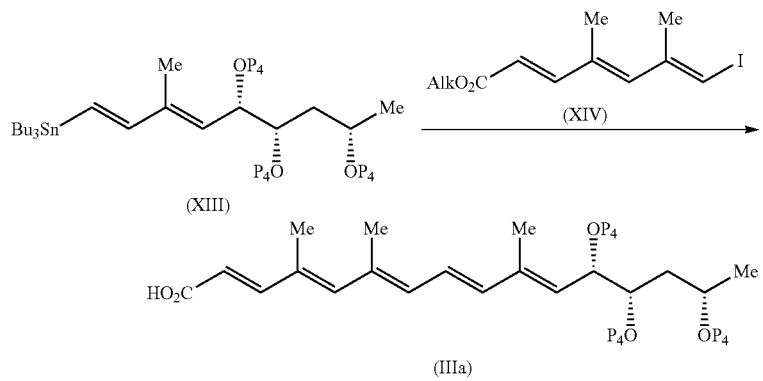

This reaction may be carried out by:

Protecting the hydroxyl group with a $P_3$ protecting group; and

Conducting a cross-metathesis with acrylic acid, notably in the presence of a ruthenium carbene catalyst such as a Grubbs catalyst, in particular a second generation Grubbs catalyst.

In yet a further aspect, the compounds of formula (VI-syn) or (VI-anti) are prepared according to a reaction of asymmetric allylboration of aldehyde of formula (X):

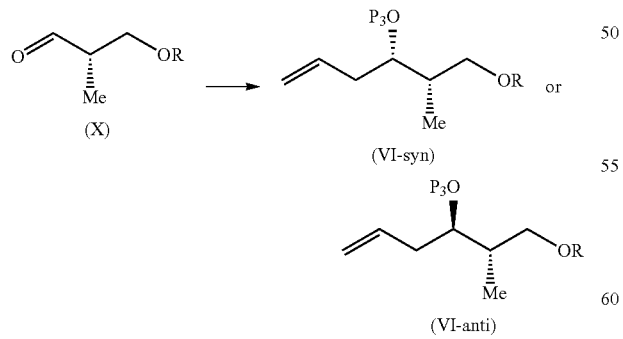

This reaction step can be carried out in the presence of (−)- or (+)-$Ipc_2Ballyl$, at −78° C., notably in $Et_2O$. Advantageously, a high diastereomeric ratio (>97:3) can be obtained in such conditions.

Wherein $P_4$ is a hydroxyl protecting group and Alk is a $C_1$-$C_6$ alkyl group.

This reaction may be carried out according to a CuTC-promoted cross-coupling reaction, notably in the presence of CuTC, $Ph_2P(O)OBu_4N$, NMP followed by treatment with LiOH, THF—$H_2O$.

In an additional aspect, the compound of formula (XIII) is prepared from a compound of formula (XV):

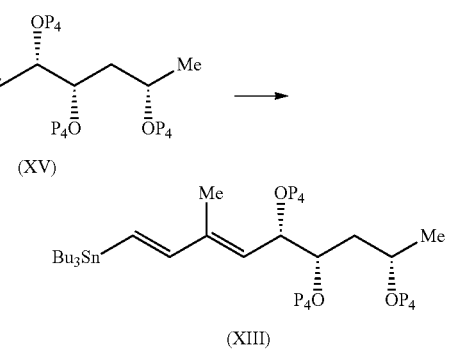

This conversion may be performed according to a three step sequence including a chromium-mediated one carbon homologation of an intermediate α,β-unsaturated aldehyde, thereby leading to the dienylstannane XIII.

More specifically, this conversion may notably comprise the steps of:

i) Reducing the ester function (—C(=O)OAlk) of the compound (XV) into an alcohol function (—CH$_2$OH), for example in the presence of an aluminium hydride such as DIBAL-H;
ii) Oxydating the obtained alcohol function into an aldehyde function (—C(=O)), for example in the presence of an oxydating agent such as MnO$_2$;
iii) Converting the aldehyde function into a function —CH=CH—SnBu$_3$, for example in the presence of CrCl$_2$, nBu$_3$SnCHBr$_2$, and LiI.

Alternatively, step iii) may be performed in two steps consisting of:
Converting the aldehyde function into a function CH=CH—I, for example in the presence of CrCl$_2$, CHI$_3$; and
Converting the —CH=CH—I into a function —CH=CH—SnBu$_3$, for example in the presence of nBuLi followed by Bu$_3$SnCl.

In yet a further aspect, the compound of formula (XV) is prepared from a compound of formula (XVI):

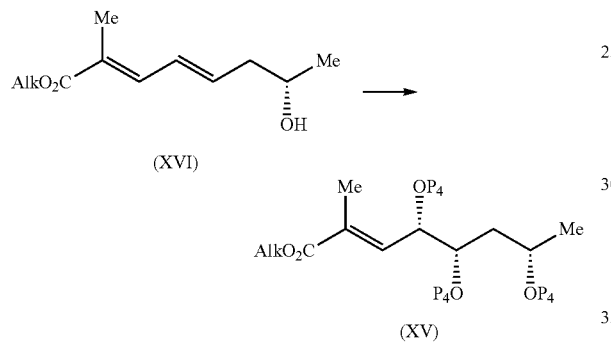

This conversion may notably include an asymmetric dihydroxylation, in particular in the presence of AD-Mix, K$_2$OsO$_4$.2H$_2$O, MeSO$_2$NH$_2$, in t-BuOH—H$_2$O. Advantageously, this reaction proceeds with complete regio- and diastereoselectivity.

In an additional aspect, the compound of formula (XVI) is prepared from a compound of formula (XVII):

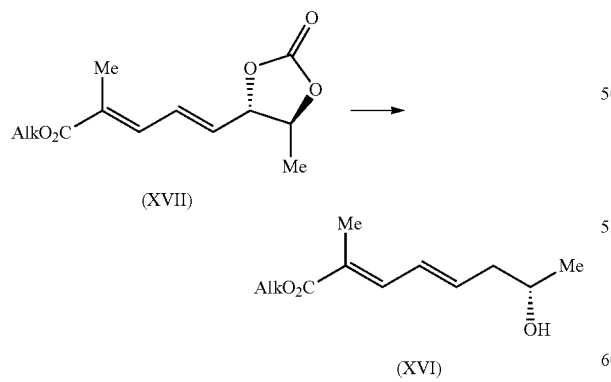

This conversion may be performed according to an allylic reduction in the presence of Pd$_2$(dba)$_3$.CHCl$_3$, Et$_3$N, HCO$_2$H.

In still another aspect, the compound of formula (XVII) is prepared from a compound of formula (XVIII):

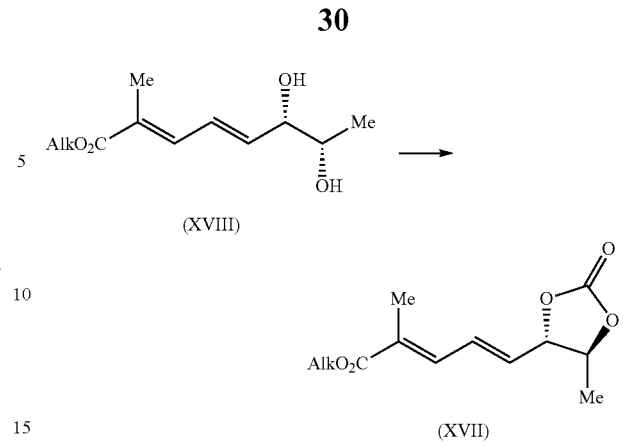

This carbonate formation may be performed in the presence of (Cl$_3$CO)$_2$CO$_3$ and of pyridine.

In a further aspect, the compound of formula (XVIII) is prepared from a compound of formula (XIX):

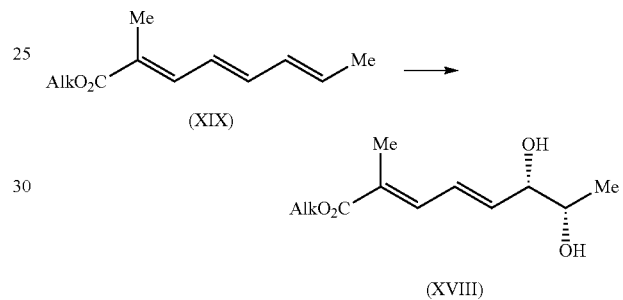

This conversion may be performed according to an asymmetric dihydroxylation, in particular in the presence of AD-Mix, K$_2$OsO$_4$.2H$_2$O, MeSO$_2$NH$_2$, in t-BuOH—H$_2$O.

In another object, the present invention relates to the compounds (VIII), (XIII), 26 and 21, as well as the racemic mixtures, enantiomers and/or diastereomers thereof. These compounds are useful as intermediates for preparing the compounds of formula (I) and/or (A)

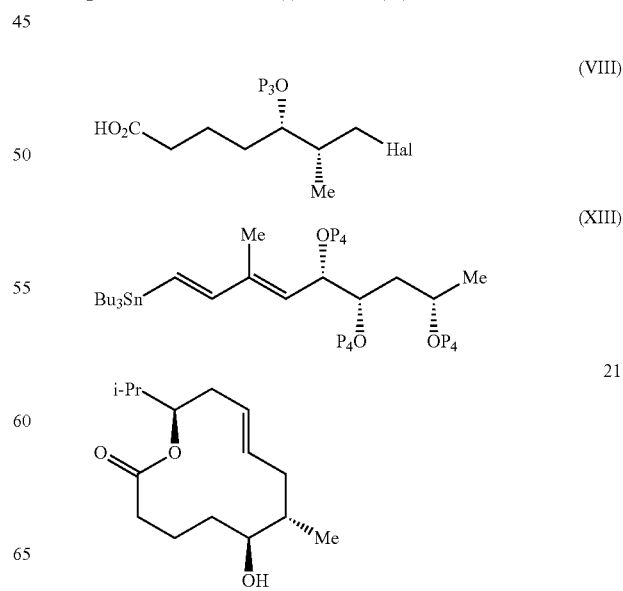

-continued

26

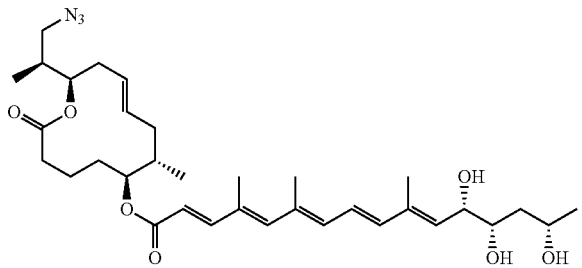

DEFINITIONS

The following terms and expressions contained herein are defined as follows:

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein, the terms "$R^x$ to $R^y$" mean the groups $R^x$ and $R^y$ as well as any group $R^i$ wherein "i" is an integer comprised in the range of values "x-y". For example, $R^1$ to $R^4$, means $R^1$, $R^2$, $R^3$, $R^4$.

As used herein, the term "alkyl" refers to a straight-chain, or branched alkyl group having 1 to 6 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, etc. The alkyl moiety of alkyl-containing groups, such as alkoxy, and alkoxyalkyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkenyl" refers to a straight chain, or branched hydrocarbon chains of 2 to 6 carbon atoms having at least one carbon-carbon double bond. A designation "$C_2$-$C_6$ alkenyl" refers to an alkenyl radical containing from 2 to 6 carbon atoms. Examples of alkenyl groups include ethenyl, propenyl, isopropenyl, 2,4-pentadienyl, etc.

As used herein, the term "alkoxy" means an alkyl-O— group, wherein the term alkyl is as defined above. Examples of alkoxy groups notably include methoxy, ethoxy, propoxy.

As used herein, the term "phenylene" refers to a phenyl group with an additional hydrogen atom removed, i.e. a moiety with the structure of:

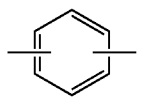

As used herein, the term "heteroarylene" refers to an aromatic group containing 5 ring carbon atoms in which one or more ring carbon atoms are replaced by at least one hetero atom such as —O—, —N—, or —S—. Examples of heteroaryl groups include pyrrolyl, furanyl, thienyl, pirazolyl, imidazolyl, thiazolyl.

As used herein, the term "cycloalkyl" refers to a saturated mono- or bicyclic alkyl ring system containing 3 to 10 carbon atoms. A designation such as "$C_5$-$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include such groups as cyclopropyl, cyclobutyl, cyclopentyl, cyclohexyl, cycloheptyl, cyclooctyl, and adamantanyl.

As used herein, the term "cycloalkenyl" refers to a partially saturated mono- or bicyclic alkyl ring system containing 3 to 10 carbon atoms. A designation such as "$C_5$-$C_7$ cycloalkenyl" refers to a cycloalkenyl radical containing from 5 to 7 ring carbon atoms. Preferred cycloalkenyl groups include those containing 5 or 6 ring carbon atoms. Examples of cycloalkenyl groups include notably pinenyl.

As used herein, the term "aryl" refers to a substituted or unsubstituted, mono- or bicyclic hydrocarbon aromatic ring system having 6 to 10 ring carbon atoms. Examples include phenyl and naphthyl. Preferred aryl groups include unsubstituted or substituted phenyl and naphthyl groups.

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorders or the disorders themselves. Such disorders include, but are not limited to inflammation, immune-mediated diseases and/or pain.

As used herein "inflammation" relates to conditions wherein attenuation or suppression of the inflammatory reaction of a subject is sought. The expression "immune-mediated diseases" relates to conditions wherein the immune system of a subject has detrimental effects on the subject. This may be in case of an abnormal activity or an overreaction of the immune system, as may be observed in autoimmune disease or in allergy. This may also be in case where a normal reaction of the immune system is unwanted, in particular to prevent graft rejection or graft-versus host disease. Accordingly, as intended herein immune-mediated diseases notably comprise autoimmune disease, allergy, graft rejection, or graft versus host disease. As intended herein, "a compound for use in treating inflammation" is considered equivalent to "a compound for use as an anti-inflammatory"; "a compound for use in the treatment of immune-mediated diseases" is considered equivalent to "a compound for use as an immunosuppressive"; and "a compound for treating pain" is considered equivalent to "a compound for use as an analgesic".

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

All other terms used in the description of the present invention have their meanings as is well known in the art.

It is recognized that compounds of the present invention may exist in various stereoisomeric forms. As such, the compounds of the present invention include both diastereomers and enantiomers. The compounds can be prepared as racemates and can be used as such, but individual enantiomers can be isolated or synthesized by the method disclosed therein or according to conventional techniques if so desired. Such racemates and individual enantiomers and mixtures thereof form part of the present invention.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

Other features of the invention will become apparent in the course of the following description of exemplary embodiments. These examples are given for illustration of the invention and are not intended to be limiting thereof.

FIGURES

FIG. 1: Synthesis of the C1-C20 fragment of C8-desmethyl mycolactones from a single chiral retron.

Figure 2:
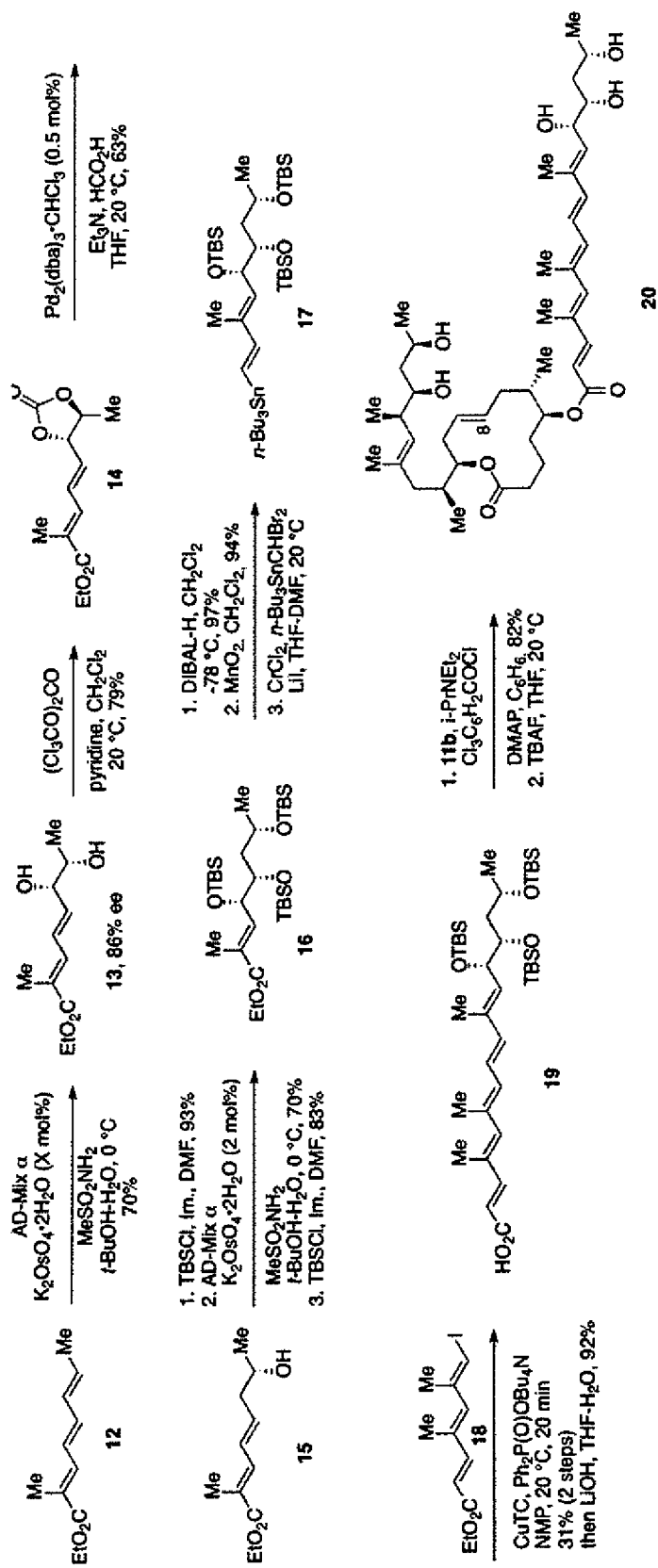

FIG. 2: Synthesis of the southern fragment of mycolactones A/B and its assembly with the C8-desmethyl core 11b.

Figure 3:
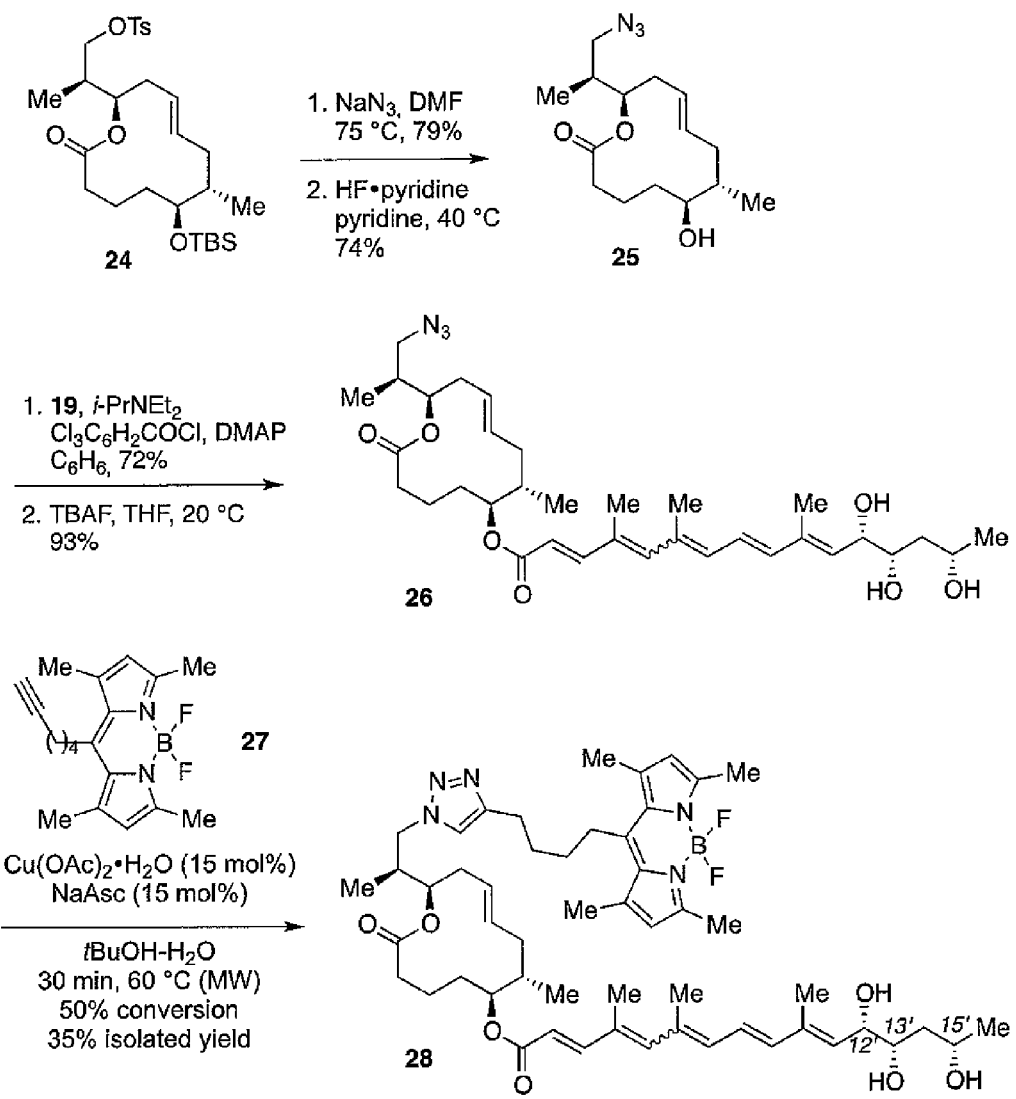

FIG. 3: Synthesis of Bodipy-mycolactone 28.

Figure 4:
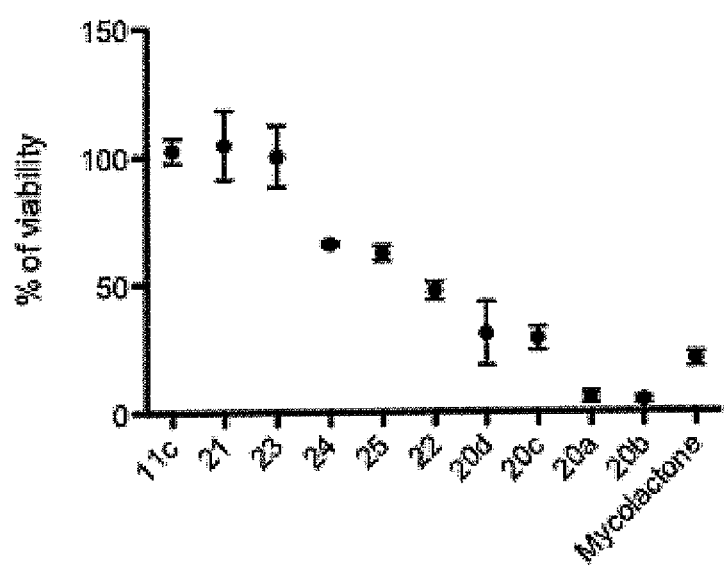

FIG. 4: Hela cell viability after 48 h of incubation with 16 µM variant or Mycolatone. Data are mean cell numbers of duplicates +/−SD.

Figure 5:
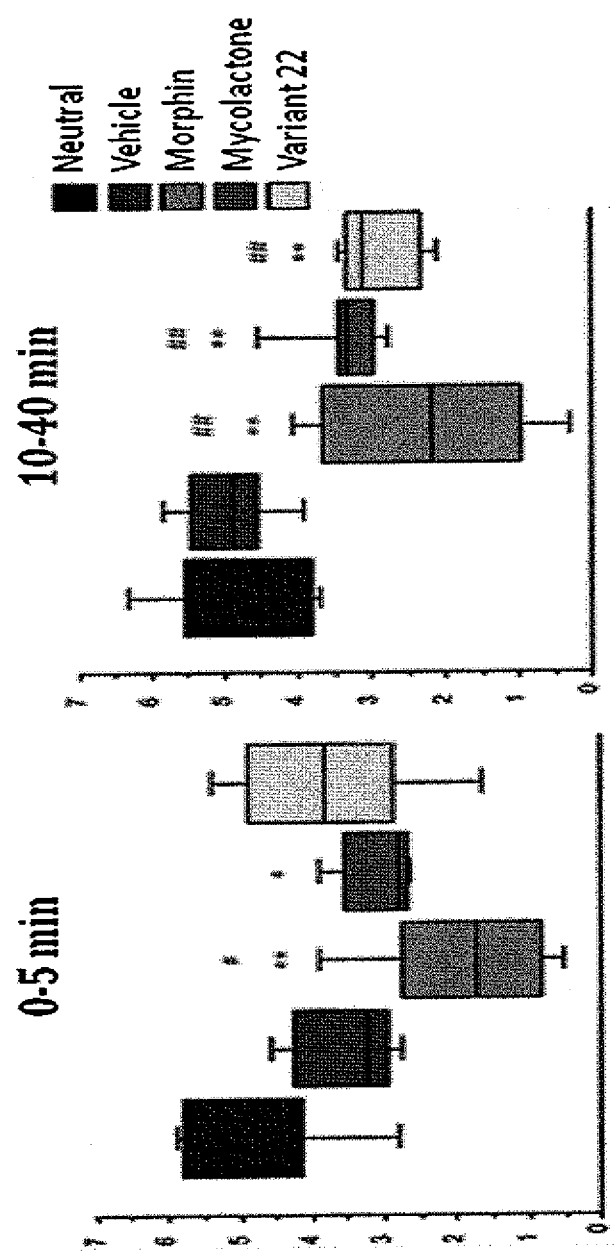

FIG. 5: Analgesic effect of mycolactone and of variant 22 against acute and inflammatory pain.

EXAMPLES

Synthesis

Materials and Methods

NMR spectra were recorded on Brucker AV 300 or AV 400 spectrometer and calibrated using undeuterated solvent as internal reference, unless otherwise indicated. Coupling constants (I) were reported in Hertz. Attached proton tests (APT) were performed to distinguish between different carbons in the $^{13}$C NMR spectra. The following abbreviations were used to explain multiplicities: s=singlet, d=doublet, t=triplet, q=quartet, m=multiplet, and b=broad. Optical rotations were recorded on a Perkin Elmer polarimeter (model 341LC) and are expressed in deg·cm$^2$·g$^{-1}$ units. High-resolution mass spectra (HRMS) were recorded on an Agilent Q-TOF (BSI) coupled with a 1100 series HPLC. Melting points were recorded on a Büchi510 melting point apparatus. All reactions were carried out in oven-dried glassware under an argon atmosphere using dry solvents, unless otherwise noted. Tetrahydrofuran (THF) was distilled under argon from sodium-benzophenone, toluene was dried using the Dry Solvent Station GT S100 developed by GlassTechnology and dichloromethane was distilled over CaH$_2$. All other anhydrous solvents were purchased from Sigma-Aldrich. Reagents were purchased from Aldrich, Acros or Alfa Aesar and used without further purification, unless otherwise noted. Yields refer to chromatographically and spectroscopically ($^1$H NMR) homogenous materials, unless otherwise noted. Reactions were monitored by thin-layer chromatography (TLC) carried out on Merck TLC silica gel 60 F254 glass-coated plates, using UV light, iodine vapor, potassium permanganate as visualizing agents. All separations were performed by flash chromatography on Merck silica gel 60 (40-63 µm) unless otherwise specified. Ozone was generated by passing 100% oxygen through an Argentox ozone generator GLX 2. Microwave reactions were performed in a CEM Intelligent Explorer (Model 541416) microwave.

Preparation of Compounds 20a to 20d.

The compounds 20a to 20d were prepared according to the schemes reported in FIGS. 1 and 2, and to the experimental conditions reported herein below. The compound 22 was prepared by adapting the synthetic routes disclosed in FIGS. 1 and 2. Compounds 28 and 29 were prepared according to or by adapting the synthetic route disclosed in FIG. 3.

-continued

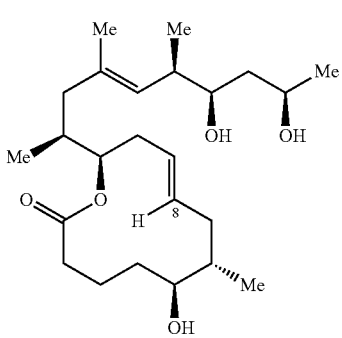

11c

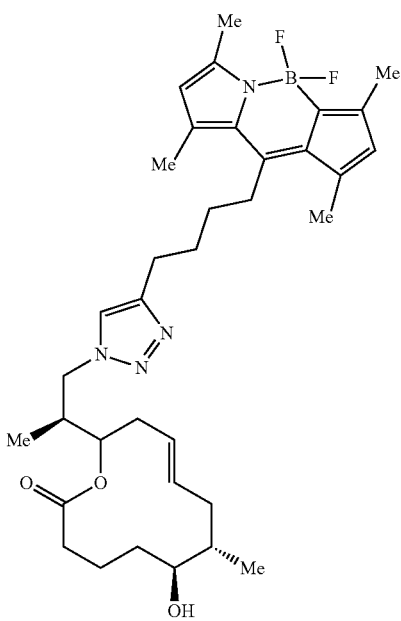

R)-3-Hydroxy-2-methylpropyl
4-methylbenzenesulfonate (2

To a solution of Roche ester (5.50 mL; 49.63 mmol), DMAP (1.20 g; 9.82 mmol) and triethylamine (10.50 mL; 74.71 mmol) in DCM (50 mL) at 0° C. was added TsCl (13.25 g; 69.50 mmol) in 3 portions. The solution was allowed to warm up to room temperature and monitored by TLC. After 4 hours at room temperature the suspension was filtered over celite, the filtrate was washed with water, dried over anhydrous sodium sulfate and concentrated under vacuum. The crude ester obtained was dissolved in toluene (100 mL) and the solution was cooled to −78° C. before dropwise addition of a solution of DIBALH (1.5 M in toluene; 76.0 mL; 114.0 mmol). The solution was allowed to warm up to room temperature and stirred overnight. The following morning the solution was cannulated into a cooled (0° C.) mixture of saturated Rochelle salt (80 mL), water (160 mL) and diethyl ether (130 mL). The mixture was stirred for 5 hours. The aqueous layer was then extracted with ethyl acetate, and the combined organic extracts were washed successively with 0.5 N HCl (80 mL), a saturated solution of sodium bicarbonate and brine. They were then dried over anhydrous sodium sulfate, filtered and concentrated. The crude compound was purified by flash chromatography on silica gel (elution with 60:40 cyclohexane/ethyl acetate solution) to yield alcohol 2 as an oil (10.53 g; 87% yield).

$^1$H NMR (300 MHz, CDCl$_3$) δ 7.80 (d, J=8.4 Hz, 2H), 7.36 (d, J=8.1 Hz, 2H), 4.04-4.01 (2H), 3.63-3.50 (2H), 2.46 (s, 3H), 2.01 (m, 1H), 0.93 (d, J=6.9 Hz, 3H).
$^{13}$C NMR (75 MHz, CDCl$_3$) δ 144.8, 132.8, 129.8, 127.8, 72.0, 63.5, 35.5, 21.6, 13.1.
$[\alpha]_D^{20}$−10.1 (c 2.5, EtOH) (litt=−9.7 (c2.93, EtOH))
HRMS calculated for C$_{11}$H$_{16}$O$_4$S+Na$^+$ 267.0662. found 267.0662 [M+Na$^+$].

(2S,3S)-3-Hydroxy-2-methylhex-5-enyl 4-methyl-benzenesulfonate (4-syn)

Procedure using the
(−)-B-methoxydiisopinocampheylborane (−)-B-methoxydiisopinocampheylborane (26.68 g; 84.34 mmol) was dissolved in diethyl ether (260 mL) and the solution was cooled to −78° C. before slow addition of a solution of allylmagnesium bromide (1.0 M in diethyl ether; 79 mL; 79.00 mmol). The solution was allowed to slowly warm up to room temperature and stirred at room temperature for one hour. Meanwhile, alcohol 2 (14.65 g; 59.97 mmol) was dissolved in DCM (60 mL) and the solution was cooled to 10° C. before addition of iodobenzene diacetate (21.40 g; 66.44 mmol) and TEMPO (0.94 g; 6.02 mmol). The orange solution was allowed to warm up to room temperature. After 2 hours, water was added to the reaction mixture and the aqueous layer was extracted with DCM; the combined organic extracts were dried over anhydrous sodium sulfate and concentrated. The crude aldehyde 3 dissolved in diethyl ether (150 mL) was slowly cannulated to the cooled (−78° C.) solution of allylborane. The temperature of the reaction mixture was maintained below −70° C. during the whole addition. The solution was then stirred for another 3 hours at −78° C. before addition of methanol (10 mL), water (84 mL) and NaBO$_3$.4H$_2$O (38.00 g; 246.98 mmol) 10 minutes later. The reaction mixture was allowed to warm up to room temperature overnight. The following morning more water was added and the aqueous layer was extracted with diethyl ether; the organic phase washed with brine, dried over anhydrous sodium sulfate, filtered and concentrated. The crude alcohol obtained was purified on an ISCO Companion on a silica cartridge (elution was as follows: start with 100% cyclohexane, ramp till 10% ethyl acetate in 5 minutes; remains at 10% ethyl acetate for 2 minutes then ramp till 15% ethyl acetate in 5 minutes; remain at 15% ethyl acetate for 8 minutes; ramp till 30% ethyl acetate in 5 minutes; remain at 30% for 10 minutes; ramp till 50% ethyl acetate in 3 minutes; remains at 50% ethyl acetate for 2 minutes; ramp till 100% ethyl acetate in 2 minutes; remains at 100% ethyl acetate for 2 minutes). [The purification can also be performed with a traditional flash chromatography on silica gel (elution:gradient from 95:5 cyclohexane/ethyl acetate to 80:20 cyclohexane/ethyl acetate). However the separation was not as efficient.

$^1$H NMR (300 MHz, CDCl$_3$) δ 7.80 (d, J=8.1 Hz, 2H), 7.36 (d, J=8.1 Hz, 2H), 5.76 (m, 1H), 5.14-5.09 (2H), 4.09 (m, 1H), 3.91 (m, 1H), 3.75 (m, 1H), 2.46 (s, 3H), 2.21-2.16 (2H), 1.94 (m, 1H), 1.59 (br s, 1H), 0.89 (d, J=6.9 Hz, 3H).
$^{13}$C NMR (75 MHz, CDCl$_3$) δ 144.8, 134.6, 132.9, 129.8, 127.9, 118.3, 72.5, 69.3, 39.1, 37.3, 21.6, 9.7.
$[\alpha]_D^{22}$+3.8 (c 1.0, CHCl$_3$) (litt=+3.2 (c 1.1, CHCl$_3$)).

Procedure using a commercial solution of
(−)-B-allyldiisopinocampheylborane

Alcohol 2 (14.65 g; 59.97 mmol) was dissolved in DCM (60 mL) and the solution was cooled to 10° C. before addition of iodobenzene diacetate (21.40 g; 66.44 mmol) and TEMPO (0.94 g; 6.02 mmol). The orange solution was stirred and allowed to warm up to room temperature. After 2 hours, water was added to the reaction mixture and the aqueous layer was extracted with DCM; the combined organic extracts were dried over anhydrous sodium sulfate and concentrated to yield aldehyde 3 that was used without further purification. Next to a cooled (−78° C.) commercial solution of (−)-B-allyidiisopinocanapheylborane (25.00 mmol in 25.0 mL of pentane) in diethyl ether (50.0 mL) was slowly added aldehyde 3 dissolved in diethyl ether (70.0 mL). The temperature of the reaction mixture was maintained below −70° C. during the whole addition. The solution was then stirred for another 3 hours at −78° C. before addition of methanol (7 mL), water (25 mL) and $NaBO_3.4H_2O$ (11.50 g; 74.74 mmol) 10 minutes later. The reaction mixture was allowed to warm up to room temperature overnight. The following morning more water was added and the aqueous layer was extracted with diethyl ether; the organic phase washed with brine, dried over anhydrous sodium sulfate, filtered and concentrated. The crude alcohol obtained was purified on an ISCO Companion on a silica cartridge (elution was as follows: start with 100% cyclohexane, ramp till 10% ethyl acetate in 5 minutes; remains at 10% ethyl acetate for 2 minutes then ramp till 15% ethyl acetate in 5 minutes; remain at 15% ethyl acetate for 8 minutes; ramp till 30% ethyl acetate in 5 minutes; remain at 30% for 10 minutes; ramp till 50% ethyl acetate in 3 minutes; remains at 50% ethyl acetate for 2 minutes; ramp till 100% ethyl acetate in 2 minutes; remains at 100% ethyl acetate for 2 minutes). Alcohol 4-syn was obtained as a colorless oil (4.96 g; 70%).

$^1H$ NMR (300 MHz, $CDCl_3$) δ 7.80 (d, J=8.1 Hz, 2H), 7.36 (d, J=8.1 Hz, 2H), 5.76 (m, 1H), 5.14-5.09 (2H), 4.09 (m, 1H), 3.91 (m, 1H), 3.75 (m, 1H), 2.46 (s, 3H), 2.21-2.16 (2H), 1.94 (m, 1H), 1.59 (br s, 1H), 0.89 (d, J=6.9 Hz, 3H).

$^{13}C$ NMR (75 MHz, $CDCl_3$) δ 144.8, 134.6, 132.9, 129.8, 127.9, 118.3, 72.5, 69.3, 39.1, 37.3, 21.6, 9.7.

$[\alpha]_D^{22}$+3.8 (c 1.0, $CHCl_3$) (litt=+3.2 (c 1.1, $CHCl_3$)).

(2S,3R)-3-Hydroxy-2-methylhex-5-enyl 4-methylbenzenesulfonate (4-anti)

Alcohol 2 (14.65 g; 59.97 mmol) was dissolved in DCM (60 mL) and the solution was cooled to 10° C. before addition of iodobenzene diacetate (21.40 g; 66.44 mmol) and TEMPO (0.94 g; 6.02 mmol). The orange solution was stirred and allowed to warm up to room temperature. After 2 hours, water was added to the reaction mixture and the aqueous layer was extracted with DCM; the combined organic extracts were dried over anhydrous sodium sulfate, filtered and concentrated to yield aldehyde 3 that was used without further purification. Next to a cooled (−78° C.) commercial solution of (+)-B-allyldiisopinocampheylborane (25.00 mmol in 25.0 mL of pentane) in diethyl ether (50.0 mL) was slowly added aldehyde 3 dissolved in diethyl ether (70.0 mL). The temperature of the reaction mixture was maintained below −70° C. during the whole addition. The solution was then stirred for another 3 hours at −78° C. before addition of methanol (7 mL), water (25 mL) and $NaBO_3.4H_2O$ (11.50 g; 74.74 mmol) 10 minutes later. The reaction mixture was allowed to warm up to room temperature overnight. The following morning more water was added and the aqueous layer was extracted with diethyl ether; the organic phase washed with brine, dried over anhydrous sodium sulfate and concentrated. The crude alcohol obtained was purified on an ISCO Companion on a silica cartridge (elution was as follows: start with 100% cyclohexane, ramp till 10% ethyl acetate in 5 minutes; remains at 10% ethyl acetate for 2 minutes then ramp till 15% ethyl acetate in 5 minutes; remain at 15% ethyl acetate for 8 minutes; ramp till 30% ethyl acetate in 5 minutes; remain at 30% for 10 minutes; ramp till 50% ethyl acetate in 3 minutes; remains at 50% ethyl acetate for 2 minutes; ramp till 100% ethyl acetate in 2 minutes; remains at 100% ethyl acetate for 2 minutes). Alcohol 4-anti was obtained as white crystals (5.45 g; 76%).

$^1H$ NMR (400 MHz, $CDCl_3$) δ 7.78 (d, J=8.4 Hz, 2H), 7.34 (d, J=8.0 Hz, 2H), 5.76 (m, 1H), 5.14-5.09 (2H); 4.09 (d, J=5.2 Hz), 3.50 (m, 1H), 2.44 (s, 3H), 2.33 (m, 1H), 2.07 (m, 1H), 1.91 (br s, 1H), 1.84 (m, 1H), 0.94 (d, J=6.8 Hz, 3H).

$^{13}C$ NMR (100 MHz, $CDCl_3$) δ 144.7, 134.1, 132.8, 129.8, 127.8, 118.7, 72.4, 70.9, 38.9, 38.2, 21.6, 13.0.

mp 45.0-46.2° C.; $[\alpha]_D^{22}$−21 (c 0.62, $CHCl_3$).

HRMS calculated for $C_{14}H_{20}O_4S+Na^+$ 307.0975. found 307.0984 $[M+Na]^+$.

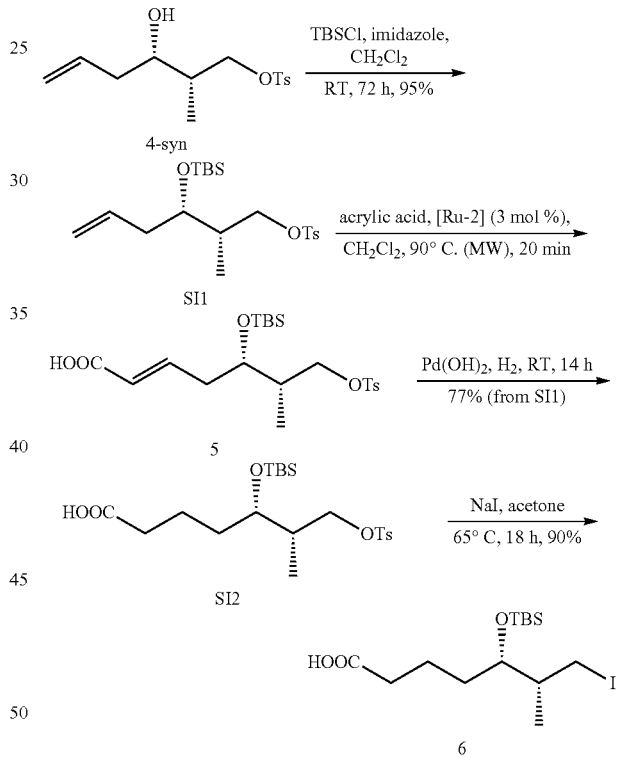

(2S,3S)-3-(tert-Butyldimethylsilyloxy)-2-methylhex-5-enyl 4-methylbenzenesulfonate (SI1)

To a solution of alcohol 4-syn (1.00 g; 3.51 mmol) in DCM (15 mL) were added imidazole (0.96 g; 14.1 mmol) and tert-butyldimethylsilyl chloride (1.27 g; 8.4 mmol). The solution was stirred at room temperature for 3 days. Then water was added and the aqueous layer was extracted using DCM, the combined organic extracts dried over anhydrous sodium sulfate, filtered and concentrated. The resulting oil was purified by flash chromatography on silica gel (elution with 80:20 cyclohexane/ethyl acetate) to afford compound SU (1.34 g; 95%).

¹H NMR (300 MHz, CDCl₃) δ 7.79 (d, J=8.4 Hz, 2H), 7.35 (d, J=8.1 Hz, 2H), 5.66 (m, 1H), 5.04-4.99 (2H), 3.98 (m, 1H); 3.85 (m, 1H), 3.75 (m, 1H), 2.46 (s, 3H), 2.20-2.12 (2H), 1.93 (m, 1H), 0.84 (d, J=7.2 Hz, 3H), 0.82 (s, 9H), 0.02 (s, 3H), −0.03 (s, 3H).
¹³C NMR (75 MHz, CDCl₃) δ 144.6, 134.5, 133.0, 129.8, 127.9, 117.2, 72.8, 71.0, 39.0, 37.0, 25.7, 25.7, 25.5, 21.6, 18.0, 10.1, −4.1, −5.0;
$[\alpha]_D^{21}$ +5.2 (c 0.8, CHCl₃)
HRMS calculated for $C_{20}H_{34}O_4SSi+Na^+$ 421.1838. found 421.1893 [M+Na]⁺.

(5S,6S)-5-(tert-butyldimethylsilyloxy)-6-methyl-7-(tosyloxy)heptanoic acid (SI2)

To a solution of SI1 (400.0 mg; 1.0 mmol) in DCM (5 mL) were added acrylic acid (0.3 mL; 4.3 mmol) and Grubbs catalyst 2$^{nd}$ generation (24 mg; 0.03 mmol). The solution was heated in a microwave at 90° C. for 20 minutes. (Note: The metathesis also takes place if the solution is stirred overnight at room temperature. In this case the yield is slightly lower.) The solution was then concentrated and filtered through a plug of silica gel (elution:ethyl acetate). The resulting oil was dissolved in ethyl acetate (14 mL) and palladium hydroxide was added to the solution. The suspension was stirred under hydrogen at room temperature overnight. The next day, the suspension was filtered through a plug of silica gel and concentrated. The crude compound was purified by flash chromatography (elution: 90:10 cyclohexane/ethyl acetate then 50:50 cyclohexane/ethyl acetate) to afford SI2 as a colorless oil (350.0 mg; 79%).
¹H NMR (300 MHz, CDCl₃) δ 7.79 (d, J=8.4 Hz, 2H), 7.35 (d, J=7.8 Hz, 2H), 4.01 (m, 1H), 3.85 (m, 1H), 3.66 (m, 1H), 2.45 (s, 3H), 2.32 (t, J=7.2 Hz, 2H), 1.92 (m, 1H), 1.66-1.24 (4H), 0.84 (d, J=6.9 Hz, 3H), 0.81 (s, 9H), 0.01 (s, 3H), −0.04 (s, 3H).
¹³C NMR (75 MHz, CDCl₃) δ 179.0, 144.7, 133.0, 129.8, 127.9, 72.6, 71.5, 37.4, 33.8, 33.1, 25.7, 21.6, 20.8, 18.0, 10.7, −4.3, −4.8.
$[\alpha]_D^{22}$ +0.8 (c 1.1, CHCl₃)
HRMS calculated for $C_{21}H_{36}O_6SSi$ 444.1929. found 444.1931 [M−H]⁻.

(5S,6R)-5-(tert-Butyldimethylsilyloxy)-7-iodo-6-methylheptanoic acid (6)

To a solution of SI2 (600.0 mg; 1.35 mmol) in acetone (15 mL) was added sodium iodide (810.0 mg; 5.40 mmol) and the solution was heated under reflux in the dark for 14 hours. The solution was cooled down to room temperature and ethyl acetate and water were added to the reaction mixture. The aqueous layer was extracted with ethyl acetate; the resulting organic extracts were rinsed with an aqueous saturated solution of sodium bisulfate, dried over anhydrous sodium sulfate, filtered and concentrated. The crude oil obtained was purified by flash chromatography over silica gel (elution: 80:20 cyclohexane/ethyl acetate) to afford 6 as a colorless oil (488 mg; 90%).
¹H NMR (300 MHz, CDCl₃) δ 3.74 (m, 1H), 3.32 (3, 1H), 3.05 (m, 1H), 2.41-2.35 (2H), 1.85 (m, 1H), 1.70-1.45 (4H), 0.98 (d, J=6.6 Hz, 3H), 0.09 (s, 3H), 0.07 (s, 3H).
¹³C NMR (75 MHz, CDCl₃) δ 179.6, 73.8, 40.9, 33.9, 33.1, 25.8, 20.6, 18.1, 14.7, 12.4, −4.3, −4.4.
$[\alpha]_D^{22}$ +11.7 (c 1.7, CHCl₃).

(5S,6S)-5-(tert-Butyldimethylsilyloxy)-6-methylnon-8-enoic acid (7)

To a solution of 6 (200.0 mg; 0.50 mmol) and FeCl₃ (20.0 mg; 0.12 mmol) in dry THF (2.2 mL) at 0° C. was added freshly distilled TMEDA (0.15 mL; 1.0 mmol) followed by a solution of vinylmagnesium bromide (1.0 M in THF; 2.0 mL; 2.0 mmol) over 30 minutes. The dark brown reaction mixture was stirred at 0° C. for another 30 minutes before addition of a 0.5 N HCl solution till the pH turned acidic. The aqueous layer was extracted with ethyl acetate; the combined organic phases dried over anhydrous sodium sulfate, filtered and concentrated. The crude compound was purified by flash chromatography over silica gel (elution: 80:20 cyclohexane/ethyl acetate) to afford 7 as a yellowish oil (76.7 mg; 51%).
¹H NMR (400 MHz, CDCl₃) δ 5.77 (m, 1H), 5.03-4.97 (2H), 3.57 (m, 1H), 2.38-2.34 (2H), 2.27 (m, 1H), 1.84-1.40 (6H), 0.90 (s, 6H), 0.84 (d, J=6.8 Hz, 3H), 0.47 (s, 6H).
¹³C NMR (100 MHz, CDCl₃) δ 180.1, 138.1, 115.5, 75.1, 37.9, 36.8, 34.2, 32.6, 25.9, 21.1, 18.1, 14.2, −4.3, −4.4.
$[\alpha]_D^{21}$ −1.8 (c 0.7, CHCl₃)

(5S,6S)-((2S,3R)-2-Methyl-1-(tosyloxy)hex-5-en-3-yl) 5-(tert-butyldimethylsilyloxy)-6-methylnon-8-enoate (8)

To a solution of acid 7 (553.0 mg; 1.84 mmol) and DMAP (265.0 mg; 2.17 mmol) in DCM (2.0 mL) at 0° C. was added DCC (453.0 mg; 2.20 mmol) followed by a solution of alcohol 4-anti (530 mg; 1.87 mmol) in DCM (1.5 mL) 30 minutes later. The mixture was allowed to warm up to room temperature and stirred for 14 hours. The mixture was then filtered, rinsed with DCM and concentrated. The crude ester was purified by flash chromatography over silica gel (elution: 95:5 cyclohexane/ethyl acetate) to afford 8 as a colorless oil (857.0 mg; 82%).
¹H NMR (300 MHz, CDCl₃) δ 7.77 (d, J=8.4 Hz, 2H), 7.35 (d, J=8.1 Hz, 2H), 5.83-5.60 (2H), 5.06-4.97 (4H), 4.86 (m, 1H), 4.05 (m, 1H), 3.89 (m, 1H), 3.55 (m, 1H), 2.46 (s, 3H), 2.38-2.18 (4H), 2.10 (m, 1H), 1.83-1.24 (7H), 0.95 (d, J=6.9 Hz, 3H), 0.89 (s, 9H), 0.82 (d, J=6.9 Hz, 3H), 0.04 (s, 6H).
¹³C NMR (75 MHz, CDCl₃) δ 172.7, 144.8, 138.1, 132.9, 129.8, 127.9, 118.2, 115.5, 75.2, 73.2, 71.2, 38.0, 36.6, 35.9, 35.7, 34.4, 32.5, 25.9, 21.7, 21.5, 18.2, 14.2, 13.4, −4.3, −4.4.
$[\alpha]_D^{20}$ −25.8 (c 0.8, CHCl₃)
HRMS calculated for $C_{30}H_{50}O_6SSi$ Na⁺ 589.2990. found 589.2982 [M+Na]⁺.

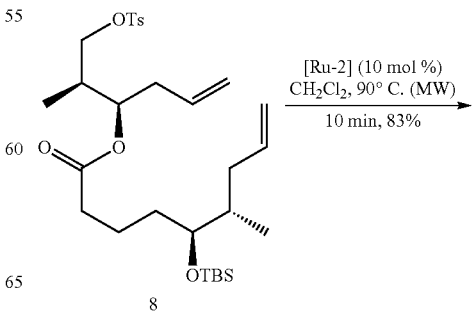

8

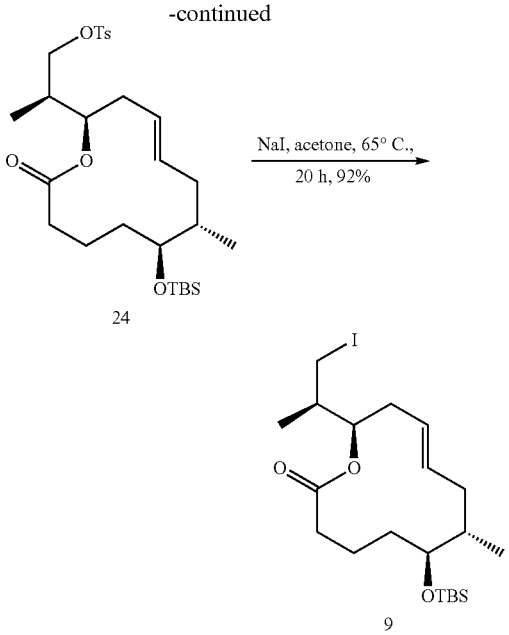

S)-2-((2R,7S,8S,E)-8-(tert-Butyldimethylsilyloxy)-7-methyl-12-oxooxacyclododec-4-en-2-yl)propyl 4-methylbenzenesulfonate (24

To a solution of ester 8 (55.0 mg; 0.10 mmol) in DCM (12 mL) was added Grubbs catalyst $2^{nd}$ generation (8.2 mg; 0.010 mmol). The solution was heated in a microwave at 90° C. for 10 minutes. It was then concentrated under reduced pressure. The crude compound was purified by preparative TLC (elution: 80:20 cyclohexane/ethyl acetate) to afford 24 as a colorless oil (43.3 mg; 83%). (Note: The metathesis also takes place if the solution is stirred 48 hours at room temperature. In this case the yield is slightly lower.)

$^1$H NMR (300 MHz, CDCl$_3$) δ 7.80 (d, J=8.4 Hz, 2H), 7.36 (d, J=8.1 Hz, 2H), 5.40 (m, 1H), 5.10 (m, 1H), 4.84 (m, 1H), 4.04 (m, 1H), 3.84 (m, 1H), 3.33 (m, 1H), 2.46 (s, 3H), 2.41 (m, 1H), 2.25 (m, 1H), 2.13-1.97 (2H), 1.94-1.85 (2H), 1.78-1.70 (2H), 1.65 (m, 1H), 1.60-1.39 (3H), 0.96 (d, J=6.9 Hz, 3H), 0.95 (d, J=6.6 Hz, 3H), 0.89 (s, 9H), 0.04 (s, 6H).

$^{13}$C NMR (75 MHz, CDCl$_3$) δ 173.0, 144.8, 136.3, 132.8, 129.8, 128.0, 124.0, 77.3, 71.6, 71.5, 37.9, 37.3, 36.6, 36.3, 35.6, 32.6, 26.9, 25.9, 21.7, 21.4, 18.2, 13.5, −4.2.

HRMS calculated for $C_{28}H_{46}O_6SSi+Na^+$ 561.2677. found 561.2669 [M+Na$^+$].

(6S,7S,12R,E)-6-(tert-Butyldimethylsilyloxy)-12-((R)-1-iodopropan-2-yl)-7-methyloxacyclododec-9-en-2-one (9)

To a solution of the previous lactone SI3 (442.0 mg; 0.82 mmol) in acetone (20 mL) was added sodium iodide (413.0 mg; 2.8 mmol) and the solution was heated under reflux in the dark for 14 hours. The solution was cooled down to room temperature and ethyl acetate and water were added to the reaction mixture. The aqueous layer was extracted with ethyl acetate, the combined organic layers rinsed with an aqueous saturated solution of sodium bisulfate, dried over anhydrous sodium sulfate, filtered and concentrated. The crude oil obtained was purified by flash chromatography over silica gel (elution: 95:5 cyclohexane/ethyl acetate then 90:10 cyclohexane/ethyl acetate) to afford 9 as a colorless oil (374.0 mg; 92%).

$^1$H NMR (300 MHz, CDCl$_3$) δ 5.45 (m, 1H), 5.17 (m, 1H), 4.85 (m, 1H), 3.63-3.27 (2H), 2.99 (m, 1H), 2.54 (m, 1H), 2.37-2.27 (2H), 2.11 (m, 1H), 2.01-1.43 (8H), 1.08 (d, J=6.9 Hz, 3H), 0.95 (d, J=6.6 Hz, 3H), 0.89 (s, 9H), 0.04 (s, 6H)

$^{13}$C NMR (75 MHz, CDCl$_3$) δ 173.1, 136.2, 124.1, 77.4, 73.5, 40.1, 37.9, 36.5, 36.3, 35.8, 32.6, 25.9, 21.4, 18.2, 17.2, 10.6, −4.2, −4.8.

(6S,7S,9E,12R)-12-[(2S,4E,6R,7R,9R)-7,9-bis[(tert-Butyldimethylsilyl)oxy]-4,6-dimethyldec-4-en-2-yl]-6-[(tert-butyldimethylsilyl)oxy]-7-methyl-1-oxacyclododec-9-en-2-one (11a)

To a solution of naphthalene (255.0 mg; 2.0 mmol) in THF (0.7 mL) was added lithium (13.0 mg; 1.9 mmol) cut into small pieces and previously washed with cyclohexane, methanol and diethyl ether successively. The suspension was stirred at room temperature for 3 hours before addition of a solution of zinc chloride (125.0 mg; 0.92 mmol; previously flame-dried twice) in THF (1.0 mL) and the reaction mixture was stirred for another 30 minutes. The suspension was then centrifuged and the supernatant was removed before addition of a solution of alkyl iodide 9 (60.0 mg; 0.12 mmol) in benzene/DMF (15:1, 0.7 mL); the reaction mixture was then stirred for 45 minutes. Meanwhile, a solution of vinyl iodide 10 (38.0 mg; 0.07 mmol) in NMP (0.45 mL) was added to a mixture of Pd(PPh$_3$)$_4$ (10.3 mg; 0.009 mmol) and LiCl (31.0 mg; 0.7 mmol; previously flame-dried) in NMP (0.3 mL). Next the supernatant of the alkylzinc iodide solution was added via cannula and the resulting reaction mixture was degassed and stirred at room temperature for 30 minutes and then at 55° C. for 15 hours. The cooled reaction mixture was poured into a mixture of water and ethyl acetate. The mixture was extracted with ethyl acetate and the combined extracts were washed with saturated aqueous NaHCO$_3$, dried over anhydrous sodium sulfate, filtered and concentrated. The crude compound was purified by flash chromatography over silica gel (elution:gradient from 90:10 to 80:20 cyclohexane/ethyl acetate) to afford 11a as a yellow oil (35.0 mg; 63%).

$^1$H NMR (400 MHz, CDCl$_3$) δ 5.42 (m, 1H), 5.20 (m, 1H), 5.12 (d, J 9.9 Hz, 1H), 4.75 (m, 1H), 3.88 (m, 1H), 3.57 (m, 1H), 3.33 (m, 1H), 2.53 (m, 1H), 2.46 (m, 1H), 2.25-2.23 (2H), 2.14-2.03 (3H), 1.98-1.91 (2H), 1.83 (m, 1H), 1.79-1.51 (8H), 1.57 (d, J=4.0 Hz, 3H), 1.45-1.39 (2H), 1.12 (d, J=6.0 Hz, 3H), 0.94 (d, J=6.4 Hz, 3H), 0.88-0.86 (27H), 0.80 (d, J=6.8 Hz, 3H), 0.04 (s, 18H).

$^{13}$C NMR (100 MHz, CDCl$_3$) δ 173.3, 135.6, 131.6, 130.4, 125.1, 77.5, 75.0, 73.1, 66.0, 45.0, 43.0, 38.1, 37.6, 36.3, 36.0, 35.4, 34.9, 32.8, 26.0, 25.93, 25.92, 24.0, 21.44, 21.42, 18.13, 18.11 (2C), 16.0, 15.8, 14.5, −4.0, −4.2, −4.3, −4.4, −4.7, −4.8.

$[α]_D^{21}$ −9.2 (c 0.4, CHCl$_3$).

HRMS calculated for $C_{42}H_{84}O_5SSi+Na^+$ 775.5519. found 775.5507 [M+Na$^+$].

(6S,7S,9E,12R)-12-[(2S,4E,6R,7R,9R)-7,9-bis[(tert-Butyldimethylsilyl)oxy]-4,6-dimethyldec-4-en-2-yl]-6-hydroxy-7-methyl-1-oxacyclododec-9-en-2-one (11b)

To a solution of 11a (30.0 mg; 0.04 mmol) in THF (0.9 mL), in a Nalgene® tube, at 0° C. was added a mixture of THF/pyridine (65:35) followed by a solution of hydrogen fluoride-pyridine (0.25 mL). The reaction was stirred at 0° C. for 3 h 30. It was quenched by slow addition of a saturated solution of sodium bicarbonate and stirred for 5 minutes. The aqueous layer was extracted with ethyl acetate and the ethyl acetate extracts were washed successively with a 15% solution of copper sulfate and brine before being dried over anhydrous sodium sulfate, filtered and concentrated. The resulting crude compound was purified by preparative TLC plate (elution: 80:20 cyclohexane/ethyl acetate) to afford alcohol 11b as a colorless oil (10.8 mg; 42%).

$^1$H NMR (300 MHz, CDCl$_3$) δ 5.43 (m, 1H), 5.23-5.03 (2H), 4.78 (m, 1H), 3.94 (m, 1H), 3.69 (m, 1H), 3.32 (m, 1H), 2.64-2.52 (2H), 2.29-1.58 (14H), 1.43 (m, 1H), 1.30-1.24 (3H), 1.21 (d, J=6.9 Hz, 3H), 0.97-0.83 (27H), 0.10 (s, 3H), 0.09 (s, 3H), 0.04 (s, 6H).

$^{13}$C NMR (100 MHz, CDCl$_3$) δ 173.5, 135.8, 132.9, 129.1, 124.9, 77.5, 76.1, 74.5, 66.2, 43.3, 42.1, 40.0, 38.4, 38.0, 36.3, 36.0, 35.0, 34.7, 32.7, 25.9, 23.9, 21.5, 18.3 (2C), 17.4, 16.0, 14.6, −4.17, −4.23, −4.4, −4.8.

HRMS calculated for C$_{36}$H$_{70}$O$_5$Si$_2$+Na$^+$ 661.4654. found 661.4655 [M+Na$^+$].

(6S,7S,9E)-12-[(2S,4E,6R)-7,9-Dihydroxy-4,6-dimethyldec-4-en-2-yl]-6-hydroxy-7-methyl-1-oxacyclododec-9-en-2-one (11c)

To a solution of 11a (7.0 mg; 0.04 mmol) in THF (0.7 mL), in a Nalgene® tube, at 0° C. was added a pyridine (0.2 mL) followed by a solution of hydrogen fluoride-pyridine (0.1 mL). The reaction was stirred at 0° C. for 18 hours. It was quenched by slow addition of a saturated solution of sodium bicarbonate followed by sodium carbonate powder till the bubbling stopped. The aqueous layer was extracted with ethyl acetate and the organic phase was washed successively with a 15% solution of copper sulfate and brine before being dried over anhydrous sodium sulfate, filtered and concentrated. The resulting crude compound was purified by preparative TLC plate (elution: 50:50 cyclohexane/ethyl acetate) to afford alcohol 11c as a colorless oil (3.1 mg; 81%).

$^1$H NMR (400 MHz, CDCl$_3$) δ 5.42 (m, 1H), 5.25 (m, 1H), 5.01-4.95 (2H), 4.04 (m, 1H), 3.68 (m, 1H), 3.50 (m, 1H), 2.82 (m, 1H), 2.60 (m, 1H), 2.36-1.98 (6H), 1.91-1.82 (4H), 1.70-1.63 (4H), 1.45-1.37 (4H), 1.21 (d, J=6.4 Hz, 3H), 0.99 (d, J=6.8 Hz, 3H), 0.96 (d, J=6.8 Hz, 3H), 0.89 (d, J=6.4 Hz, 3H); $^{13}$C NMR (100 MHz, CDCl$_3$) δ 174.8, 135.2, 134.4, 128.6, 127.4, 77.6, 75.0, 71.2, 69.0, 44.0, 40.9, 39.6, 38.0, 37.4, 35.6, 34.7, 34.5, 33.5, 23.9, 20.1, 16.9, 16.8, 16.3, 14.9.

HRMS calculated for C$_{24}$H$_{42}$O$_5$+Na$^+$ 433.2927. found 433.2923 [M+Na$^+$].

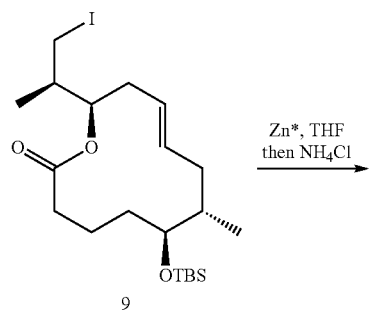

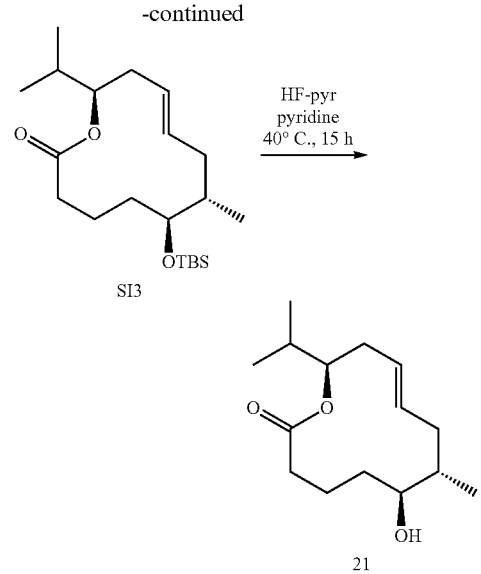

(6S,7S,9E,12R)-6-(tert-Butyldimethylsilyloxy)-12-isopropyl-7-methyloxacyclododec-9-en-2-one (SI3)

To a solution of naphthalene (255.0 mg; 2.0 mmol) in THF (0.7 mL) was added lithium (13.0 mg; 1.9 mmol) cut into small pieces and previously washed with cyclohexane, methanol and diethyl ether successively. The suspension was stirred at room temperature for 3 hours before addition of a solution of zinc chloride (125.0 mg; 0.92 mmol; previously flame-dried twice) in THF (1.0 mL) and the reaction mixture was stirred for another 30 minutes. The suspension was then centrifuged and the supernatant was removed before addition of a solution of alkyl iodide 9 (49.4 mg; 0.10 mmol) in benzene/DMF (15:1, 0.86 mL); the reaction mixture was then stirred for 45 minutes. An aqueous saturated solution of ammonium chloride was then slowly added to the reaction mixture. After 5 minutes of stirring water, and ethyl acetate were added. The aqueous layer was extracted with ethyl acetate and the organic layer was washed with saturated aqueous NaHCO$_3$, dried over anhydrous sodium sulfate, filtered and concentrated. The crude compound was purified by flash chromatography over neutral alumina (elution: gradient from 95:5 to 50:50 cyclohexane/ethyl acetate) to afford SI3 as a colorless oil (22.0 mg; 60%).

$^1$H NMR (300 MHz, CDCl$_3$) δ 5.43 (m, 1H), 5.19 (m, 1H), 4.75 (m, 1H), 3.34 (m, 1H), 2.54 (m, 1H), 2.27 (m, 1H), 2.14-1.90 (2H), 1.84-1.57 (7H), 1.45 (m, 1H), 0.96-0.89 (18H), 0.04 (s, 6H).

$^{13}$C NMR (75 MHz, CDCl$_3$) δ 173.4, 135.6, 125.1, 77.4, 75.6, 38.0, 36.3, 36.1, 35.9, 32.8, 32.4, 25.9, 21.4, 18.5, 18.32, 18.28, −4.2, −4.8.

(6S,7S,9E,12R)-6-hydroxy-12-isopropyl-7-methyloxacyclododec-9-en-2-one (21)

To a solution of SI3 (30.0 mg; 0.04 mmol) in pyridine (4.4 mL), in a Nalgene® tube, at 0° C. was added a solution of hydrogen fluoride-pyridine (1.5 mL). The reaction was then allowed to warm up to room temperature and then heated at 40° C. for 12 hours. The cool reaction mixture was quenched by slow addition of a saturated solution of sodium bicarbonate followed by sodium carbonate powder till the bubbling stopped. The aqueous layer was extracted with ethyl acetate and the ethyl acetate extracts were washed successively with a 15% solution of copper sulfate and brine before being dried over anhydrous sodium sulfate, filtered and concentrated. The resulting crude compound was purified by preparative TLC plate (elution: 80:20 cyclohexane/ethyl acetate) to afford alcohol 21 as a colorless solid (30.8 mg; 89%).

$^1$H NMR (300 MHz, CDCl$_3$) δ 5.43 (m, 1H), 5.26 (m, 1H), 4.89 (m, 1H), 3.51 (m, 1H), 2.45-2.29 (2H), 2.56-2.13 (2H), 2.04 (m, 1H), 1.93-1.63 (5H), 1.52-1.43 (2H), 0.97 (d, J=6.6 Hz, 3H), 0.91 (d, J 6.9 Hz, 3H), 0.89 (d, J 6.6 Hz, 3H).

$^{13}$C NMR (75 MHz, CDCl$_3$) δ 174.4, 134.2, 127.1, 77.3, 73.4, 38.1, 37.0, 36.3, 35.2, 33.2, 32.4, 19.6, 18.6, 18.1, 18.0.

HRMS calculated for $C_{15}H_{26}O_3+Na^+$ 277.1777. found 277.1770 [M+Na$^+$].

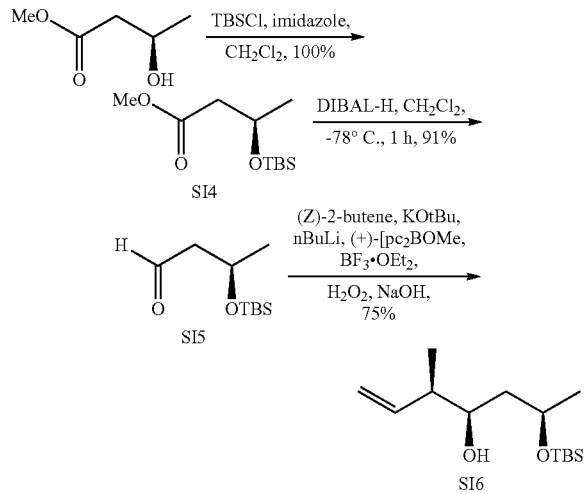

R)-Methyl 3-(tert-butyldimethylsilyloxy)butanoate (SI4

To a solution of methyl 3-(R)-hydroxybutyrate (3.5 g, 29.6 mmol) in dichloromethane (130 mL) were added imidazole (8 g, 119 mmol, 4 eq.) and TBDMSCl (8.9 g, 59.3 mmol, 2 eq.) at 0° C. The solution was left to warm up to room temperature and stirred for 18 h. The reaction mixture was hydrolyzed with water and diluted with dichloromethane. The aqueous phase was extracted twice with dichloromethane and the combined organic phases were washed with brine. After being dried over magnesium sulfate and filtered the organic phases were concentrated under reduced pressure. The crude product was purified by flash chromatography (elution with cyclohexane/ethyl acetate 90:10) to give SI4 (6.80 g, 29.6 mmol, 100%) as a colorless oil.

$^1$H NMR (CDCl$_3$, 300 MHz) δ 4.28 (ddq, J=5.4, 7.7, 6.1 Hz, 1H), 3.66 (s, 3H), 2.48 (dd, J=7.7, 14.5 Hz, 1H), 2.37 (dd, J=5.3, 14.5 Hz, 1H), 1.19 (d, J=6.1 Hz, 3H), 0.86 (s, 9H), 0.06 (s, 3H), 0.04 (s, 3H). The spectral data are in agreement with those reported in the literature.[10]

$^{13}$C NMR (CDCl$_3$, 75 MHz) δ 172.1, 65.8, 51.4, 44.7, 25.7 (3×C), 23.9, 17.9, −4.5, −5.1.

The spectral data are in agreement with those reported in the literature.[11]

R)-3-(tert-Butyldimethylsilyloxy)butanal (SI5

To a solution of SI4 (13.9 g, 60 mmol) in dichloromethane (60 mL) at −78° C. was added dropwise DIBAL-H (40 mL, 1.5 M in toluene, 1.1 eq.). After being stirred at −78° C. for 1 h, diethyl ether was added, followed by a saturated aqueous solution of Rochelle salts. The resulting solution was stirred at room temperature for 12 h, and the aqueous layer was extracted three times with diethyl ether. The combined organic layers were washed with brine. After being dried over magnesium sulfate, filtered, and concentrated under reduced pressure, the crude product was filtered through silica gel (eluted with dichloromethane) to give SI5 (11.03 g, 54.6 mmol, 91%) as a colorless oil.

$^1$H NMR (CDCl$_3$, 300 MHz) δ 9.79 (dd, J=2.1, 2.7 Hz, 1H), 4.35 (dqd, J=5.0, 6.2, 6.4 Hz, 1H), 2.55 (ddd, J=2.7, 6.4, 15.7 Hz, 1H), 2.46 (ddd, J=2.1, 5.0, 15.7 Hz, 1H), 1.24 (d, J=6.2 Hz, 3H), 0.87 (s, 9H), 0.07 (s, 3H), 0.06 (s, 3H).

$^{13}$C NMR (CDCl$_3$, 75 MHz) δ 202.3, 65.7, 52.9, 25.7 (3×C), 23.9, 17.9, −4.4, −5.1.

The spectral data are in agreement with those reported in the literature.[12]

(3R,4R,6R)-6-(tert-Butyldimethylsilyloxy)-3-methylhept-1-en-4-ol (SI6)

To a solution of t-BuOK (7.6 g, 67.8 mmol) in THF (465 mL) at −78° C. was added Z-2-butene (9.51 g, 170 mmol), followed by n-BuLi (27 mL, 2.5 M in hexane, 67.5 mmol). The bright yellow suspension was stirred at −78° C. for 5 min, −45° C. for 10 min, and then −78° C. for 15 min. A solution of (−)-Ipc$_2$BOMe (25 g, 79 mmol) in diethyl ether (58 mL) was then added via cannula. The solution was stirred at −78° C. for 30 min, and then BF$_3$·Et$_2$O (11 mL, 87 mmol) was added followed immediately by a solution of SI5 (9.28 g, 46 mmol) in THF (58 mL). After being stirred at −78° C. for 3 h, the reaction mixture was quenched by addition of 3 N NaOH (150 mL). H$_2$O$_2$ (30%, 75 mL) was then added carefully and the resulting mixture was stirred vigorously at room temperature for 12 h. The mixture was then diluted with ethyl acetate and washed with water and brine. The organic phase was then dried over magnesium sulfate, filtered and concentrated under reduced pressure. The crude product was purified by flash chromatography (cyclohexane/ethyl acetate 20:1) to give SI6 (8.95 g, 34.7 mmol, 75%) as a colorless oil.

$^1$H NMR (CDCl$_3$, 300 MHz) δ 5.78 (ddd, J=7.3, 10.8, 16.9, 1H), 5.02 (ddd, J=1.2, 1.9, 16.9, 1H), 5.01 (ddd, J=1.0, 1.2, 10.8 Hz, 1H), 4.03 (dqd, J=3.8, 6.0, 9.7 Hz, 1H), 3.6 (ddd, J=1.8, 5.4, 9.7 Hz, 1H), 2.21 (m, 1H), 1.58 (ddd, J=1.8, 3.8, 14.4 Hz, 1H), 1.43 (dt, J=14.4, 9.7 Hz, 1H), 1.15 (d, J=6.0 Hz, 3H), 1.00 (d, J=6.8 Hz, 3H), 0.88 (s, 9H), 0.09 (s, 3H), 0.08 (s, 3H).

$^{13}$C NMR (CDCl$_3$, 75 MHz) δ 141.0, 114.7, 74.7, 70.3, 43.7, 42.5, 25.8 (3×C), 24.5, 17.8, 14.9, −3.9, −4.8.

[α]$^{20}_D$=−20.9 (c 1, CHCl$_3$)

HRMS (ESI) calculated for $C_{14}H_{31}O_2Si$: m/z 259.2087 ([M+H]$^+$). found: m/z 259.2083 ([M+H]$^+$).

The spectral data are in agreement with those reported in the literature.[13]

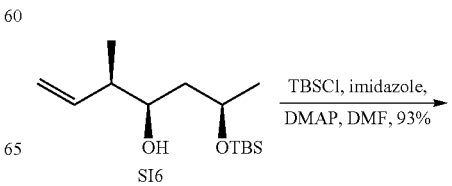

-continued

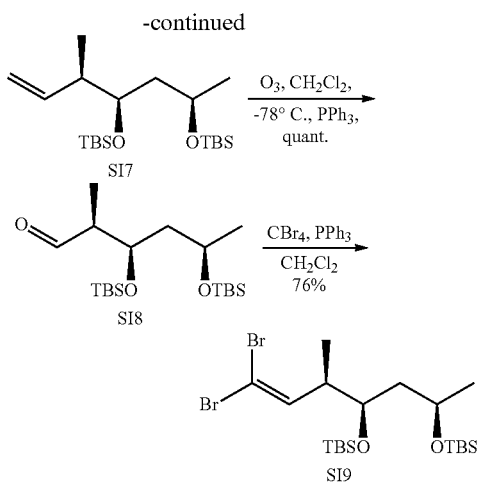

(2R,4R,5R)-2,4-bis(tert-Butyldimethylsilyloxy)-5-methylhept-6-ene (SI7)

To a solution of SI6 (6.44 g, 25 mmol) in DMF (125 mL) were added tert-butyldimethylsilyl chloride (9.42 g, 62.5 mmol, 2.5 eq.), imidazole (3.4 g, 50 mmol, 2 eq.) and DMAP (610 mg, 5 mmol, 0.2 eq.). The reaction mixture was stirred at room temperature for 20 h and was then hydrolysed with water. The aqueous layer was extracted with a mixture of cyclohexane/dichloromethane (90:10). The combined organic phases were washed with water, brine, and dried over magnesium sulfate, filtered and concentrated under reduced pressure. The crude product was purified by flash chromatography (elution with cyclohexane/ethyl acetate 25:1) to give SI7 (8.6 g, 23.25 mmol, 93%) as a colorless oil.

$^1$H NMR (CDCl$_3$, 300 MHz) δ 5.9 (ddd, J=6.3, 11.1, 17.4 Hz, 1H), 5.00 (ddd, 1.2, 1.7, 11.1 Hz, 1H), 4.98 (ddd, J=1.4, 1.7, 17.4 Hz, 1H), 3.90 (ddq ap. sextet, J=6.3 Hz, 1H), 3.67 (ddd, J=3.7, 5.6, 6.5 Hz, 1H), 2.332 (m, 1H), 1.60 (m, 1H), 1.48 (ddd, J=5.6, 6.8, 13.5 Hz, 1H), 1.12 (d, J=6.0 Hz, 3H), 0.94 (d, J=6.9 Hz, 3H), 0.88 (s, 9H), 0.87 (s, 9H), 0.05 (s, 3H), 0.04 (s, 3H), 0.03 (s, 6H).

$^{13}$C NMR (CDCl$_3$, 75 MHz) δ 141.4, 113.8, 72.9, 65.9, 43.7, 42.2, 25.9 (6×C), 23.7, 17.8 (2×C), 13.7, −4.3 (3×C), −4.7.

The spectral data are in agreement with those reported in the literature.

$[α]^{20}_D$=+15.5 (c 1.1, CHCl$_3$)

(2S,3R,5R)-3,5-bis(tert-Butyldimethylsilyloxy)-2-methylhexanal (SI8)

A solution of SI7 (1 g, 2.69 mmol) in dichloromethane (15 mL) at −78° C. was saturated with ozone until a blue color persisted. The solution was then purged with argon until disappearance of the blue coloration and triphenylphosphine (740 mg, 2.82 mmol) was added. The solution was left to warm up to room temperature and stirred for 12 h before being concentrated under reduced pressure. The excess of triphenylphosphine oxide was removed by filtration (washing with diethyl ether) to give SI8 (1 g, 2.69 mmol, 100%).

$^1$H NMR (CDCl$_3$, 300 MHz) δ 9.75 (d, J=0.6 Hz, 1H), 4.37 (ddd, J=2.8, 6.1, 7.7 Hz, 1H), 3.83 (ap sextet, J=5.7 Hz, 1H), 2.48 (dq, J=2.8, 6.7 Hz, 1H), 1.68-1.62 (2H), 1.16 (d, J=6.0 Hz, 3H), 1.05 (d, J=6.7 Hz, 3H), 0.88 (s, 9H), 0.86 (s, 9H), 0.07 (s, 3H), 0.06 (s, 3H), 0.04 (s, 3H), 0.03 (s, 3H).

$^{13}$C NMR (CDCl$_3$, 75 MHz) δ 205.1, 68.7, 65.6, 50.5, 40.2, 25.8 (3×C), 25.7 (3×C), 23.9, 17.9 (2×C), 6.9, −4.1 (2×C), −4.2 (2×C).

The spectral data are in agreement with those reported in the literature.

(2R,4R,5R)-2,4-bis(tert-Butyldimethylsilyloxy)-7,7-dibromo-5-methylhept-6-ene (SI9)

To a solution of CBr$_4$ (4.64 g, 14 mmol, 3 eq.) in dichloromethane (14 mL) was added triphenylphosphine (7.36 g, 28 mmol, 6 eq.), and the reaction mixture was stirred for 30 min at 0° C. Triethylamine (3.1 mL) and a solution of SI8 (1.75 g, 4.68 mmol) in dichloromethane (2.5 mL) were added. After being stirred at 0° C. for 3 h, the reaction mixture was hydrolyzed with an aqueous saturated solution of NaHCO$_3$. The aqueous phase was extracted with dichloromethane and the combined organic phases were washed with brine. After being dried over MgSO$_4$, filtered and concentrated under reduced pressure, the crude product was purified by flash chromatography (cyclohexane/ethyl acetate 30:1) to give SI9 (1.9 g, 3.56 mmol, 76%) as a colorless oil.

$^1$H NMR (CDCl$_3$, 300 MHz) δ 6.40 (d, J=9.7 Hz, 1H), 3.86 (ddq ap. qd, J=6.1, 12.2 Hz, 1H), 3.77 (dt, J=3.3, 6.5 Hz, 1H), 2.58 (ddq, J=3.3, 6.8, 9.7 Hz, 1H), 1.62-1.57 (2H), 1.15 (d, J=6.1 Hz, 3H), 0.96 (d, J=6.8 Hz, 3H), 0.89 (s, 9H), 0.88 (s, 9H), 0.06 (s, 6H), 0.05 (s, 6H).

$^{13}$C NMR (CDCl$_3$, 75 MHz) δ 142.3, 87.5, 70.8, 65.7, 44.6, 42.7, 25.1 (6×C), 24.0, 18.0 (2×C), 12.4, −4.2 (2×C), −4.7 (2×C).

The spectral data are in agreement with those reported in the literature.

$[α]^{20}_D$=−12.6 (c 1.3, CHCl$_3$)

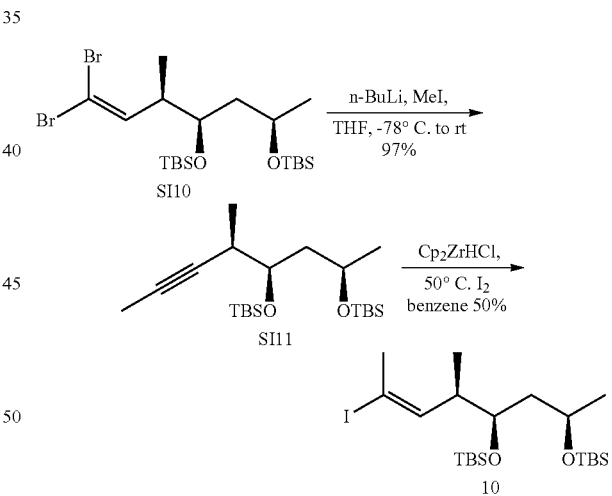

(2R,4R,5R)-2,4-bis(tert-Butyldimethylsilyloxy)-5-methyloct-6-yne (SI10)

To a solution of SI9 (767 mg, 1.43 mmol) in THF (15 mL) at −78° C. was added n-BuLi (1.64 mL, 2.5 M in hexane). After being stirred at −78° C. for 30 min, MeI (1.35 mL) was added and the reaction mixture was stirred at room temperature for 2 h. The reaction mixture was then diluted with ethyl acetate and hydrolyzed with an aqueous saturated solution of NaHCO$_3$. The aqueous phase was extracted twice with ethyl acetate and the combined organic phases were washed with brine and dried over magnesium sulfate.

After being filtered and concentrated under reduced pressure, SI10 (533 mg, 1.39 mmol, 97%) was obtained as a colorless oil.

$^1$H NMR (CDCl$_3$, 300 MHz) δ 3.98 (ddq ap. sext, J=6.3, 1H), 3.67 (td, J=5.1, 6.6 Hz, 1H), 2.49 (m, 1H), 1.83 (ddd, J=1.9, 6.6, 13.1 Hz, 1H), 1.77 (d, J=2.5 Hz, 3H), 1.56 (m, 1H), 1.14 (d, J=6.3 Hz, 3H), 1.07 (d, J=6.9 Hz, 3H), 0.89 (s, 18H), 0.09-0.06 (12H).

$[α]^{20}_D$=+8.5 (c 0.4, CHCl$_3$)

The spectral data are in agreement with those reported in the literature.

$^{13}$C NMR (CDCl$_3$, 75 MHz) δ 82.1, 73.8, 72.6, 65.9, 44.5, 32.2, 25.9 (3×C), 25.8 (3×C), 23.8, 18.1 (2×C), 16.3, 3.5, −4.3, −4.5 (2×C), −4.7.

HRMS (ESI) calculated for C$_{21}$H$_{45}$O$_2$Si$_2$: m/z 385.2952 ([M+H]$^+$). found: m/z 385.2928 ([M+H]$^+$).

E-(2R,4R,5R)-7-Iodo-2,4-bis(tert-butyldimethylsilyloxy)-5-methyloct-6-ene (10)

A solution of SI10 (1.25 g, 3.25 mmol) in benzene (8.4 mL) was added to Cp$_2$ZrHCl (1.77 g, 6.87 mmol, 2.1 eq.). The reaction mixture was protected from the light and stirred at 50° C. for 2 h before being cooled to −15° C. A solution of I$_2$ (684 mg, 6.67 mmol, 2 eq.) in dichloromethane was added until the solution became brown. The resulting solution was stirred 30 min, before being poured into a mixture of 1:1 saturated aqueous NaHCO$_3$ saturated aqueous Na$_2$S$_2$O$_3$. The reaction mixture was diluted with ethyl acetate and the aqueous phase was extracted. The combined organic phases were washed successively with a saturated aqueous solution of Na$_2$S$_2$O$_3$, with a saturated aqueous solution of NaHCO$_3$, with brine and dried over MgSO$_4$. After being filtered and concentrated under reduced pressure, the crude product was purified by Flash chromatography eluting with cyclohexane/toluene 100:1 to give 10 (825 mg, 1.1 mmol, 50%).

$^1$H NMR (CDCl$_3$, 300 MHz) δ 6.13 (dd, J=1.5, 10.0 Hz, 1H), 3.87 (dqd ap. sextet, J=6.0 Hz, 1H), 3.65 (m, 1H), 2.52 (m, 1H), 2.38 (d, J=1.5 Hz, 3H), 1.64-1.56 (2H), 1.13 (d, J=6.0 Hz, 3H), 0.91 (d, J=6.8 Hz, 3H), 0.89 (s, 9H), 0.88 (s, 9H), 0.05 (s, 6H), 0.04 (s, 6H).

$^{13}$C NMR (CDCl$_3$, 75 MHz) δ 145.0, 93.1, 71.8, 65.8, 44.9, 40.3, 27.9, 25.9 (3×C), 25.8 (3×C), 24.0, 18.1 (2×C), 14.1, −4.2, −4.6 (2×C), −4.7.

The spectral data are in agreement with those reported in the literature.

$[α]^{20}_D$=+22.1 (c 1, CHCl$_3$)

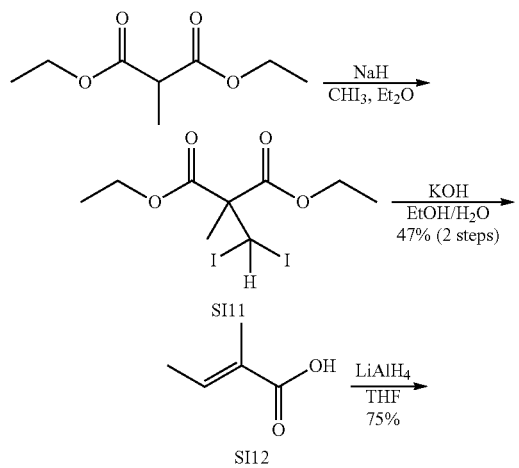

Diethyl 2-(diiodomethyl)-2-methylmalonate (SI11)

To a solution of sodium hydride (55% in oil, 8.2 g, 1.1 eq.) in anhydrous diethyl ether (250 mL) was slowly added diethyl methylmalonate (29.4 mL, 171 mmol) during 1 h with a vigorous stirring and the resulting mixture was refluxed for a further 2.5 h. Iodoform (74 g, 1.1 eq.) was added and the mixture refluxed for 20 h. After being cooled to 0° C., 10% aqueous HCl (80 mL) was added and the mixture stirred for 10 min. The aqueous phase was extracted with diethyl ether, and the combined organic phases were dried on magnesium sulfate, filtered and concentrated. The crude product was purified by Flash chromatography on silica gel (elution with: cyclohexane/ethyl acetate 100:2) to give SI11 as a pink oil.

$^1$H NMR (CDCl$_3$, 300 MHz) δ 5.77 (s, 1H), 4.22 (q, J=7.1 Hz, 4H), 1.79 (s, 3H), 1.29 (t, J=7.1 Hz, 6H).

$^{13}$C NMR (CDCl$_3$, 75 MHz) δ 165.8 (2×C), 62.5 (2×C), 61.9, 20.1 (2×C), 13.8, −25.9.

The spectral data are in agreement with those reported in the literature.[14]

E)-3-iodo-2-methylacrylic acid (SI12

To a solution of SI11 in EtOH-water (130:25 mL) was added KOH (19 g). The mixture was refluxed for 24 h. After being cooled to room temperature the solvent was removed under reduced pressure and the residue redissolved in 10% aqueous K$_2$CO$_3$ (100 mL) and washed twice with CH$_2$Cl$_2$. The basic solution was acidified with 12M HCl, and extracted with CH$_2$Cl$_2$. The combined extracts were dried on MgSO$_4$, filtered and concentrated under reduce pressure to give SI12 (15.6 g, 73 mmol, 43%) as a white powder. Only the (E)-isomer could be detected by NMR analysis.

$^1$H NMR (CDCl$_3$, 300 MHz) δ 8.02 (s, 1H), 2.00 (s, 3H).

$^{13}$C NMR (CDCl$_3$, 75 MHz) δ 168.3, 138.9, 101.8, 19.8.

The spectral data are in agreement with those reported in the literature.

E)-3-Iodo-2-methylprop-2-en-1-ol (SI13

To a cooled (0° C.) solution of SI12 (350 mg, 1.65 mmol) in dry THF was slowly added over 30 min LiAlH$_4$ (63 mg, 1.66 mmol, 1 eq). After being stirred at room temperature for a further 4.5 h, 60 μL of water were added, followed by 60 μL of an aqueous solution of NaOH 3N, and 180 μL of water, Celite and diethyl ether. The reaction mixture was stirred at room temperature for 12 h and filtered over Celite. The solvent was concentrated under reduced pressure to give SI13 (242 mg, 1.23 mmol, 75%) as a yellow oil.

$^1$H NMR (CDCl$_3$, 300 MHz) δ 6.26 (d, J=1.2 Hz, 1H), 4.11 (s, 2H), 1.82 (s, 3H).

$^{13}$C NMR (CDCl$_3$, 75 MHz) δ 147.2, 77.3, 67.1, 21.3.

The spectral data are in agreement with those reported in the literature.

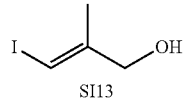

SI13

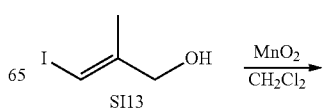

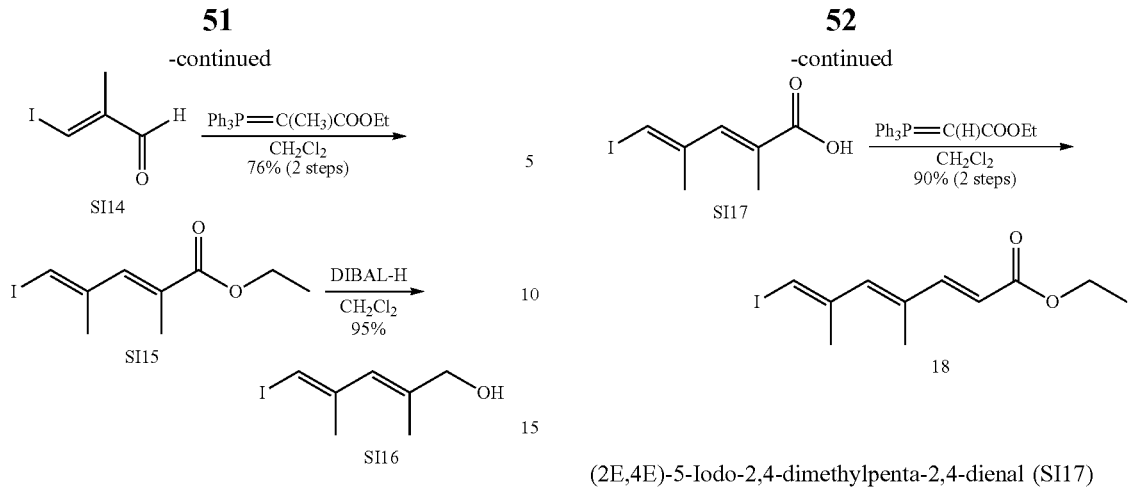

E)-3-Iodo-2-methylprop-2-en-1-al (SI14

To a solution of SI13 (5.57 g, 28 mmol) in CH$_2$Cl$_2$ (100 mL) was added activated MnO$_2$ (17 g, 520 mmol, 18 eq.). The reaction mixture was stirred at room temperature for 20 hand refluxed for a further 20 h. After being cooled to room temperature the reaction mixture was filtered through a bed of Celite. The resulting yellow solution of aldehyde SI14 was used in the next step without further purification.

(2E,4E)-Ethyl 5-iodo-2,4-dimethylpenta-2,4-dienoate (SI15)

To a solution of SI14 in CH$_2$Cl$_2$ at 0° C. was added (1-ethoxycarbonylethylidene)triphenylphosphorane (10.2 g, 28 mmol, 1 eq.). The solution was stirred at room temperature for 7 h. Solvent was removed under reduced pressure and flash chromatography (cyclohexane/ethyl acetate 100:1) of the residue gave SI15 (5.96 g, 21.3 mmol, 76% over 2 steps) as a yellow oil.
$^1$H NMR (CDCl$_3$, 300 MHz) δ 7.05 (s, 1H), 6.40 (s, 1H), 4.22 (q, J=7.1 Hz, 2H), 2.01 (d, 0.6 Hz, 3H), 1.95 (d, J=1.5 Hz, 3H), 1.31 (t, J=7.1 Hz, 3H).
$^{13}$C NMR (CDCl$_3$, 75 MHz) δ 168.2, 1417, 138.6, 128.3, 85.2, 60.9, 24.5, 14.3, 14.2.

(2E,4E)-5-Iodo-2,4-dimethylpenta-2,4-dien-1-ol (SI16)

To a solution of SI15 (5.78 g, 20.6 mmol) in CH$_2$Cl$_2$ at 0° C. (100 mL) was slowly added DIBAL-H (33 mL, 49.8 mmol, 2.4 eq.). After being stirred at 0° C. for 5.5 h, an aqueous saturated solution of Rochelle salts and diethyl ether were added to the reaction mixture. The solution was then stirred for 12 h at room temperature. The aqueous phase was extracted three times with diethyl ether. The combined extracts were washed with brine, dried over MgSO$_4$, filtered and concentrated. The residue was purified by Flash chromatography on silica gel (cyclohexane/ethyl acetate 20:1) to give SI16 (4.69 g, 19.7 mmol, 95%) as a yellow oil.
$^1$H NMR (CDCl$_3$, 300 MHz) δ 6.05 (s, 1H), 5.89 (s, 1H), 4.04 (s, 2H), 1.93 (s, 3H), 1.74 (s, 3H).
$^{13}$C NMR (CDCl$_3$, 75 MHz) δ 144.2, 137.4, 125.4, 79.9, 68.1, 25.0, 15.4.

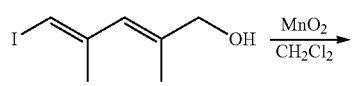

(2E,4E)-5-Iodo-2,4-dimethylpenta-2,4-dienal (SI17)

To a solution of SI16 (4.06 g, 17 mmol) in CH$_2$Cl$_2$ (80 mL) was added activated MnO$_2$ (8 g, 255 mmol, 15 eq.). The reaction mixture was refluxed for 20 h. After being cooled to room temperature, the mixture was filtered through a bed of Celite and the residue washed with CH$_2$Cl$_2$. The resulting yellow solution of SI17 was used in the next step without further purification.
$^1$H NMR (C$_6$D$_6$, 300 MHz) δ 9.11 (s, 1H), 6.13 (s, 1H), 5.87 (s, 1H), 1.62 (s, 3H), 1.53 (s, 3H).

(2E,4E,6E)-Ethyl 7-iodo-4,6-dimethylhepta-2,4,6-trienoate (18)

To a solution of SI17 in CH$_2$Cl$_2$ at 0° C. was added (carbethoxymethylene)triphenylphosphorane (8.8 g, 25.5 mmol, 1.5 eq.). The solution was stirred at room temperature for 6 h and refluxed for a further 18 h. Solvent was removed under reduced pressure, and the crude product was purified by Flash chromatography (cyclohexane/ethyl acetate 10:1) to give 18 (5.25 g, 17 mmol, 100% over 2 steps) as a yellow oil. A (E)/(Z)=96:4 mixture could be detected by $^1$H analysis.
$^1$H NMR (C$_6$D$_6$, 300 MHz) δ 7.42 (dd, J=0.6, 15.6 Hz, 1H), 5.94 (d, J=15.6 Hz, 1H), 5.91 (s, 1H), 5.60 (s, 1H), 4.10 (q, J=7.1 Hz, 2H), 1.61 (d, J=0.6 Hz, 3H), 1.36 (d, J=0.9 Hz, 3H), 1.02 (t, J=7.1 Hz, 3H).
$^{13}$C NMR (C$_6$D$_6$, 75 MHz) δ 166.7, 148.9, 144.1, 138.4, 133.9, 118.9, 84.5, 60.2, 24.6, 14.4, 13.5.
HRMS (ESI) calculated for C$_{11}$H$_{16}$IO$_2$: m/z 307.0189 ([M+H]$^+$). found: m/z 307.0181 ([M+H]$^+$).

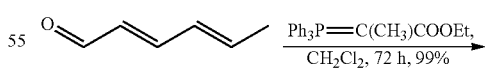

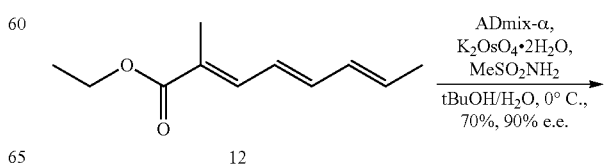

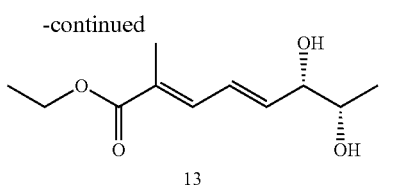

13

(2E,4E,6E)-Ethyl 2-methylocta-2,4,6-trienoate (12)

To a solution of (1-ethoxycarbonylethylidene)triphenylphosphorane (6.51 g, 17.9 mmol, 1.3 mmol) in dichloromethane (40 mL) at 0° C. was added trans-hexadienal (commercially available as a (E,E/E,Z)=87:13 mixture) (1.5 mL, 13.59 mmol) in solution in dichloromethane (3 mL). The reaction mixture was stirred at room temperature for 72 h. After being concentrated under reduced pressure, the crude product was purified by Flash chromatography (cyclohexane/ethyl acetate 100:1 to 10:1) to give 12 (2.43 g, 13.4 mmol, 99%) as a yellow oil. A (E,E,E/E,E,Z)=86:14 mixture could be detected by $^1$H analysis.

$^1$H NMR (CDCl$_3$, 300 MHz) δ 7.22 (dd, J=1.1, 11.3 Hz, 1H), 6.52 (dd, J=10.4, 14.8 Hz, 1H), 6.38 (dd, J=11.3, 14.8 Hz, 1H), 6.21 (ddq, J=1.5, 10.4, 14.4 Hz, 1H), 5.92 (dq, J=6.8, 14.4 Hz, 1H), 4.22 (q, J=7.2 Hz, 2H), 1.96 (d, J=1.1 Hz, 3H), 1.85 (d, J=6.8 Hz, 3H), 1.32 (t, J=7.2 Hz, 3H).

$^1$H NMR (CDCl$_3$, 75 MHz) δ 168.3, 139.5, 138.3, 133.8, 131.6, 129.3, 125.3, 60.3, 18.4, 14.2, 12.6.

The spectral data are in agreement with those reported in the literature.[15]

(2E,4E,6S,7S)-Ethyl 6,7-dihydroxy-2-methylocta-2,4-dienoate (13)

To a solution of AD-mix α (7.7 g) in a mixture of t-BuOH and water (27.5: 27.5 mL) were added methanesulfonamide (520 mg, 5.47 mmol, 1.02 eq.) and potassium osmate dihydrate (12 mg, 0.033 mmol, 0.6%). The reaction mixture was stirred at room temperature until both phases were clear, and then cooled at 0° C. whereupon the inorganic salts partially precipitate. 12 (963 mg, 5.34 mmol) was then added and the reaction mixture was stirred at 0° C. for 15 h. Sodium sulfite (8.2 g) was then added at 0° C. The reaction mixture was stirred at room temperature for 15 min and the aqueous phase was extracted 3 times with ethyl acetate. The combined organic layers were washed with an aqueous solution of potassium hydroxide (2N), with brine and dried over magnesium sulfate. After being filtered and concentrated under reduced pressure, the crude product was purified by flash chromatography (cyclohexane/ethyl acetate 8:2) to give 13 (800 mg, 3.73 mmol, 70%, 86% e.e) as a yellow oil.

$^1$H NMR (CDCl$_3$, 300 MHz) δ 7.17 (d, J=11.4 Hz, 1H), 6.65 (ddd, J=1.1, 11.4, 15.2 Hz, 1H), 6.03 (dd, J=6.31, 15.2 Hz, 1H), 4.21 (q, J=7.1 Hz, 2H), 4.00 (dd ap. t, J=6.3 Hz, 1H), 3.69 (dq ap. p, J=6.3 Hz, 1H), 1.96 (d, J=1.1 Hz, 3H), 1.30 (t, J=7.2 Hz, 3H), 1.21 (d, J=6.3 Hz, 3H).

$^{13}$C NMR (CDCl$_3$, 75 MHz) δ 168.3, 139.2, 138.2, 128.2, 127.4, 76.9, 70.7, 60.7, 19.0, 14.2, 12.7.

HRMS (ESI) calculated for C$_{11}$H$_{18}$O$_4$Na: m/z 237.1097 ([M+Na]$^+$). found: m/z 237.1096 ([M+Na]$^+$).

[α]$^{20}_D$=−4.3 (c 0.7, CHCl$_3$)

(2S,2'S)-((2S,3S,4E,6E)-8-Ethoxy-7-methyl-8-oxoocta-4,6-diene-2,3-diyl)bis(2-methoxy-2-phenylacetate) (SI18)

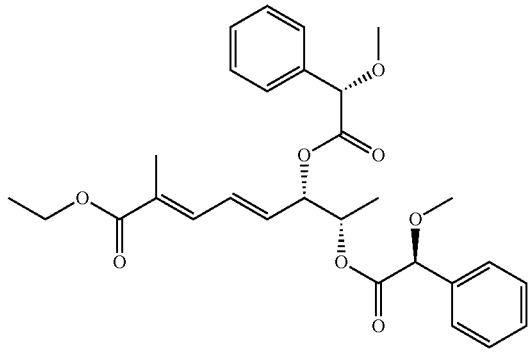 [SMILES: CCOC(=O)/C(C)=C/C=C/[C@H](OC(=O)[C@@H](OC)c1ccccc1)[C@H](C)OC(=O)[C@@H](OC)c1ccccc1]

To a solution of 13 (18 mg, 0.084 mmol) were added (S)-2-methoxy-2-phenylacetic acid (54 mg, 0.32 mmol, 3.9 eq.), DMAP (10 mg, 0.084 mmol, 1 eq.), CSA (15 mg, 0.065 mmol, 0.8 eq.) and DCC (69 mg, 0.33 mmol, 3.9 eq.). The reaction mixture was stirred at room temperature for 15 h, before being filtered, concentrated under reduced pressure and purified by preparative TLC (heptane/ethyl acetate 70:30). SI18 (31 mg, 0.061 mmol, 73%, d.e: 93:7) was obtained as colorless oil.

$^1$H NMR (CDCl$_3$, 300 MHz) δ 7.45-7.31 (10H), 7.29 (d, J=13.8 Hz, 1H), 6.78 (dd, J=1.2, 11.7 Hz, 1H), 6.28 (dd, J=11.7, 13.8 Hz, 1H), 5.35 (m, 1H), 5.01 (dd, J=3.7, 6.5 Hz, 1H), 4.72 (s, 1H), 4.67 (s, 1H), 4.22 (q, J=7 Hz, 2H), 3.36 (s, 3H), 3.33 (s, 3H), 1.81 (dd, J=1.2 Hz, 3H), 1.33 (t, J=7.2 Hz, 3H), 0.94 (d, J=6.5 Hz, 3H).

$^{13}$C NMR (CDCl$_3$. 75 MHz) δ 169.7, 169.6, 167.9, 136.2, 136.1, 136.0, 132.5, 129.2, 129.1, 128.9, 128.8, 128.6 (4×C), 127.2 (2×C), 127.1 (2×C), 82.4, 82.2, 75.1, 71.1, 60.7, 57.3, 57.2, 15.6, 14.3, 12.7.

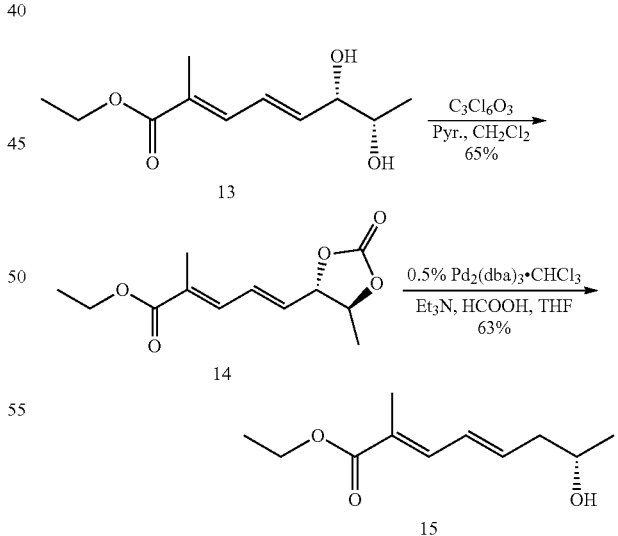

(2E,4E)-Ethyl 2-methyl-5-((4S,5S)-5-methyl-2-oxo-1,3-dioxolan-4-yl)penta-2,4-dienoate (14)

To a solution of 13 (3.36 g, 15.7 mmol) and pyridine (5.44 mL) in dichloromethane (16 mL) at 0° C. was slowly added a solution of triphosgene (2.72 g, 9.1 mmol, 0.6 eq.) in dichloromethane (6.5 mL). After being stirred at 0° C. for 3 h the reaction mixture was hydrolyzed at 0° C. with a saturated aqueous solution of ammonium chloride. The aqueous layer was extracted three times with diethyl ether and the combined organic layers were washed with an aqueous saturated solution of sodium bicarbonate, with brine and dried over magnesium sulfate. After being filtered and concentrated under reduced pressure, the crude product was purified by Flash chromatography on silica gel (elution: cyclohexane/ethyl acetate 20:1) to give 14 (2.98 g, 12.4 mmol, 79%). A 84:16 mixture of diastereoisomers could be detected by $^1$H analysis.

$^1$H NMR (CDCl$_3$, 300 MHz) δ 7.13 (d, J=11.4 Hz, 1H), 6.69 (dd, J=11.4, 15.1 Hz, 1H), 5.95 (dd, J=7.4, 15.1 Hz, 1H), 4.71 (dd ap. t, J=7.4 Hz, 1H), 4.45 (dq, J=6.2, 12.3 Hz, 1H), 4.20 (q, J=7.1 Hz, 2H), 1.96 (s, 3H), 1.48 (d, J=6.2 Hz, 3H), 1.28 (t, J=7.1 Hz, 3H).

$^{13}$C NMR (CDCl$_3$, 75 MHz) δ 167.6, 153.9, 134.8, 131.3, 131.1, 130.8, 83.3, 78.4, 60.9, 18.0, 14.1, 12.8.

$[α]^{20}_D$=−47.5 (c 0.6, CHCl$_3$)

(7S,2E,4E)-Ethyl
7-hydroxy-2-methylocta-2,4-dienoate (15)

To a solution of 14 (100 mg, 0.41 mmol) in THF (1 mL) were added Pd$_2$(dba)$_3$.CHCl$_3$ (1.8 mg, 0.002 mmol, 0.5%), triethylamine (140 μL, 2 eq.) and formic acid (40 μL, 2 eq.). The reaction mixture was stirred at room temperature for 96 h. After being diluted with diethyl ether, water was added, and the water layer was extracted with diethyl ether. The organic layer was washed with an aqueous saturated solution of sodium carbonate, with brine, dried over magnesium sulfate, filtered and concentrated under reduced pressure. The reaction mixture was purified by preparative TLC (heptane/ethyl acetate 7:3) to give 15 (50 mg, 0.26 mmol, 63%) as a colorless oil.

$^1$H NMR (CDCl$_3$, 300 MHz) δ 7.15 (d, J=11.3 Hz, 1H), 6.41 (dd, J=11.3 Hz, 15.0 Hz, 1H), 6.06 (td, J=7.5, 15.0 Hz, 1H), 4.2 (q, J=7.1 Hz, 2H), 3.89 (dd, J=6.2, 12.2 Hz, 1H), 2.36-2.31 (2H), 1.91 (d, J=0.9 Hz, 3H), 1.28 (t, J=7.1 Hz, 3H), 1.20 (d, J=6.2 Hz, 3H).

$^{13}$C NMR (CDCl$_3$, 75 MHz) δ 168.5, 137.9, 137.8, 128.9, 126.2, 67.2, 60.5, 43.0, 23.0, 14.3, 12.6.

HRMS (ESI) calculated for C$_{11}$H$_{19}$O$_3$: m/z 199.1329 ([M+H]$^+$). found: m/z 199.1334 ([M+H]$^+$).

$[α]^{20}_D$=+6.5 (c 1, CHCl$_3$)

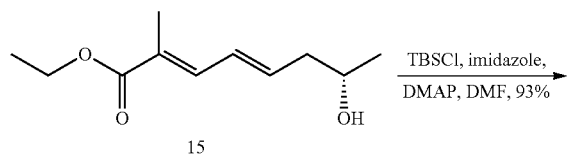

15

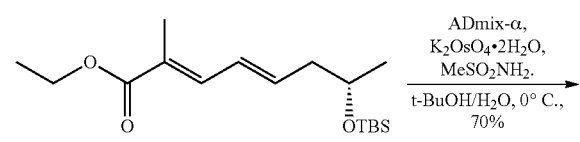

SI19

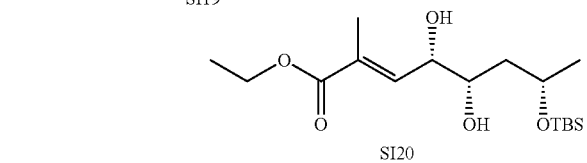

SI20

(7S,2E,4E)-Ethyl 7-(tert-butyldimethylsilyloxy)-2-methylocta-2,4-dienoate (SI19)

To a solution of 15 (1.15 g, 5.8 mmol) in DMF (29 mL) were added tert-butyldimethylsilyl chloride (1.75 g, 11.6 mmol, 2 eq.), imidazole (790 mg, 11.6 mmol, 2 eq.) and DMAP (142 mg, 1.16 mmol, 0.2 eq.). The reaction mixture was stirred at room temperature for 24 h, and then hydrolyzed with water. The aqueous layer was extracted three times with a mixture of cyclohexane and dichloromethane (9:1). The combined organic layers were washed with brine, dried over magnesium sulfate, filtered and concentrated under reduced pressure. The crude product was purified by preparative TLC plate (heptane/ethyl acetate 9:1) to give SI19 (1.68 g, 5.38 mmol, 93%) as a colorless oil.

$^1$H NMR (CDCl$_3$, 300 MHz) δ 7.14 (d, J=11.3 Hz, 1H), 6.35 (dd, J=11.3, 15.1 Hz, 1H), 6.06 (td, J=7.5, 15.1 Hz, 1H), 4.2 (q, J=7.1 Hz, 2H), 3.88 (qd ap. q, J=6.4 Hz, 1H), 2.3 (dd ap. t, J=6.4 Hz, 2H), 1.92 (s, 3H), 1.3 (t, J=7.1 Hz, 3H), 1.14 (d, J=6.4 Hz, 3H), 0.87 (s, 9H), 0.04 (s, 3H), 0.03 (s, 3H).

$^{13}$C NMR (CDCl$_3$, 75 MHz) & 168.7, 139.2, 138.3, 135.9, 128.0, 68.1, 60.5, 43.5, 25.8 (3×C), 23.6, 18.1, 14.3, 12.5, −4.5, −4.7.

$[α]^{20}_D$=−5.5 (c 1.4, CHCl$_3$)

HRMS (ESI) calculated for C$_{17}$H$_{33}$O$_3$Si: m/z 313.2198 ([M+H]$^+$). found: m/z 313.2204 ([M+H]$^+$).

(4S,5S,7S,E)-Ethyl 7-(tert-butyldimethylsilyloxy)-4,5-dihydroxy-2-methyloct-2-enoate (SI20)

To a solution of AD-mix α (1.58 g) in a mixture of t-BuOH and water (9.5:9.5 mL) were added methanesulfonamide (91 mg, 0.96 mmol, 0.9 eq.) and potassium osmiate dihydrate (8.4 mg, 0.022 mmol, 2%). The reaction mixture was stirred at room temperature until both phases were clear, and then cooled at 0° C. whereupon the inorganic salts partially precipitate. SI19 (358 mg, 1.14 mmol) was then added and the reaction mixture was stirred at 0° C. for 15 h. Sodium sulfite (2.87 g) was then added at 0° C. The reaction mixture was stirred at room temperature for 15 min and the water phase was extracted three times with ethyl acetate. The combined organic layers were washed with an aqueous solution of potassium hydroxide (2N), with brine and dried over magnesium sulfate. After being filtered and concentrated under reduced pressure, the crude product was purified by flash chromatography (cyclohexane/ethyl acetate 8:2) to give SI20 (276 mg, 0.80 mmol, 70%) as a yellow oil.

$^1$H NMR (CDCl$_3$, 300 MHz) δ 6.66 (qd, J=1.4, 8.9 Hz, 1H), 4.21 (q, J 7.2 Hz, 2H), 4.19 (m, 1H), 4.12 (m, 1H), 3.74 (tq, J=2.6, 6.2 Hz, 1H), 1.92 (d, J=1.4 Hz, 3H), 1.62-1.51 (2H), 1.30 (t, J=7.2 Hz, 3H), 1.19 (d, J=6.2 Hz, 3H), 0.90 (s, 9H), 0.13 (s, 3H), 0.12 (s, 3H).

$^{13}$C NMR (CDCl$_3$, 75 MHz) δ 167.7, 138.8, 131.4, 74.0, 71.8, 69.9, 60.8, 41.2, 25.8 (3×C), 24.5, 17.8, 14.2, 13.3, −3.8, −4.8.

$[α]^{20}_D$=+9.1 (c 0.8, CHCl$_3$)

HRMS (ESI) calculated for C$_{17}$H$_{34}$O$_5$SiNa: m/z 369.2067 ([M++Na]$^+$). found: m/z 369.2072 ([M+Na]$^+$).

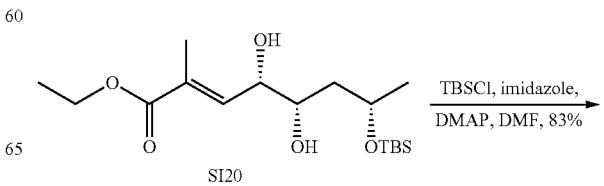

SI20

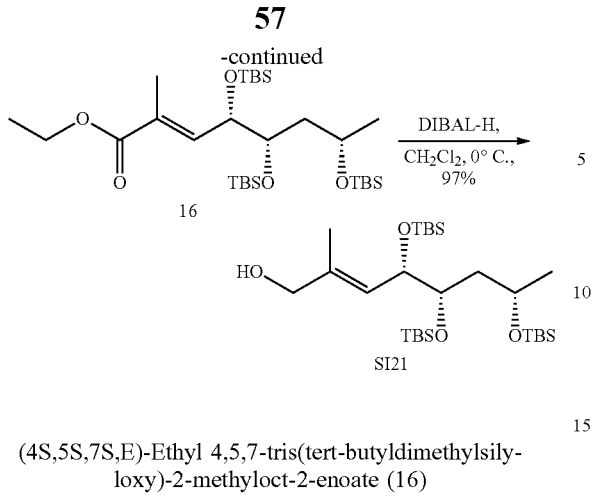

(4S,5S,7S,E)-Ethyl 4,5,7-tris(tert-butyldimethylsilyloxy)-2-methyloct-2-enoate (16)

To a solution of SI21 (240 mg, 0.69 mmol) in DMF (5 mL) were added tert-butyldimethylsilyl chloride (626 mg, 4.16 mmol, 6 eq.), imidazole (190 mg, 2.76 mmol, 4 eq.) and DMAP (20 mg, 0.16 mmol, 0.2 eq.). The reaction mixture was stirred at room temperature for 24 h, and then hydrolysed with water. The aqueous layer was extracted three times with a cyclohexane/dichloromethane mixture (9:1). The combined organic layers were washed with brine, dried over magnesium sulfate, filtered and concentrated under reduced pressure. The crude product was purified by chromatography on silica gel (eluting with cyclohexane/ethyl acetate 20:1) to give 16 as a colorless oil (330 mg, 0.57 mmol, 83%).

$^1$H NMR (CDCl$_3$, 300 MHz) δ 6.72 (dd, J=1.3, 8.9 Hz, 1H), 4.39 (dd, J=3.5, 8.9 Hz, 1H), 4.20 (q, J=7.1 Hz, 2H), 3.89 (m, 1H), 3.67 (ddd, J=3.5, 4.8, 8.0 Hz, 1H), 1.87 (d, J=1.3 Hz, 3H), 1.83 (ddd, J=4.9, 7.7, 12.9 Hz, 1H), 1.61 (ddd, J=5.8, 7.8, 12.9 Hz, 1H), 1.29 (t, J=7.1 Hz, 3H), 1.14 (d, J=6.0 Hz, 3H), 0.87 (s, 27H), 0.05 (s, 3H), 0.04 (s, 3H), 0.03 (s, 6H), 0.02 (s, 3H), 0.01 (s, 3H).

$^{13}$C NMR (CDCl$_3$, 75 MHz) δ 168.0, 141.3, 127.9, 73.2, 71.4, 65.9, 60.6, 42.8, 25.9 (3×C), 25.8 (3×C), 25.7 (3×C), 23.5, 18.1, 18.0, 17.9, 14.2, 13.4, −4.2, −4.3, −4.5 (2×C), −4.7, −4.8.

The spectral data are in agreement with those reported in the literature.[16]

$[α]_{20}^D$=−25.6 (c 1.3, CHCl$_3$)

HRMS (ESI) calculated for C$_{29}$H$_{62}$O$_5$Si$_3$Na: m/z 597.3797 ([M+Na]$^+$). found: m/z 597.3794 ([M+Na]$^+$).

(4S,5S,7S,E)-4,5,7-tris(tert-Butyldimethylsilyloxy)-2-methyloct-2-en-1-ol (SI21)

To a solution of 16 (300 mg, 0.52 mmol) in dichloromethane (3 mL) was added DIBAL-H (0.55 mL, 1.5 M in toluene, 1.6 eq.). The reaction mixture was stirred at 0° C. for 1 h and a saturated aqueous solution of Rochelle salts was added. After being stirred for 12 h, the aqueous layer was extracted three times with diethyl ether. The combined organic layers were washed with brine, dried over magnesium sulfate, filtered and concentrated under reduced pressure to give SI21 as a colorless oil (271 mg, 0.51 mmol, 97%).

$^1$H NMR (CDCl$_3$, 300 MHz) δ 5.46 (dd, J=1.1, 9.1 Hz, 1H), 4.33 (dd, J=3.8, 9.1 Hz, 1H), 4.01 (s, 2H), 3.90 (m, 1H), 3.60 (td, J=3.8, 7.9 Hz, 1H), 1.83 (ddd, J=3.9, 8.4, 13.3 Hz, 1H), 1.71 (d, J=1.1 Hz, 3H), 1.59 (ddd, J=5.0, 8.3, 13.3 Hz, 1H), 1.13 (d, J=6.0 Hz, 3H), 0.88 (s, 9H), 0.87 (s, 9H), 0.86 (s, 9H), 0.05 (s, 6H), 0.04 (s, 3H), 0.03 (s, 3H), 0.02 (s, 3H), −0.02 (s, 3H).

The spectral data are in agreement with those reported in the literature.

$[α]_{20}^D$=−17.7 (c 0.7, CHCl$_3$)

HRMS (ESI) calculated for C$_{27}$H$_{60}$O$_4$Si$_3$Na: m/z 555.3692 ([M+Na]$^+$). found: m/z 555.3686 ([M+Na]$^+$).

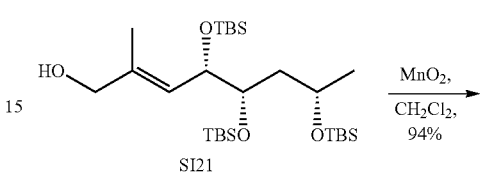

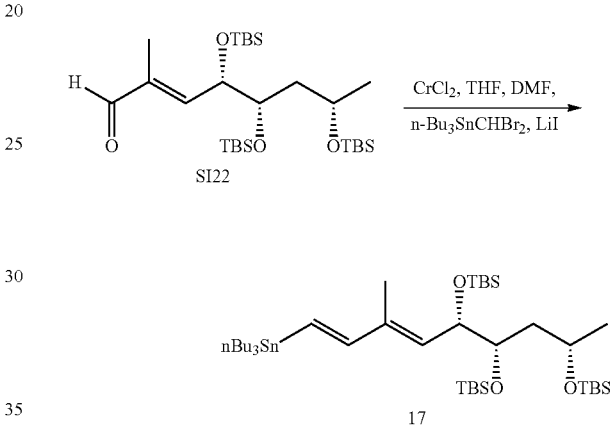

(4S,5S,7S,E)-4,5,7-tris(tert-Butyldimethylsilyloxy)-2-methyloct-2-enal (SI22)

To a solution of SI21 (215 mg, 0.40 mmol) in CH$_2$Cl$_2$ (4 mL) was added activated MnO$_2$ (529 mg, 6.15 mmol, 15 eq.). After being refluxed for 20 h the reaction mixture was filtered over a bed of Celite and washed with CH$_2$Cl$_2$. Solvent was removed under reduced pressure to give SI22 (200 mg, 0.38 mmol, 94%) as a yellow oil.

$^1$H NMR (CDCl$_3$, 300 MHz) δ 9.45 (s, 1H), 6.44 (dd, J=1.3, 8.4 Hz, 1H), 4.56 (dd, J=3.7, 8.4 Hz, 1H), 3.91 (m, 1H), 3.72 (td, J=3.9, 8.1 Hz, 1H), 1.90 (ddd, J=4.0, 8.2, 13.2 Hz, 1H), 1.80 (d, J=1.3 Hz, 3H), 1.61 (m, 1H), 1.15 (d, J=6.0 Hz, 3H), 0.88 (s, 9H), 0.87 (s, 9H), 0.86 (s, 9H), 0.05--0.02 (18H).

$^{13}$C NMR (CDCl$_3$, 75 MHz) δ 195.6, 152.8, 138.9, 73.3, 71.2, 65.7, 42.4, 25.9 (3×C), 25.8 (3×C), 25.7 (3×C), 23.3, 18.1, 18.0, 17.9, 10.2, −4.1, −4.3, −4.4, −4.5 (2×C), −4.6.

(5S,6S,8S)-6-[(tert-Butyldimethylsilyl)oxy]-2,2,3,3,8,10,10,11,11-nonamethyl-5-[(1E,3E)-2-methyl-4-(tributylstannyl)buta-1,3-dien-1-yl]-4,9-dioxa-3,10-disiladodecane (17)

To a solution of CrCl$_2$ (244 mg, 1.98 mmol, 10 eq.) in THF (3.2 mL) was slowly added DMF (0.146 mL). The reaction mixture was stirred at room temperature for 15 min and cooled to 0° C. A solution of SI22 (105 mg, 0.198 mmol) and tri-n-butylstannyldibromomethane[17] (184 mg, 0.40 mmol, 2 eq.) in THF (1.2 mL) was then added and the reaction mixture was stirred at 0° C. for 5 min; at which point a solution of LiI (106 mg, 0.79 mmol, 4 eq.) in THF (1.5 mL) was added. The reaction mixture was protected from light and stirred at room temperature for 18 h. The reaction mixture was hydrolyzed with water and the aqueous layer was extracted three times with $Et_2O$. The combined organic layers were washed with brine, dried over $MgSO_4$, filtered and concentrated under reduced pressure. 17 thus obtained was used without further purification.

1H), 6.35 (s, 1H), 6.27 (d, J 11.2 Hz, 1H), 5.86 (d, J=15.5 Hz, 1H), 5.58 (d, J=8.9 Hz, 1H), 4.43 (dd, J=3.6, 8.9 Hz, 1H), 4.22 (q, J=7.1 Hz, 2H), 3.91 (td, J=5.8, 7.6 Hz, 1H), 3.64 (td, J=3.6, 7.6 Hz, 1H), 2.05 (s, 3H), 2.02 (s, 3H), 1.85 (s, 3H), 1.80 (m, 1H), 1.62 (m, 1H), 1.31 (t, J=7.1 Hz, 3H), 1.14 (d, J=5.8 Hz, 3H), 0.88 (s, 9H), 0.87 (s, 9H), 0.86 (s, 9H), 0.05 (s, 9H), 0.04 (s, 3H), 0.02 (s, 3H), −0.02 (s, 3H).

$^{13}C$ NMR ($CDCl_3$, 75 MHz, 4'E isomer) δ 167.5, 150.7, 143.7, 139.8, 135.1, 134.6, 134.3, 134.0, 132.2, 123.7, 116.2, 73.7, 71.4, 66.1, 60.2, 42.7, 25.9 (6C), 25.8 (3C), 23.5, 18.1, 18.0, 17.9, 17.1, 14.4, 14.2, 13.5, −4.1 (2C), −4.3, −4.5, −4.6, −4.7.

HRMS (ESI) calculated for $C_{39}H_{74}O_5Si_3Na$: m/z 729.4736 ([M+Na]$^+$). found: m/z 729.4730 ([M+Na]$^+$).

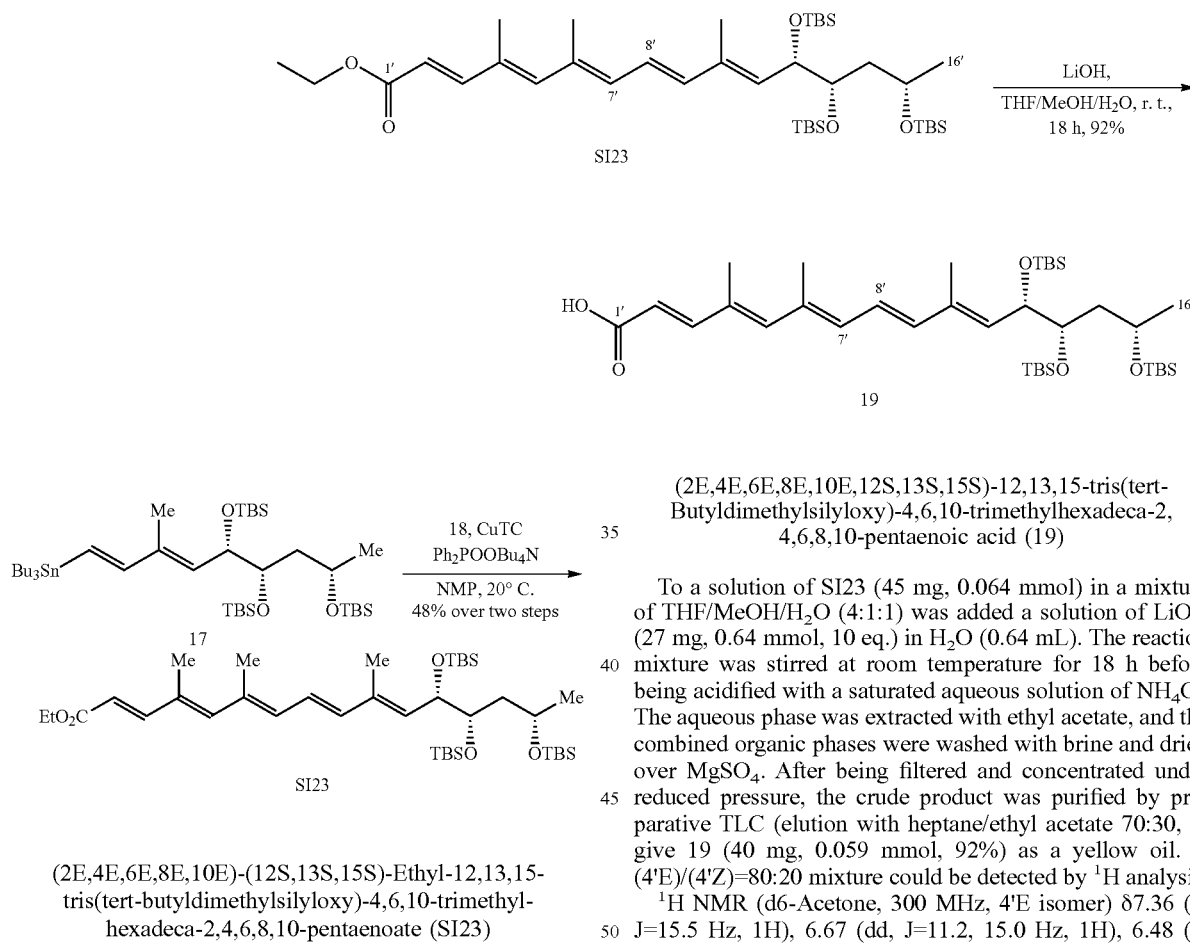

(2E,4E,6E,8E,10E)-(12S,13S,15S)-Ethyl-12,13,15-tris(tert-butyldimethylsilyloxy)-4,6,10-trimethyl-hexadeca-2,4,6,8,10-pentaenoate (SI23)

To a solution of 17 and tetra-n-butylammoniumdiphenylphosphinate[18] (169 mg, 0.37 mmol) in NMP (1.1 mL) was added 0.1 mL of a stock solution of 18 in NMP (125 mg, 0.39 mmol in 0.75 mL). After the addition of CuTC[19] (76 mg, 0.40 mmol), the remaining solution of 18 (0.65 mL) was added dropwise over 5 min. The reaction mixture was stirred at room temperature for 40 min and then diluted with $Et_2O$. The mixture was filtered through a pad of neutral alumina. The filtrate was then washed with water, brine, dried over $MgSO_4$, filtered, and concentrated. The crude product was purified by preparative TLC (elution with heptane/ethyl acetate 90:10) to give SI23 (67 mg, 0.095 mmol, 48% over two steps) as a yellow oil. A (4'E)/(4'Z)=92:8 mixture could be detected by $^1H$ analysis.

$^1H$ NMR ($CDCl_3$, 300 MHz, 4'E isomer) δ 7.37 (d, J=15.5 Hz, 1H), 6.50 (dd, J=11.1, 15.5 Hz, 1H), 6.37 (d, J=15.5 Hz,

(2E,4E,6E,8E,10E,12S,13S,15S)-12,13,15-tris(tert-Butyldimethylsilyloxy)-4,6,10-trimethylhexadeca-2,4,6,8,10-pentaenoic acid (19)

To a solution of SI23 (45 mg, 0.064 mmol) in a mixture of THF/MeOH/$H_2O$ (4:1:1) was added a solution of LiOH (27 mg, 0.64 mmol, 10 eq.) in $H_2O$ (0.64 mL). The reaction mixture was stirred at room temperature for 18 h before being acidified with a saturated aqueous solution of $NH_4Cl$. The aqueous phase was extracted with ethyl acetate, and the combined organic phases were washed with brine and dried over $MgSO_4$. After being filtered and concentrated under reduced pressure, the crude product was purified by preparative TLC (elution with heptane/ethyl acetate 70:30, to give 19 (40 mg, 0.059 mmol, 92%) as a yellow oil. A (4'E)/(4'Z)=80:20 mixture could be detected by $^1H$ analysis.

$^1H$ NMR (d6-Acetone, 300 MHz, 4'E isomer) δ7.36 (d, J=15.5 Hz, 1H), 6.67 (dd, J=11.2, 15.0 Hz, 1H), 6.48 (d, J=15.0 Hz, 1H), 6.46 (s, 1H), 6.39 (d, J=11.2 Hz, 1H), 5.87 (d, J=15.5 Hz, 1H), 5.67 (d, J=9.1 Hz, 1H), 4.58 (dd, J=3.4, 9.1 Hz, 1H), 4.01 (m, 1H), 3.78 (m, 1H), 2.09 (s, 3H), 2.06 (s, 3H), 1.94 (s, 3H), 1.87 (m, 1H), 1.66 (m, 1H), 1.17 (d, J=6.0 Hz, 3H), 0.91 (27H), 0.09 (18H).

$^{13}C$ NMR (d6-Acetone, 75 MHz, (4'E isomer) δ169.2, 152.6, 145.3, 141.2, 137.1, 136.4, 136.0, 135.7, 134.2, 126.3, 118.1, 76.3, 73.0, 67.7, 44.9, 27.4 (6C), 27.3 (3C), 25.2, 22.2, 18.2 (3C), 15.3, 14.8, −2.7, −2.9, −3.0, −3.1, −3.3, −3.4.

HRMS-ESI calculated for $C_{37}H_{69}O_5Si_3$: m/z 677.4458 ([M−H]$^−$). found: m/z 677.4467 ([M−H]$^−$).

The acid 19 was photoisomerized in acetone for 1 h, using a green fluorescent bulb, in order to obtain 19 with a 4'Z/4'E=48:52 ratio as detected by $^1H$ NMR.

Spectrum emission of the fluorescent bulb at 5 cm: 365, 405, 435, 486, 541, 545, 576, 578, 610 nm.

Compound SI24

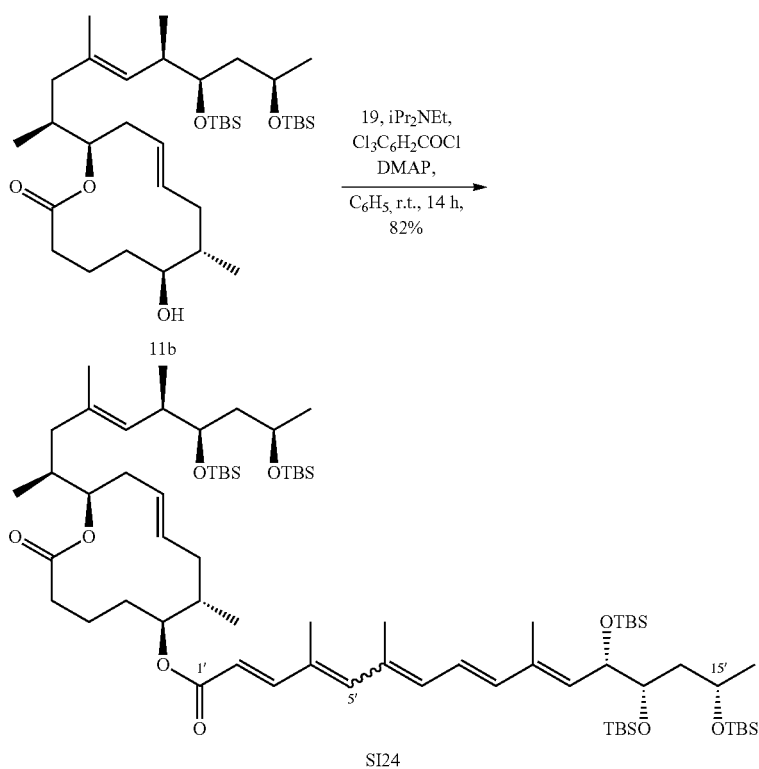

To a solution of 19 (40 mg, 0.056 mmol) in benzene (0.4 mL) were added diisopropylethylamine (35 μL, 0.19 mmol, 6.7 eq.), 2,4,6-trichlorobenzoyl chloride (20 μL, 0.12 mmol, 4 eq.), and DMAP (32 mg). The reaction mixture was stirred at room temperature for 15 min and a solution of 11b (18 mg, 0.028 mmol) in benzene (0.3 mL) was added. After being stirred at room temperature for 14 h, an aqueous saturated solution of sodium hydrogenocarbonate was added to the reaction mixture. The aqueous layer was extracted three times with benzene. The combined organic layers were washed with brine, dried over MgSO$_4$, filtered and concentrated under reduced pressure. The crude product was purified on preparative TLC (eluting with heptane/ethyl acetate 95:5) to give SI24 (30 mg, 0.023 mmol, 82%) as a yellow oil. A (4'E)/(4'Z)=70:30 mixture could be detected by $^1$H analysis.

$^1$H NMR (CDCl$_3$, 300 MHz, 4'E isomer) δ 7.34 (d, J=15.4 Hz, 1H), 6.49 (dd, J=10.8, 14.9 Hz, 1H), 6.36 (d, J=15.5 Hz, 1H), 6.33 (s, 1H), 6.27 (d, J=11.5 Hz, 1H), 5.82 (d, J=15.1 Hz, 1H), 5.57 (d, J=8.9 Hz, 1H), 5.42 (m, 1H), 5.21-5.09 (2H), 5.04 (d, J=9.4 Hz, 1H), 4.77 (ddd, J=2.1, 5.6, 11.5 Hz, 1H), 4.42 (dd, J=3.6, 9.2 Hz, 1H), 3.90 (m, 1H), 3.64 (m, 1H), 3.57 (m, 1H), 3.32 (dd, J=4.0, 9.1 Hz, 1H), 2.55 (m, 1H), 2.52 (m, 1H), 2.44 (m, 1H), 2.24 (m, 1H), 2.15 (m, 1H), 2.10 (m, 1H), 2.05 (s, 3H), 2.02 (s, 3H), 1.97 (m, 1H), 1.94-1.92 (2H), 1.84 (s, 6H), 1.80-1.59 (10H), 1.53 (s, 3H), 1.26-1.23 (3H), 1.13 (d, J=6.0 Hz, 3H), 0.93 (d, J=6.7 Hz, 3H), 0.90 (s, 9H), 0.88 (s, 18H), 0.87 (s, 9H), 0.86 (s, 9H), 0.78 (d, J=6.7 Hz, 3H), 0.05 (s, 9H), 0.03 (s, 6H), 0.02 (s, 9H), 0.01 (s, 6H).

$^{13}$C NMR (CDCl$_3$, 75 MHz, 4'E isomer) δ 173.3, 166.9, 150.6, 143.5, 141.4, 139.7, 135.6, 135.1, 134.6, 134.2, 134.1, 132.2, 131.9, 130.6, 125.0, 116.5, 75.0, 73.6, 72.9, 72.8, 71.3, 68.2, 66.0, 42.8, 42.6, 41.7, 38.0, 37.3, 36.3, 35.9, 35.6, 34.9, 32.7, 30.3, 25.9 (12C), 25.8 (3C), 23.4, 21.4, 20.8, 18.3 (2×C), 18.1 (2×C), 17.9, 17.1, 15.9, 15.6, 14.5, 14.2, 13.5, −4.1 (2×C), −4.2 (2×C), −4.3, −4.4, −4.5, −4.6, −4.7, −4.8.

HRMS (ESI) calculated for C$_{73}$H$_{138}$O$_9$Si$_5$Na: m/z 1321.9079 ([M+Na]$^+$). found: m/z 1321.9082 ([M+Na]$^+$).

Compound 20a

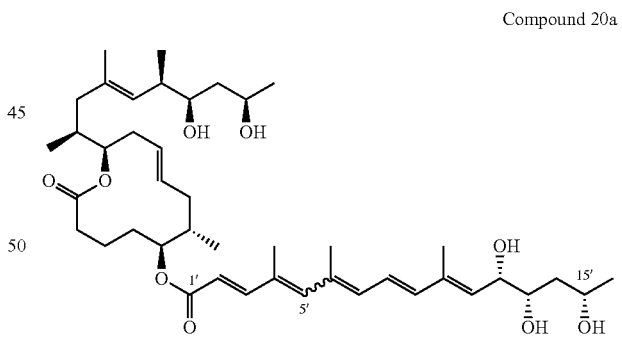

To a solution of SI24 (11 mg) in THF (2.1 mL) was added TBAF (0.17 mL, 20 eq.). The solution was stirred at room temperature for 12 h. For stabilities issues of 20a, the reaction was quenched at 60% of conversion. CaCO$_3$ (34 mg), Dowex 50WX8-400 (94 mg) and MeOH (0.2 mL) were added and the reaction mixture was stirred for 20 min. After being filtered and concentrated under reduced pressure, the crude product was purified by preparative TLC (CH$_2$Cl$_2$/MeOH 90:10). The recovered trial was recycled. After one recycle, 20a was obtained (2 mg). A (4'E)/(4'Z)=42:58 mixture could be detected by $^1$H analysis.

$^1$H NMR (d6-Acetone, 400 MHz, 4'Z isomer) δ7.90 (d, J=15.5 Hz, 1H), 6.64 (dd, J=11.1, 15.5, Hz, 1H), 6.45 (d, J=15.5 Hz, 1H), 6.33 (s, 1H), 6.17 (d, J=11.1 Hz, 1H), 5.92 (d, J=15.5 Hz, 1H), 5.61 (d, J=8.2 Hz, 1H), 5.45 (m, 1H), 5.22 (m, 1H), 5.20 (m, 1H), 5.05 (d, J=9.4 Hz, 1H), 4.84 (ddd, J=2.1, 5.3, 11.3 Hz, 1H), 419 (m, 1H), 4.20 (s, 1H, OH), 4.04 (s, 1H, OH), 3.90 (m, 1H), 3.68 (m, 1H), 3.51 (s, 1H, OH), 3.44 (m, 1H), 3.30 (m, 1H), 2.42 (m, 1H), 2.40 (m, 1H), 2.30 (m, 1H), 2.12 (m, 1H), 2.10 (m, 1H), 2.02 (s, 3H), 1.96 (m, 1H), 1.95 (m, 1H), 1.92-1.87 (7H), 1.80 (m, 1H), 1.77 (m, 1H), 1.76-1.73 (2H), 1.65 (m, 1H), 1.62-1.59 (4H), 1.53-1.49 (2H), 1.47-1.44 (2H), 1.25 (m, 1H), 1.20 (d, J=6.2 Hz, 3H), 0.90 (6H), 0.85 (d, J=6.7 Hz, 6H).

$^{13}$C NMR (d6-Acetone, 100 MHz, 4'Z isomer) δ 174.6, 168.1, 145.2, 144.0, 142.8, 138.3, 136.9, 136.8, 135.9, 135.6, 134.6, 133.1, 132.2, 127.9, 126.2, 120.9, 76.8, 76.4, 76.3, 74.2, 73.4, 70.9, 68.7, 45.2, 43.1, 42.8, 41.2, 40.3, 37.3, 36.5, 36.2, 35.4, 25.2, 22.2, 21.1, 20.9, 20.7, 18.6, 18.0, 17.2, 16.1, 15.4, 14.4.

$^1$H NMR (d6-Acetone, 400 MHz, 4'E isomer) δ 7.34 (d, J=15.5 Hz, 1H), 6.64 (dd, J=11.2, 15.5, Hz, 1H), 6.40 (d, J=15.5 Hz, 1H), 6.39 (s, 1H), 6.38 (d, J=11.2 Hz, 1H), 5.87 (d, J=15.5 Hz, 1H), 5.61 (d, J=8.2 Hz, 1H), 5.45 (m, 1H), 5.22 (m, 1H), 5.20 (m, 1H), 5.05 (d, J=9.4 Hz, 1H), 4.84 (ddd, J=2.1, 5.3, 11.3 Hz, 1H), 4.29 (m, 1H), 4.20 (s, 1H, OH), 4.04 (s, 1H, OH), 3.90 (m, 1H), 3.68 (m, 1H), 3.50 (s, 1H, OH), 3.44 (m, 1H), 3.30 (m, 1H), 2.42 (m, 1H), 2.40 (m, 1H), 2.30 (m, 1H), 2.12 (m, 1H), 2.10 (m, 1H), 2.02 (s, 3H), 1.96 (m, 1H), 1.95 (m, 1H), 1.92-1.87 (7H), 1.80 (m, 1H), 1.77 (in, 1H), 1.76-1.73 (2H), 1.65 (m, 1H), 1.62-1.59 (4H), 1.53-1.49 (2H),1.47-1.44 (2H), 1.25 (m, 1H), 1.20 (d, J=6.2 Hz, 3H), 0.90 (6H), 0.85 (d, J=6.7 Hz, 6H).

$^{13}$C NMR (d6-Acetone, 100 MHz, 4'E isomer) δ 174.6, 168.1, 152.0, 141.3, 141.0, 138.3, 137.1, 136.9, 136.8, 135.8, 134.6, 133.1, 132.2, 127.9, 126.2, 118.8, 76.7, 76.4, 76.3, 74.1, 73.3, 70.8, 68.6, 45.1, 42.9, 42.8, 41.3, 40.3, 37.3, 36.5, 36.2, 35.4, 25.1, 22.2, 21.1, 20.9, 20.7, 18.6, 18.1, 17.2, 16.1, 15.4, 14.4.

HRMS-ESI calculated for $C_{43}H_{68}O_9Na$: m/z 751.4761 ([M+Na]$^+$). found: m/z 751.4736 ([M+Na]$^+$).

Compound SI25

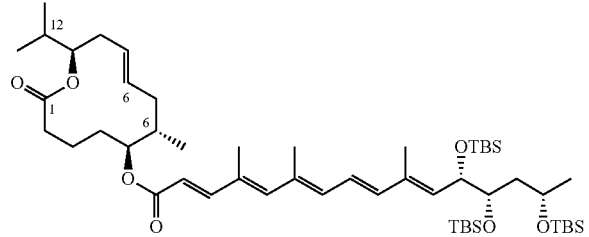

To a solution of 19 (60 mg, 0.089 mmol) in benzene (0.7 mL) were added diisopropylethylamine (62 μL, 0.34 mmol, 5.6 eq.), 2,4,6-trichlorobenzoyl chloride (29 μL; 0.18 mmol, 3 eq.), and DMAP (55 mg). The reaction mixture was stirred at room temperature for 15 min and 24 (15 mg, 0.059 mmol) was added. After being stirred at room temperature for 14 h, an aqueous saturated solution of sodium hydrogenocarbonate was added to the reaction mixture. The aqueous layer was extracted three times with benzene. The combined organic layers were washed with brine, dried over MgSO$_4$, filtered and concentrated under reduced pressure. The crude product was purified on preparative TLC eluting with benzene/heptane 60:40) to give SI25 (47 mg, 0.051 mmol, 87%) as a yellow oil. A (4'E)/(4'Z) 85:15 mixture could be detected by $^1$H analysis.

$^1$H NMR (CDCl$_3$, 300 MHz, 4'E isomer) δ 7.37 (d, J=15.5 Hz, 1H), 6.51 (dd, J=14.8, 11.2 Hz, 1H), 6.37 (d, J=14.8 Hz, 1H), 6.36 (s, 1H), 6.28 (d, J 11.2 Hz, 1H), 5.86 (d, J=15.52 Hz, 1H), 5.59 (d, J=8.8 Hz, 1H), 5.51 (m, 1H), 5.30 (m, 1H), 4.83-4.74 (2H), 4.44 (dd, J=9.1, 3.9 Hz, 1H), 3.91 (m, 1H), 3.65 (td, J=7.8, 3.9 Hz, 1H), 2.49 (m, 1H), 2.30 (m, 1H), 2.15-2.06 (2H), 2.06 (s, 3H), 2.03 (s, 3H), 1.98-1.96 (m, 1H), 1.86 (s, 3H), 1.87-1.61 (6H), 1.15 (d, J=6.0 Hz, 3H), 0.95 (s, 3H), 0.93 (s, 3H), 0.92 (s, 3H), 0.90 (s, 3H), 0.89 (s, 9H), 0.88 (s, 9H), 0.87 (s, 9H), 0.06 (s, 9H), 0.04 (s, 3H), 0.02 (s, 3H), −0.02 (s, 3H).

$^{13}$C NMR (CDCl$_3$, 75 MHz, 4'E isomer) δ 173.0, 166.8, 150.7, 143.6, 139.8, 135.1, 134.8, 134.6, 134.3, 134.0, 132.2, 126.0, 123.7, 116.4, 78.6, 75.9, 73.6, 71.4, 66.0, 42.7, 38.0, 36.1, 35.5, 34.4, 32.3, 29.6, 25.9 (6C), 25.8 (3C), 23.5, 20.3, 19.2, 18.5, 18.2, 18.1 (2×C), 17.9, 17.1, 14.2, 13.5, −4.2 (2×C), −4.3, −4.5, −4.6, −4.7.

HRMS (ESI) calculated for $C_{52}H_{94}O_7Si_3Na$: m/z 937.6199 ([M+Na]$^+$). found: m/z 937.6187 ([M+Na]$^+$).

Compound 22

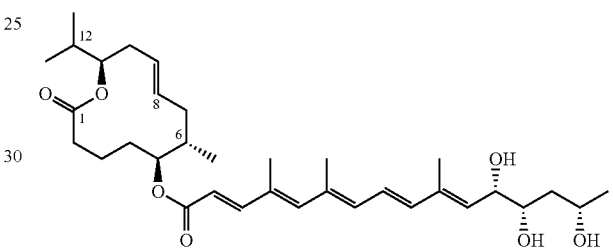

To a solution of SI25 (47 mg, 0.051 mmol) in THF (0.3 mL) was added TBAF (0.46 mmol, 1M in THF, 9 eq). The solution was stirred at room temperature for 4 h. CaCO$_3$ (90 mg), Dowex 50WX8-400 (285 mg) and MeOH (0.6 mL) were added and the reaction mixture was stirred for 1 h. After being filtered and concentrated under reduced pressure, the crude product was purified by preparative TLC (CH$_2$Cl$_2$/MeOH 90:10) to give 22 (29 mg, 0.050 mmol, 98%). A (4'E)/(4'Z)=83:17 mixture could be detected by analysis.

$^1$H NMR (CDCl$_3$, 300 MHz) δ 7.34 (d, J=15.5 Hz, 1H), 6.56 (dd, 11.1, 15.1 Hz, 1H), 6.35 (s, 1H), 6.33 (d, J=15.1 Hz, 1H), 6.22 (d, J=11.1 Hz, 1H), 5.85 (d, J=15.5 Hz, 1H), 5.50 (d, J=8.9 Hz, 1H), 5.44 (m, 1H), 5.26 (m, 1H), 4.81-4.70 (2H), 4.28 (dd, J=7.4, 8.6 Hz, 1H), 4.05 (m, 1H), 3.76-3.70 (2H), 2.47 (m, 1H), 2.29 (m, 1H), 2.12-2.08 (2H), 2.04 (s, 3H), 2.01 (s, 3H), 1.90 (m, 1H), 1.84-1.68 (6H), 1.53-1.51 (2H), 1.19 (d, J=6.9 Hz, 3H), 0.93 (s, 3H), 0.91 (s, 3H), 0.90 (s, 3H), 0.89 (s, 3H).

$^{13}$C NMR (CDCl$_3$, 75 MHz) δ 173.0, 166.8, 150.5, 143.3, 141.0, 138.4, 135.1, 134.7, 134.4, 132.6, 131.1, 126.0, 125.2, 116.7, 78.7, 75.9, 75.8, 72.1, 68.5, 40.4, 38.0, 36.1, 35.5, 34.4, 32.3, 29.6, 24.1, 20.3, 19.2, 18.5, 18.2, 17.1, 14.2, 13.3.

HRMS-EST calculated for $C_{34}H_{56}NaO_7$: m/z 595.3605 ([M+Na]$^+$). found: m/z 595.3595 ([M+Na]$^+$).

Following this general procedure, compounds 22b-o were prepared by esterification of compound 21 with carboxylic acids 19b-o followed by global deprotection of the three tert-butyldimethylsilyl ethers.

(6S,7S,9E,12R)-7-methyl-2-oxo-12-(propan-2-yl)-1-oxacyclododec-9-en-6-yl(2E,4E,6E,8E,10E,12S,13S,15R)-12,13,15-trihydroxy-4,6,10-trimethylhexadeca-2,4,6,8,10-pentaenoate (compound 22b)

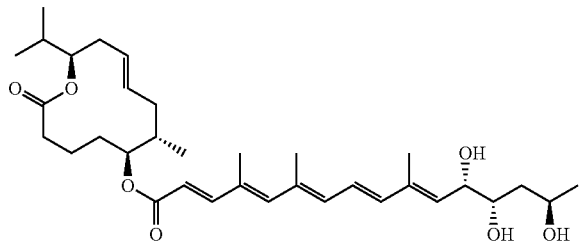 [SMILES: CC(=C\C=C\C(C)=C\[C@H](O)[C@@H](O)C[C@@H](C)O)/C=C(C)/C=C/C(=O)O[C@H]1CCCC(=O)O[C@@H](C(C)C)C/C=C/C[C@@H]1C]

A (4'E)/(4'Z)=43:57 mixture could be detected by $^1$H analysis.

$^1$H NMR (Acetone-d6, 400 MHz) δ 7.93 (d, J=15.8 Hz, 1H, Z isomer), 7.37 (d, J=15.5 Hz, 1H, E isomer), 6.63 (dd, J=11.0, 14.4 Hz, 1H), 6.47 (s, 1.14), 6.36 (d, J=14.4 Hz, 1H), 6.17 (d, J=11.0 Hz, 1H), 5.90 (d, J=15.5 Hz, 1H), 5.57 (m, 1H), 5.49 (m, 1H), 5.30 (m, 1H), 4.78-4.67 (2H), 4.28 (dd, J=7.0, 8.7 Hz, 1H), 4.01 (m, 1H), 3.79-3.70 (2H), 3.56 (m, 1H), 3.30 (m, 1H), 2.47 (m, 1H), 2.29 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (2H), 1.54-1.49 (2H), 1.13 (d, J=6.1 Hz, 3H), 0.92 (s, 3H), 0.90 (s, 3H), 0.87 (s, 3H).

HRMS (ESI) calculated for $C_{34}H_{52}O_7Na$: m/z 595.3605 ([M+Na]$^+$). found: m/z 595.3619 ([M+Na]$^+$).

(6S,7S,9E,12R)-7-methyl-2-oxo-12-(propan-2-yl)-1-oxacyclododec-9-en-6-yl(2E,4E,6E,8E,10E,12R,13R,15R)-12,13,15-trihydroxy-4,6,10-trimethylhexadeca-2,4,6,8,10-pentaenoate (compound 22c)

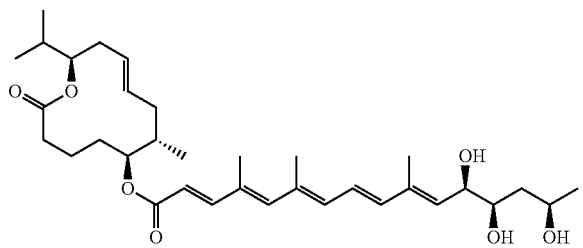 [SMILES: CC(=C\C=C\C(C)=C\[C@@H](O)[C@H](O)C[C@@H](C)O)/C=C(C)/C=C/C(=O)O[C@H]1CCCC(=O)O[C@@H](C(C)C)C/C=C/C[C@@H]1C]

A (4'E)/(4'Z)=60:40 mixture could be detected by $^1$H analysis.

$^1$H NMR (Acetone-d6, 300 MHz) δ 7.93 (d, J=15.7 Hz, 1H, Z isomer), 7.38 (d, J=15.6 Hz, 1H, E isomer), 6.63 (dd, J=11.1, 14.5 Hz, 1H), 6.48 (s, 1H), 6.38 (d, J=14.5 Hz, 1H), 6.18 (d, J=11.1 Hz, 1H), 5.91 (d, J=15.5 Hz, 1H), 5.64-5.57 (2H), 5.30 (m, 1H), 4.81-4.67 (2H), 4.28 (m, 1H), 4.26 (m, 1H), 4.06 (m, 1H), 4.02-3.90 (2H), 3.69 (m, 1H), 2.51 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (2H), 1.54-1.49 (2H), 1.13 (d, J=6.1 Hz, 3H), 0.92 (s, 3H), 0.90 (s, 3H), 0.87 (s, 3H).

HRMS (ESI) calculated for $C_{34}H_{52}O_7Na$: m/z 595.3605 ([M+Na]$^+$). found: m/z 595.3588 ([M+Na]$^+$).

(6S,7S,9E,12R)-7-methyl-2-oxo-12-(propan-2-yl)-1-oxacyclododec-9-en-6-yl(2E,4E,6E,8E,10E,13S,15S)-13,15-dihydroxy-4,6,10-trimethylhexadeca-2,4,6,8,10-pentaenoate (compound 22d)

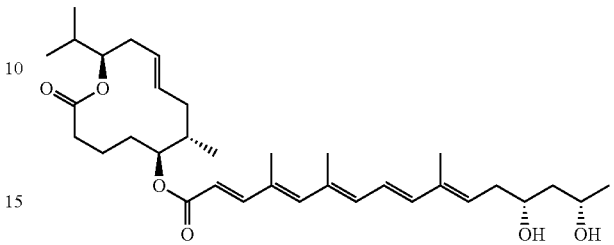

A (4'E)/(4'Z)=41:59 mixture could be detected by $^1$H analysis.

NMR $^1$H (Acetone d-6, 300 MHz) δ 7.93 (d, J=15.5 Hz, 1H, Z isomer), 7.36 (d, J=15.5 Hz, 1H, E isomer), 6.63 (dd, J=11.1, 14.5 Hz, 1H), 6.48 (s, 1H), 6.38 (d, J=14.5 Hz, 1H), 6.17 (d, J=11.1 Hz, 1H), 5.89 (d, J=15.5 Hz, 1H), 5.71 (m, 1H), 5.50 (m, 1H), 5.28 (m, 1H), 4.78-4.63 (2H), 4.27 (m, 1H), 4.11 (m, 1H), 3.97 (m, 1H), 3.85 (m, 1H), 2.51 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (2H), 1.54-1.49 (2H), 1.13 (d, J=6.1 Hz, 3H), 0.92 (s, 3H), 0.90 (s, 3H), 0.87 (s, 3H).

HRMS (ESI) calculated for $C_{34}H_{52}O_6Na$: m/z 579.3656 ([M+Na]$^+$). found: m/z 579.3659 ([M+Na]$^+$).

(6S,7S,9E,12R)-7-methyl-2-oxo-12-(propan-2-yl)-1-oxacyclododec-9-en-6-yl(2E,4E,6E,8E,10E,13S)-13-hydroxy-4,6,10-trimethylhexadeca-2,4,6,8,10-pentaenoate (compound 22e)

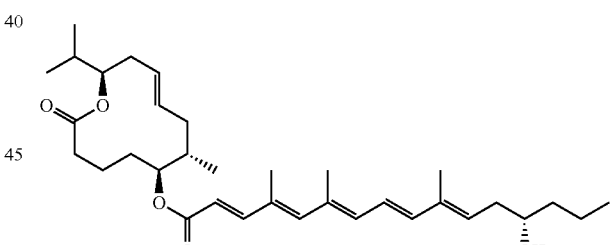

Compound 22e exists as a mixture of three isomers in a 44:25:31 ratio and a few diagnostic chemical shifts of the first (44%) and third (31%) isomers could be identified in proton NMR.

$^1$H NMR (Acetone-d6, 400 MHz) δ 7.93 (d, J=15.8 Hz, 1H, diagnostic chemical shift of the first isomer), 7.44 (d, J=15.5 Hz, 1H), 7.37 (d, J=15.6 Hz, 1H, diagnostic chemical shift of the third isomer), 6.63 (dd, J=11.1, 15.0 Hz, 1H), 6.47 (s, 1H), 6.36 (d, J=15.0 Hz, 1H), 6.17 (d, J=11.1 Hz, 1H), 5.89 (d, J=15.5 Hz, 1H), 5.74 (m, 1H), 5.50 (m, 1H), 5.30 (m, 1H), 4.78-4.67 (2H), 3.68-3.65 (2H), 2.50 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (4H), 1.54-1.49 (4H), 1.19 (s, 3H), 0.92 (s, 3H), 0.90 (s, 3H), 0.87 (s, 3H).

HRMS (ESI) calculated for $C_{34}H_{52}O_5Na$: m/z 563.3707 ([M+Na]$^+$). found: m/z 563.3704 ([M+Na]$^+$).

(6S,7S,9E,12R)-7-methyl-2-oxo-12-(propan-2-yl)-1-oxacyclododec-9-en-6-yl 3-[(1E,3E,5S,6S,8S)-5,6,8-trihydroxy-3-methylnona-1,3-dien-1-yl]benzoate (compound 22f)

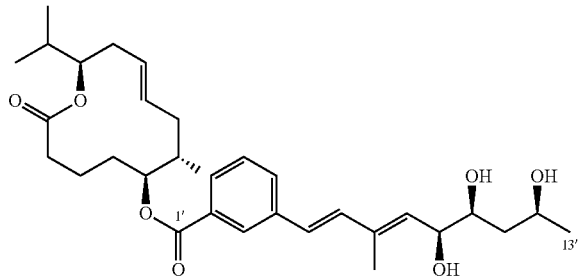 [SMILES: CC(/C=C/c1cccc(C(=O)O[C@H]2CCCC(=O)O[C@@H](C(C)C)C/C=C/C[C@@H]2C)c1)=C\[C@H](O)[C@@H](O)C[C@H](C)O]

$^1$H NMR (Acetone-d6, 300 MHz) δ 8.12 (s, 1H), 7.90 (d, J=7.7 Hz, 1H), 7.79 (d, J=7.7 Hz, 1H), 7.48 (dd ap t, J=7.8 Hz, 1H), 7.02 (d, J=16.1 Hz, 1H), 6.72 (d, J=16.1 Hz, 1H), 5.73 (d, J=8.9 Hz, 1H), 5.55 (m, 1H), 5.33 (m, 1H), 4.89 (m, 1H), 4.78 (ddd, J=2.4, 6.2, 11.5 Hz, 1H), 4.33 (dd, J=6.2, 8.9 Hz, 1H), 4.06 (s, 1H), 4.03 (s, 1H), 4.00 (m, 1H), 3.68 (m, 1H), 2.51 (m, 1H), 2.35 (m, 1H), 2.20-2.10 (2H), 2.06 (s, 3H), 1.94-1.92 (2H), 1.80-1.75 (2H), 1.82-1.76 (4H), 1.54-1.51 (2H), 1.12 (d, J 6.1 Hz, 3H), 0.96 (d, J=5.6 Hz, 3H), 0.96 (d, J=7.0 Hz, 3H), 0.90 (d, JT 7.0 Hz, 3H).

HRMS (ESI) calculated for $C_{32}H_{46}O_7Na$: m/z 565.3135 ([M+Na]$^+$). found: m/z 565.3142 ([M+Na]$^+$).

(6S,7S,9E,12R)-7-methyl-2-oxo-12-(propan-2-yl)-1-oxacyclododec-9-en-6-yl(2E,4E,6E,8E,10E,12S,13S)-12,13-dihydroxy-4,6,10-trimethylhexadeca-2,4,6,8,10-pentaenoate (compound 22g)

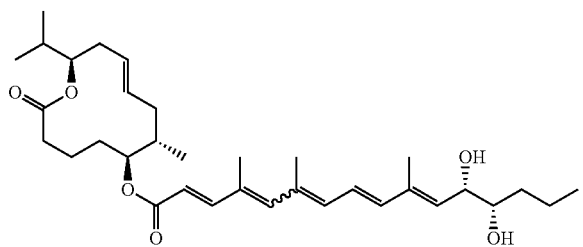 [SMILES: CCC[C@H](O)[C@@H](O)/C=C(C)/C=C/C=C(C)C=C(C)/C=C/C(=O)O[C@H]1CCCC(=O)O[C@@H](C(C)C)C/C=C/C[C@@H]1C]

A (4'E)/(4'Z)=47:53 mixture could be detected by $^1$H analysis.

$^1$H NMR (Acetone-d6, 400 MHz) δ 7.93 (d, J=15.6 Hz, 1H, Z isomer), 7.37 (d, J=15.5 Hz, 1H, E isomer), 6.63 (dd, J=11.1, 15.0 Hz, 1H), 6.47 (s, 1H), 6.36 (d, J=15.0 Hz, 1H), 6.16 (d, J=11.1 Hz, 1H), 5.89 (d, J=15.5 Hz, 1H), 5.58 (m, 1H), 5.50 (m, 1H), 5.30 (m, 1H), 4.78-4.67 (2H), 4.22 (d, J=7.1, 8.5 Hz, 1H), 3.60-3.56 (2H), 3.40 (m, 1H), 2.50 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (2H), 1.54-1.49 (4H), 1.19 (s, 3H), 0.92 (s, 3H), 0.90 (s, 3H), 0.87 (s, 3H).

HRMS (ESI) calculated for $C_{34}H_{52}O_6Na$: m/z 579.3656 ([M+Na]$^+$). found: m/z 579.3649 ([M+Na]$^+$).

(6S,7S,9E,12R)-7-methyl-2-oxo-12-(propan-2-yl)-1-oxacyclododec-9-en-6-yl(2E,4E,6E,8E,10E,12R,13R)-12,13-dihydroxy-4,6,10-trimethylhexadeca-2,4,6,8,10-pentaenoate (compound 22h)

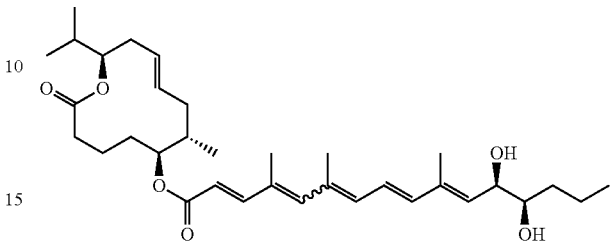

A (4'E)/(4'Z)=52:48 mixture could be detected by $^1$H analysis.

$^1$H NMR (Acetone-d6, 300 MHz) δ 7.93 (d, J=15.6 Hz, 1H, Z isomer), 7.37 (d, J=15.5 Hz, 1H, E isomer), 6.63 (dd, J=11.1, 15.0 Hz, 1H), 6.47 (s, 1H), 6.36 (d, J=15.0 Hz, 1H), 6.15 (d, J=11.1 Hz, 1H), 5.89 (d, J=15.5 Hz, 1H), 5.56 (d, J=8.5 Hz, 1H), 5.50 (m, 1H), 5.30 (m, 1H), 4.78-4.67 (2H), 4.22 (d, J=6.9, 8.9 Hz, 1H), 3.90 (m, 1H), 3.60 (m, 1H), 3.40 (m, 1H), 2.50 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (2H), 1.54-1.49 (4H), 1.19 (s, 3H), 0.92 (s, 3H), 0.90 (s, 3H), 0.87 (s, 3H).

HRMS (ESI) calculated for $C_{34}H_{52}O_6Na$: m/z 579.3656 ([M+Na]$^+$). found: m/z 579.3655 ([M+Na]$^+$).

(6S,7S,9E,12R)-7-methyl-2-oxo-12-(propan-2-yl)-1-oxacyclododec-9-en-6-yl(2E,4E,6E,8E,10E,12S)-12-hydroxy-4,6,10-trimethylhexadeca-2,4,6,8,10-pentaenoate (compound 22i)

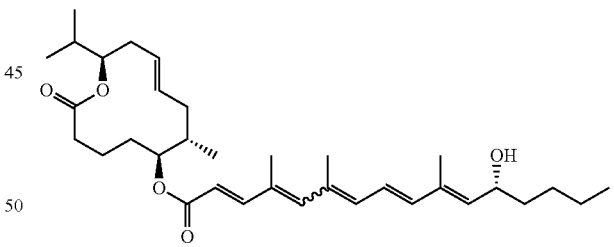

A (4'E)/(4'Z)=54:46 mixture could be detected by $^1$H analysis.

$^1$H NMR (Acetone-d6, 300 MHz) δ 7.93 (d, J=15.6 Hz, 1H, Z isomer), 7.37 (d, J=15.5 Hz, 1H, E isomer), 6.63 (dd, J=11.3, 15.0 Hz, 1H), 6.47 (s, 1H), 6.36 (d, J=15.0 Hz, 1H), 6.17 (d, J=11.3 Hz, 1H), 5.89 (d, J=15.6 Hz, 1H), 5.58-5.50 (2H), 5.29 (m, 1H), 4.79-4.66 (2H), 4.46 (m, 1H), 3.60 (m, 1H), 2.49 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (4H), 1.54-1.49 (4H), 1.28 (s, 3H), 0.92 (s, 3H), 0.90 (s, 3H), 0.87 (s, 3H).

HRMS (ESI) calculated for $C_{34}H_{52}O_5Na$: m/z 563.3707 ([M+Na]$^+$). found: m/z 563.3700 ([M+Na]$^+$).

(6S,7S,9E,12R)-7-methyl-2-oxo-12-(propan-2-yl)-1-oxacyclododec-9-en-6-yl(2E,4E,6E,8E,10E,15S)-15-dihydroxy-4,6,10-trimethylhexadeca-2,4,6,8,10-pentaenoate (compound 22j)

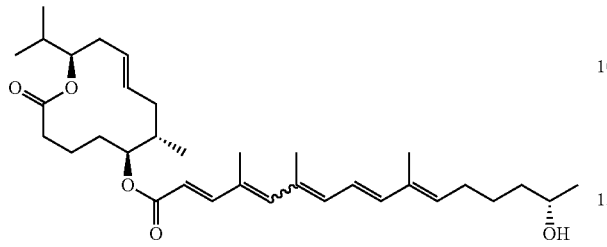

Compound 22j exists as a mixture of three isomers in a 42:27:31 ratio and a few diagnostic chemical shifts of the first (42%) and third (31%) isomers could be identified in proton NMR.

¹H NMR (Acetone-d6, 400 MHz) δ 7.93 (d, J=15.8 Hz, 1H, diagnostic chemical shift of the first isomer), 7.44 (d, J=15.5 Hz, 1H), 7.37 (d, J=15.6 Hz, 1H, diagnostic chemical shift of the third isomer), 6.63 (dd, J=11.1, 15.0 Hz, 1H), 6.47 (s, 1H), 6.36 (d, J=15.0 Hz, 1H), 6.17 (d, J=11.1 Hz, 1H), 5.89 (d, J=15.5 Hz, 1H), 5.74 (m, 1H), 5.50 (m, 1H), 5.30 (m, 1H), 4.78-4.67 (2H), 3.71 (m, 1H), 3.58 (m, 1H), 2.50 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (4H), 1.54-1.49 (4H), 1.19 (s, 3H), 0.92 (s, 3H), 0.90 (s, 3H), 0.87 (s, 3H).

HRMS (ESI) calculated for $C_{34}H_{52}O_5Na$: m/z 563.3707 ([M+Na]⁺). found: m/z 563.3679 ([M+Na]⁺).

(6S,7S,9E,12R)-7-methyl-2-oxo-12-(propan-2-yl)-1-oxacyclododec-9-en-6-yl 3-[(1E,3E,5E,7S,8S,10S)-7,8,10-trihydroxy-5-methylundeca-1,3,5-trien-1-yl]benzoate (compound 22k)

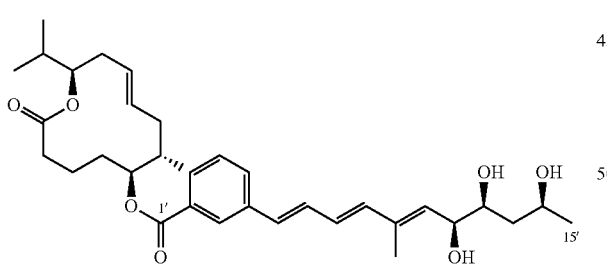

¹H NMR (Acetone-d6, 300 MHz) δ 8.09 (dd, J=7.2, 8.0 Hz, 1H), 7.91 (dd, J=7.8, 14.7 Hz, 1H), 7.74 (d, J=7.7 Hz, 1H), 7.47 (dd ap. t, J=7.7 Hz, 1H), 7.02 (d, J=16.6 Hz, 1H), 6.78 (m, 1H), 6.57-6.39 (2H including 6.51 (s, 1H)), 5.60 (m, 1H), 5.52 (m, 1H), 5.32 (m, 1H), 4.89 (m, 1H), 4.74 (m, 1H), 4.29 (m, 1H), 4.04 (m, 1H), 3.94 (m, 1H), 3.68 (m, 1H), 2.51 (m, 1H), 2.35 (m, 1H), 2.07-2.04 (5H), 1.95-1.92 (2H), 1.80-1.75 (4H), 1.70-1.62 (4H), 1.54-1.49 (2H), 1.11 (d, J=6.3 Hz, 3H), 0.96 (d, J=5.7 Hz, 3H), 0.92 (d, J=6.9 Hz, 3H), 0.90 (d, J=6.9 Hz, 3H).

HRMS (ESI) calculated for $C_{34}H_{48}O_7Na$: m/z 591.3292 ([M+Na]⁺). found: m/z 591.3285 ([M+Na]⁺).

(6S,7S,9E,12R)-7-methyl-2-oxo-12-(propan-2-yl)-1-oxacyclododec-9-en-6-yl(2E)-3-{3-[(1E,3E,5S,6S,8S)-5,6,8-trihydroxy-3-methylnona-1,3-dien-1-yl]phenyl}prop-2-enoate (compound 22l)

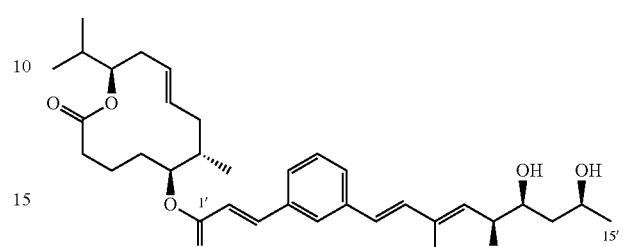

¹H NMR (Acetone-d6, 300 MHz) δ 7.88 (s, 1H), 7.70 (d, J=16.0 Hz, 1H), 7.56 (dd ap. t, J=7.3 Hz, 1H), 7.53 (d, J=7.3 Hz, 1H), 7.41 (d, J=7.3 Hz, 1H), 7.07 (d, J=16.3 Hz, 1H), 6.68 (d, J=16.3 Hz, 1H), 6.63 (d, J=16.0 Hz, 1H), 5.72 (d, J=8.9 Hz, 1H), 5.53 (m, 1H), 5.30 (m, 1H), 4.80-4.72 (2H), 4.32 (dd, J=6.3, 8.9 Hz, 1H), 4.06-3.94 (2H), 3.70 (ddd, J=3.6, 6.3, 9.7 Hz, 1H), 2.49 (m, 1H), 2.32 (m, 1H), 2.20-2.10 (2H), 2.06 (s, 3H), 2.00-1.90 (2H), 1.96-1.94 (4H), 1.80-1.69 (4H), 1.57-1.50 (2H), 1.12 (d, J=6.1 Hz, 3H), 0.93 (s, 3H), 0.90 (s, 3H), 0.88 (s, 3H).

HRMS (ESI) calculated for $C_{34}H_{48}O_7Na$: m/z 591.3292 ([M+Na]⁺). found: m/z 591.3289 ([M+Na]⁺).

(6S,7S,9E,12R)-7-methyl-2-oxo-12-(propan-2-yl)-1-oxacyclododec-9-en-6-yl(2E,4E)-4,6-dimethylhepta-2,4,6-trienoate (compound 22m)

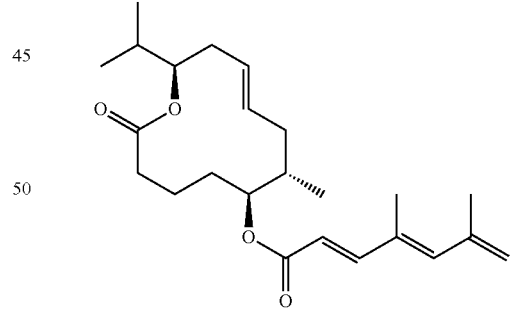

A (4'E)/(4'Z)=87:13 mixture could be detected by ¹H analysis.

¹H NMR (CDCl₃, 300 MHz) δ 7.93 (d, J=15.8 Hz, 1H, Z isomer), 7.33 (d, J=15.6 Hz, 1H, E isomer), 6.26 (s, 1H), 5.88 (d, J=15.6 Hz, 1H), 5.45 (m, 1H), 5.27 (m, 1H), 5.17 (s, 1H), 5.00 (s, 1H), 4.82-4.73 (2H), 2.48 (m, 1H), 2.29 (m, 1H), 2.16-2.00 (4H), 1.88-1.68 (6H), 1.96 (s, 3H), 1.93 (s, 3H), 0.93 (s, 3H), 0.91 (s, 3H), 0.89 (s, 3H).

HRMS (ESI) calculated for $C_{24}H_{36}O_4Na$: m/z 411.2505 ([M+Na]⁺). found: m/z 411.2497 ([M+Na]⁺).

(6S,7S,9E,12R)-7-methyl-2-oxo-12-(propan-2-yl)-1-oxacyclododec-9-en-6-yl(2E,4E,6E,8E,10E,12R,13S,15S)-12,13,15-trihydroxy-4,6,10-trimethylhexadeca-2,4,6,8,10-pentaenoate (compound 22n)

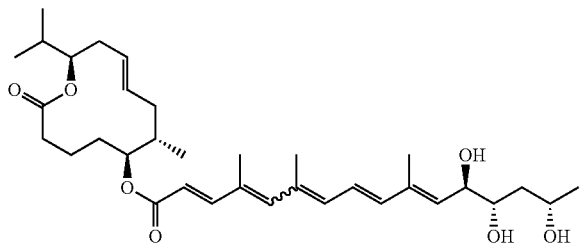 [SMILES: CC(=C/C=C/C(C)=C/[C@@H](O)[C@@H](O)C[C@H](C)O)C=C(C)/C=C/C(=O)O[C@H]1CCCC(=O)O[C@@H](C(C)C)C/C=C/C[C@@H]1C]

A (4'E)/(4'Z) 56:44 mixture could be detected by ¹H analysis.

¹H NMR (Acetone-d6, 400 MHz) δ 7.93 (d, J=15.6 Hz, 1H, Z isomer), 7.37 (d, J=15.5 Hz, 1H, E isomer), 6.63 (dd, J=11.1, 15.0 Hz, 1H), 6.47 (s, 1H), 6.36 (d, J=15.0 Hz, 1H), 6.17 (d, J=11.1 Hz, 1H), 5.89 (d, J=15.5 Hz, 1H), 5.68 (d, J=8.5 Hz, 1H), 5.50 (m, 1H), 5.30 (m, 1H), 4.78-4.67 (2H), 4.38 (m, 1H), 4.04 (m, 1H), 3.88 (m, 1H), 3.81 (m, 1H), 3.69 (m, 1H), 3.63 (m, 1H), 2.49 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (2H), 1.54-1.49 (2H), 1.13 (d, J=6.1 Hz, 3H), 0.92 (s, 3H), 0.90 (s, 3H), 0.87 (s, 3H).

HRMS (ESI) calculated for $C_{34}H_{52}O_7Na$: m/z 595.3605 ([M+Na]⁺). found: m/z 595.3600 ([M+Na]⁺).

(6S,7S,9E,12R)-7-methyl-2-oxo-12-(propan-2-yl)-1-oxacyclododec-9-en-6-yl(2E,4E,6E,8E,10E,12S,13R,15S)-12,13,15-trihydroxy-4,6,10-trimethylhexadeca-2,4,6,8,10-pentaenoate (compound 22o)

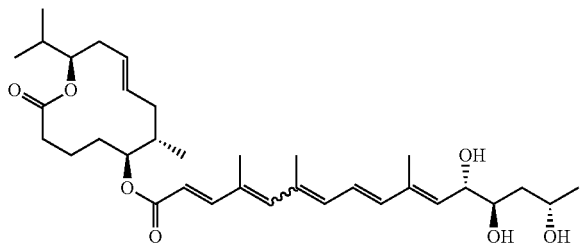 [SMILES: CC(=C/C=C/C(C)=C/[C@H](O)[C@H](O)C[C@H](C)O)C=C(C)/C=C/C(=O)O[C@H]1CCCC(=O)O[C@@H](C(C)C)C/C=C/C[C@@H]1C]

A (4'E)/(4'Z)=65:35 mixture could be detected by ¹H analysis.

¹H NMR (Acetone-d6, 400 MHz) δ 7.92 (d, J=15.6 Hz, 1H, Z isomer), 7.37 (d, J=15.5 Hz, 1H, E isomer), 6.63 (dd, J=11.1, 15.0 Hz, 1H), 6.47 (s, 1H), 6.36 (d, J=15.0 Hz, 1H), 6.17 (d, J=11.1 Hz, 1H), 5.89 (d, J=15.5 Hz, 1H), 5.66 (m, 1H), 5.50 (m, 1H), 5.30 (m, 1H), 4.78-4.66 (2H), 4.37 (m, 1H), 4.18 (s, 1H), 4.09 (s, 1H), 3.99 (m, 1H), 3.85 (s, 1H), 3.80 (m, 1H), 2.50 (m, 1H), 2.32 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (2H), 1.54-1.49 (2H), 1.13 (d, J 6.1 Hz, 3H), 0.92 (s, 3H), 0.90 (s, 3H), 0.87 (s, 3H).

HRMS (ESI) calculated for $C_{34}H_{52}O_7Na$: m/z 595.3605 ([M+Na]⁺). found: m/z 595.3618 ([M+Na]+).

(2E,8E,10E,12S,13S)-((6S,7S,12R,E)-12-((2S,6R,7R,9R,E)-7,9-dihydroxy-4,6-dimethyldec-4-en-2-yl)-7-methyl-2-oxooxacyclododec-9-en-6-yl) 12,13-dihydroxy-4,6,10-trimethylhexadeca-2,4,6,8,10-pentaenoate (Compound 20e)

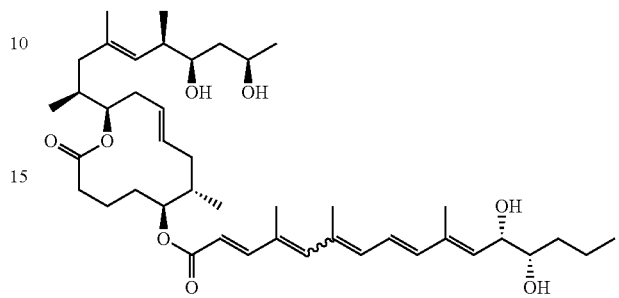

A (4'E)/(4'Z)=43:57 mixture could be detected by ¹H analysis.

¹H NMR (Acetone-d6, 400 MHz, 4'E isomer) δ 7.90 (d, J=15.5 Hz, 1H, Z isomer), 7.34 (d, J=15.6 Hz, 1H), 6.64 (dd, J=10.8, 14.7 Hz, 1H), 6.47 (s, 1H), 6.38 (d, J=10.8 Hz, 1H), 5.87 (d, J 15.6 Hz, 1H), 5.61 (m, 1H), 5.45 (m, 1H), 5.22 (m, 1H), 5.20 (m, 1H), 5.06 (d, J=9.4 Hz, 1H), 4.84 (m, 1H), 4.22 (m, 1H), 3.90 (m, 1H), 3.60 (m, 1H), 3.51 (m, 1H), 3.42-3.38 (3H), 2.42 (m, 1H), 2.40 (m, 1H), 2.30 (m, 1H), 2.12 (m, 1H), 2.10 (1H), 2.02 (s, 3H), 1.96 (m, 1H), 1.95 (m, 1H), 1.92-1.84 (8H), 1.80 (m, 1H), 1.77 (m, 1H), 1.75-1.70 (4H), 1.65 (m, 1H), 1.62-1.56 (4H), 1.52-1.48 (2H), 1.48-1.42 (2H), 1.26 (m, 1H), 1.25 (d, J=6.2 Hz, 3H), 1.00-0.96 (6H), 0.88-0.83 (6H).

HRMS (ESI) calculated for $C_{43}H_{68}O_8Na$: m/z 735.4806 ([M+Na]⁺). found: m/z 735.4799 ([M+Na]⁺).

(6S,7S,12R)-7-methyl-2-oxo-12-(propan-2-yl)-1-oxacyclododecan-6-yl(2E,4E,6E,8E,10E,12S,13S,15S)-12,13,15-trihydroxy-4,6,10-trimethylhexadeca-2,4,6,8,10-pentaenoate (compound C-004)

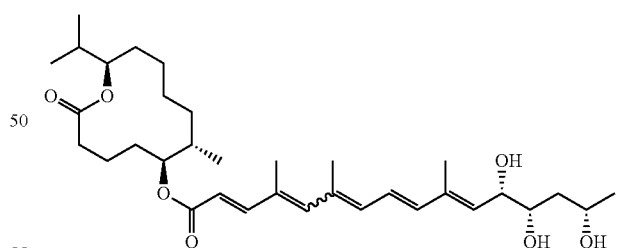

A (4'E)/(4'Z)=74:26 mixture could be detected by ¹H analysis.

¹H NMR (Acetone-d6, 300 MHz) δ 7.93 (d, J=15.6 Hz, 1H, Z isomer), 7.37 (d, J=15.5 Hz, 1H, E isomer), 6.63 (dd, J=11.1, 15.0 Hz, 1H), 6.47 (s, 1H), 6.36 (d, J=15.0 Hz, 1H), 6.17 (d, J=11.1 Hz, 1H), 5.89 (d, J 15.5 Hz, 1H), 5.59 (d, J=8.8 Hz, 1H), 4.74-4.60 (2H), 4.28-4.25 (2H), 4.07-3.94 (3H), 3.66 (m, 1H), 2.59 (m, 1H), 2.12-2.08 (2H), 2.06 (s, 3H), 1.97 (s, 3H), 1.95-1.92 (2H), 1.90 (s, 3H), 1.80-1.75 (4H), 1.70-1.62 (4H), 1.54-1.49 (4H), 1.13 (d, J=6.1 Hz, 3H), 0.92 (s, 3H), 0.90 (s, 3H), 0.87 (s, 3H).

HRMS (ESI) calculated for $C_{34}H_{54}O_7Na$: m/z 597.3762 ([M+Na]+). found: m/z 597.3750 ([M+Na]+).

Cyclohexyl(2E,4E,6E,8E,10E,12S,13S,15S)-12,13,15-trihydroxy-4,6,10-trimethylhexadeca-2,4,6,8,10-pentaenoate (compound C-002)

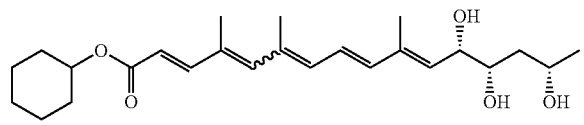 [SMILES: CC(=C/C=C/C(C)=C/[C@H](O)[C@@H](O)C[C@H](C)O)C=C(C)/C=C/C(=O)OC1CCCCC1]

A (4'E)/(4'Z)=60:40 mixture could be detected by $^1H$ analysis.

$^1$H NMR (Acetone-d6, 300 MHz) δ 7.93 (d, J=15.9 Hz, 1H, Z isomer), 7.34 (d, J=15.6 Hz, 1H, E isomer), 6.63 (dd, J=11.1, 14.5 Hz, 1H), 6.46 (s, 1H), 6.38 (d, J=14.5 Hz, 1H), 6.16 (d, J=11.1 Hz, 1H), 5.92 (d, J=15.6 Hz, 1H), 5.60 (d, J=9.1 Hz, 1H), 4.77 (m, 1H), 4.30-4.20 (2H), 4.02-3.91 (2H), 3.69-3.58 (2H), 2.04 (s, 3H), 1.97 (s, 3H), 1.90 (s, 3H), 1.87-1.68 (6H), 1.54-1.34 (6H), 1.13 (d, J=6.2 Hz, 3H).

HRMS (ESI) calculated for $C_{25}H_{38}O_5Na$: m/z 441.2611 ([M+Na]+). found: m/z 441.2609 ([M+Na]+).

(2E,4E,6E,8E,10E,12S,13S,15S)-Isopropyl 12,13,15-tris(tert-butyldimethylsilyloxy)-4,6,10-trimethyl-hexadeca-2,4,6,8,10-pentaenoate (SI26)

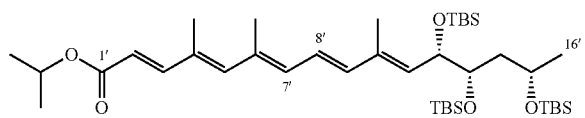 [SMILES: CC(=C\C=C\C(C)=C\[C@H](O[Si](C)(C)C(C)(C)C)[C@H](C[C@H](C)O[Si](C)(C)C(C)(C)C)O[Si](C)(C)C(C)(C)C)/C=C(C)/C=C/C(=O)OC(C)C]

To a solution of 19 (23 mg, 0.034 mmol) in benzene (0.2 mL) were added diisopropylethylamine (21 μL, 0.11 mmol, 4 eq.), 2,4,6-trichlorobenzoyl chloride (10 μL, 0.06 mmol, 2 eq.), and DMAP (18 mg). The reaction mixture was stirred at room temperature for 15 min and isopropanol (25 μL) was added. After being stirred at room temperature for 14 h, an aqueous saturated solution of sodium hydrogenocarbonate was added to the reaction mixture. The aqueous layer was extracted three times with benzene. The combined organic layers were washed with brine, dried over MgSO4, filtered and concentrated under reduced pressure. The crude product was purified on preparative TLC (eluting with benzene/heptane 60:40) to give SI26 (18 mg, 0.025 mmol, 74%) as a yellow oil. A (4'E)/(4'Z)=86:14 mixture could be detected by $^1H$ analysis.

$^1$H NMR (CDCl3, 300 MHz, 4'E isomer) δ 7.35 (d, J=15.5 Hz, 1H), 6.50 (dd, J=14.9, 10.9 Hz, 1H), 6.36 (d, J=14.9 Hz, 1H), 6.34 (s, 1H), 6.27 (d, J=10.9 Hz, 1H), 5.84 (d, J=15.5 Hz, 1H), 5.58 (d, J=9.0 Hz, 1H), 5.10 (td, J=12.5, 6.3 Hz, 1H), 4.43 (dd, J=9.0, 3.6 Hz, 1H), 3.91 (m, 1H), 3.64 (td, J=7.9, 4.0 Hz, 1H), 2.05 (s, 3H), 2.02 (s, 3H), 1.85 (s, 3H), 1.60 (m, 2H), 1.29 (s, 3H), 1.27 (s, 3H), 1.14 (d, J=5.9 Hz, 3H), 0.88 (s, 9H), 0.87 (s, 9H), 0.86 (s, 9H), 0.05 (s, 9H), 0.04 (s, 3H), 0.02 (s, 3H), −0.03 (s, 3H).

$^{13}$C NMR (CDCl3, 75 MHz, 4'E isomer) δ 167.1, 150.5, 143.5, 142.7, 141.2, 139.7, 135.0, 134.6, 134.2, 132.2, 123.7, 116.7, 73.7, 71.4, 67.3, 66.1, 42.7, 25.9 (3×C), 25.8 (6×C), 23.5, 21.9, 18.2, 18.1, 17.9, 17.1, 14.2, 13.5, −4.1 (2×C), −4.3, −4.5, −4.6, −4.7.

HRMS (ESI) calculated for $C_{40}H_{76}O_5Si_3Na$: m/z 743.4893[M+Na]+). found: m/z 743.4886 ([M+Na]+).

(2E,4E,6E,8E,10E,12S,13S,15S)-isopropyl 12,13,15-trihydroxy-4,6,10-trimethylhexadeca-2,4,6,8,10-pentaenoate (23)

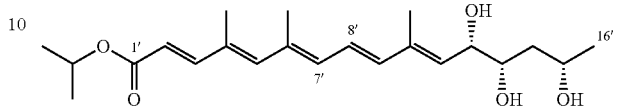

To a solution of SI26 (18 mg, 0.025 mmol) in THF (0.13 mL) was added TBAF (225 μL, 0.225 mmol, 9 eq.). The solution was stirred at room temperature for 12 h. CaCO3 (45 mg), Dowex 50WX8-400 (140 mg) and MeOH (0.3 mL) were added and the reaction mixture was stirred for 1 h. After being filtered and concentrated under reduced pressure, the crude product was purified by preparative TLC (CH2Cl2/MeOH 90:10) to give 23 (9 mg, 96%). A (4'E)/(4'Z)=80:20 mixture could be detected by $^1H$ analysis.

$^1$H NMR (CDCl3, 300 MHz) δ 7.34 (d, J=15.5 Hz, 1H), 6.57 (dd, J=15.1, 11.1 Hz, 1H), 6.34 (s, 1H), 6.33 (d, J=15.1 Hz, 1H), 6.22 (d, J=10.0 Hz, 1H), 5.85 (d, J=15.5 Hz, 1H), 5.50 (d, J=9.3 Hz, 1H), 5.09 (td, J=12.5, 6.3 Hz, 1H), 4.29 (m, 1H), 4.05 (m, 1H), 3.74 (m, 1H), 3.59 (s, 1H, —OH), 2.99 (s, 1H, —OH), 2.37 (s, 1H, —OH), 2.04 (s, 3H), 2.01 (s, 3H), 1.91 (s, 3H), 1.54-1.52 (2H), 1.29 (s, 3H), 1.27 (s, 3H), 1.20 (d, J=6.1 Hz, 3H).

$^{13}$C NMR (CDCl3, 75 MHz) δ 167.0, 150.3, 143.1, 138.5, 138.2, 135.2, 134.3, 133.5, 130.9, 125.2, 117.1, 75.8, 72.1, 68.6, 67.4, 40.4, 24.2, 21.9 (2×C), 17.2, 14.2, 13.4.

HRMS-ESI calculated for $C_{22}H_{34}NaO_5$: m/z 401.2298 ([M+Na]+). found: m/z 401.2285 ([M+Na]+).

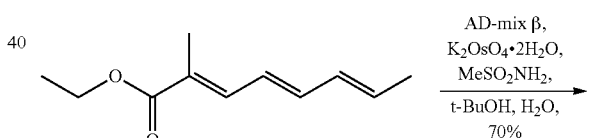

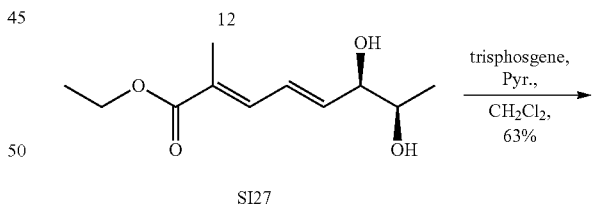

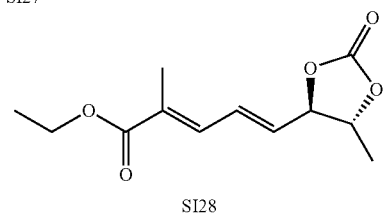

(2E,4E,6R,7R)-Ethyl 6,7-dihydroxy-2-methylocta-2,4-dienoate (SI27)

To a solution of AD-mix β (7.77 g) in a mixture of t-BuOH and water (27.5:27.5 mL) were added methanesulfonamide (520 mg, 5.5 mmol, 1 eq.) and potassium osmiate dehydrate (12 mg, 0.03 mmol, 0.6%). The reaction mixture was stirred at room temperature until both phases were clear, and then cooled at 0° C. whereupon the inorganic salts partially precipitate. 12 (1 g, 5.5 mmol) was then added and the reaction mixture was stirred at 0° C. for 15 h. Sodium sulfite (8.2 g) was then added at 0° C. The reaction mixture was stirred at room temperature for 15 min and the water phase was extracted 3 times with ethyl acetate. The combined organic layers were washed with an aqueous solution of potassium hydroxide (2N), with brine and dried over magnesium sulfate. After being filtered and concentrated under reduced pressure, the crude product was purified by flash chromatography (cyclohexane/ethyl acetate 8:2) to give SI27 (800 mg, 3.73 mmol, 70%) as a yellow oil.

$^1$H NMR (CDCl$_3$, 300 MHz) δ 7.17 (d, J=11.5 Hz, 1H), 6.65 (ddd, J=1.2, 11.4, 15.2 Hz, 1H), 6.03 (dd, J=6.31, 15.2 Hz, 1H), 4.21 (q, J=7.1 Hz, 2H), 4.00 (dd ap. t, J=6.3 Hz, 1H), 3.69 (dq ap. p, J=6.3 Hz, 1H), 1.96 (d, J=1.2 Hz, 3H), 1.30 (s, t, J=7.1 Hz, 3H), 1.21 (d, J=6.3 Hz, 3H).

$^{13}$C NMR (CDCl$_3$, 75 MHz) δ 168.3, 139.2, 138.2, 128.2, 127.4, 76.9, 70.7, 60.7, 19.0, 14.2, 12.7.

$[α]^{20}_D$=+8.8 (c 1, CHCl$_3$)

(2E,4E)-Ethyl 2-methyl-5-((4R,5R)-5-methyl-2-oxo-1,3-dioxolan-4-yl)penta-2,4-dienoate (SI28)

To a solution of SI27 (860 mg, 4.0 mmol) and pyridine (1.4 mL) in dichloromethane (4.7 mL) at 0° C. was added slowly a solution of triphosgene (712 mg, 2.4 mmol, 0.6 eq., 1.7 M in dichloromethane). After being stirred at 0° C. for 3 h the reaction mixture was hydrolyzed at 0° C. with a saturated aqueous solution of ammonium chloride. The water layer was extracted three times with diethyl ether and the combined organic layers were washed with an aqueous saturated solution of sodium bicarbonate, with brine, dried over magnesium sulfate. After being filtered and concentrated under reduced pressure, the crude product was purified by Flash chromatography on silica gel (elution: cyclohexane/ethyl acetate 20:1) to give SI28 (375 mg, 2.5 mmol, 63%).

$^1$H NMR (CDCl$_3$, 300 MHz) δ 7.15 (d, J=11.4 Hz, 1H), 6.71 (ddd, J=11.4, 15.1 Hz, 1H), 5.96 (dd, J=7.4, 15.1 Hz, 1H), 4.72 (dd ap. t, J=7.4 Hz, 1H), 4.46 (m, 1H), 4.23 (q, J=7.1 Hz, 2H), 1.99 (d, J=1.1 Hz, 3H), 1.51 (d, J=6.2 Hz, 3H), 1.31 (t, J=7.1 Hz, 3H).

$^{13}$C NMR (CDCl$_3$, 75 MHz) δ 167.7, 153.9, 134.8, 131.4, 131.1, 130.9, 83.4, 78.4, 60.9, 18.1, 14.2, 12.9.

$[α]^{20}_D$=+45.4 (c 2, CHCl$_3$)

HRMS (ESI) calculated for C$_{12}$H$_{16}$O$_5$Na: m/z 263.0889 ([M+Na]$^+$). found: m/z 263.0886 ([M+Na]$^+$).

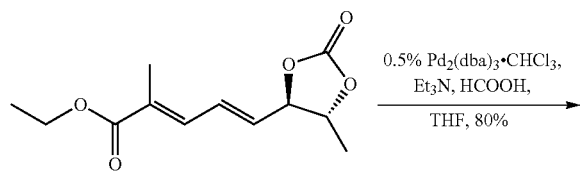

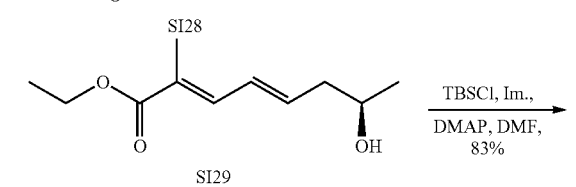

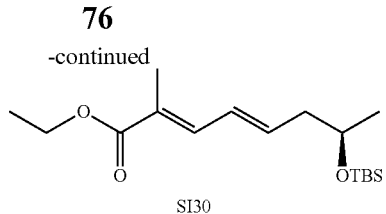

(7R,2E,4E)-Ethyl 7-hydroxy-2-methylocta-2,4-dienoate (SI29) To a solution of SI28 (560 mg, 2.33 mmol) in THF (5.1 mL) were added Pd$_2$(dba)$_3$.CHCl$_3$ (11 mg, 0.012 mmol, 0.5%), triethylamine (0.78 mL, 2 eq.) and formic acid (223 μL, 2 eq.). The reaction mixture was stirred at room temperature for 96 h. After being diluted with diethyl ether, water was added, and the aqueous layer was extracted. The organic layer was washed with an aqueous saturated solution of sodium carbonate, with brine, dried over magnesium sulfate, filtered and concentrated under reduced pressure. The reaction mixture was purified by flash chromatography on silica gel (heptane/ethyl acetate 90:10) to give SI29 (370 mg, 1.87 mmol, 80%) as a colorless oil.

$^1$H NMR (CDCl$_3$, 300 MHz) δ 7.17 (d, J=11.3 Hz, 1H), 6.44 (dd, J=11.3 Hz, 15.0 Hz, 1H), 6.07 (td, J=7.5, 15.0 Hz, 1H), 4.20 (q, J=7.1 Hz, 2H), 3.92 (dq ap. dd, J=6.2, 12.2 Hz, 1H), 2.36-2.31 (2H), 1.93 (d, J=0.9 Hz, 3H), 1.30 (t, J=7.1 Hz, 3H), 1.23 (d, J=6.2 Hz, 3H).

$^{13}$C NMR (CDCl$_3$, 75 MHz) δ 168.5, 137.9, 137.8, 128.9, 126.2, 67.2, 60.5, 43.0, 23.0, 14.3, 12.6.

$[α]^{20}_D$=−8.6 (c 0.8, CHCl$_3$)

R,2E,4E)-Ethyl 7-(tert-butyldimethylsilyloxy)-2-methylocta-2,4-dienoate (SI30

To a solution of SI29 (370 mg, 1.87 mmol) in DMF (14 mL) were added TBSCl (825 mg. 5.48 mmol, 2.9 eq.), imidazole (371 mg, 5.45 mmol, 2.9 eq.) and DMAP (66 mg, 0.55 mmol, 0.3 eq.). The reaction mixture was stirred at room temperature for 24 h, and was hydrolyzed. The aqueous phase was extracted three times with a mixture of cyclohexane/dichloromethane 9:1. The combined organic layers were washed with brine, dried over MgSO$_4$, filtered and concentrated. The residue was purified by flash chromatography on silica gel (eluant: cyclohexane/ethyl acetate 95:5) to afford SI30 (484 mg, 1.55 mmol, 83%) as a yellow oil.

$^1$H NMR (CDCl$_3$, 300 MHz) δ 7.15 (d, J=11.4 Hz, 1H), 6.35 (dd, J=11.3, 15.1 Hz, 1H), 6.06 (td, J=7.4, 15.1 Hz, 1H), 4.20 (q, J=7.1 Hz, 2H), 3.88 (qd ap. dd, J=6.4, 12.0 Hz, 1H), 2.31 (dd ap. t, J=6.4 Hz, 2H), 1.92 (d, J=0.9 Hz, 3H), 1.30 (t, J=7.1 Hz, 3H), 1.14 (d, J=6.4 Hz, 3H), 0.87 (s, 9H), 0.04 (s, 3H), 0.03 (s, 3H).

$^{13}$C NMR (CDCl$_3$, 75 MHz) δ 168.6, 139.2, 138.2, 128.0, 125.4, 68.1, 60.4, 43.5, 25.8 (3×C), 23.6, 18.1, 14.3, 12.5, −4.5, −4.7.

$[α]^{20}_D$=+3.8 (c 1.7, CHCl$_3$)

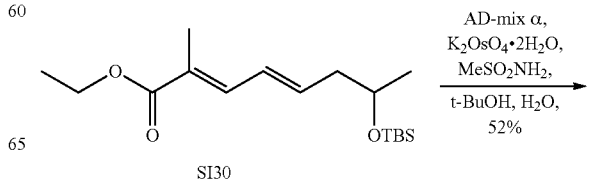

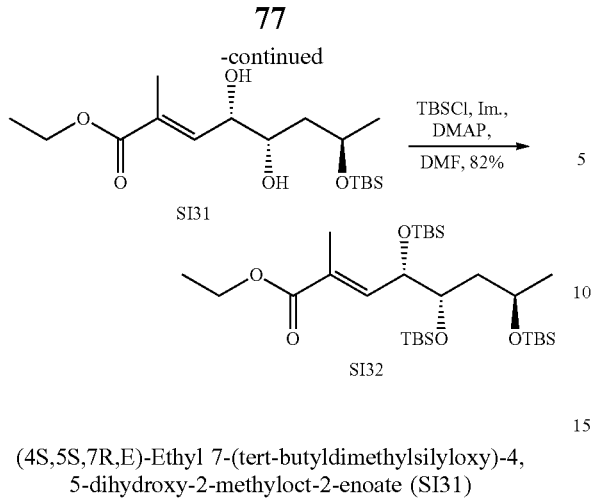

(4S,5S,7R,E)-Ethyl 7-(tert-butyldimethylsilyloxy)-4,5-dihydroxy-2-methyloct-2-enoate (SI31)

To a solution of AD-mix α (9 g) in a mixture of t-BuOH and water (54:54 mL) were added methanesulfonamide (520 mg, 5.45 mmol, 0.85 eq.) and potassium osmiate dihydrate (45 mg, 0.12 mmol, 1.9%). The reaction mixture was stirred at room temperature until both phases were clear, and then cooled at 0° C. whereupon the inorganic salts partially precipitate. SI31 (2 g, 6.4 mmol) was then added and the reaction mixture was stirred at 0° C. for 15 h. Sodium sulfite (3 g) was then added at 0° C. The reaction mixture was stirred at room temperature for 15 min and the water phase was extracted 3 times with ethyl acetate. The combined organic layers were washed with an aqueous solution of potassium hydroxide (2N), with brine, dried over magnesium sulfate. After being filtered and concentrated under reduce pressure, the crude product was purified by flash chromatography (cyclohexane/ethyl acetate 8:2) to give SI31 (1.64 g, 4.7 mmol, 73%) as a yellow oil.

$^1$H NMR (CDCl$_3$, 300 MHz) δ 6.66 (qd, J=1.5, 8.7 Hz, 1H), 4.21 (q, J=7.2 Hz, 2H), 4.19 (m, 1H), 4.12 (m, 1H), 3.94 (tq, J=2.6, 6.2 Hz, 1H), 1.92 (d, 0.1-1.5 Hz, 3H), 1.62-1.51 (2H), 1.29 (t, J=7.2 Hz, 3H), 1.24 (d, J=6.2 Hz, 3H), 0.90 (s, 9H), 0.13 (s, 3H), 0.12 (s, 3H).

$^{13}$C NMR (CDCl$_3$, 75 MHz) δ 165.2, 141.9, 130.9, 73.0, 72.5, 66.7, 61.9, 43.6, 26.4 (3×C), 26.1, 17.8 14.6, 13.4, −4.2, −4.7.

HRMS-ESI calculated for C$_{17}$H$_{34}$O$_5$SiNa: m/z 369.2071 ([M+Na]$^+$). found: m/z 369.2067 ([M+Na]$^+$).

[α]$^{20}$D=−14.4 (c 1.3, CHCl$_3$)

(4S,5S,7R,E)-Ethyl 4,5,7-tris(tert-butyldimethylsilyloxy)-2-methyloct-2-enoate (SI32)

To a solution of SI31 (190 mg, 0.55 mmol) in DMF (4.2 mL) were added tert-butyldimethylsilyl chloride (516 mg, 3.42 mmol, 6.2 eq.), imidazole (163 mg, 2.40 mmol, 4.4 eq.) and DMAP (17 mg, 0.14 mmol, 0.25 eq.). The reaction mixture was stirred at room temperature for 24 h, and then hydrolysed. The aqueous layer was extracted 3 times with a cyclohexane/dichloromethane mixture (9:1). The combined organic layers were washed with brine, dried over magnesium sulfate, filtered and concentrated under reduced pressure. The crude product was purified by chromatography on silica gel (elution with cyclohexane/ethyl acetate 20:1) to give SI32 as a colorless oil (259 mg, 0.45 mmol, 82%).

$^1$H NMR (MeOD, 300 MHz) δ 6.73 (dd, J=1.3, 8.9 Hz, 1H), 4.49 (dd, J=3.4, 8.9 Hz, 1H), 4.21 (q, J=7.1 Hz, 2H), 4.11 (dd, J=6.2, 12.7 Hz, 1H), 3.91 (m, 1H), 1.88 (d, J=1.3 Hz, 3H), 1.50-1.41 (2H), 1.30 (t, J=7.1 Hz, 3H), 1.21 (d, J=6.2 Hz, 3H), 0.90 (27H), 0.09 (18H).

$^{13}$C NMR (MeOD, 75 MHz) δ 160.2, 142.5, 129.8, 75.0, 74.2, 67.1, 62.0, 45.3, 26.6 (3×C), 26.5 (3×C), 26.4 (3×C), 25.1, 19.1 (3×C), 14.6, 14.1, −3.3, −3.7, −3.8, −3.9, −4.1, −4.4.

HRMS-ESI calculated for C$_{29}$H$_{62}$NaO$_5$Si$_3$: m/z 597.3797 ([M+Na]$^+$). found: m/z 597.3791 ([M+Na]$^+$).

[α]$^{20}$D=−22.4 (c 0.6, CHCl$_3$)

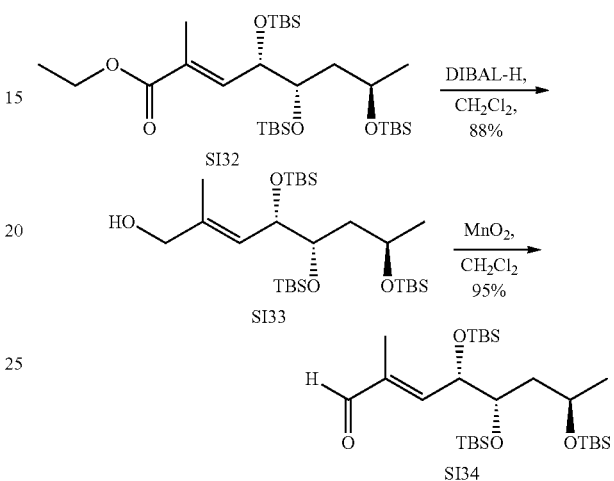

(4S,5S,7R,E)-4,5,7-tris(tert-Butyldimethylsilyloxy)-2-methyloct-2-en-1-ol (SI33)

To a solution of SI33 (385 mg, 0.67 mmol) in dichloromethane (4 mL) was added DIBAL-H (1 mL, 1.5 M in toluene, 2.2 eq.). The reaction mixture was stirred at 0° C. for 1 h and a saturated aqueous solution of Rochelle salts was added. After being stirred for 12 h, the aqueous layer was extracted three times with diethyl ether. The combined organic layers were washed with brine, dried over magnesium sulfate, filtered and concentrated under reduced pressure. The crude product is purified by Flash chromatography eluting with cyclohexane/ethyl acetate 15:1) to give SI33 as a colorless oil (315 mg, 0.59 mmol, 88%).

$^1$H NMR (CDCl$_3$, 300 MHz) δ 5.44 (dd, J=1.1, 9.0 Hz, 1H), 4.36 (dd, J=3.6, 9.0 Hz, 1H), 4.02 (s, 2H), 4.06 (m, 1H), 3.80 (ddd, J=3.6, 5.7, 6.8 Hz, 1H), 1.89 (ddd ap. td, J=6.3, 13.4 Hz, 1H), 1.70 (d, J=1.1 Hz, 3H), 1.41 (m, 1H), 1.18 (d, J=6.1 Hz, 3H), 0.89-0.86 (27H), 0.08-0.01 (18H).

$^{13}$C NMR (CDCl$_3$, 75 MHz) δ 136.9, 125.3, 73.6, 72.2, 68.8, 65.9, 43.4, 26.0 (3×C), 25.9 (3×C), 25.8 (3×C), 24.6, 18.2, 18.1, 18.0, 14.7, −3.8, −4.0, 4.2, −4.3, −4.5, −4.7.

[α]$^{20}$D=−11.7 (c 0.7, CHCl$_3$)

E-(4S,5S,7R)-4,5,7-tris(tert-Butyldimethylsilyloxy)-2-methyloct-2-enal (SI34)

To a solution of SI33 (278 mg, 0.52 mmol) in dichloromethane (4 mL) was added MnO$_2$ (1.03 g, 11.8 mmol, 20 eq.). The reaction mixture was heated under reflux for 24 h before being filtered on a bed of Celite. After being concentrated under reduced pressure, SI34 was obtained as a colorless oil (267 mg, 0.50 mmol, 96%).

$^1$H NMR (CDCl$_3$, 300 MHz) δ 9.45 (s, 1H), 6.42 (dd, J=1.3, 8.3 Hz, 1H), 4.58 (dd, J=3.7, 8.3 Hz, 1H), 4.05 (m,

1H), 3.92 (m, 1H), 1.90 (m, 1H), 1.81 (d, J=1.3 Hz, 3H), 1.42 (m, 1H), 1.19 (d, J=6.1 Hz, 3H), 0.89 (s, 18H), 0.86 (s, 9H), 0.09 (18H).
$^{13}$C NMR (CDCl$_3$, 75 MHz) δ 195.4, 152.7, 123.0, 73.7, 72.7, 65.7, 43.5, 25.9 (3×C), 25.8 (3×C), 25.7 (3×C), 24.7, 17.9 (3×C), 10.3, −3.6, −3.9, −4.2, −4.5, −4.6, −4.8.

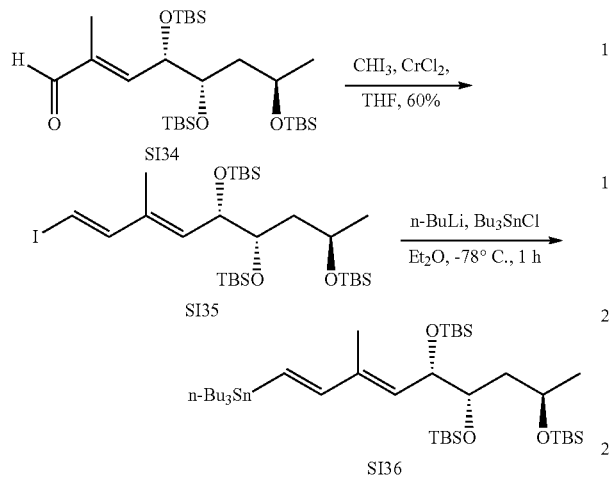

(1E,3E)-(5S,6S,810-tris-(tert-Butyldimethylsilyloxy)-1-iodo-3-methyl-nona-1,3-diene (SI35)

To a suspension of CrCl$_2$ (2.00 g, 16.28 mmol, 8 eq.) in THF (18 mL) was added dropwise a solution of SI34 (1.45 g, 2.73 mmol) and CHI$_3$ (3.2 g, 8.1 mmol, 3 eq.) in THF (12 mL). The reaction mixture was stirred at room temperature for 12 h before being diluted with diethyl ether and water. The aqueous phase was extracted three times, and the combined organic phases were washed with water and brine. After being dried over magnesium sulfate, filtered and concentrated under reduced pressure, the crude product was purified by Flash chromatography (eluting with cyclohexane/toluene 100:1) to give SI35 (1.08 g, 1.65 mmol, 60%) as a colorless oil.

$^1$H NMR (C$_6$D$_6$, 300 MHz) δ 7.07 (d, J=14.7 Hz, 1H), 6.02 (d, J=14.7 Hz, 1H), 5.51 (d, J=9.0 Hz, 1H), 4.50 (dd, J=3.6, 9.0 Hz, 1H), 4.18 (td, J=6.1, 7.5 Hz, 1H), 4.00 (m, 1H), 2.10 (ddd, J=4.5, 7.5, 13.7 Hz, 1H), 1.59 (d, J=0.8 Hz, 3H), 1.58 (m, 1H), 1.23 (d, J=6.1 Hz, 3H), 1.02 (s, 9H), 0.97 (s, 9H), 0.93 (s, 9H), 0.16 (s, 3H), 0.15 (s, 3H), 0.14 (s, 3H), 0.12 (s, 3H), 0.11 (s, 3H), 0.09 (s, 3H).
$^{13}$C NMR (C$_6$D$_6$, 75 MHz) δ 149.5, 135.7, 133.6, 76.4, 74.2, 72.7, 66.3, 43.9, 26.3 (3×C), 26.1 (3×C), 26.0 (3×C), 25.1, 18.4, 18.3, 18.2, 13.1, −3.3, −3.8, −3.9, −4.2 (2×C), −4.6.
HRMS-ESI calculated for C$_{28}$H$_{59}$INaO$_3$Si$_3$: m/z 677.2709 ([M+Na]$^+$). found: m/z 677.2702 ([M+Na]$^+$).
[α]$^{20}_D$=−30.3 (c 1.1, CHCl$_3$)

(5S,6S,8R)-6-[(tert-Butyldimethylsilyl)oxy]-2,2,3,3,8,10,10,11,11-nonamethyl-5-[(1E,3E)-2-methyl-4-(tributylstannyl)buta-1,3-dien-1-yl]-4,9-dioxa-3,10-disiladodecane (SI36)

To a solution of SI35 (350 mg, 0.53 mmol) in Et$_2$O (2.75 mL) at −78° C. was added n-BuLi (525 µL, 1.6 M in hexane, 0.84 mmol, 1.6 eq.) and the reaction mixture was stirred for 20 min. Bu$_3$SnCl (300 µL, 1.1 mmol, 2 eq.) was then added to the solution and the reaction mixture was allowed to warm to room temperature for 1 h. The reaction mixture was hydrolyzed with a saturated aqueous NaHCO$_3$ solution. The aqueous phase was extracted twice with Et$_2$O. The combined organic phases were washed with brine, dried over MgSO$_4$, filtered and concentrated under reduced pressure. The crude material SI36 was used without further purification.

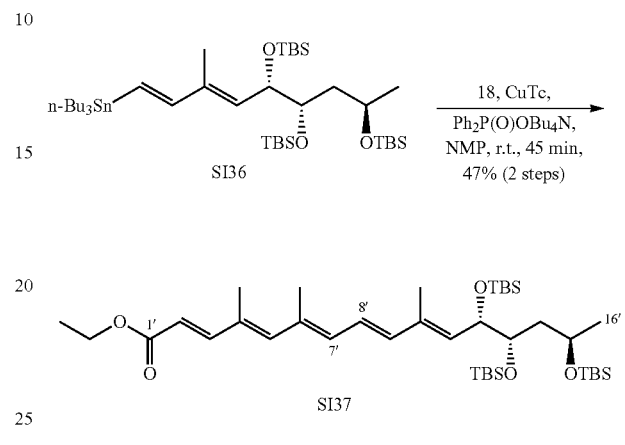

(2E,4E,6E,8E,10E)-(12S,13S,15R)-Ethyl-12,13,15-tris(tert-butyldimethylsilyloxy)-4,6,10-trimethyl-hexadeca-2,4,6,8,10-pentaenoate (SI37)

To a solution of SI36 and tetrabutylammonium diphenylphosphate (457 mg, 0.99 mmol) in NMP (3 mL) was added 0.2 mL of a stock solution of 18 in NMP (335 mg, 1.1 mmol, in 2 mL). After the addition of CuTC (204 mg, 1.07 mmol, 2 eq.), the remaining solution of 18 (1.8 mL) was added dropwise over 5 min. The reaction mixture was stirred at room temperature for 40 min, and then diluted with Et$_2$O. The mixture was filtered through a pad of neutral alumina with washing. The filtrate was then washed with water, with brine, dried over MgSO$_4$, filtered, and concentrated. The crude product was purified by preparative TLC eluting with heptane/ethyl acetate 90:10 to give SI37 (190 mg, 0.25 mmol, 47% over 2 steps) as a yellow oil. A (4'E)/(4'Z)=95:5 mixture could be detected by $^1$H analysis.

$^1$H NMR (CDCl$_3$, 300 MHz, 4'E isomer) δ7.37 (d, J 15.5 Hz, 1H), 6.50 (dd, J=10.9, 15.0 Hz, 1H), 6.36 (d, J=15.0 Hz, 1H), 6.35 (s, 1H), 6.26 (d, J=10.9 Hz, 1H), 5.86 (d, J=15.5 Hz, 1H), 5.55 (d, J=8.9 Hz, 1H), 4.46 (dd, J=3.5, 9.0 Hz, 1H), 4.22 (q, J=7.1 Hz, 2H), 4.05 (m, 1H), 3.82 (m, 1H), 2.05 (s, 3H), 2.02 (s, 3H), 1.92 (m, 1H), 1.85 (s, 3H), 1.42 (m, 1H), 1.31 (t, J=7.1 Hz, 3H), 1.18 (d, J=6.0 Hz, 3H), 0.89 (s, 9H), 0.87 (s, 18H), 0.08 (s, 12H), 0.03 (s, 3H), −0.02 (s, 3H).
$^{13}$C NMR (CDCl$_3$, 75 MHz, 4'E isomer) δ 167.5, 150.7, 143.7, 139.7, 135.1, 134.6, 134.1, 134.0, 132.2, 123.7, 116.2, 74.0, 72.9, 65.9, 60.2, 43.7, 26.0 (3×C), 25.9 (3×C), 25.8 (3×C), 24.6, 18.2, 18.1, 18.0, 17.1, 14.4, 14.2, 13.6, −3.7, −4.0, −4.2, −4.3, −4.4, −4.7.
HRMS-ESI calculated for C$_{39}$H$_{74}$NaO$_5$Si$_3$: m/z 729.4736 ([M+Na]$^+$). found: m/z 729.4725 ([M+Na]$^+$).

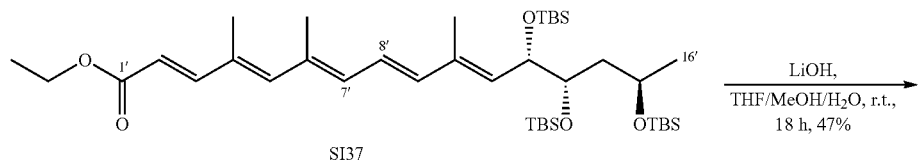

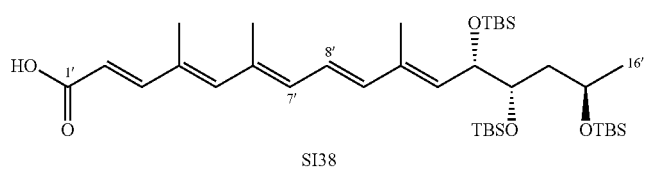

(2E,4E,6E,8E,10E,12S,13S,15R)-12,13,15-tris(tert-Butyldimethylsilyloxy)-4,6,10-trimethylhexadeca-2,4,6,8,10-pentaenoic acid (SI38)

To a solution of SI37 (100 mg, 0.14 mmol) in a mixture of THF/MeOH/H$_2$O (3.5:0.9:0.9 mL) was added a solution of LiOH (58 mg, 1.26 mmol, 9 eq.) in H$_2$O (1.5 mL). The reaction mixture was stirred at room temperature for 18 h before being acidified with a saturated aqueous solution of NH$_4$Cl. The aqueous phase was extracted with ethyl acetate, and the combined organic phases were washed with brine and dried over MgSO$_4$. After being filtered and concentrated under reduced pressure, the crude product was purified by preparative TLC eluting with heptane/ethyl acetate 70:30, to give SI38 (45 mg, 0.066 mmol, 47%). A (4'E)/(4'Z)=88:12 mixture could be detected by $^1$H analysis. The acid was then photoisomerized in acetone for 1 h, using a green fluorescent bulb, in order to obtain SI38 with a 4'Z/4'E=56:44 ratio as detected by $^1$H NMR.

$^1$H NMR (d6-Acetone, 300 MHz, 4'Z isomer) δ 7.94 (d, J=15, 6 Hz, 1H), 6.66 (dd, J=11.2, 15.3 Hz, 1H), 6.40 (d, J=14.8 Hz, 1H), 6.34 (s, 1H), 6.19 (d, J=11.1 Hz, 1H), 5.92 (d, J=16.0 Hz, 1H), 5.63 (d, J=9.7 Hz, 1H), 4.57 (dd, J=3.4, 9.1 Hz, 1H), 4.13 (m, 1H), 3.92 (m, 1H), 2.03 (s, 3H), 1.97 (s, 3H), 1.93 (s, 3H), 1.88 (m, 1H), 1.49 (m, 1H), 1.20 (d, J=7.0 Hz, 3H), 0.91-0.89 (27H), 0.14 (s, 6H), 0.12-0.11 (6H), 0.09 (s, 3H), 0.04 (s, 3H).

$^{13}$C NMR (d6-Acetone, 75 MHz, 4'Z isomer) δ 169.2, 152.6, 144.5, 142.8, 141.0, 137.3, 136.0, 135.9, 135.4, 132.9, 126.1, 120.4, 75.7, 74.5, 67.7, 45.5, 27.4 (3×C), 27.3 (6×C), 26.2, 19.6, 18.6, 18.2, 15.5, 14.9, −2.4, −2.7, −2.9, −3.1 (2×C), −3.4.

$^1$H NMR (d6-Acetone, 300 MHz, 4'E isomer) δ 7.36 (d, J=15.5 Hz, 1H), 6.66 (dd, J=11.2, 15.0 Hz, 1H), 6.47 (d, J=15.0 Hz, 1H), 6.46 (s, 1H), 6.38 (d, J=11.2 Hz, 1H), 5.87 (d, J=15.5 Hz, 1H), 5.61 (d, J=8.9 Hz, 1H), 4.57 (dd, J=3.4, 9.1 Hz, 1H), 4.13 (m, 1H), 3.92 (m, 1H) 2.09 (s, 3H), 2.03 (s, 3H), 1.93 (s, 3H), 1.88 (m, 1H), 1.49 (m, 1H), 1.20 (d, J=7.0 Hz, 3H) 0.91-0.89 (27H), 0.14 (s, 6H), 0.12-0.11 (6H), 0.09 (s, 3H), 0.04 (s, 3H).

$^{13}$C NMR (d6-Acetone, 75 MHz, 4'E isomer) δ 169.2, 152.6, 145.2, 142.9, 141.3, 137.1, 136.4, 135.9, 135.2, 132.9, 126.1, 118.1, 75.7, 74.4, 67.7, 45.5, 27.4 (3×C), 27.3 (6×C), 26.2, 19.6, 18.6, 18.2, 15.5, 14.9, −2.4, −2.7, −2.9, −3.1 (2×C), −3.4.

HRMS-ESI calculated for C$_{37}$H$_{69}$O$_5$Si$_3$: m/z 677.4460 ([M−H]$^−$). found: m/z 677.4458 ([M−H]$^−$).

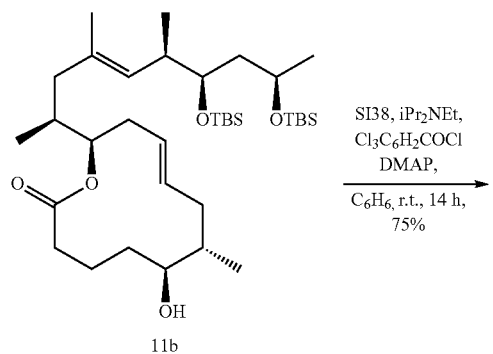

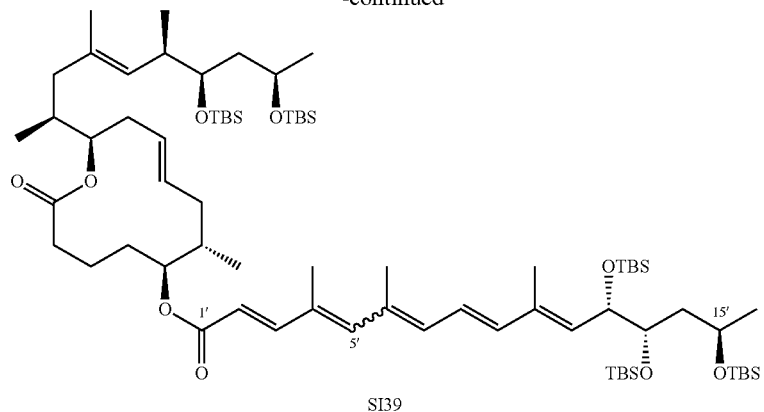

SI39

Compound SI39

To a solution of SI38 (27 mg, 0.040 mmol, 2 eq) in benzene (0.2 mL) were added diisopropylethylamine (27 μL, 0.15 mmol), 2,4,6-trichlorobenzoyl chloride (15 μL, 0.09 mmol), and DMAP (24.5 mg). The reaction mixture was stirred at room temperature for 15 min, and a solution of 11b (13 mg, 0.02 mmol) was added. After being stirred at room temperature for 14 h, an aqueous saturated solution of sodium hydrogenocarbonate was added to the reaction mixture. The aqueous layer was extracted three times with benzene. The combined organic layers were washed with brine, dried over MgSO$_4$, filtered and concentrated under reduced pressure. The crude product was purified on preparative TLC eluting with heptane/ethyl acetate 95:5 to give SI39 (19 mg, 0.015 mmol, 75%) as a yellow oil. A (4'E)/(4'Z)=53:47 mixture could be detected by $^1$H analysis.

$^1$H NMR (CDCl$_3$, 300 MHz, 4'Z isomer) δ 7.94 (d, J=15.6 Hz, 1H), 6.45 (dd, J=10.7, 14.8 Hz, 1H), 6.33 (d, J 15.0 Hz, 1H), 6.24 (s, 1H), 6.14 (d, J=10.6 Hz, 1H), 5.86 (d, J=15.5 Hz, 1H), 5.54 (d, J=8.7 Hz, 1H), 5.42 (m, 1H), 5.21-5.08 (2H), 5.04 (d, J=9.6 Hz, 1H), 4.77 (m, 1H), 4.45 (dd, J=3.45, 9.0 Hz, 1H), 4.05 (m, 1H), 3.82 (m, 1H), 3.57 (m, 1H), 3.32 (dd, J=4.1, 9.1 Hz, 1H), 2.55 (m, 1H), 2.52 (m, 1H), 2.44 (m, 1H), 2.24 (m, 1H), 2.15 (m, 1H), 2.10 (m, 1H), 2.05 (s, 3H), 2.02 (s, 3H), 1.97 (m, 1H), 1.94-1.92 (2H), 1.84 (s, 6H), 1.80-1.59 (10H), 1.53 (s, 3H), 1.26-1.23 (3H), 1.13 (d, J=6.0 Hz, 3H), 0.93 (d, J 6.7 Hz, 3H), 0.90 (s, 9H), 0.88 (s, 18H), 0.87 (s, 9H), 0.86 (s, 9H), 0.78 (d, J=6.7 Hz, 3H), 0.05 (s, 9H), 0.03 (s, 6H), 0.02 (s, 9H), 0.01 (s, 6H).

$^{13}$C NMR (CDCl$_3$, 75 MHz, 4'Z isomer) δ173.3, 166.9, 150.5, 142.6, 141.4, 139.4, 135.6, 135.1, 134.5, 134.1, 134.0, 133.6, 131.9, 130.8, 123.8, 118.6, 75.0, 73.9, 72.9, 72.8, 71.3, 68.3, 65.9, 43.7, 42.8, 41.7, 38.0, 37.3, 36.3, 35.9, 35.6, 34.9, 32.7, 29.8, 25.9 (12×C), 25.8 (3×C), 24.5, 21.2, 20.7, 18.3 (2×C), 18.1 (2×C), 17.5, 17.1, 15.9, 15.6, 14.5, 14.2, 13.6, −3.7, −4.1, −4.2, −4.3 (2×C), −4.4, −4.5, −4.7 (2×C), −4.8.

$^1$H NMR (CDCl$_3$, 300 MHz, 4'E isomer) δ 7.35 (d, J=15.4 Hz, 1H), 6.50 (dd, J=11.1, 15.4 Hz, 1H), 6.36 (d, J=15.0 Hz, 1H), 6.33 (s, 1H), 6.29 (d, J=10.4 Hz, 1H), 5.82 (d, J=15.5 Hz, 1H), 5.52 (d, J=8.7 Hz, 1H), 5.42 (m, 1H), 5.21-5.08 (2H), 5.04 (d, J=9.6 Hz, 1H), 4.77 (m, 1H), 4.45 (dd, J=3.45, 9.0 Hz, 1H), 4.05 (m, 1H), 3.82 (m, 1H), 3.57 (m, 1H), 3.32 (dd, J=4.1, 9.1 Hz, 1H), 2.55 (m, 1H), 2.52 (m, 1H), 2.44 (m, 1H), 2.24 (m, 1H), 2.15 (m, 1H), 2.10 (m, 1H), 2.05 (s, 3H), 2.02 (s, 3H), 1.97 (m, 1H), 1.94-1.92 (2H), 1.84 (s, 6H), 1.80-1.59 (10H), 1.53 (s, 3H), 1.26-1.23 (3H), 1.13 (d, J=6.0 Hz, 3H), 0.93 (d, J=6.7 Hz, 3H), 0.90 (s, 9H), 0.88 (s, 18H), 0.87 (s, 9H), 0.86 (s, 9H), 0.78 (d, J=6.7 Hz, 3H), 0.05 (s, 9H), 0.03 (s, 6H), 0.02 (s, 9H), 0.01 (s, 6H).

$^{13}$C NMR (CDCl$_3$, 75 MHz, 4'E isomer) δ173.3, 166.9, 150.5, 143.6, 141.4, 139.7, 135.6, 135.2, 134.5, 134.1, 134.0, 132.2, 131.9, 130.6, 125.0, 116.5, 75.0, 73.9, 72.9, 72.8, 71.3, 68.3, 65.9, 43.7, 42.8, 41.7, 38.0, 37.3, 36.3, 35.9, 35.6, 34.9, 32.7, 29.7 25.9 (12×C), 25.8 (3×C), 24.5, 21.4, 20.8, 18.3 (2×C), 18.1 (2×C), 17.5, 17.1, 15.9, 15.6, 14.5, 14.2, 13.6, −3.7, −4.1, −4.2, −4.3 (2×C), −4.4, −4.5, −4.7 (2×C), −4.8.

HRMS (ESI) calculated for C$_{73}$H$_{138}$O$_9$Si$_5$Na: m/z 1322.9104 ([M+Na]$^+$). found: m/z 1322.9103 ([M+Na]$^+$).

Compound 20b

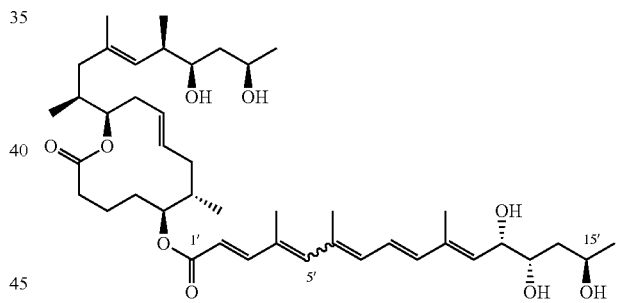

To a solution of SI39 (10 mg) in THF (2.0 mL) was added TBAF (0.17 mL, 20 eq.). The solution was stirred at room temperature for 12 h. For stabilities issues of 20b, the reaction was quenched at 65% of conversion. CaCO$_3$ (34 mg), Dowex 50WX8-400 (94 mg) and MeOH (0.2 mL) were added and the reaction mixture was stirred for 20 min. After being filtered and concentrated under reduced pressure, the crude product was purified by preparative TLC (CH$_2$Cl$_2$/MeOH 90:10). The recovered triol was recycled. After one recycle, 20b was obtained (2 mg). A (4'E)/(4'Z)=57:43 mixture could be detected by $^1$H analysis.

$^1$H NMR (d6-Acetone, 400 MHz, 4'Z isomer) δ 7.91 (d, J=15.5 Hz, 1H), 6.64 (dd, J=11.2, 15.5 Hz, 1H), 6.45 (d, J=15.5 Hz, 1H), 6.33 (s, 1H), 6.17 (d, J=11.1 Hz, 1H), 5.92 (d, J=15.5 Hz, 1H), 5.57 (d, J=9.2 Hz, 1H), 5.45 (m, 1H), 5.22 (m, 1H), 5.20 (m, 1H), 5.05 (d, J=9.4 Hz, 1H), 4.83 (m, 1H), 4.26 (m, 1H), 4.01 (m, 1H) 3.91 (m, 1H, OH), 3.81 (m, 1H, OH), 3.73 (m, 1H), 3.65 (s, 1H, OH), 3.52 (m, 1H, OH),3.44 (m, 1H), 3.34 (m, 1H, OH), 3.30 (m, 1H), 2.45-2.42 (2H), 2.30 (m, 1H), 2.27 (m, 1H), 2.20 (m, 1H), 2.16-2.13 (3H), 2.02 (s, 3H) 1.96-1.94 (4H), 1.82-1.74 (6H), 1.62 (s, 3H), 1.62-1.59 (2H), 1.49-1.45 (2H), 1.25 (d, J=6.2 Hz, 3H), 1.13 (d, J=6.2 Hz, 3H), 0.99-0.96 (6H), 0.85 (d, J=6.7 Hz, 6H).

$^{13}$C NMR (d6-Acetone, 100 MHz, 4'Z isomer) δ 174.6, 168.1, 145.2, 144.0, 142.8, 138.2, 136.9, 136.1, 135.9, 135.6, 134.5, 133.1, 132.1, 127.9, 126.2, 120.9, 76.4, 76.2, 74.2, 73.8, 73.5, 70.9, 65.8, 45.2, 43.6, 43.1, 41.2, 40.3, 37.3, 36.5, 36.3, 35.4, 25.6, 22.1, 21.2, 20.9, 20.7, 18.6, 18.0, 17.2, 16.1, 14.8, 14.4.

$^{1}$H NMR (d6-Acetone, 400 MHz, 4'E isomer) δ 7.34 (d, J=15.3 Hz, 1H), 6.64 (dd, J=11.2, 15.5 Hz, 1H), 6.40 (d, J=15.5 Hz, 1H), 6.39 (s, 1H), 6.38 (d, J=11.2 Hz, 1H), 5.87 (d, J=15.5 Hz, 1H), 5.57 (d, J=9.2 Hz, 1H), 5.45 (m, 1H), 5.22 (m, 1H), 5.20 (m, 1H), 5.05 (d, J=9.4 Hz, 1H), 4.83 (m, 1H), 4.26 (m, 1H), 4.01 (m, 1H) 3.91 (m, 1H, OH), 3.81 (m, 1H, OH), 3.73 (m, 1H), 3.65 (s, 1H, OH), 3.52 (m, 1H, OH), 3.44 (m, 1H), 3.34 (m, 1H, OH), 3.30 (m, 1H), 2.45-2.42 (2H), 2.30 (m, 1H), 2.27 (m, 1H), 2.20 (m, 1H), 2.16-2.13 (3H), 2.02 (s, 3H) 1.96-1.94 (4H), 1.82-1.74 (6H), 1.62 (s, 3H), 1.62-1.59 (2H), 1.49-1.45 (2H), 1.25 (d, J=6.2 Hz, 3H), 1.13 (d, J=6.2 Hz, 3H), 0.99-0.96 (6H), 0.85 (d, J=6.7 Hz, 6H).

$^{13}$C NMR (d6-Acetone, 100 MHz, 4'E isomer) δ 174.6, 168.1, 152.0, 141.3, 141.0, 138.2, 137.2, 136.9, 136.1, 135.8, 134.6, 133.1, 132.1, 127.9, 126.2, 118.8, 76.4, 76.3, 74.2, 73.8, 73.5, 70.8, 65.8, 45.1, 43.6, 43.1, 41.3, 40.3, 37.3, 36.5, 36.3, 35.4, 25.4, 22.1, 21.1, 20.9, 20.7, 18.6, 18.1, 17.2, 16.1, 14.8, 14.4.

HRMS-ESI calculated for $C_{43}H_{68}O_9$: m/z 751.4761 ([M+Na]$^+$). found: m/z 751.4762 ([M+Na]$^+$).

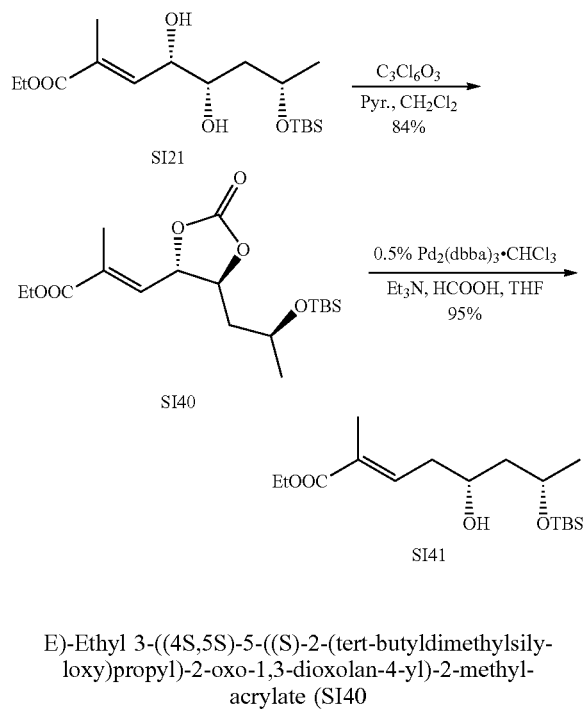

E)-Ethyl 3-((4S,5S)-5-((S)-2-(tert-butyldimethylsilyloxy)propyl)-2-oxo-1,3-dioxolan-4-yl)-2-methylacrylate (SI40

To a solution of SI21 (220 mg, 0.64 mmol) and pyridine (222 µL) in dichloromethane (1 mL) at 0° C. was slowly added a solution of triphosgene (95 mg, 0.32 mmol, 0.5 eq.). The reaction mixture was stirred at 0° C. for 3 h before being hydrolyzed by adding an aqueous saturated solution of NH$_4$Cl. The aqueous phase was extracted three times with diethylether and the combined organic phases were washed with an aqueous saturated solution of sodium bicarbonate, with brine, and dried over magnesium sulfate. After being filtered and concentrated under reduced pressure, the crude product was purified by Flash chromatography on silica gel (elution: cyclohexane/ethyl acetate 80:20) to give SI40 (200 mg, 0.54 mmol, 84%).

$^{1}$H NMR (CDCl$_3$, 300 MHz) δ 6.65 (qd, J=1.4, 8.8 Hz, 1H), 5.13 (dd, J=7.7, 8.8 Hz, 1H), 4.57 (dt, J=4.8, 7.7 Hz, 1H), 4.24 (q, J=7.1 Hz, 2H), 4.04 (dd, J=5.9, 11.7 Hz, 1H), 2.03 (m, 1H), 1.97 (d, J=1.4 Hz, 3H), 1.79 (m, 1H), 1.31 (t, J=7.1 Hz, 3H), 1.21 (d, J=5.9 Hz, 3H), 0.86 (s, 9H), 0.06 (s, 3H), 0.03 (s, 3H).

$^{13}$C NMR (CDCl$_3$, 75 MHz) δ 166.3, 154.1, 135.3, 132.4, 78.9, 77.9, 64.7, 61.4, 41.9, 26.9, 25.7, 23.3, 17.9, 14.1, 13.5, −4.4, −5.0.

[α]$^{20}_D$=−39.4 (c 1.0, CHCl$_3$)

(5R,7S,E)-Ethyl 7-(tert-butyldimethylsilyloxy)-5-hydroxy-2-methyloct-2-enoate (SI41)

To a solution of SI40 (154 mg, 0.41 mmol) in THF (1.75 mL) were added Pd$_2$(dba)$_3$·CHCl$_3$ (15 mg, 0.016 mmol, 0.4%), Et$_3$N (0.35 mL, 2 eq.) and formic acid (100 µL, 2 eq.). The reaction mixture was stirred at room temperature for 24 h before being diluted with Et$_2$O and hydrolyzed with an aqueous saturated solution of Na$_2$CO$_3$. The aqueous phase was extracted three times with Et$_2$O. The combined organic phases were washed with brine, dried over MgSO$_4$, filtered and concentrated under reduced pressure. The crude product was purified by TLC preparative eluting with heptane/ethyl acetate to give 90:10) to give SI41 (128 mg, 0.39 mmol, 95%) as a colorless oil.

$^{1}$H NMR (CDCl$_3$, 300 MHz) δ 6.80 (qt ap. td, J=1.2, 7.4 Hz, 1H), 4.18 (q, J=7.1 Hz, 2H), 4.08 (m, 1H), 3.93 (m, 1H), 2.43-2.25 (2H), 1.84 (d, J=1.2 Hz, 3H), 1.58-1.52 (2H), 1.29 (t, J=7.1 Hz, 3H), 1.18 (d, J=6.1 Hz, 3H), 0.89 (s, 9H), 0.12 (s, 3H), 0.10 (s, 3H).

$^{13}$C NMR (CDCl$_3$, 75 MHz) δ 168.0, 137.8, 129.6, 70.8, 70.3, 60.5, 45.0, 36.8, 25.8 (3×C), 24.6, 17.8, 14.3, 12.7, −3.8, −4.8.

[α]$^{20}_D$=+47.1 (c 0.4, CHCl$_3$)

HRMS-ESI calculated for $C_{17}H_{34}NaO_4Si$: m/z 353.2118 ([M+Na]$^+$). found: m/z 353.2113 ([M+Na]$^+$).

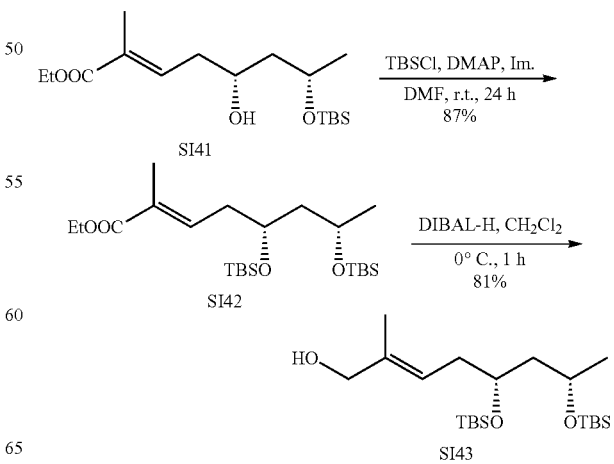

(5R,7S,E)-Ethyl 5,7-bis(tert-butyldimethylsilyloxy)-2-methyloct-2-enoate (SI42)

To a solution of SI41 (100 mg, 0.30 mmol) in DMF (2 mL) were added TBSCl (313 mg, 2.08 mmol, 7 eq.), imidazole (80 mg, 1.17 mmol, 4 eq.) and DMAP (17 mg, 0.14 mmol, 0.5 eq.). The reaction mixture was stirred at room temperature for 24 h before being hydrolyzed. The aqueous phase was extracted three times with a mixture of cyclohexane/dichloromethane 90:10. The combined organic layers were washed with brine, dried over MgSO$_4$, filtered and concentrated. The residue was purified by TLC preparative (cyclohexane/ethyle acetate 90:10) to give SI42 (114 mg, 0.26 mmol, 87%) as a colorless oil.

$^1$H NMR (CDCl$_3$, 300 MHz) 6.82 (ddq ap. dt, J=1.3, 7.4 Hz, 1H), 4.18 (q, J=7.1 Hz, 2H), 3.92-3.85 (2H), 2.43-2.24 (2H), 1.83 (d, J=1.3 Hz, 3H), 1.71 (m, 1H), 1.50 (m, 1H), 1.29 (t, J=1.3 Hz, 3H), 1.14 (d, J=6.0 Hz, 3H), 0.88 (s, 9H), 0.87 (s, 9H), 0.06 (s, 3H), 0.05 (s, 3H), 0.04 (s, 3H), 0.01 (s, 3H).

$^{13}$C NMR (CDCl$_3$, 75 MHz) δ 168.1, 138.8, 125.8, 68.9, 65.8, 60.4, 47.7, 36.6, 25.8 (6×C), 24.0, 18.1 (2×C), 14.3, 12.7, −4.2, −4.4, −4.5, −4.6.

$[α]^{20}_D$=+16.9 (c 0.4, CHCl$_3$)

HRMS-ESI calculated for C$_{23}$H$_{48}$NaO$_4$Si$_2$: m/z 467.2983 ([M+Na]$^+$). found: m/z 467.2980 ([M+Na]$^+$).

(5R,7S,E)-5,7-bis(tert-Butyldimethylsilyloxy)-2-methyloct-2-en-1-ol (SI43)

To a solution of SI42 (640 mg, 1.44 mmol) in dichloromethane (6 mL) was added DIBAL-H (3.15 mL, 1.0 M in toluene, 2.2 eq.). The reaction mixture was stirred at 0° C. for 1 h before being hydrolyzed with an aqueous saturated solution of Rochelle's salts. The reaction mixture thus obtained was stirred at room temperature for 12 h. The aqueous phase was extracted with Et$_2$O three times. The combined organic phases were washed with water, brine and dried over MgSO$_4$. After filtration and concentration under reduced pressure, SI43 was obtained as a colorless oil (470 mg, 1.17 mmol, 81%).

$^1$H NMR (CDCl$_3$, 300 MHz) δ 5.47 (qd ap. td, J=1.0, 7.2 Hz, 1H), 4.01 (s, 2H), 3.90 (tt ap. dd, J=6.8, 12.5 Hz, 1H), 3.78 (qd, J=5.7, 11.7 Hz, 1H), 2.20 (dd, J=6.8 Hz, 2H), 1.67 (m, 3H), 1.12 (d, J=5.7 Hz, 3H), 0.88 (s, 9H), 0.87 (s, 9H), 0.04 (s, 12H). The spectral data are in agreement with those reported in the literature.[20]

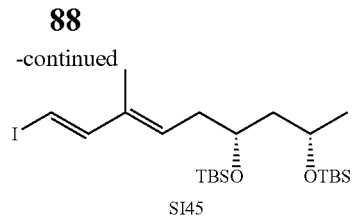

SI45

(5R,7S,E)-5,7-bis(tert-Butyldimethylsilyloxy)-2-methyloct-2-enal (SI44)

To a solution of SI43 (589 mg, 1.36 mmol) in dichloroethane (7 mL) was added MnO$_2$ (2.3 g, 26 mmol, 19 eq.). The reaction mixture was heated under reflux for 24 h before being filtered on a bed of Celite. After being concentrated under reduced pressure, SI44 was obtained as a yellow oil (510 mg, 1.27 mmol, 93%).

$^1$H NMR (CDCl$_3$, 300 MHz) δ 9.42 (s, 1H), 6.60 (dt, J=6.7, 1.3 Hz, 1H), 4.01 (m, 1H), 3.89 (m, 1H), 2.64-2.33 (2H), 1.75 (s, 3H), 1.73 (m, 1H), 1.51 (m, 1H), 1.14 (d, J=6.1 Hz, 3H), 0.88 (s, 18H), 0.06 (s, 6H), 0.04 (s, 6H).

The spectral data are in agreement with those reported in the literature.

(1E,3E)-(6S,8S)-bis-(tert-Butyldimethylsilyloxy)-1-iodo-3-methyl-nona-1,3-diene (SI45)

To a suspension of CrCl$_2$ (332 mg, 2.7 mmol, 6 eq.) in THF (2 mL) was added dropwise a solution of SI44 (180 mg, 0.45 mmol) and CHI$_3$ (531 mg, 1.35 mmol, 3 eq.) in THF (1.5 mL). The reaction mixture was stirred at room temperature for 12 h before being diluted with diethyl ether and water. The aqueous phase was extracted three times, and the combined organic phases were washed with water and brine. After being dried over magnesium sulfate, filtered and concentrated under reduced pressure, the crude product was purified by flash chromatography (cyclohexane/toluene 100:1) to give SI45 (140 mg, 0.26 mmol, 59%) as a colorless oil.

$^1$H NMR (C$_6$D$_6$, 300 MHz) δ 7.07 (d, J=14.6 Hz, 1H), 5.94 (d, J=14.6 Hz, 1H), 5.42 (t, J=7.4 Hz, 1H), 3.89 (m, 1H), 3.82 (m, 1H), 2.20-2.16 (2H), 1.82 (ddd ap. td, J=13.5, 6.5 Hz, 1H), 1.52 (ddd ap. td, J=13.5, 6.2 Hz, 1H), 1.39 (d, J=8.8 Hz, 3H), 1.09 (d, J=6.0 Hz, 3H), 0.99 (s, 9H), 0.98 (s, 9H), 0.08 (s, 3H), 0.07 (s, 6H), 0.04 (s, 3H).

$^{13}$C NMR (C$_6$D$_6$, 75 MHz) δ 149.7, 136.1, 130.6, 74.2, 69.6, 66.1, 47.9, 36.3, 26.1 (3×C), 26.0 (3×C), 24.1, 18.2 (2×C), 12.0, −4.1, −4.2, −4.4, −4.6.

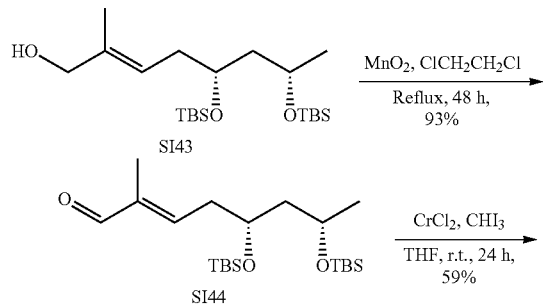

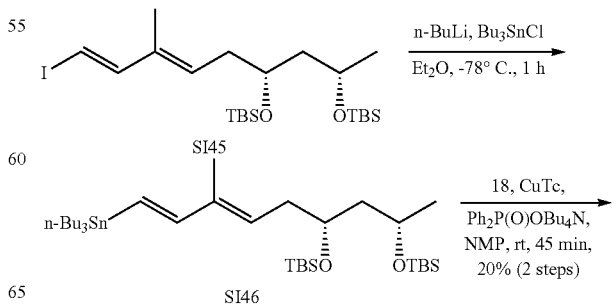

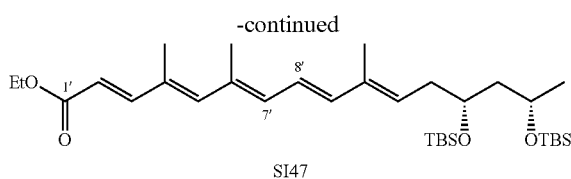

SI47

(5S,7R)-2,2,3,3,5,9,9,10,10-nonamethyl-7-((2E,4E)-3-methyl-5-(tributylstannyl)penta-2,4-dienyl)-4,8-dioxa-3,9-disilaundecane (SI46)

To a solution of SI45 (240 mg, 0.46 mmol) in Et$_2$O (2.4 mL) at −78° C. was added n-BuLi (560 μL, 1.6 M in hexane, 0.90 mmol, 2 eq.) and the reaction mixture was stirred for 20 min. Bu$_3$SnCl (260 μL, 0.98 mmol, 2 eq.) was then added to the solution and the reaction mixture was allowed to warm to room temperature for 1 h. The reaction mixture was hydrolyzed with a saturated aqueous NaHCO$_3$ solution. The aqueous phase was extracted twice with Et$_2$O. The combined organic phases were washed with brine, dried over MgSO$_4$, filtered and concentrated under reduced pressure. The crude material SI46 was used without further purification.

(2E,4E,6E,8E,10E)-(3S,5S)-Ethyl13,15-bis(tert-butyldimethylsilyloxy)-4,6,10-trimethylhexadeca-2,4,6,8,10-pentaenoate (SI47)

To a solution of SI46 and tetrabutylammonium diphenylphosphate (600 mg, 1.30 mmol) in NMP (2.6 mL) was added 0.2 mL of a stock solution of 18 in NMP (275 mg, 0.9 mmol, in 1.6 mL). After the addition of CuTC (180 mg, 0.95 mmol, 2 eq.), the remaining solution of 18 (1.4 mL) was added dropwise over 5 min. The reaction mixture was stirred at room temperature for 40 min, and then diluted with Et$_2$O. The mixture was filtered through a pad of neutral alumina. The filtrate was then washed with water, with brine, dried over MgSO$_4$, filtered, and concentrated. The crude product was purified by TLC preparative (elution with heptane/ethyl acetate 90:10) to give SI47 (50 mg, 0.09 mmol, 20% over 2 steps) as a yellow oil. A (4'E)/(4'Z)=89:11 mixture could be detected by $^1$H analysis.

$^1$H NMR (CDCl$_3$, 300 MHz, 4'E isomer) δ 7.37 (d, J=15.5 Hz, 1H), 6.48 (dd, J=10.8, 15.0 Hz, 1H), 6.38 (m, 1H), 6.35 (s, 1H), 6.25 (d, J 9.4 Hz, 1H), 5.85 (d, J=15.5 Hz, 1H), 5.62 (m, 1H), 4.23 (q, J=7.1 Hz, 2H), 3.90 (m, 1H), 3.82 (m, 1H), 2.39-2.32 (2H), 2.04 (s, 3H), 2.02 (s, 3H), 1.81 (s, 3H), 1.69 (m, 1H), 1.49 (m, 1H), 1.30 (t, J=7.1 Hz, 3H), 1.12 (d, J=6.0 Hz, 3H), 0.88 (s, 18H), 0.05-0.03 (12H).

$^{13}$C NMR (CDCl$_3$, 75 MHz, 4'E isomer) δ 167.6, 150.9, 145.2, 143.9, 140.0, 135.6, 131.2, 129.1, 124.8, 122.4, 115.8, 69.5, 65.9, 60.1, 47.4, 36.5, 35.5, 25.9 (3×C), 25.8 (3×C), 23.8, 18.1, 18.0, 17.0, 14.1, 12.7, −4.3, −4.4, −4.6, −4.8.

HRMS (ESI) calculated for C$_{33}$H$_{64}$NO$_4$Si$_2$: m/z 594.4368 ([M+NH$_4$]$^+$). found: m/z 594.4352 ([M+NH$_4$]$^+$).

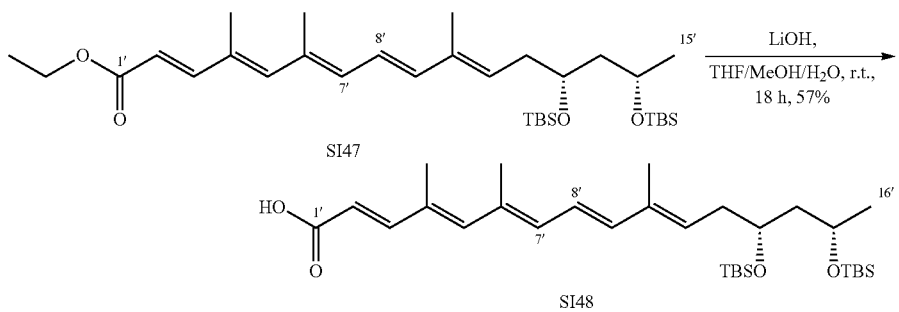

(2E,4E,6E,8E,10E,13S,15S)-13,15-bis(tert-Butyldimethylsilyloxy)-4,6,10-trimethylhexadeca-2,4,6,8,10-pentaenoic acid (SI48)

To a solution of SI47 (33 mg, 0.057 mmol) in a mixture of THF/MeOH/H$_2$O (1.2 mL/0.3 mL/0.3 mL) was added a solution of LiOH (24 mg, 0.57 mmol) in H$_2$O (0.57 mL). The reaction mixture was stirred at room temperature for 18 h before being acidified with an NH$_4$Cl saturated aqueous solution. The aqueous phase was extracted with ethyl acetate, and the combined organic phases were washed with brine and dried over MgSO$_4$. After being filtered and concentrated under reduced pressure, the crude product was purified by TLC preparative (elution with heptane/ethyl acetate 70:30) to give SI48 (17 mg, 0.031 mmol, 57%). A (4'E)/(4'Z)=86:14 mixture could be detected by $^1$H analysis.

$^1$H NMR (CDCl$_3$, 300 MHz, 4'E isomer) δ 7.46 (d, J=15.4 Hz, 1H), 6.45 (dd, J=10.8, 15.5 Hz), 6.40 (m, 1H), 6.38 (m, 1H), 6.30 (s, 1H), 5.85 (d, J=15.5 Hz, 1H), 5.63 (m, 1H), 3.89 (m, 1H), 3.83 (m, 1H), 2.37-2.32 (2H), 2.06 (s, 3H), 2.03 (s, 3H), 1.81 (s, 3H), 1.66 (m, 1H), 1.52 (m, 1H), 1.13 (d, J=6.0 Hz, 3H), 0.88 (s, 18H), 0.05-0.03 (12H).

$^{13}$C NMR (CDCl$_3$, 75 MHz, 4'E isomer) δ 172.5, 153.3, 145.2, 140.5, 136.4, 135.5, 132.5, 131.5, 122.4, 114.7, 69.5, 65.9, 47.4, 36.5, 35.5, 25.9 (3×C), 25.8 (3×C), 23.8, 18.1, 18.0, 17.0, 14.1, 12.7, −4.3, −4.4, −4.6, −4.8.

HRMS (ESI) calculated for C$_{31}$H$_{55}$O$_4$Si$_2$: m/z 547.3648 ([M−H]$^−$). found: m/z 547.3649 ([M−H]$^−$).

The acid SI48 was photoisomerized in acetone for 1, h, using a green fluorescent bulb, in order to obtain SI48 with a 4'Z/4'E=50:50 ratio as detected by $^1$H NMR.

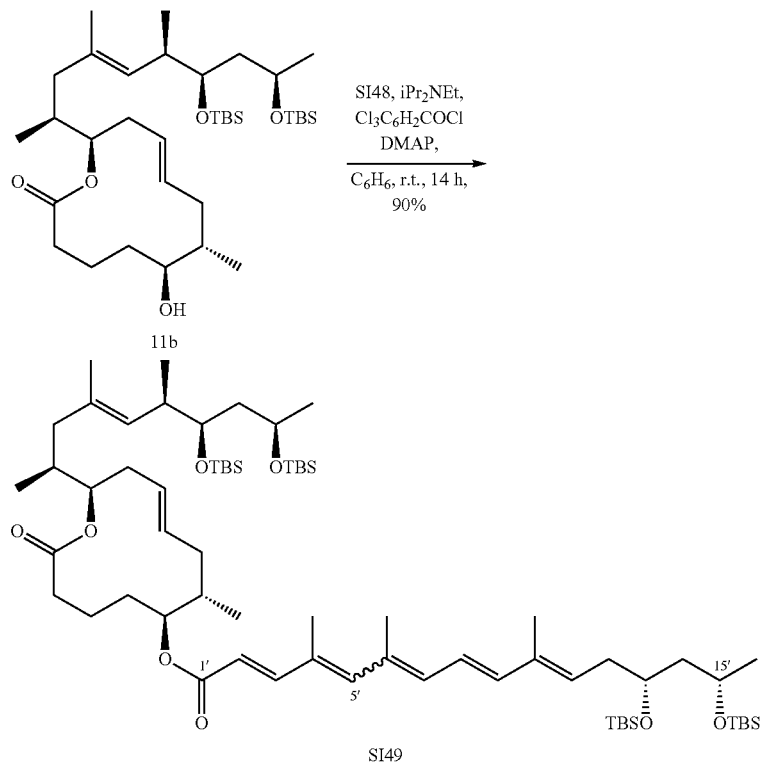

Compound SI49

To a solution of SI48 (25 mg, 0.045 mmol, 2.25 eq.) in benzene (0.30 mL) were added diisopropylethylamine (30 µL, 0.16 mmol, 3.6 eq.), 2,4,6-trichlorobenzoyl chloride (15 µL, 0.09 mmol, 2 eq.), DMAP (28 mg). The reaction mixture was stirred at room temperature for 15 min and a solution of 11b (13 mg, 0.02 mmol) in benzene (0.3 mL) was added. After being stirred at room temperature for 14 h, an aqueous saturated solution sodium hydrogenocarbonate was added to the reaction mixture. The aqueous layer was extracted three times with benzene. The combined organic layers were washed with brine, dried over MgSO$_4$, filtered and concentrated under reduced pressure. The crude product was purified on preparative TLC eluting with heptane/ethyl acetate 95:5 to give SI49 (21 mg, 0.018 mmol, 90%) as a yellow oil.

HRMS (ESI) calculated for $C_{67}H_{124}O_8Si_4Na$: m/z 1192.8291 ([M+Na]$^+$). found: m/z 1192.8285 ([M+Na]$^+$).

Compound 20d

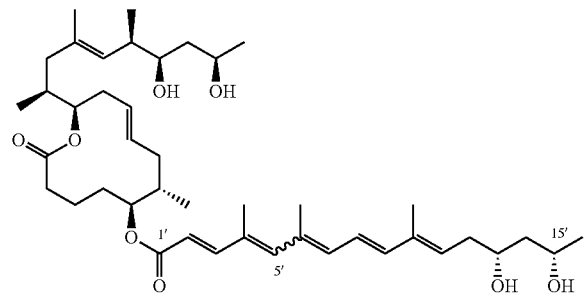 [SMILES: CC(=C/C=C/C(C)=C/[C@H](O)[C@@H](O)C[C@@H](C)O)C=C(C)/C=C/C(=O)O[C@H]1CCCC(=O)O[C@@H]([C@@H](C)C/C(C)=C/[C@@H](C)[C@H](O)C[C@@H](C)O)C/C=C/C[C@@H]1C]

To a solution of SI49 (8 mg) in THF (1.5 mL) was added TBAF (0.14 mL, 20 eq.). The solution was stirred at room temperature for 12 h. For stabilities issues of 20d, the reaction was quenched at 60% of conversion. CaCO$_3$ (35 mg), Dowex 50WX8-400 (95 mg) and MeOH (0.2 mL) were added and the reaction mixture was stirred for 20 min. After being filtered and concentrated under reduced pressure, the crude product was purified by preparative TLC (CH$_2$Cl$_2$/MeOH 90:10). The recovered triol was recycled. After one recycle, 20d was obtained (2 mg). A (4'E)/(4'Z)=47:53 mixture could be detected by $^1$H analysis.

$^1$H NMR (d6-Acetone, 400 MHz, 4'Z isomer) δ 7.92 (d, J=15.7 Hz, 1H), 6.51 (dd, J=11.0, 15.4 Hz, 1H), 6.45 (d, J=15.5 Hz, 1H), 6.32 (s, 1H), 6.15 (d, J=11.5 Hz, 1H), 5.91 (d, J=15.7 Hz, 1H), 5.72 (m, 1H), 5.45 (m, 1H), 5.19 (m, 1H), 5.06 (d, J=9.6 Hz, 1H), 4.83 (m, 1H), 4.09 (s, 1H, OH), 3.97 (m, 1H), 3.86 (m, 1H), 3.51 (m, 1H), 3.42 (m, 1H, OH), 2.45-2.28 (5H), 2.06 (s, 3H), 2.02 (s, 3H), 1.97 (s, 3H), 1.84 (s, 3H), 1.80-1.74 (8H), 1.64 (s, 3H), 1.63-1.58 (2H), 1.53-1.47 (5H), 1.26 (d, J=6.3 Hz, 3H), 1.12 (d, J=6.1 Hz, 3H), 0.97 (d, J=6.7 Hz, 3H), 0.90 (d, J=9.7 Hz, 3H), 0.85 (d, J 6.8 Hz, 3H).

$^{13}$C NMR (d6-Acetone, 100 MHz, 4'Z isomer) δ 173.6, 167.1, 144.5, 143.1, 141.0, 140.6, 137.3, 136.6, 135.9, 135.4, 133.5, 131.9, 131.1, 126.9, 125.9, 117.5, 75.3, 73.2, 73.1, 72.2, 69.9, 68.2, 46.4, 45.7, 44.2, 44.1, 42.1, 40.3, 39.2, 38.0, 37.4, 36.3, 35.5, 34.4, 24.4, 21.1, 20.0, 19.7, 17.1, 16.2, 15.1, 14.3, 12.7.

$^1$H NMR (d6-Acetone, 400 MHz, 4'E isomer) δ 7.34 (d, J=15.6 Hz, 1H), 6.52 (dd, J=10.5, 14.9 Hz, 1H), 6.44 (d, J 15.5 Hz, 1H), 6.34 (s, 1H), 6.32 (d, J=10.5 Hz, 1H); 5.87 (d, J=15.7 Hz, 1H), 5.72 (m, 1H), 5.45 (m, 1H), 5.19 (m, 1H), 5.06 (d, J=9.6 Hz, 1H), 4.83 (m, 1H), 4.09 (s, 1H, OH), 3.97 (m, 1H), 3.86 (m, 1H), 3.51 (m, 1H), 3.42 (m, 1H, OH), 2.45-2.28 (5H), 2.06 (s, 3H), 2.02 (s, 3H), 1.97 (s, 3H), 1.84 (s, 3H), 1.80-1.74 (8H), 1.64 (s, 3H), 1.63-1.58 (2H), 1.53-1.47 (5H), 1.26 (d, J=6.3 Hz, 3H), 1.12 (d, J=6.1 Hz, 3H), 0.97 (d, J=6.7 Hz, 3H), 0.90 (d, J=9.7 Hz, 3H), 0.85 (d, J=6.8 Hz, 3H).

$^{13}$C NMR (d6-Acetone, 100 MHz, 4'E isomer) δ 173.6, 167.1, 151.2, 141.0, 140.6, 137.3, 136.6, 135.9, 135.4, 133.5, 132.6, 131.7, 131.1, 126.9, 123.5, 119.7, 75.4, 73.2, 73.1, 72.2, 69.9, 68.2, 46.4, 45.7, 44.2, 44.1, 42.1, 40.3, 39.3, 38.0, 37.4, 36.3, 35.2, 34.4, 24.5, 21.1, 20.1, 19.9, 17.1, 16.2, 15.1, 14.3, 12.7.

HRMS-ESI calculated for $C_{43}H_{68}NaO_8$: m/z 735.4812 ([M+Na]$^+$). found: m/z 735.4821 ([M+Na]$^+$).

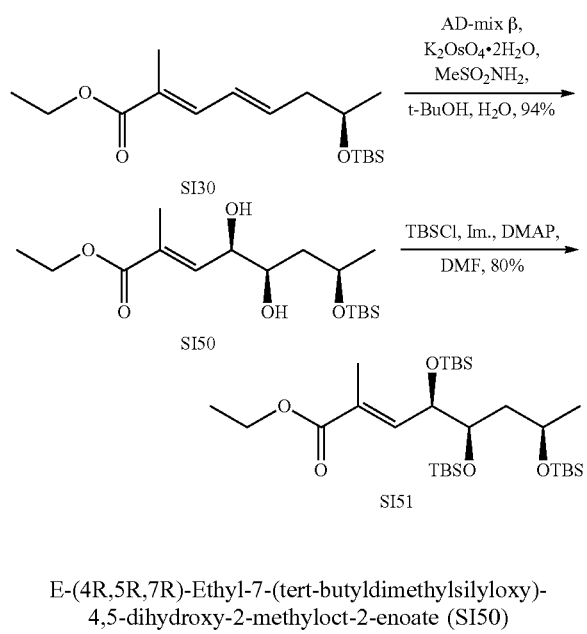

E-(4R,5R,7R)-Ethyl-7-(tert-butyldimethylsilyloxy)-4,5-dihydroxy-2-methyloct-2-enoate (SI50)

To a solution of AD-mix β (3.3 g) in a mixture of t-BuOH and water (20:20 mL) were added methanesulfonamide (190 mg, 2 mmol, 1 eq.) and potassium osmiate dihydrate (16 mg, 0.044 mmol, 2%). The reaction mixture was stirred at room temperature until both phases were clear, and then cooled at 0° C. whereupon the inorganic salts partially precipitate. SI30 (750 mg, 2.39 mmol) was then added and the reaction mixture was stirred at 0° C. for 15 h. Sodium sulfite (6 g) was then added. The reaction mixture was stirred at room temperature for 15 min and the aqueous phase was extracted three times with ethyl acetate. The combined organic layers were washed with an aqueous solution of potassium hydroxide (2N), with brine and dried over magnesium sulfate. After being filtered and concentrated under reduced pressure, the crude product was purified by flash chromatography (cyclohexane/ethyl acetate 8:2) to give SI50 (746 mg, 2.25 mmol, 94%) as a yellow oil.

$^1$H NMR (CDCl$_3$, 300 MHz) δ 6.66 (qd, J=1.4, 9.0 Hz, 1H), 4.30-4.15 (2H), 4.20 (m, 1H), 4.10 (m, 1H), 3.96 (s, 1H, —OH), 3.74 (m, 1H), 2.77 (d, J=3.7 Hz, 1H, —OH), 1.92 (d, J=1.4 Hz, 3H), 1.30 (t, J=7.1 Hz, 3H), 1.20 (d, J=6.1 Hz, 3H), 0.90 (s, 9H), 0.13 (s, 3H), 0.12 (s, 3H).

$^{13}$C NMR (CDCl$_3$, 75 MHz) δ 167.7, 138.8, 131.3, 74.0, 71.8, 69.8, 60.8, 41.2, 25.8 (3×C), 24.5, 17.8, 14.2, 13.3, −3.8, −4.8.

$[α]^{20}_D$=−11.6 (c 0.8, CHCl$_3$)

HRMS-ESI calculated for $C_{17}H_{34}NaO_5Si$: m/z 369.2067 ([M+Na]$^+$). found: m/z 369.2070 ([M+Na]$^+$).

(4R,5R,7R,E)-Ethyl 4,5,7-tris(tert-butyldimethylsilyloxy)-2-methyloct-2-enoate (SI51)

To a solution of SI50 (460 mg, 1.33 mmol) in DMF (8 mL) were added TBSCl (1.2 g, 7.96 mmol, 6 eq.), imidazole (362 mg, 5.32 mmol, 4 eq.) and DMAP (55 mg, 0.45 mmol, 0.3 eq.). The reaction mixture was stirred at room temperature for 24 h before being hydrolyzed. The aqueous phase was extracted three times with a mixture cyclohexane/dichloromethane 90:10. The combined organic layers were washed with brine, dried over MgSO$_4$, filtered and concentrated. The residue was purified by flash chromatography on silica gel (eluant: cyclohexane/ethyl acetate 20:1) to give SI51 (610 mg, 1.06 mmol, 80%) as a colorless oil.

$^1$H NMR (CDCl$_3$, 300 MHz) δ 6.72 (dd, J=1.3, 8.9 Hz, 1H), 4.39 (dd, J=3.5, 8.9 Hz, 1H), 4.20 (q, J=7.1 Hz, 2H), 3.89 (m, 1H), 3.67 (dd, J=3.5, 4.8, 8.0 Hz, 1H), 1.87 (d, J=1.3 Hz, 3H), 1.83 (ddd, J=4.9, 7.7, 12.9 Hz, 1H), 1.61 (ddd, J=5.8, 7.8, 12.9 Hz, 1H), 1.29 (t, J=7.1 Hz, 3H), 1.14 (d, J=6.0 Hz, 3H), 0.87 (s, 27H), 0.05 (s, 3H), 0.04 (s, 3H), 0.03 (s, 6H), 0.02 (s, 3H), 0.01 (s, 3H).

$^{13}$C NMR (CDCl$_3$, 75 MHz) δ 168.0, 141.3, 127.9, 73.2, 71.4, 65.9, 60.6, 42.8, 25.9 (3×C), 25.8 (3×C), 25.7 (3×C), 23.5, 18.1, 18.0, 17.9, 14.2, 13.4, −4.2, −4.3, −4.4, −4.5, −4.7, −4.8.

$[α]^{20}_D$=+21.9 (c 1, CHCl$_3$)

HRMS-ESI calculated for $C_{29}H_{62}NaO_5Si_3$: m/z 597.3797 ([M+Na]$^+$). found: m/z 597.3794 ([M+Na]$^+$).

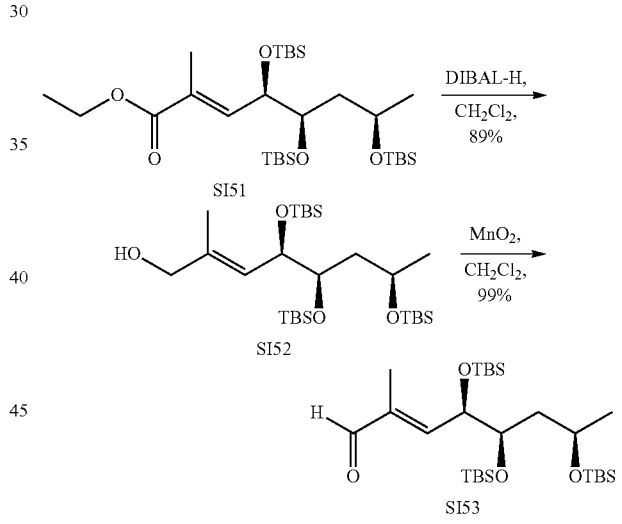

(4R,5R,7R,E)-4,5,7-tris(tert-Butyldimethylsilyloxy)-2-methyloct-2-en-1-ol (SI52)

To a solution of SI51 (590 mg, 1.03 mmol) in dichloromethane (6 mL) was added DIBAL-H (1.45 mL, 2.18 mmol, 1.5 M in toluene, 1.6 eq.). The reaction mixture was stirred at 0° C. for 1 h before being hydrolyzed with a saturated aqueous solution of Rochelle's salts. The reaction mixture thus obtained was stirred at room temperature for 12 h. The aqueous phase was extracted with Et$_2$O three times. The combined organic phases were washed with water, brine and dried over MgSO$_4$. After filtration and concentration under reduced pressure, SI52 was obtained as a colorless oil (490 mg, 0.92 mmol, 89%).

$^1$H NMR (CDCl$_3$, 300 MHz) δ 5.48 (qd ap. dd, J=1.1, 9.1 Hz, 1H), 4.35 (dd, J=3.7, 9.1 Hz, 1H), 4.03 (d, J=3.9 Hz,

2H), 3.92 (m, 1H), 3.62 (td, J=3.8, 7.9 Hz, 1H), 1.84 (ddd, J=3.9, 8.3, 13.1 Hz, 1H), 1.73 (d, J=1.1 Hz, 3H), 1.62 (ddd, J=5.0, 8.3, 13.3 Hz, 1H), 1.15 (d, J=6.0 Hz, 3H), 0.90 (s, 9H), 0.89 (s, 9H), 0.88 (s, 9H), 0.07 (s, 6H), 0.06 (s, 3H), 0.03 (s, 3H), 0.02 (s, 3H), −0.02 (s, 3H).

$[\alpha]^{20}_D$=+17.9 (c 1.5, CHCl$_3$)

HRMS-ESI calculated for C$_{27}$H$_{60}$NaO$_4$Si$_3$: m/z 555.3691 ([M+Na]$^+$). found: m/z 555.3689 ([M+Na]$^+$).

(4R,5R,7R,E)-4,5,7-tris(tert-Butyldimethylsilyloxy)-2-methyloct-2-enal (SI53)

To a solution of SI52 (490 mg, 0.93 mmol) in dichloroethane (6 mL) was added MnO$_2$ (3 g, 34 mmol, 36 eq.). The reaction mixture was heated under reflux for 24 h before being filtered on a bed of Celite. After being concentrated under reduced pressure, SI53 was obtained as a colorless oil (490 mg, 0.92 mmol, 99%).

$^1$H NMR (CDCl$_3$, 300 MHz) δ 9.45 (s, 1H), 6.44 (dd, J=1.3, 8.4 Hz, 1H), 4.56 (dd, J=3.7, 8.4 Hz, 1H), 3.91 (m, 1H), 3.72 (td, J=3.9, 8.1 Hz, 1H), 1.90 (ddd, J=4.0, 8.2, 13.2 Hz, 1H), 1.80 (d, J 1.3 Hz, 3H), 1.61 (m, 1H), 1.15 (d, J=6.0 Hz, 3H), 0.88 (s, 9H), 0.87 (s, 9H), 0.86 (s, 9H), 0.05--0.02 (18H).

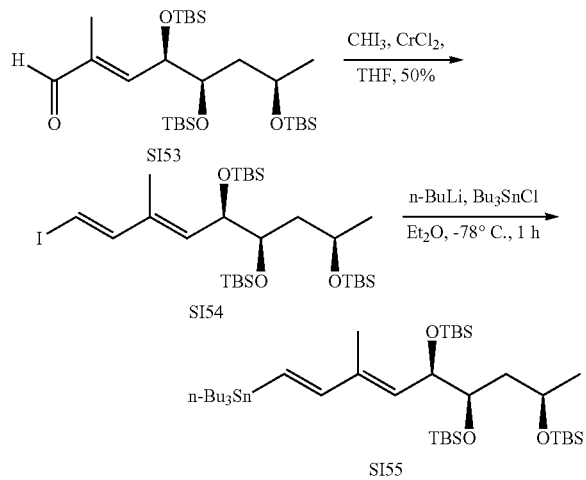

(1E,3E)-(5R,6R,8R)-tris-(tert-Butyldimethylsilyloxy)-1-iodo-3-methyl-nona-1,3-diene (SI54)

To as suspension of CrCl$_2$ (705 mg, 5.7 mmol, 6 eq.) in THF (6 mL) was added dropwise a solution of SI53 (490 mg, 0.92 mmol) and CHI$_3$ (1.13 g, 2.87 mmol, 3 eq.) in THF (4 mL). The reaction mixture was stirred at room temperature for 12 h before being diluted with diethyl ether. The aqueous phase was extracted three times, and the combined organic phases were washed with water and brine. After being dried over magnesium sulfate, filtered and concentrated under reduced pressure, the crude product was purified by flash chromatography eluting with cyclohexane/toluene (100:1) to give SI54 (300 mg, 0.46 mmol, 50%) as a colorless oil.

$^1$H NMR (C$_6$D$_6$, 300 MHz) δ 7.00 (d, J=14.6 Hz, 1H), 6.00 (d, J=14.6 Hz, 1H), 5.52 (d, J=9.1 Hz, 1H), 4.48 (dd, J=3.7, 9.1 Hz, 1H), 4.08 (m, 1H), 3.81 (td, J=3.7, 7.8 Hz, 1H), 2.09 (ddd, J=4.4, 7.8, 13.4 Hz, 1H), 1.86 (ddd, J=5.6, 7.5, 13.4 Hz, 1H), 1.55 (d, J=1.1 Hz, 3H), 1.26 (d, J=5.9 Hz, 3H), 1.00 (s, 9H), 0.96 (s, 9H), 0.92 (s, 9H), 0.13 (s, 6H), 0.09 (s, 3H), 0.08 (s, 3H), 0.05 (s, 3H), 0.01 (s, 3H).

$^{13}$C NMR (C$_6$D$_6$, 75 MHz) δ 149.3, 135.2, 133.8 76.5, 73.9, 71.5, 66.3, 43.4, 26.1 (9×C), 23.9, 18.3 (2×C), 18.2, 12.9, −4.0 (3×C), −4.3 (2×C), −4.5.

$[\alpha]^{20}_D$=+26.6 (c 1.1, CHCl$_3$)

HRMS-ESI calculated for C$_{28}$H$_{59}$INaO$_3$Si$_3$: m/z 677.2708 ([M+Na]$^+$). found: m/z 677.2700 ([M+Na]$^+$).

(5R,6R,8R)-6-[(tert-Butyldimethylsilyl)oxy]-2,2,3,3,8,10,10,11,11-nonamethyl-5-[(1E,3E)-2-methyl-4-(tributylstannyl)buta-1,3-dien-1-yl]-4,9-dioxa-3,10-disiladodecane (SI55)

To a solution of SI54 (290 mg, 0.44 mmol) in Et$_2$O (2.3 mL) at −78° C. was added n-BuLi (438 μL, 1.6 M in hexane, 0.70 mmol, 1.6 eq.) and the reaction mixture was stirred for 20 min. Bu$_3$SnCl (248 μL, 0.93 mmol, 2.1 eq.) was then added to the solution and the reaction mixture was allowed to warm to room temperature for 1 h. The reaction mixture was hydrolyzed with saturated aqueous NaHCO$_3$ solution. The aqueous phase was extracted twice with Et$_2$O. The combined organic phases were washed with brine, dried over MgSO$_4$, filtered and concentrated under reduced pressure. The crude SI55 was used without further purification.

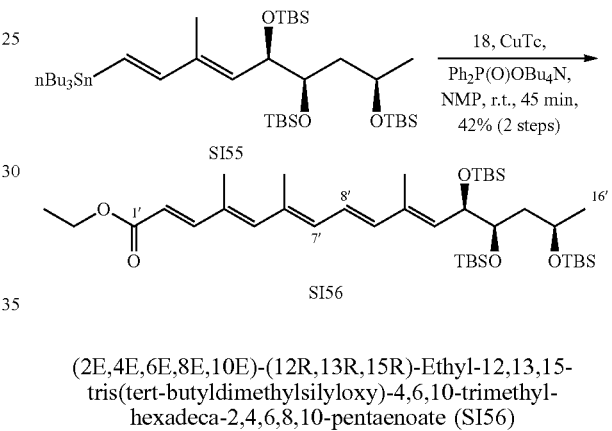

(2E,4E,6E,8E,10E)-(12R,13R,15R)-Ethyl-12,13,15-tris(tert-butyldimethylsilyloxy)-4,6,10-trimethyl-hexadeca-2,4,6,8,10-pentaenoate (SI56)

To a solution of SI55 and tetrabutylammonium diphenylphosphate (378 mg, 0.82 mmol) in NMP (2.5 mL) was added 0.2 mL of the following solution: 278 mg of 18 (0.91 mmol, 2.1 eq.) in NMP (1.7 mL). After the addition of CuTC (170 mg, 0.89 mmol, 2 eq.), the remaining solution of 18 (1.5 mL) was added dropwise for 5 min. The reaction mixture was stirred at room temperature for 40 min, and then diluted with Et$_2$O. The mixture was filtered through a pad of neutral alumina. The filtrate was then washed with water, with brine, dried over MgSO$_4$, filtered, and concentrated. The crude product was purified by preparative TLC eluting with heptane/ethyl acetate 90:10 to give SI56 (135 mg, 0.18 mmol, 42% over 2 steps) as a yellow oil. A (4'E)/(4'Z)=89:11 mixture could be detected by $^1$H analysis.

$^1$H NMR (CDCl$_3$, 300 MHz) δ 7.37 (d, J=15.5 Hz, 1H), 6.50 (dd, J=11.0, 14.9 Hz, 1H), 6.37 (d, J=11.7 Hz, 1H), 6.35 (s, 1H), 6.27 (d, J=11.0 Hz, 1H), 5.86 (d, J=15.5 Hz, 1H), 5.58 (d, J=9.0 Hz, 1H), 4.43 (dd, J=3.7, 9.0 Hz, 1H), 4.22 (q, J=7.1 Hz, 2H), 3.91 (m, 1H), 3.64 (m, 1H), 2.05 (s, 3H), 2.02 (s, 3H), 1.85 (s, 3H), 1.80 (m, 1H), 1.62 (m, 1H), 1.31 (t, J=7.1 Hz, 3H), 1.13 (d, J=6.0 Hz, 3H), 0.88 (s, 9H), 0.87 (s, 9H), 0.86 (s, 9H), 0.05 (s, 9H), 0.04 (s, 3H), 0.02 (s, 3H), −0.02 (s, 3H).

$^{13}$C NMR (CHCl$_3$, 75 MHz) δ 167.5, 150.8, 143.7, 139.8, 135.2, 134.6, 134.3, 134.1, 132.2, 123.7, 116.1, 73.6, 71.3, 66.0, 60.2, 42.7, 25.9 (6×C), 25.8 (3×C), 23.5, 18.1, 18.0, 17.9, 17.1, 14.3, 14.2, 13.5, −4.2 (2×C), −4.3, −4.5, −4.6, −4.7.

HRMS-ESI calculated for $C_{39}H_{74}NaO_5Si_3$: m/z 729.4736 ([M+Na]$^+$). found: m/z 729.4721 ([M+Na]$^+$).

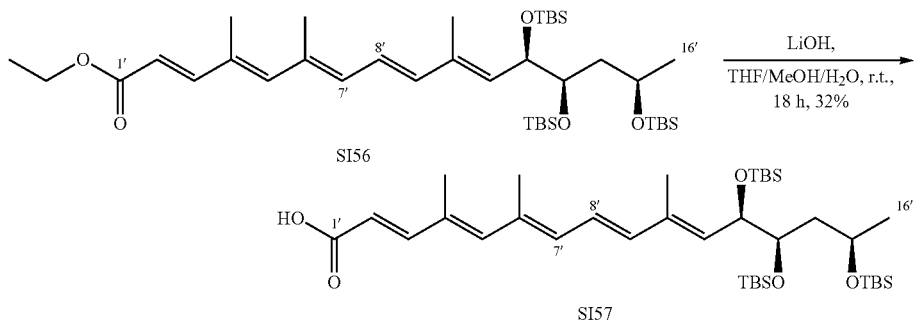

(2E,4E,6E,8E,10E,12R,13R,15R)-12,13,15-tris(tert-Butyldimethylsilyloxy)-4,6,10-trimethylhexadeca-2,4,6,8,10-pentaenoic acid (SI57)

To a solution of SI56 (130 mg, 0.18 mmol) in a mixture of THF/MeOH/H$_2$O (4.3 mL/1.1 mL/1.1 mL) was added a solution of LiOH (94 mg, 2 mmol) in H$_2$O (2 mL). The reaction mixture was stirred at room temperature for 18 h before being acidified with a saturated aqueous solution of NH$_4$Cl. The aqueous phase was extracted with ethyl acetate, and the combined organic phases were washed with brine and dried over MgSO$_4$. After being filtered and concentrated under reduced pressure, the crude product was purified by preparative TLC eluting with heptane/ethyl acetate 70:30, to give SI57 (39 mg, 0.057 mmol, 32%). A (4'E)/(4'Z)=79:21 mixture could be detected by $^1$H analysis.

$^1$H NMR (d6-Acetone, 300 MHz) δ 7.36 (d, J=15.5 Hz, 1H), 6.67 (dd, J=11.2, 14.9 Hz, 1H), 6.48 (d, J=14.9 Hz, 1H), 6.46 (s, 1H), 6.39 (d, J=11.2 Hz, 1H), 5.87 (d, J=15.5 Hz, 1H), 5.67 (d, J 9.1 Hz, 1H), 4.58 (dd, J=3.4, 9.1 Hz, 1H), 4.00 (m, 1H), 3.78 (m, 1H), 2.09 (s, 3H), 2.06 (s, 3H), 1.94 (s, 3H), 1.87 (m, 1H), 1.66 (m, 1H), 1.17 (d, 1=6.0 Hz, 3H), 0.90 (27H), 0.09 (18H).

$^{13}$C NMR (d6-Acetone, 75 MHz) δ 169.2, 152.5, 145.2, 141.2, 140.9, 137.1, 136.7, 136.3, 135.9, 134.2, 126.2, 118.2, 75.3, 73.0, 67.7, 44.9, 27.4 (6×C), 27.3 (3×C), 25.2, 18.2 (3×C), 15.3, 14.8, −2.8, −2.9, −3.0, −3.1, −3.3, −3.4.

HRMS (ESI) calculated for $C_{37}H_{69}O_5Si_3$: m/z 677.4458 ([M−H]$^-$). found: m/z 677.4462 ([M−H]$^-$).

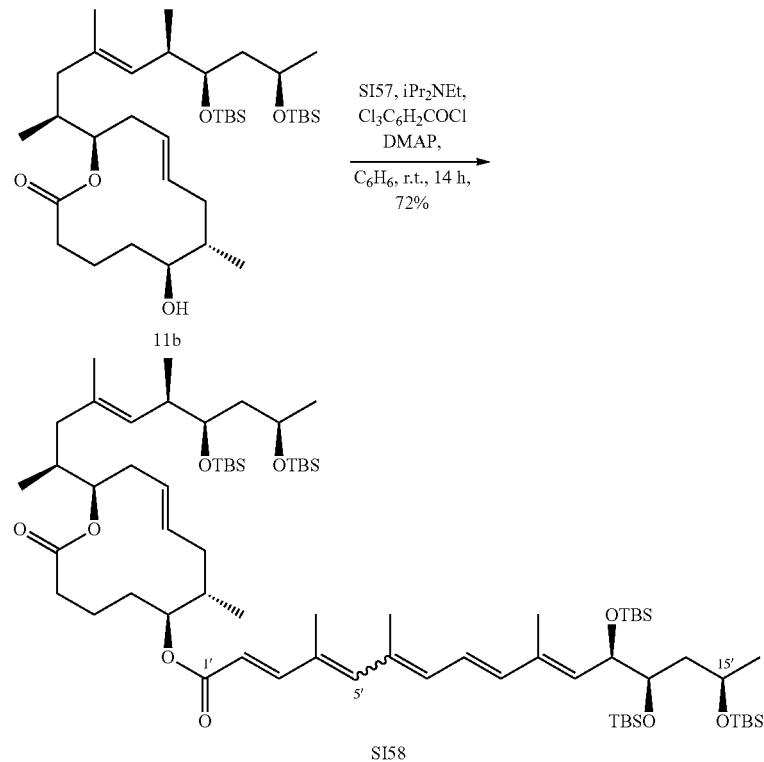

To a solution of SI57 (39 mg, 0.11 mmol, 4.4 eq.) in benzene (0.40 mL) were added diisopropylethyl amine (38 µL, 0.20 mmol, 3.6 eq.), 2,4,6-trichlorobenzoyl chloride (21 µL, 0.12 mmol, 2 eq.) and DMAP (35 mg). The reaction mixture was stirred at room temperature for 15 min and a solution of 11b (16 mg, 0.025 mmol) in benzene (0.3 mL) was added. After being stirred at room temperature for 14 h, an aqueous saturated solution of sodium hydrogenocarbonate was added to the reaction mixture. The aqueous layer was extracted three times with benzene. The combined organic layers were washed with brine, dried over MgSO$_4$, filtered and concentrated under reduced pressure. The crude product was purified on preparative TLC eluting with heptane/ethyl acetate (95:05) to give SI58 (23 mg, 0.018 mmol, 72%) as a yellow oil. A (4'E)/(4'Z)=54:46 mixture could be detected by $^1$H analysis.

$^1$H NMR (CDCl$_3$, 300 MHz, 4'Z isomer) δ 7.94 (d, J=15.5 Hz, 1H), 6.46 (dd, J=11.0, 14.8 Hz, 1H), 6.34 (d, J=14.9 Hz, 1H), 6.25 (s, 1H), 6.16 (d, J=11.0 Hz, 1H), 5.86 (d, J=15.5 Hz, 1H), 5.55 (d, J=8.1 Hz, 1H), 5.42 (m, 1H), 5.21-5.09 (2H), 5.04 (d, J=9.2 Hz, 1H), 4.76 (m, 1H), 4.43 (dd, J=3.6, 9.1 Hz, 1H), 3.90 (m, 1H), 3.63 (m, 1H), 3.57 (m, 1H), 3.33 (dd, J=4.1, 9.2 Hz, 1H), 2.55 (m, 1H), 2.52 (m, 1H), 2.24 (m, 1H), 2.15 (m, 1H), 2.10 (m, 1H), 2.05 (s, 3H), 2.02 (s, 3H), 1.97 (m, 1H), 1.94-1.92 (2H), 1.84 (s, 6H), 1.80-1.59 (10H), 1.53 (s, 3H), 1.26-1.23 (4H), 1.14 (d, J=6.0 Hz, 3H), 0.94 (d, J=6.7 Hz, 3H), 0.90 (s, 9H), 0.88 (s, 18H), 0.87 (s, 9H), 0.86 (s, 9H), 0.78 (d, J=6.6 Hz, 3H), 0.05 (s, 12H), 0.03 (s, 12H), 0.02 (s, 6H).

$^1$H NMR (CDCl$_3$, 75 MHz, 4'Z isomer) δ 173.3, 166.9, 150.6, 142.6, 141.4, 139.5, 135.6, 135.1, 134.6, 134.1, 134.0, 133.6, 131.9, 130.8, 123.8, 118.6, 75.0, 73.9, 72.9, 72.8, 71.3, 68.4, 66.1, 43.7, 42.8, 41.7, 38.0, 37.3, 36.3, 35.9, 35.6, 34.9, 32.7, 30.3, 25.9 (12×C), 25.8 (3×C), 23.5, 21.4, 20.7, 18.3 (2×C), 18.1 (3×C), 17.1, 15.9, 15.6, 14.5, 14.2, 13.6, −4.1, −4.2 (2×C), −4.3, −4.4 (2×C), −4.5, −4.6, −4.7, −4.8.

$^1$H NMR (CDCl$_3$, 300 MHz, 4'E isomer) δ 7.34 (d, J=15.5 Hz, 1H), 6.49 (dd, J=10.8, 14.9 Hz, 1H), 6.36 (d, J=15.5 Hz, 1H), 6.33 (s, 1H), 6.27 (d, J=11.3 Hz, 1H), 5.82 (d, J=15.5 Hz, 1H), 5.57 (d, J=8.1 Hz, 1H), 5.42 (m, 1H), 5.21-5.09 (2H), 5.04 (d, J=9.2 Hz, 1H), 4.76 (m, 1H), 4.43 (dd, J=3.6, 9.1 Hz, 1H), 3.90 (m, 1H), 3.63 (m, 1H), 3.57 (m, 1H), 3.33 (dd, J=4.2, 9.2 Hz, 1H), 2.55 (m, 1H), 2.52 (m, 1H), 2.24 (m, 1H), 2.15 (m, 1H), 2.10 (m, 1H), 2.05 (s, 3H), 2.02 (s, 3H), 1.97 (m, 1H), 1.94-1.92 (2H), 1.84 (s, 6H), 1.80-1.59 (10H), 1.53 (s, 3H), 1.26-1.23 (4H), 1.14 (d, J=6.0 Hz, 3H), 0.94 (d, J=6.7 Hz, 3H), 0.90 (s, 9H), 0.88 (s, 18H), 0.87 (s, 9H), 0.86 (s, 9H), 0.78 (d, J=6.6 Hz, 3H), 0.05 (s, 12H), 0.03 (s, 12H), 0.02 (s, 6H).

$^{13}$C NMR (CHCl$_3$, 75 MHz, 4'E isomer) δ 173.3, 166.9, 150.6, 143.6, 141.5, 139.8, 135.6, 135.1, 134.7, 134.3, 134.1, 132.2, 131.9, 130.6, 125.0, 116.7, 75.0, 73.6, 72.9, 72.8, 71.3, 68.3, 66.1, 42.9, 42.7, 41.7, 38.0, 37.3, 36.3, 35.9, 35.6, 34.9, 32.7, 30.3, 25.9 (12×C), 25.8 (3×C), 23.5, 21.3, 20.8, 18.3 (2×C), 18.1 (3×C), 17.1, 15.9, 15.6, 14.5, 14.2, 13.5, −4.1, −4.2 (2×C), −4.3, −4.4 (2×C), −4.5, −4.6, −4.7, −4.8.

To a solution of SI58 (10 mg) in THF (2.0 mL) was added TBAF (0.17 mL, 20 eq.). The solution was stirred at room temperature for 12 h. For stabilities issues of 20c, the reaction was quenched at 60% of conversion. CaCO$_3$ (34 mg), Dowex 50WX8-400 (94 mg) and MeOH (0.2 mL) were added and the reaction mixture was stirred for 20 min. After being filtered and concentrated under reduced pressure, the crude product was purified by preparative TLC (CH$_2$Cl$_2$/MeOH 90:10). The recovered triol was recycled. After one recycle, 20c was obtained (2 mg). A (4'E)/(4'Z)=52:48 mixture could be detected by $^1$H analysis.

$^1$H NMR (d6-Acetone, 300 MHz, 4'Z isomer) δ 7.91 (d, J=15.6 Hz, 1H), 6.64 (dd, J=11.1, 15.5 Hz, 1H), 6.45 (d, J=15.5 Hz, 1H), 6.33 (s, 1H), 6.16 (d, J=11.1 Hz, 1H), 5.93 (d, J=15.6 Hz, 1H), 5.59 (d, J=8.2 Hz, 1H), 5.45 (m, 1H), 5.23 (m, 1H), 5.19 (m, 1H), 5.05 (d, J=9.4 Hz, 1H), 4.83 (m, 1H), 4.28 (m, 1H), 4.22 (s, 1H, OH), 4.04 (s, 1H, OH), 3.95 (m, 1H), 3.67 (m, 1H), 151 (s, 1H, OH), 3.43 (m, 1H), 3.31 (m, 1H), 2.43 (m, 1H), 2.40 (m, 1H), 2.30 (m, 1H), 2.13 (m, 1H), 2.10 (m, 1H), 2.02 (s, 3H) 1.96 (m, 1H), 1.95 (m, 1H), 1.92-1.87 (7H), 1.80 (m, 1H), 1.77 (m, 1H), 1.76-1.73 (2H), 1.65 (m, 1H), 1.62-1.59 (4H), 1.53-1.49 (2H), 1.47-1.44 (2H), 1.25 (m, 1H), 1.20 (d, J=6.2 Hz, 3H), 0.90 (6H), 0.85 (d, J=6.7 Hz, 6H).

$^{13}$C NMR (d6-Acetone, 75 MHz, 4'Z isomer) δ 174.6, 168.0, 145.2, 144.0 142.8, 138.3, 136.9, 136.8, 136.0, 135.6, 134.5, 133.1, 132.1, 127.8, 126.1, 120.9, is 76.8, 76.4, 76.2, 74.2, 73.3, 70.9, 68.7, 45.2, 43.1, 42.8, 41.2, 40.2, 37.3, 36.4, 36.2, 35.4, 25.2, 22.1, 21.1, 20.9, 20.7, 18.6, 18.1, 17.2, 16.1, 15.4, 14.4.

$^1$H NMR (d6-Acetone, 300 MHz, 4'E isomer) δ 7.34 (d, J=15.6 Hz, 1H), 6.67 (dd, J=11.2, 15.5 Hz, 1H), 6.42 (d, J=15.5 Hz, 1H), 6.39 (s, 1H), 6.36 (d, J 11.2 Hz, 1H), 5.87 (d, J=15.6 Hz, 1H), 5.58 (d, J=8.2 Hz, 1H), 5.45 (m, 1H), 5.23 (m, 1H), 5.19 (m, 1H), 5.05 (d, J=9.4 Hz, 1H), 4.83 (m, 1H), 4.28 (m, 1H), 4.22 (s, 1H, OH), 4.04 (s, 1H, OH), 3.95 (m, 1H), 3.67 (m, 1H), 3.51 (s, 1H, OH), 3.43 (m, 1H), 3.31 (m, 1H), 2.43 (m, 1H), 2.40 (m, 1H), 2.30 (m, 1H), 2.13 (m, 1H), 2.10 (m, 1H), 2.02 (s, 3H) 1.96 (m, 1H), 1.95 (m, 1H), 1.92-1.87 (7H), 1.80 (m, 1H), 1.77 (m, 1H), 1.76-1.73 (2H), 1.65 (m, 1H), 1.62-1.59 (4H), 1.53-1.49 (2H), 1.47-1.44 (2H), 1.25 (m, 1H), 1.20 (d, J=6.2 Hz, 3H), 0.90 (6H), 0.85 (d, J=6.7 Hz, 6H).

$^{13}$C NMR (d6-Acetone, 75 MHz, 4'E isomer) δ 174.6, 168.0, 152.0, 141.3, 140.1, 138.3, 137.1, 136.9, 136.8, 135.8, 134.5, 133.1, 132.1, 127.8, 126.1, 118.7, 76.8, 76.4, 76.2, 74.2, 73.3, 70.9, 68.7, 45.1, 43.1, 42.8, 41.3, 40.2, 37.3, 36.4, 36.2, 35.4, 25.2, 22.1, 21.2, 20.9, 20.7, 18.6, 18.1, 17.2, 16.1, 15.4, 14.4.

HRMS-ESI calculated for C$_{43}$H$_{68}$NaO$_9$: m/z 751.4755 ([M+Na]$^+$). found: m/z 751.4775 ([M+Na]$^+$).

Compound SI20c

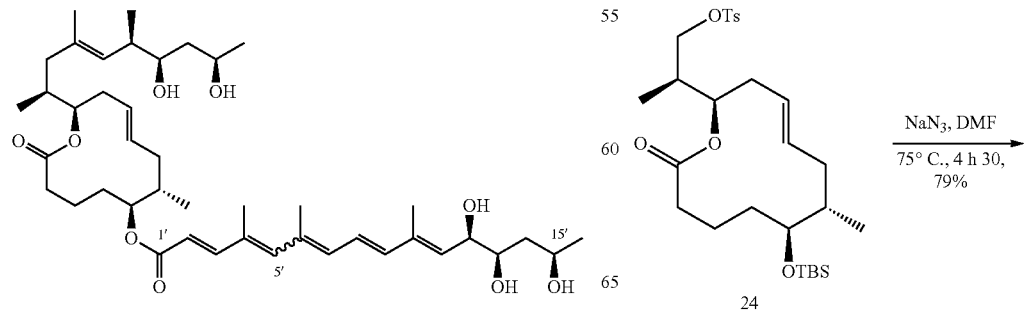

24

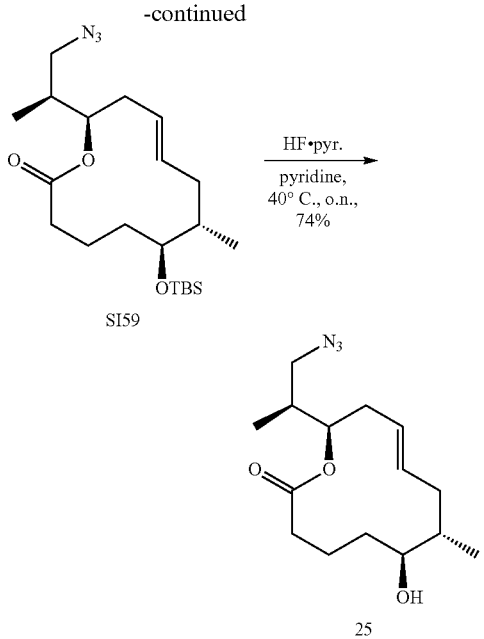

SI59

(6S,7S,12R,E)-12-((S)-1-azidopropan-2-yl)-6-(tert-butyldimethylsilyloxy)-7-methyloxacyclododec-9-en-2-one (SI59)

To a solution of 24 (300 mg, 0.56 mmol) in DMF (3.5 mL) was added NaN₃ (70 mg, 1.08 mmol, 1.9 eq.). The reaction mixture was heated at 75° C. for 4 h 30, before being cooled to 0° C. and diluted with water and diethyl ether. The aqueous phase was extracted three times with diethyl ether. The combined organic phases were washed with brine, dried over MgSO₄, filtered, and concentrated under reduced pressure. The crude product was purified by flash chromatography (cyclohexane/ethyl acetate 95:5 to 80:20) to give SI59 (182 mg, 0.44 mmol, 79%) as a colorless oil.

$^1$H NMR (CDCl$_3$, 300 MHz) δ 5.42 (m, 1H), 5.14 (m, 1H), 4.83 (m, 1H), 3.35 (dd, J=5.0, 12.2 Hz, 1H), 3.30 (m, 1H), 3.10 (dd, J=7.7, 12.2 Hz, 1H), 2.51 (ddd, J=3.4, 4.2, 11.9 Hz, 1H), 2.28 (m, 1H), 2.06 (m, 1H), 1.99-1.88 (3H), 1.86-1.83 (2H), 1.75-1.68 (2H), 1.61-1.55 (2H), 0.99 (d, J=6.5 Hz, 3H), 0.92 (d, J=6.7 Hz, 3H), 0.86 (s, 9H), 0.01 (s, 6H).

$[α]^{20}_D$=−105.9 (c 0.2, CHCl$_3$)

IR: 2096 cm$^{-1}$ (N$_3$)

(6S,7S,12R,E)-12-((S)-1-azidopropan-2-yl)-6-hydroxy-7-methyloxacyclododec-9-en-2-one (25)

To a solution of SI59 (20 mg, 0.05 mmol) in pyridine (1.6 mL) at 0° C. was added HF.pyridine (0.57 mL). The reaction mixture was heated at 40° C. overnight, before being neutralized by the addition of a saturated aqueous solution of NaHCO$_3$. The aqueous phase was extracted three times with diethyl ether. The organic phases were combined, washed with an aqueous solution of CuSO$_4$ (15%), dried over MgSO$_4$, filtered and concentrated under reduced pressure. The crude product was purified by preparative TLC (heptane/ethyl acetate 50:50) to give 25 (10.9 mg, 0.037 mmol, 74%) as a colorless oil.

$^1$H NMR (CDCl$_3$, 300 MHz) δ 5.43 (m, 1H), 5.22 (m, 1H), 4.97 (ddd, J=2.5, 6.7, 11.6 Hz, 1H), 3.46 (m, 1H), 3.37 (dd, J=5.1, 12.2 Hz, 1H), 3.4 (dd, J=7.5, 12.2 Hz, 1H), 2.45-2.33 (2H), 2.24-2.13 (2H), 2.00-1.79 (3H), 1.72-1.59 (3H), 1.54-1.42 (2H), 1.01 (d, J=6.6 Hz, 3H), 0.99 (d, J=6.4 Hz, 3H).

$^{13}$C NMR (CDCl$_3$, 75 MHz) δ 174.0, 135.0, 126.1, 73.9, 73.3, 54.0, 38.0, 37.9, 36.8, 36.5, 35.2, 33.0, 19.3, 18.3, 14.5.

Compound SI60

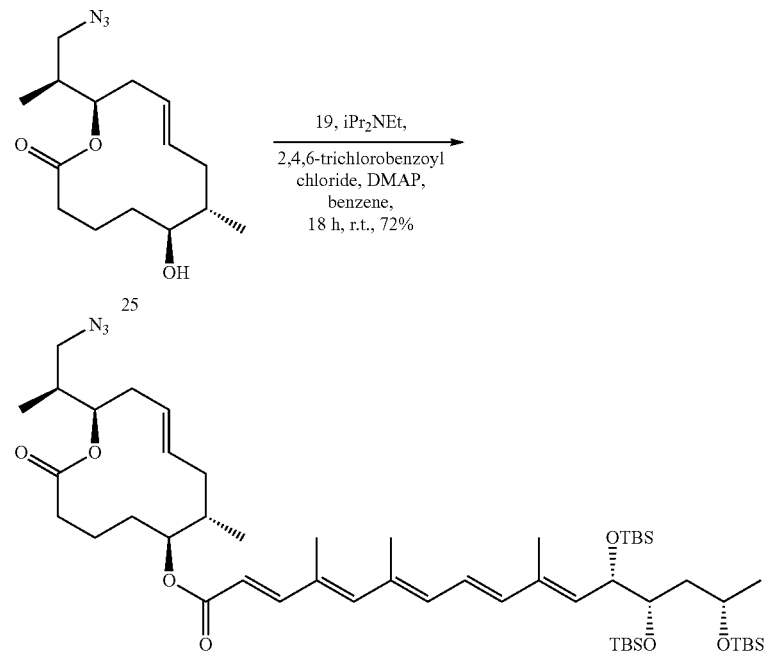

SI60

To a solution of 25 (80 mg, 0.12 mmol) in benzene (0.7 mL) were added diisopropylethylamine (70 μL, 0.39 mmol), 2,4,6-trichlorobenzoyl chloride (38 μL, 0.23 mmol) and DMAP (62 mg). The reaction mixture was stirred at room temperature for 15 min and a solution of 19 (20 mg, 0.068 mmol) in benzene (0.6 mL) was added. After being stirred at room temperature for 18 h, an aqueous saturated solution sodium of hydrogenocarbonate was added to the reaction mixture. The aqueous layer was extracted three times with benzene. The combined organic layers were washed with brine, dried over MgSO$_4$, filtered and concentrated under reduced pressure. The crude product was purified on preparative TLC eluting with heptane/ethyl acetate 95:05) to J=5.9 Hz, 3H), 1.00 (d, J=6.8 Hz, 3H), 0.92 (d, J=6.3 Hz, 3H), 0.87 (s, 9H), 0.86 (s, 9H), 0.85 (s, 9H), 0.04 (s, 9H), 0.03 (s, 3H), 0.01 (s, 3H), −0.04 (s, 3H).

$^{13}$C NMR (CDCl$_3$, 75 MHz, 4'E isomer) δ 172.8, 166.8, 150.8, 143.7, 139.8, 135.4, 135.2, 134.6, 134.3, 134.1, 132.2, 125.1, 123.7, 116.3, 78.4, 73.6, 72.8, 71.3, 66.0, 54.1, 42.6, 37.9, 37.8, 36.5, 35.4, 34.3, 29.5, 25.9 (6×C), 25.8 (3×C), 23.5, 20.4, 19.1, 18.2, 18.1, 17.9, 17.1, 14.4, 14.2, 13.5, −4.2 (2×C), −4.3, −4.5, −4.6, −4.7.

HRMS-ESI calculated for C$_{52}$H$_{93}$N$_3$O$_7$Si$_3$Na: m/z 978.6213 ([M+Na]$^+$). found: m/z 962.6203 ([M+Na]$^+$).

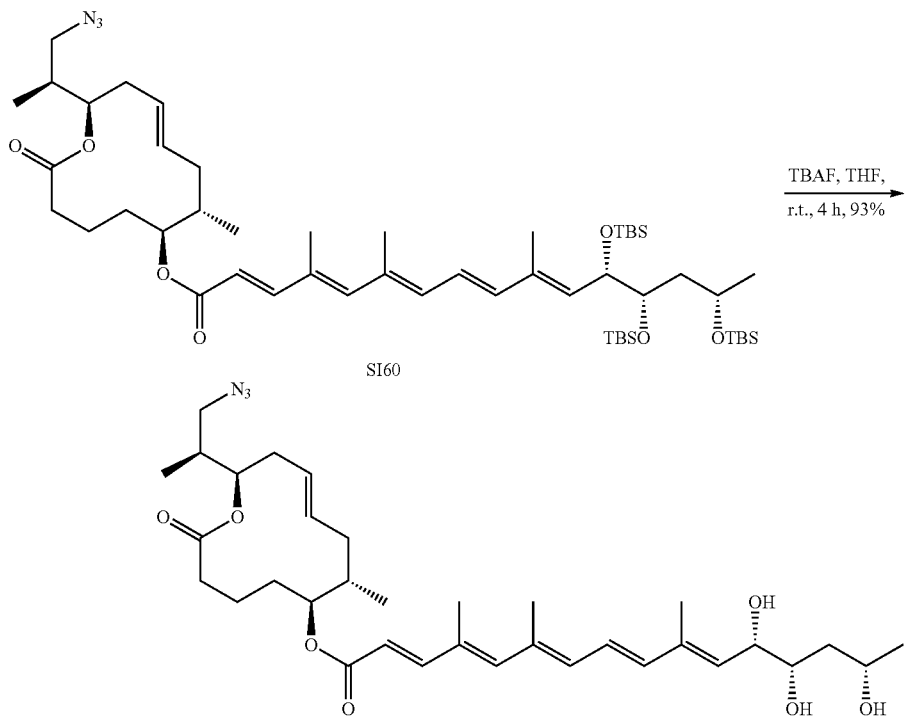

Compound 26 give SI60 (55 mg, 0.058 mmol, 72%) as a yellow oil. A (4'E)/(4'Z)=50:50 mixture could be detected by $^1$H analysis.

$^1$H NMR (CDCl$_3$, 300 MHz, 4'Z isomer) δ 7.94 (d, J=15.6 Hz, 1H), 6.48 (dd, J=11.3, 14.6 Hz, 1H), 6.36 (d, J=14.7 Hz, 1H), 6.24 (s, 1H), 6.15 (d, J=11.3 Hz, 1H), 5.87 (d, J 15.6 Hz, 1H), 5.57 (d, J=8.3 Hz, 1H), 5.42 (m, 1H), 5.20 (m, 1H), 4.89 (m, 1H), 4.73 (m, 1H), 4.46 (dd, J=3.6, 9.1 Hz, 1H), 3.90 (m, 1H), 3.62 (m, 1H), 3.37 (m, 1H), 3.12 (m, 1H), 2.48 (m, 1H), 2.33 (m, 1H), 2.19-2.08 (2H), 2.04 (s, 3H), 2.02 (s, 3H), 1.95-1.85 (2H), 1.84 (s, 3H), 1.79-1.56 (8H), 1.13 (d, J 5.9 Hz, 3H),1.00 (d, J=6.8 Hz, 3H), 0.92 (d, J=6.3 Hz, 3H), 0.87 (s, 9H), 0.86 (s, 9H), 0.85 (s, 9H), 0.04 (s, 9H), 0.03 (s, 3H), 0.01 (s, 3H), −0.04 (s, 3H).

$^1$H NMR (CDCl$_3$, 300 MHz, 4'E isomer) δ 7.36 (d, J 15.5 Hz, 1H), 6.50 (dd, J=11.4, 15.0 Hz, 1H), 6.36 (d, J=14.7 Hz, 1H), 6.35 (s, 1H), 6.29 (d, J=11.4 Hz, 1H), 5.84 (d, J=15.5 Hz, 1H), 5.54 (d, J=8.6 Hz, 1H), 5.42 (m, 1H), 5.20 (m, 1H), 4.89 (m, 1H), 4.73 (m, 1H), 4.46 (dd, J=3.6, 9.1 Hz, 1H), 3.90 (m, 1H), 3.62 (m, 1H), 3.37 (m, 1H), 3.12 (m, 1H), 2.48 (m, 1H), 2.33 (m, 1H), 2.19-2.08 (2H), 2.04 (s, 3H), 2.02 (s, 3H), 1.95-1.85 (2H), 1.84 (s, 3H), 1.79-1.56 (8H), 1.13 (d, To a solution of SI160 (55 mg, 0.057 mmol) in THF (0.5 mL) was added TBAF (0.52 mL, 1M in THF). The reaction mixture was stirred at room temperature for 4 h. CaCO$_3$ (106 mg), Dowex 50WX8-400 (320 mg) and MeOH (0.7 mL) were added and the reaction mixture was stirred for 45 min. After being filtered over Celite and concentrated under reduced pressure, the crude product was purified by preparative TLC (CH$_2$Cl$_2$/MeOH 90:10) to give 26 (32.5 mg, 0.053 mmol, 93%). A (4'E)/(4'Z) 52:48 mixture could be detected by $^1$H analysis.

$^1$H NMR (d6-Acetone, 300 MHz, 4'Z isomer) δ 7.92 (d, J=15.6 Hz, 1H), 6.66 (dd, J=11.2 Hz, 14.7 Hz, 1H), 6.45 (d, J=14.5 Hz, 1H), 6.34 (s, 1H), 6.16 (d, J=11.0 Hz, 1H), 5.94 (d, J=15.6 Hz, 1H), 5.60 (m, 1H), 5.53 (m, 1H), 5.28 (m, 1H), 4.89 (m, 1H), 4.69 (m, 1H), 4.28 (m, 1H), 4.18 (m, 1H, OH), 4.02 (m, 1H, OH), 3.99 (m, 1H), 3.65 (m, 1H), 3.47 (dd, J=5.2, 12.3 Hz, 1H), 3.23 (dd, J=7.3, 12.3 Hz, 1H), 2.86 (s, 1H, OH), 2.52 (m, 1H), 2.40 (m, 1H), 2.21 (m, 1H), 2.09 (s, 3H), 2.02 (s, 3H), 1.90 (s, 3H), 1.82 (m, 1H), 1.70-1.65 (5H), 1.55-1.52 (5H), 1.11 (d, J=6.0 Hz, 3H), 0.99 (d, J=6.8 Hz, 3H), 0.90 (d, J=6.2 Hz, 3H).

$^{13}$C NMR (d6-Acetone, 100 MHz, 4'Z isomer) δ 173.8, 167.8, 145.3, 144.1, 142.8, 138.3, 136.9, 136.3, 135.8, 135.6, 133.1, 127.5, 126.2, 120.6, 80.1, 76.7, 74.3, 73.3, 68.7, 55.6, 42.8, 39.5, 37.9, 37.0, 36.0, 25.2, 22.0, 21.6, 20.8, 18.6, 18.1, 15.4 15.3, 14.4.

$^1$H NMR (d6-Acetone, 300 MHz, 4'E isomer) δ 7.36 (d, J=15.5 Hz, 1H), 6.64 (dd, J=11.7, 15.5 Hz, 1H), 6.47 (s, 1H), 6.40 (d, J=15.5 Hz, 1H), 6.36 (d, J=11.7 Hz, 1H), 5.89 (d, J=15.5 Hz, 1H), 5.60 (m, 1H), 5.53 (m, 1H), 5.28 (m, 1H), 4.89 (m, 1H), 4.69 (m, 1H), 4.28 (m, 1H), 4.18 (m, 1H, OH), 4.02 (m, 1H, OH), 3.99 (m, 1H), 3.65 (m, 1H), 3.47 (dd, J=5.2, 12.3 Hz, 1H), 3.23 (dd, J=7.3, 12.3 Hz, 1H), 2.86 (s, 1H, OH), 2.52 (m, 1H), 2.40 (m, 1H), 2.21 (m, 1H), 2.09 (s, 3H), 2.02 (s, 3H), 1.90 (s, 3H), 1.82 (m, 1H), 1.70-1.65 (5H), 1.55-1.52 (5H), 1.11 (d, J=6.0 Hz, 3H), 0.99 (d, J=6.8 Hz, 3H), 0.90 (d, J=6.2 Hz, 3H).

$^{13}$C NMR (d6-Acetone, 75 MHz, 4'E isomer) δ 173.8, 167.8, 152.2, 141.3, 141.0, 138.2, 137.2, 136.9, 136.3, 135.9, 133.1, 127.5, 126.2, 118.4, 80.1, 76.7, 74.3, 73.3, 68.7, 55.6, 42.8, 39.7, 37.9, 36.9, 36.0, 25.2, 22.0, 21.6, 20.8, 18.6, 18.1, 15.4, 15.3, 14.4.

HRMS-ESI calculated for $C_{34}H_{51}N_3O_7Na$: m/z 636.3619 ([M+Na]$^+$). found: m/z 636.3608 ([M+Na]$^+$).

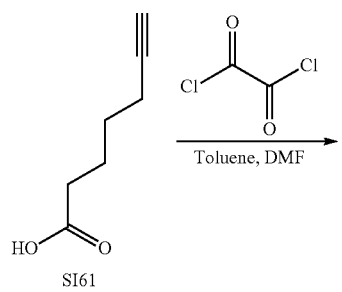

SI61

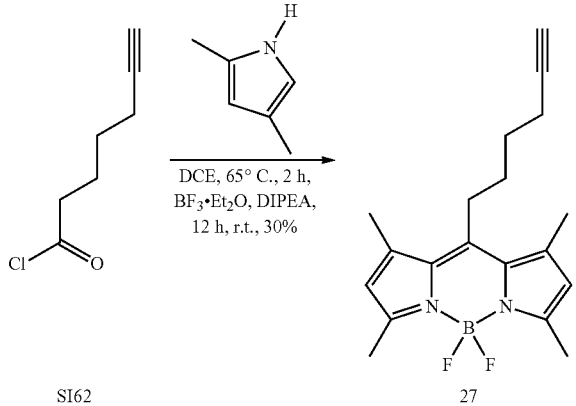

SI62     27

4,4-Difluoro-8-(hept-6-yne)-1,3,5,7-tetramethyl-4-bora-3a,4a-diaza-s-indacene (27)

Oxalylchloride (518 μL, 5.94 mmol, 1.5 eq.) was added dropwise to a solution of hept-6-ynoic acid SI61 (0.5 mL, 3.96 mmol) in toluene (19 mL). A catalytic amount of DMF (2 drops) was added and the solution was stirred at room temperature for 3 h. After concentration, the residue was co-evaporated with toluene and the resulting crude hept-6-ynoyl chloride was used without further purification. A 1M solution of hept-6-ynoyl chloride in dichloroethane was made up and 2,4-dimethyl-1H-pyrrole (856 μL, 8.32 mmol, 2.1 eq.) was added. The resulting reaction mixture was stirred at 65° C. for 2 h. After cooling to room temperature, BF$_3$.OEt$_2$ (2.45 mL, 19.8 mmol, 0.5 eq.) was added over 5 min, followed by the dropwise addition of diisopropylethyl amine (2.76 mL, 15.84 mmol, 4 eq.). Argon was then bubbled for 5 min through the solution, and the reaction mixture was stirred for 12 h at room temperature, before being washed with water and extracted with ethyl acetate. The organic phase was dried over MgSO$_4$, filtered and concentrated under reduced pressure. The crude product was purified by flash chromatography (cyclohexane/ethyl acetate 80:20) to give 27 (390 mg, 1.19 mmol, 30%) as a red oil that slowly crystallizes.

$^1$H NMR (CDCl$_3$, 300 MHz) δ 6.27 (s, 2H), 3.14-3.09 (2H), 2.75 (s, 6H), 2.62 (s, 6H), 2.51-2.47 (2H), 2.21 (m, 1H), 1.97-1.93 (4H).

$^{13}$C NMR (CDCl$_3$, 75 MHz) δ 153.6 (2×C), 145.8 (2×C), 140.3 (2×C), 131.3, 121.5 (2×C), 83.6, 68.9, 30.4, 28.7, 27.6, 18.0 (2×C), 16.1 (2×C), 14.3.

The spectral data are in agreement with those reported in the literature.[21]

$^{11}$B NMR (CDCl$_3$, 128 MHz) δ 3.87 (t, J 33.2 Hz)

Compound 28

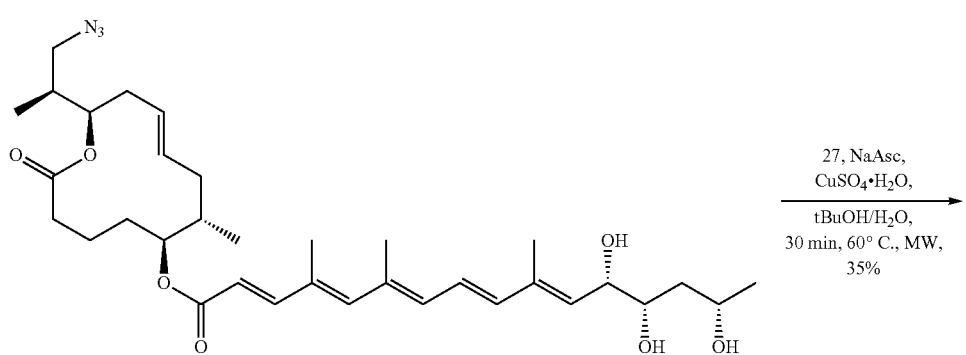

27, NaAsc, CuSO$_4$·H$_2$O,
tBuOH/H$_2$O,
30 min, 60° C., MW,
35%

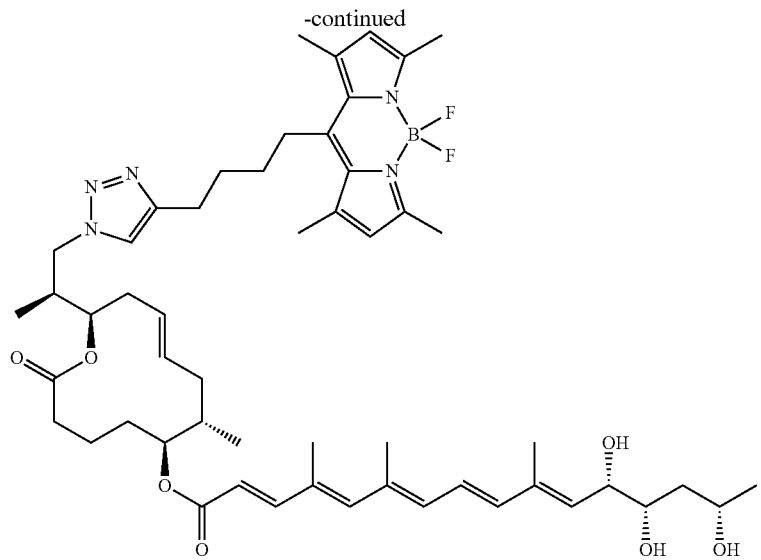

28

To a solution of 26 (14 mg, 0.023 mmol) in a mixture of t-BuOH (0.125 mL) and water (0.075 mL) were added a solution of sodium ascorbate (14 μL, 15%) in water, a solution of CuSO$_4$.5H$_2$O (17 μL, 15%) in water and 27 (8.3 mg, 0.025 mmol, 1.1 eq.). The reaction mixture was heated for 30 min at 60° C. (MW irradiation), before being purified by preparative TLC (heptane/ethyl acetate 20:80) to give 28 (8 mg, 0.008 mmol, 35%). A (4'E)/(4'Z)=50:50 mixture could be detected by $^1$H analysis.

$^1$H NMR (d6-Acetone, 400 MHz, 4'Z isomer) δ 7.92 (d, J=15.6 Hz, 1H), 7.74 (s, 1H), 6.66 (dd, J=11.5 Hz, 15.0 Hz, 1H), 6.45 (d, J=15.5 Hz, 1H), 6.33 (s, 1H), 6.17 (s, 2H), 6.16 (d, J=11.5 Hz, 1H), 5.94 (d, J=15.6 Hz, 1H), 5.60 (m, 1H), 5.52 (m, 1H), 5.26 (m, 1H), 5.20 (m, 1H), 4.89 (m, 1H), 4.68 (m, 1H), 4.47 (dd, J=13.79, 5.15 Hz, 1H), 4.28 (m, 1H), 4.22 (m, 1H, OH), 4.16 (m, 1H), 4.02 (m, 1H, OH), 3.99 (m, 1H), 3.67 (m, 1H), 3.07-3.02 (2H), 2.83-2.77 (3H), 2.52 (m, 1H), 2.45 (s, 6H), 2.43 (s, 6H), 2.35-2.30 (2H), 2.25-2.19 (3H), 2.09 (s, 3H), 2.03 (s, 3H), 1.91 (s, 3H), 1.82 (m, 1H), 1.76-1.66 (8H), 1.54-1.51 (2H), 1.12 (d, J=6.1 Hz, 3H), 0.91 (d, J=6.2 Hz, 3H), 0.85 (d, J 6.9 Hz, 3H).

$^{13}$C NMR (d6-Acetone, 75 MHz, 4'Z isomer) δ 174.0, 167.8, 155.3 (2×C), 148.7 (2×C), 145.4, 144.1, 142.8, 138.3, 137.0 (3×C), 136.3, 135.9, 135.8, 135.7, 134.2, 133.1, 127.3, 126.1, 123.8, 123.4 (2×C), 120.6, 80.1, 76.8, 74.6, 73.3, 68.7, 53.6, 42.8, 40.5, 39.6, 38.0, 36.9, 36.0, 33.0, 29.9, 26.9, 25.3, 22.0, 21.7, 20.8, 18.6, 18.1, 17.4 (4×C), 15.4, 15.3, 14.4.

$^1$H NMR (d6-Acetone, 400 MHz, 4'E isomer) δ 7.74 (s, 1H), 7.37 (d, J=15.4 Hz, 1H), 6.64 (dd, J=11.2, 14.8 Hz, 1H), 6.46 (s, 1H), 6.40 (d, J=14.8 Hz, 1H), 6.36 (d, J=11.2 Hz, 1H), 6.17 (s, 2H), 5.89 (d, 15.5 Hz, 1H), 5.60 (m, 1H), 5.53 (m, 1H), 5.28 (m, 1H), 5.20 (m, 1H), 4.89 (m, 1H), 4.68 (m, 1H), 4.47 (dd, J=13.79, 5.15 Hz, 1H), 4.28 (m, 1H), 4.22 (m, 1H), 4.16 (m, 1H), 4.02 (m, 1H, OH), 3.99 (m, 1H), 3.67 (m, 1H), 3.07-3.02 (2H), 2.83-2.77 (3H), 2.52 (m, 1H), 2.45 (s, 6H), 2.43 (s, 6H), 2.35-2.30 (2H), 2.25-2.19 (3H), 2.09 (s, 3H), 2.03 (s, 3H), 1.91 (s, 3H), 1.82 (m, 1H), 1.76-1.66 (8H), 1.54-1.51 (2H), 1.12 (d, J=6.1 Hz, 3H), 0.91 (d, J=6.2 Hz, 3H), 0.85 (d, J=6.9 Hz, 3H).

$^{13}$C NMR (d6-Acetone, 75 MHz, 4'E isomer) δ 174.0, 167.8, 155.3 (2×C), 152.2, 148.7 (2×C), 141.4, 140.9, 138.3, 137.2 137.0 (3×C), 136.3, 135.9, 135.8, 134.2, 133.1, 127.3, 126.1, 123.8, 123.4 (2×C), 118.3, 80.1, 76.8, 74.6, 73.3, 68.7, 53.6, 42.8, 40.5, 39.6, 38.0, 36.9, 36.0, 33.0, 29.9, 26.9, 25.3, 22.0, 21.6, 20.8, 18.6, 18.1, 17.4 (4×C), 15.4, 15.3, 14.4.

$^{11}$B NMR (d6-Acetone, 128 MHz) δ 3.54 (t, J=32.4 Hz)
$^{19}$F NMR (d6-Acetone, 373 MHz) δ −141.60−−141.89 (overlap of two quadruplets with J=32.2 Hz)
HRMS-ESI calculated for C$_{53}$H$_{74}$BF$_2$N$_5$O$_7$Na: m/z 964.5550 ([M+Na]$^+$). found: m/z 964.5534 ([M+Na]$^+$).

2,2-difluoro-8-(4-{1-[(2S)-2-[(2R,4E,7S,8S)-8-hydroxy-7-methyl-12-oxo-1-oxacyclododec-4-en-2-yl]propyl]-1H-1,2,3-triazol-4-yl}butyl)-4,6,10,12-tetramethyl-1λ$^5$,3-diaza-2λ$^4$-boratricyclo[7.3.0.0$^{3,7}$]dodeca-1 (12),4,6,8,10-pentaen-1-ylium, (compound 29)

To a solution of 25 (10 mg; 0.034 mmol) in tBuOH/H$_2$O (1:1; 130 μL/130 μL) were added an aqueous solution of sodium ascorbate (50 μL; 15%), an aqueous solution of CuSO$_4$.5H$_2$O (80 μL; 10%) and 27 (11 mg; 0.034 mmol). The reaction mixture was warmed at 60° C. for 24 h before being diluted with diethyl ether and water. The aqueous phase was extracted three times with diethyl ether. The combined organic phases were washed with brine, dried over magnesium sulfate filtered and concentrated under reduced pressure. The crude product was purified by preparative TLC (Hexane/ethyl acetate=25:75) to give 29 as a red oil (18 mg; 0.029; 85%).

$^1$H NMR (CDCl$_3$, 300 MHz) δ 7.31 (s; 1H); 6.03 (s; 2H); 5.45 (m; 1H); 5.20 (m; 1H); 4.95 (m; 1H); 4.42 (dd; J=5.1; 13.9 Hz; 1H); 4.07 (dd; J=8.1; 13.9 Hz; 1H); 3.44 (m; 1H); 3.00-2.94 (2H); 2.80-2.74 (2H); 2.50 (s; 6H); 2.37 (s; 6H); 2.31-2.25 (2H); 1.97-1.93 (2H); 1.93-1.75 (5H); 1.72-1.58 (6F1); 1.52-1.47 (2H); 0.99 (d; J=6.7 Hz; 3H); 0.85 (d; J=6.9 Hz; 3H).

$^{13}$C NMR (CDCl$_3$, 75 MHz) δ 174.1; 153.8; 147.3; 146.0; 140.3; 135.4; 131.4; 125.5; 121.6; 121.4; 74.3; 73.3; 52.2; 38.6; 38.0; 36.6; 35.2; 32.9; 31.4; 29.7; 28.1; 25.4; 19.2; 18.6; 16.4; 14.4; 14.1.

HRMS-ESI Calculated for $C_{34}H_{48}BF_2N_5O_3Na$: m/z 646.3716 ([M+Na]⁺). found: m/z 646.3706 ([M+Na]⁺).

Following the procedure for the synthesis of compound 29, compound 26 was reacted with the appropriate commercially available alkyne. After work-up and purification, compounds 28b and 28c were obtained.

(6S,7S,9E,12R)-12[(2S)-1-(4-pentyl-1H-1,2,3-triazol-1-yl)propan-2-yl]-7-methyl-2-oxo-1-oxacyclododec-9-en-6-yl(2E,4E,6E,8E,10E,12S,13R,15S)-12,13,15-trihydroxy-4,6,10-trimethylhexadeca-2,4,6,8,10-pentaenoate (compound 28b)

A (4'E)/(4'Z)=42:58 mixture could be detected by ¹H analysis.

¹H NMR (Acetone-d6, 300 MHz) δ 7.92 (d, J=15.6 Hz, 1H, Z isomer), 7.70 (s, 1H), 7.37 (d, J=15.4 Hz, 1H, E isomer), 6.63 (dd, 111.1, 15.0 Hz, 1H), 6.47 (s, 1H), 6.36 (d, J=15.0 Hz, 1H), 6.17 (d, J=11.1 Hz, 1H), 5.89 (d, J=15.5 Hz, 1H), 5.60 (d, J=8.7 Hz, 1H), 5.50 (m, 1H), 5.30 (m, 1H), 4.90 (m, 1H), 4.70 (m, 1H), 4.47 (dd, J=5.4, 13.7 Hz, 1H), 4.28 (m, 1H), 4.16 (dd, J=8.8, 13.7 Hz, 1H), 4.04 (m, 1H), 3.67 (m, 1H), 2.67-2.60 (2H), 2.51 (m, 1H), 2.43 (m, 1H), 2.34 (m, 1H), 2.21 (m, 1H), 2.09 (s, 3H), 1.98 (s, 3H), 1.96-1.87 (2H), 1.90 (s, 3H), 1.80-1.75 (2H), 1.70-1.60 (8H), 1.54-1.51 (4H), 1.35-1.28 (4H), 1.12 (d, J 6.1 Hz, 3H), 0.91 (s, 3H), 0.87 (s, 3H).

HRMS (ESI) calculated for $C_{41}H_{63}N_3O_7Na$: m/z 732.4558 ([M+Na]⁺). found: m/z 732.4548 ([M+Na]⁺).

(6S,7S,9E,12R)-12-[(2S)-1-{4-[(1S)-1-hydroxyethyl]-1H-1,2,3-triazol-1-yl}propan-2-yl]-7-methyl-2-oxo-1-oxacyclododec-9-en-6-yl(2E,4E,6E,8E,10E,12S,13R,15S)-12,13,15-trihydroxy-4,6,10-trimethylhexadeca-2,4,6,8,10-pentaenoate (compound 28c)

A (4'E)/(4'Z)=42:58 mixture could be detected by ¹H analysis.

¹H NMR (Acetone-d6, 300 MHz) δ 7.92 (d, J=15.6 Hz, 1H, Z isomer), 7.70 (s, 1H), 7.37 (d, J=15.4 Hz, 1H, E isomer), 6.63 (dd, J=11.1, 15.0 Hz, 1H), 6.47 (s, 1H), 6.36 (d, J=15.0 Hz, 1H), 6.17 (d, J=11.1 Hz, 1H), 5.89 (d, J=15.5 Hz, 1H), 5.60 (d, J=9.5 Hz, 1H), 5.50 (m, 1H), 5.30 (m, 1H), 4.99-4.88 (2H), 4.70 (m, 1H), 4.50 (dd, J=5.3, 13.8 Hz, 1H), 4.30-4.18 (3H), 4.04 (m, 1H), 3.95 (m, 1H), 3.67 (m, 1H), 3.58 (m, 1H), 2.51 (m, 1H), 2.43 (m, 1H), 2.34 (m, 1H), 2.21 (m, 1H), 2.09 (s, 3H), 1.98 (s, 3H), 1.96-1.87 (2H), 1.90 (s, 3H), 1.80-1.75 (2H), 1.70-1.60 (4H), 1.54-1.51 (2H), 1.48 (d, J=6.5 Hz, 3H), 1.35-1.28 (2H), 1.12 (d, J=6.1 Hz, 3H), 0.91 (s, 3H), 0.87 (s, 3H).

Biological Data

1. Immunomodulatory Effects

Materials and Methods

All variants described hereinabove were tested for biological activity in the 0.4-16 μM range, using mycolactones A/B purified from M. ulcerans 1615 (ATCC 35840) as a reference.

Stock solutions (4 mM) prepared in dimethyl sulfoxide (DMSO) for all compounds, were kept at −20° C. They were diluted on the day of the experiment in cell culture medium. In all cases, mycolactone-treated samples were compared with solvent-treated controls. Four types of tests reflecting the major effects of mycolactone on the biology of human cells were used: (A) effect on global cell metabolic activity, (B) on cell viability, (C) on activation-induced production of cytokine and (D) on cell trafficking.

(A) The cytopathic activity of mycolactone and variants was assessed in a [3-(4,5-Dimethylthiazol-2-yl)-2,5-Diphenyltetrazolium Bromide] (MTT) assay, using the epithelial HeLa cell line (ATCC®; CCL-2) as a model. Briefly, HeLa cells were plated in 96-well plates ($10^4$ cells/well) in Dulbecco's Modified Eagle culture medium supplemented with 10% fetal calf serum and 2 mM L-Glutamine. After 16 h, mycolactone or variants dilutions (final concentration 0.4-8 μM) were added to the wells, and incubated with the cells for 48 h, prior to the addition of MTT at 50 μg/ml. After 4 h, culture supernatants were removed and the formed formazan crystals dissolved in dimethyl sulfoxide (DMSO) for absorbance measurement.

(B) HeLa cell death being negligible in the concentration and time frame conditions used in (A), the cytotoxicity of 16 μM mycolactone and variants was evaluated after 48 h of incubation by cell exclusion of the Trypan Blue dye. Here, one part of Trypan blue (0.4% in phosphate-buffered saline PBS) was mixed with one part cell suspension (recovered from cell culture wells by trypsin treatment). The mixture was incubated for 3 min at room temperature and unstained (viable) and stained (nonviable) cells counted separately with a hemacytometer.

(C) The immunosuppressive activity of mycolactone and variants was measured on Jurkat T cells (ATCC®; TIB-152™ clone E6-1), as models of human T lymphocytes. Cells were inoculated in 96-well plates ($5 \times 10^5$ cells/well in RPMI 1640 medium supplemented with 10% fetal calf serum and 2 mM L-Glutamine) then incubated with serial dilutions of the various compounds for 4 h, and stimulated for 20 h with 50 ng/ml phorbol-12-myristate-13-acetate (PMA) and 1 μg/ml calcium ionophore. The production of IL-2 was then assessed in culture supernatants by ELISA.

(D) The effect of mycolactone and variants on T cell homing was assessed through their inhibitory effect on the expression of CD62-L receptor by human peripheral blood cells (PBLs). Human PBLs were isolated from total blood by Ficoll density gradient centrifugation. They were incubated in 96-well plates ($10^5$ cells/well in RPMI 1640 medium supplemented with 10% fetal calf serum and 2 mM L-Glutamine) with mycolactone or variant for 72 h. Cells were then fixed for 20 min in 4% paraformaldehyde (PFA) and stained with an anti-CD62-L antibody coupled with phycoerythrin in a solution of PBS, BSA 0.5%, saponin 0.05%, then analysed by flow cytometry.

Results and Conclusions

The results of A, C and D tests are summarized in the table below and those of B in FIG. 4. Data correspond to mean absorbance measurements (A, C), mean cell numbers (B) or mean fluorescence intensities (D). They are expressed as percentages, relatively to solvent-treated controls and are representative of at least two independent experiments. For each variant and experiment, the $IC_{50}$ value (concentration at which the compound induces 50% of mycolactone maximal activity) and corresponding % of mycolactone activity are shown.

CD62-L expression by lymphocytes. Similar results were obtained with the fluorescent derivatives 28 and 29.

Notably, the variant 22 corresponding to the core and southern C1'-C16' fragment showed no cytotoxic nor cytopathic effect at concentrations <16 μM, while inducing significant reduction of IL-2 production and CD62-L expression at concentrations >4 μM.

Compared to mycolactones A/B, the C8-desmethyl mycolactones A/B variants 20a and 20b showed equivalent cytotoxicity at 16 μM but a cytopathic activity reduced by 4 fold. Particularly noteworthy is the role of the C12'-hydroxyl: when this functional group is deleted or differentially oriented, as in compounds 20d and 20c compared to compound 20a respectively, both the cytopathic and cytotoxic activities are significantly reduced. This demonstrates that overall the compounds according to the invention are expected to be less cytopathic than natural mycolactones.

| Compound | Conc. (μM) | Metabolic activity (MA: mean absorbance) (A) | | Cytokine production (M.A.: mean absorbance) (C) | | CD62-L expression (MFI: mean fluorescence intensity) (D) | |
|---|---|---|---|---|---|---|---|
| | | % relative to control | % inhibition relative to control (100 − (100 × MA (mycolactone)/ MA (solvent)) | % relative to control | % inhibition relative to control (100 − (100 × MA (mycolactone)/ MA (solvent)) | % relative to control | % inhibition relative to control (100 − (100 × MFI (mycolactone)/ MFI (solvent)) |
| Mycolactone | 0.4 | 70 | 3.5 (100%) | 99 | 0.1 (100%) | 100 | <0.03 (100%) |
| | 4 | 80 | | 100 | | 100 | |
| | 8 | 100 | | 100 | | 100 | |
| 22 | 0.4 | 0 | NA | 15 | 3 (3.3%) | ND | 3.7 (0.8%) |
| | 4 | 0 | | 58 | | 60 | |
| | 8 | 0 | | 95 | | 70 | |
| 11c | 0.4 | 0 | 16 (20%) | 0 | 8 (1.2%) | ND | 16 (0.2%) |
| | 4 | 30 | | 30 | | 20 | |
| | 8 | 40 | | 50 | | 40 | |
| 20a | 0.4 | 0 | 14 (25%) | 0 | 6 (1.6%) | ND | ND |
| | 4 | 10 | | 40 | | ND | |
| | 8 | 30 | | 70 | | ND | |
| 20b | 0.4 | 0 | 15 (23%) | 20 | 4 (2.5%) | ND | 8 (0.4%) |
| | 4 | 10 | | 55 | | 0 | |
| | 8 | 15 | | 92 | | 50 | |
| 20c | 0.4 | 0 | >16 (<20%) | 18 | 6.5 (1.5%) | ND | >16 (<0.2%) |
| | 4 | 20 | | 35 | | 0 | |
| | 8 | 25 | | 65 | | 10 | |
| 20d | 0.4 | 0 | >16 (<20%) | 12 | 7.3 (1.4%) | ND | NA |
| | 4 | 20 | | 30 | | 0 | |
| | 8 | 25 | | 55 | | 0 | |
| 28 | 0.4 | 0 | >16 (<20%) | 20 | 4 (2.5%) | ND | ND |
| | 4 | 20 | | 50 | | ND | |
| | 8 | 35 | | 70 | | ND | |
| 29 | 0.4 | 0 | 16 (20%) | 18 | 3 (3.3%) | ND | 2 (1.5%) |
| | 4 | 30 | | 70 | | 100 | |
| | 8 | 40 | | 95 | | 100 | |

NA: no activity,
ND: not done

Mycolactone led to a complete blockade of the activation-induced production of IL-2 by human lymphocytes at concentrations >0.4 μM. At these doses, mycolactone also markedly reduced cell viability and totally suppressed the expression of CD62-L.

Variant 11c, possessing the core and northern C14-C20 fragment, was not cytotoxic in the conditions tested but showed inhibitory effect on the metabolic activity of HeLa cells. It also showed immunosuppressive activity, evidenced by significant inhibition of both IL-2 production and 2. Analgesic Effects The analgesic properties of the compounds of the invention may be confirmed with animal pain models well-known to one of skill in the art, such as the formalin-induced acute pain model and the carrageenan-induced inflammatory pain model (Encyclopedia of Psychopharmacology, Volume 2, P. 111)

The analgesic properties of Mycolactone and variant 22 were tested in the formalin-induced acute pain model (Encyclopedia of Psychopharmacology, Volume 2, p. 111).

Briefly, Mycolactone and variant 22 were administered intraperitoneally at 0.5 and 5 mg/kg respectively, 60 minutes before the subcutaneous injection of 10 µl of a 5% formalin solution of the right hind-leg. Two negative control groups, injected with PBS (neutral) or ethanol vehicle (vehicle) were tested in the same conditions. A group injected with 3 mg/kg morphin 15 minutes before formalin injection was used as a positive reference.

The time spent in licking/biting and the number of jumps during the early phase (0-5 min) and the late phase (10-40 min) were recorded, as indicators of acute and inflammatory pain, respectively. The graphs in FIG. 5 compare the global score of pain (rank sum of licking/biting time and jump number) in the five groups of animals (Mann-Whitney test on trimmed means; n≥6; *P<0.05 **P<0.01 vs. neutral; # P<0.05, # P<0.01 vs. vehicle.

They show that mycolactone displays significant activity against acute and inflammatory pain, while variant 22 is effective against inflammatory pain.

In the carrageenan test, the maximum mechanic pressure that can be applied on inflamed tissues before animals withdraw their leg is recorded.

REFERENCES

[1] a) M. T. Silva, F. Portaels, J. Pedrosa, *Lancet Infect. Dis.* 2009, 9, 699; b) C. Demangel, T. P. Stinear, S. T. Cole, *Nat. Rev. Microbiol.* 2009, 10, 50; c) D. S. Walsh, F. Portaels, W. M. Meyers, *Clin. Microbiol. Newsletter* 2009, 31, 119; d) H. Hong, C. Demangel, S. J. Pidot, P. F. Leadlay, T. Stinear, *Nat. Prod. Rep.* 2008, 25, 447; d) M. Wansbrough-Jones, R. Phillips, *The Lancet* 2006, 367, 1849; e) V. Sizaire, F. Nackers, E. Comte, F. Portaels, *Lancet Infect. Dis.* 2006, 6, 288; f) P. D. R. Johnson, T. Stinear, P. L. C. Small, G. Pluschke, R. W. Merritt, F. Portaels, K. Huygen, J. A. Hayman, K. Asiedu, *PLoS. Med* 2005, 2, e108; g) T. van der Werf, T. Stinear, Y. Stienstra, W. T. A. van der Graaf, P. L. Small, *Lancet* 2003, 362, 1062.

[2] S. J. Pidot, K. Asiedu, M. Käser, J. A. M. Fyfe, T. P. Stinear, *PLoS. Negl. Trop. Dis.* 2010, 4, e663.

[3] a) W. A. Nienhuis, Y. Stienstra, W. A. Thompson, P. C. Awuah, K. M. Abass, W. Tuah, N. Y. Awua-Boateng, E. O. Ampadu, V. Siegmund, J. P. Schouten, O. Adjei, G. Bretzel, T. S. van der Werf, *The Lancet* 2010, 375, 664; b) S. Etuaful, B. Carbonnelle, J. Grosset, S. Lucas, C. Horsfield, R. Phillips, M. Evans, D. Ofori-Adjei, E. Klustse, J. Owusu-Boateng, G. K. Amedofu, P. Awuah, E. Ampadu, G. Amofah, K. Asiedu, M. Wansbrough-Jones, *Antimicrob. Agents. Chemother.* 2005, 49, 3182.

[4] T. S. van der Werf, W. T. A. van der Graaf, J. W. Tappero, K. Asiedu, *Lancet* 1999, 354, 1013.

[5] Hong, H., Demangel, C., Pidot, S. J., Leadlay, P. F. and Stinear, T. (2008) Mycolactones: immunosuppressive and cytotoxic polyketides produced by aquatic mycobacteria. *Nat Prod Rep,* 25:447-454.

[6] Demangel, C., Stinear, T. P. and Cole, S. T. (2009) Buruli ulcer: reductive evolution enhances pathogenicity of *Mycobacterium ulcerans*. *Nat Rev Microbiol,* 7:50-60.

[7a] Coutanceau, E., Marsollier, L., Brosch, R., Perret, E., Goossens, P., Tanguy, M., Cole, S. T., Small, P. L. C. and Demangel, C. (2005) Modulation of the host immune response by a transient intracellular stage of *Mycobacterium ulcerans*: the contribution of endogenous mycolactone toxin. *Cell Microbiol,* 7(8):1187-96.

[7b] Coutanceau, E., Decalf, J., Babon, A., Winter, N., Cole, S. T., Albert, M. L. and Demangel, C. (2007) Selective suppression of dendritic cell functions by *Mycobacterium ulcerans* toxin mycolactone. *J Exp Med,* 204(6):1395-1403.

[7c] Guenin-Macé, L., Carrette, F., Asperti-Boursin, F., Le Bon, A., Caleechum, L., Di Bartolo, V., Fontanet, A., Bismuth, G. and Demangel, C. (2011) Mycolactone impairs T cell homing by suppressing microRNA control of L-selectin expression. *Proc. Natl. Acad. Sci. USA,* 108:12833-12838.

[8] a) A. Guérinot, S. Reymond, J. Cossy, *Angew. Chem. Int. Ed.* 2007, 46, 6521; See also: b) G. Cahiez, C. Duplais, A. Moyeux, *Org. Lett.* 2007, 9, 3253; c) B. D. Sherry, A. Fürstner, *Acc. Chem. Res.* 2008, 41, 1500.

[9] A. Mve-Obiang, R. E. Lee, F. Portaels, P. L. C. Small, *Infect. Immun.* 2003, 71, 774.

[10] Ishiyama H., Ishibashi M., Ogawa A., Yoshida S., Kobayashi J.-I., *J. Org. Chem.* 1997, 62, 3831

[11] Coffey D. S., McDonald A. I., Overman L. E., Rabinowitz M. H., Renhowe P. A., *J. Am. Chem. Soc.* 2000, 122, 4893.

[12] Keck G. E., Palani A., MeHardy S. F., *J. Org. Chem.* 1994, 59, 3113

[13] Song F., Fidanze S., Benowitz A., Kishi Y., *Tetrahedron* 2007, 67, 5739

[14] Baker R., Castro J. L., *J. Chem. Soc., Perkin Trans.* 11990, 47.

[15] Burr D. A., Chen X. B., Vederas J. C., *Org. Lett.* 2007, 9, 161

[16] Song F., Fidanze S., Benowitz A., Kishi Y., *Org. Lett.* 2002, 4, 647.

[17] Hodgson, D. M.; Boulton, L. T.; Maw, G. N. *Tetrahedron* 1995, 51, 3713

[18] Srogl, J.; Allred, G. D.; Liebeskind, L. S. *J. Am. Chem. Soc.* 1997, 119, 12376

[19] Allred, G. D.; Liebeskind, L. S. *J. Am. Chem. Soc.* 1996, 118, 2748.

[20] Judd T., Bischoff A., Kishi Y., Adusumilli S., Small P., *Org. Lett.,* 2004, 6, 4901

[21] Verdoes M., Hillaert U., Florea B. I., Sae-Heng M., Risseeuw M. D. P., Filippov D. V., van der Marel G. A., Overkleeft H. S., *Bioorg. Med. Chem. Lett.* 2007, 17, 6169

[22] Mycolactones A/B: a) K. L. Jackson, W. Li, C.-L. Chen, Y. Kishi, *Tetrahedron* 2010, 66, 2263; b) F. Song, S. Fidanze, A. B. Benowitz, Y. Kishi, *Tetrahedron* 2007, 63, 5379; c) F. Song, S. Fidanze, A. B. Benowitz, Y. Kishi, *Org. Lett.* 2002, 4, 647; Mycolactone C: d) T. C. Judd, A. Bischoff, Y. Kishi, S. Adusumilli, P. L. C. Small, *Org. Lett.* 2004, 6, 4901; Mycolactone E: e) S. Aubry, R. E. Lee, E. A. Mahrous, P. L. C. Small, D. Beachboard, Y. Kishi, *Org. Lett.* 2008, 10, 5385; Mycolactone F: f) H.-J. Kim, Y. Kishi, *J. Am. Chem. Soc.* 2008, 130, 1842; Mycolactone dia-F: g) H.-J. Kim, K. L. Jackson, Y. Kishi, H. R. Williamson, L. Mosi, P. L. C. Small, *Chem. Commun.* 2009, 7402; Minor metabolite: h) T. Spangenberg, S. Aubry, Y. Kishi, *Tetrahedron Lett.* 2010, 51, 1782.

[23] a) K.-S. Ko, M. D. Alexander, S. D. Fontaine, J. E. Biggs-Houck, J. J. La Clair, M. D. Burkart, *Org. Biomol. Chem.* 2010, 8, 5159; b) M. D. Alexander, S. D. Fontaine, J. J. La Clair, A. G. DiPasquale, A. L. Rheingold, M. D. Burkart, *Chem. Commun.* 2006, 4602.

The invention claimed is:

1. A compound of formula (I):

$$Y—O—W \quad (I)$$

wherein:

W is H or —C(=O)—X;

X is $X_{aa}$, $X_{bb}$, $X_{cc}$, $X_{dd}$ or $X_{ee}$:

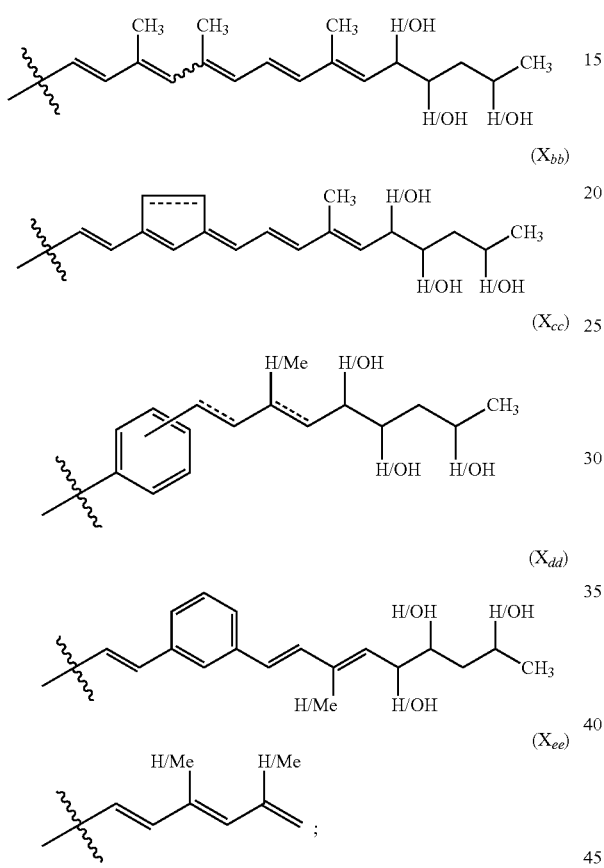

Y is Z;

Z is:

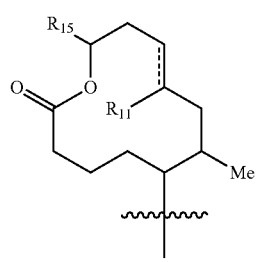

wherein $R^{15}$ is C1-C6 alkyl or L;

$R^{11}$ is H or $CH_3$;

----- is a single bond (C—C) or a double bond (C=C);

L is $L_1$, $L_2$, or $L_3$:

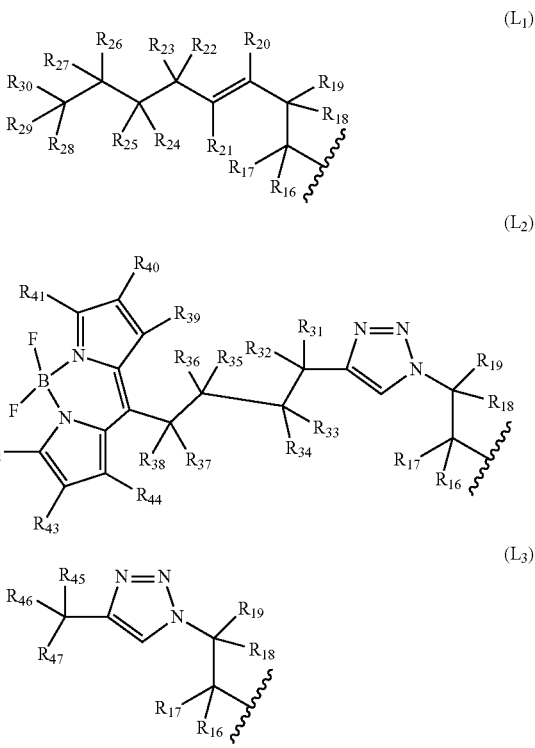

$R^{16}, R^{17}, R^{18}, R^{19}, R^{20}, R^{21}, R^{22}, R^{23}, R^{26}, R^{27}, R^{30}, R^{31}, R^{32}, R^{33}, R^{34}, R^{35}, R^{36}, R^{37}, R^{38}, R^{39}, R^{40}, R^{41}, R^{42}, R^{43}, R^{44}, R^{45}$ and $R^{46}$ are each independently selected from H and $C_1$-$C_6$ alkyl;

$R^{24}, R^{25}, R^{28}, R^{29}$ and $R^{47}$ are each independently selected from H, halogen, hydroxyl, and ($C_1$-$C_6$) alkoxy;

with the proviso that when X is Xaa or Xbb, and when $R^{15}$ is $L_1$, then $R^{11}$ cannot be $CH_3$, with the provision that when Y is selected from $C_2$-$C_6$ alkenyl, $C_3$-$C_{10}$ cycloalkyl, $C_3$-$C_{10}$ cycloalkenyl, ($C_1$-$C_6$)alkoxy($C_1$-$C_6$)alkyl, ($C_1$-$C_6$)alkoxy($C_6$-$C_{10}$)aryl, then W is —C(=O)—X;

with the exclusion of the compounds wherein:

Y is Z; W is H; ----- is C=C; $R^{11}$ is $CH_3$; $R^{15}$ is $L_1$ with $R^{16}, R^{20}, R^{22}$ and $R^{30}$ are $CH_3$; $R^{24}$ and $R^{28}$ are OH; and the other radicals $R^i$ are H;

Y is Z; W is H; ----- is C=C; $R^{11}$ is $CH_3$; $R^{15}$ is isopropyl; and the other radicals $R^i$ are H;

and the stereoisomeric forms, or mixtures of stereoisomeric forms thereof.

2. The compound of claim 1, wherein $R^{15}$ is isopropyl or $L_{1a}$:

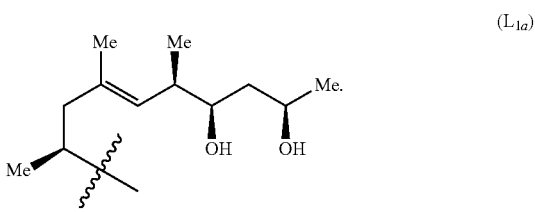 [SMILES: *[C@@H](C)C/C(C)=C/[C@@H](C)[C@H](O)C[C@@H](C)O]

3. The compound of claim 1 selected from:
cycloalkyl (2E,4E,6E,8E,10E)-12,13,15-trihydroxy-4,6,10-trimethylhexadeca-2,4,6,8,10-pentaenoate;
cycloalkenyl (2E)-3-[(3E)-3-[(2E,4E)-6,7,9-trihydroxy-4-methyldeca-2,4-dien-1-ylidene]cyclopent-1-en-1-yl] prop-2-enoate;
cycloalkenyl 3-[(1E,3E)-5,6,8-trihydroxy-3-methylnona-1,3-dien-1-yl]benzoate;
(9E)-7-methyl-2-oxo-12-(propan-2-yl)-1-oxacyclododec-9-en-6-yl (2E,4E,6E,8E,10E)-12,13,15-trihydroxy-4,6,10-trimethylhexadeca-2,4,6,8,10-pentaenoate;
(9E)-7-methyl-2-oxo-12-(propan-2-yl)-1-oxacyclododec-9-en-6-yl (2E)-3-[(3E)-3-[(2E,4E)-6, 7,9-trihydroxy-4-methyldeca-2,4-dien-1-ylidene]cyclopent-1-en-1-yl] prop-2-enoate;
(9E)-7-methyl-2-oxo-12-(propan-2-yl)-1-oxacyclododec-9-en-6-yl 3-[(1E,3E)-5,6,8-trihydroxy-3-methylnona-1,3-dien-1-yl]benzoate;
(9E)-12-[(4E)-7,9-dihydroxy-4,6-dimethyldec-4-en-2-yl]-7-methyl-2-oxo-1-oxacyclododec-9-en-6-yl (2E,4E,6E,8E,10E)-12,13,15-trihydroxy-4,6,10-trimethylhexadeca-2,4,6,8,10-pentaenoate;
(9E)-12-[(4E)-7,9-dihydroxy-4,6-dimethyldec-4-en-2-yl]-7-methyl-2-oxo-1-oxacyclododec-9-en-6-yl 3-[(1E,3E)-6,8-dihydroxy-3-methylnona-1,3-dien-1-yl]benzoate;
(9E)-12-[(4E)-7,9-dihydroxy-4,6-dimethyldec-4-en-2-yl]-7-methyl-2-oxo-1-oxacyclododec-9-en-6-yl (2E)-3-[(3E)-3-[(2E,4E)-7,9-dihydroxy-4-methyldeca-2,4-dien-1-ylidene]cyclopent-1-en-1-yl]prop-2-enoate;
(6S,7S,9E,12R)-12-[(2S,4E,6R,7R,9R)-7,9-dihydroxy-4,6-dimethyldec-4-en-2-yl]-7-methyl-2-oxo-1-oxacyclododec-9-en-6-yl (2E,4E,6E,8E,10E,12 S,13 S,15S)-12,13,15-trihydroxy-4,6,10-trimethylhexadeca-2,4,6,8,10-pentaenoate (compound 20a);
(6S,7S,9E,12R)-12-[(2S,4E,6R,7R,9R)-7,9-dihydroxy-4,6-dimethyldec-4-en-2-yl]-7-methyl-2-oxo-1-oxacyclododec-9-en-6-yl (2E,4E,6E,8E,10E,12S,13 S,15R)-12,13,15-trihydroxy-4,6,10-trimethylhexadeca-2,4,6,8,10-pentaenoate (compound 20b);
(6S,7S,9E,12R)-12-[(2S,4E,6R,7R,9R)-7,9-dihydroxy-4,6-dimethyldec-4-en-2-yl]-7-methyl-2-oxo-1-oxacyclododec-9-en-6-yl (2E,4E,6E,8E,10E,12R,13R,15R)-12,13,15-trihydroxy-4,6,10-trimethylhexadeca-2,4,6,8,10-pentaenoate (compound 20c);
(6S,7S,9E,12R)-12-[(2S,4E,6R,7R,9R)-7,9-dihydroxy-4,6-dimethyldec-4-en-2-yl]-7-methyl-2-oxo-1-oxacyclododec-9-en-6-yl (2E,4E,6E,8E,10E,13R,15R)-13,15-dihydroxy-4,6,10-trimethylhexadeca-2,4,6,8,10-pentaenoate (compound 20d);
(6S,7S,9E,12R)-12-[(2S,4E,6R,7R,9R)-7,9-dihydroxy-4,6-dimethyldec-4-en-2-yl]-6-hydroxy-7-methyl-1-oxacyclododec-9-en-2-one (compound 11c);
(6S,7S,9E,12R)-7-methyl-2-oxo-12-(propan-2-yl)-1-oxacyclododec-9-en-6-yl (2E,4E,6E,8E,10E,12S,13 S,15S)-12,13,15-trihydroxy-4,6,10-trimethylhexadeca-2,4,6,8,10-pentaenoate (compound 22);
2,2-difluoro-4,6,10,12-tetramethyl-8-(4-{1-[(2S)-2-[(2R,4E,7S,8S)-7-methyl-12-oxo-8-{[(2E,4E,6E,8E,10E,12S,13 S,15S)-12,13,15-trihydroxy-4,6,10-trimethylhexadeca-2,4,6,8,10-pentaenoyl]oxy}-1-oxacyclododec-4-en-2-yl]propyl]-1H-1,2,3-triazol-4-yl}butyl)-1$\lambda^5$,3-diaza-2$\lambda^4$-boratricyclo[7.3.0.0$^{3,7}$]dodeca-1(12),4,6,8,10-pentaen-1-ylium (compound 28);
2,2-difluoro-8-(4-{1-[(2S)-2-[(2R,4E,7S,8 S)-8-hydroxy-7-methyl-12-oxo-1-oxacyclododec-4-en-2-yl]propyl]-1H-1,2,3-triazol-4-yl}butyl)-4,6,10,12-tetramethyl-1$\lambda^5$,3-diaza-2$\lambda^4$-boratricyclo[7.3.0.0$^{3,7}$]dodeca-1(12),4,6,8,10-pentaen-1-ylium (Compound 29);
(6S,7S,9E,12R)-7-methyl-2-oxo-12-(propan-2-yl)-1-oxacyclododec-9-en-6-yl (2E,4E,6E,8E,10E,12S,13 S,15R)-12,13,15-trihydroxy-4,6,10-trimethylhexadeca-2,4,6,8,10-pentaenoate (compound 22b);
(6S,7S,9E,12R)-7-methyl-2-oxo-12-(propan-2-yl)-1-oxacyclododec-9-en-6-yl (2E,4E,6E,8E,10E,12R,13R,15R)-12,13,15-trihydroxy-4,6,10-trimethylhexadeca-2,4,6,8,10-pentaenoate (compound 22c);
(6S,7S,9E,12R)-7-methyl-2-oxo-12-(propan-2-yl)-1-oxacyclododec-9-en-6-yl (2E,4E,6E,8E,10E,13 S,15S)-13,15-dihydroxy-4,6,10-trimethylhexadeca-2,4,6,8,10-pentaenoate (compound 22d);
(6S,7S,9E,12R)-7-methyl-2-oxo-12-(propan-2-yl)-1-oxacyclododec-9-en-6-yl (2E,4E,6E,8E,10E,13 S)-13-hydroxy-4,6, 10-trimethylhexadeca-2,4,6, 8,10-pentaenoate (compound 22e);
(6S,7S,9E,12R)-7-methyl-2-oxo-12-(propan-2-yl)-1-oxacyclododec-9-en-6-yl 3-[(1E,3E,5S,6S,8S)-5,6,8-trihydroxy-3-methylnona-1,3-dien-1-yl]benzoate (compound 22f);
(6S,7S,9E,12R)-7-methyl-2-oxo-12-(propan-2-yl)-1-oxacyclododec-9-en-6-yl (2E,4E,6E,8E,10E,12S,13 S)-12,13-dihydroxy-4,6,10-trimethylhexadeca-2,4,6,8,10-pentaenoate (compound 22g);
(6S,7S,9E,12R)-7-methyl-2-oxo-12-(propan-2-yl)-1-oxacyclododec-9-en-6-yl (2E,4E,6E,8E,10E,12R,13R)-12,13-dihydroxy-4,6,10-trimethylhexadeca-2,4,6,8,10-pentaenoate (compound 22h);
(6S,7S,9E,12R)-7-methyl-2-oxo-12-(propan-2-yl)-1-oxacyclododec-9-en-6-yl (2E,4E,6E,8E,10E,12S)-12-hydroxy-4,6,10-trimethylhexadeca-2,4,6,8,10-pentaenoate (compound 22i);
(6S,7S,9E,12R)-7-methyl-2-oxo-12-(propan-2-yl)-1-oxacyclododec-9-en-6-yl (2E,4E,6E,8E,10E,15S)-15-dihydroxy-4,6,10-trimethylhexadeca-2,4,6,8,10-pentaenoate (compound 22j);
(6S,7S,9E,12R)-7-methyl-2-oxo-12-(propan-2-yl)-1-oxacyclododec-9-en-6-yl 3-[(1E,3E,5E,7S,8S,10S)-7,8,10-trihydroxy-5-methylundeca-1,3,5-trien-1-yl]benzoate (compound 22k);
(6S,7S,9E,12R)-7-methyl-2-oxo-12-(propan-2-yl)-1-oxacyclododec-9-en-6-yl (2E)-3-{3-[(1E,3E,5S,6S,8S)-5,6,8-trihydroxy-3-methylnona-1,3-dien-1-yl]phenyl}prop-2-enoate (compound 22l);
(6S,7S,9E,12R)-7-methyl-2-oxo-12-(propan-2-yl)-1-oxacyclododec-9-en-6-yl (2E,4E)-4,6-dimethylhepta-2,4,6-trienoate (compound 22m);
(6S,7S,9E,12R)-7-methyl-2-oxo-12-(propan-2-yl)-1-oxacyclododec-9-en-6-yl (2E,4E,6E,8E,10E,12R,13 S,15S)-12,13,15-trihydroxy-4,6,10-trimethylhexadeca-2,4,6,8,10-pentaenoate (compound 22n);
(6S,7S,9E,12R)-7-methyl-2-oxo-12-(propan-2-yl)-1-oxacyclododec-9-en-6-yl (2E,4E,6E,8E,10E,12S,13R,15S)-12,13,15-trihydroxy-4,6,10-trimethylhexadeca-2,4,6,8,10-pentaenoate (compound 22o);
(2E,8E,10E,12 S,13 S)-((6S,7S,12R,E)-12-((2S,6R,7R,9R,E)-7,9-dihydroxy-4,6-dimethyldec-4-en-2-yl)-7-methyl-2-oxooxacyclododec-9-en-6-yl) 12,13-dihydroxy-4,6,10-trimethylhexadeca-2,4,6,8,10-pentaenoate (compound 20e);
(6S,7S,12R)-7-methyl-2-oxo-12-(propan-2-yl)-1-oxacyclododecan-6-yl (2E,4E,6E,8E,10E,12S,13 S,15S)-12,13,15-trihydroxy-4,6,10-trimethylhexadeca-2,4,6,8,10-pentaenoate (compound C-004);

Cyclohexyl (2E,4E,6E,8E,10E,12S,13S,15S)-12,13,15-trihydroxy-4,6,10-trimethylhexadeca-2,4,6,8,10-pentaenoate (compound C-002);

(6S,7S,9E,12R)-12-[(2S)-1-(4-pentyl-1H-1,2,3-triazol-1-yl)propan-2-yl]-7-methyl-2-oxo-1-oxacyclododec-9-en-6-yl (2E,4E,6E,8E,10E,12S,13R,15S)-12,13,15-trihydroxy-4,6,10-trimethylhexadeca-2,4,6,8,10-pentaenoate (compound 28b);

(6S,7S,9E,12R)-12-[(2S)-1-{4-[(1S)-1-hydroxyethyl]-1H-1,2,3-triazol-1-yl}propan-2-yl]-7-methyl-2-oxo-1-oxacyclododec-9-en-6-yl (2E,4E,6E,8E,10E,12S,13R,15S)-12,13,15-trihydroxy-4,6,10-trimethylhexadeca-2,4,6,8,10-pentaenoate (compound 28c).

4. A pharmaceutical composition comprising a compound of claim 1 and one or more pharmaceutically acceptable excipients.

5. A method of preparation of compounds of formula (I) according to claim 1, comprising the steps of:
coupling a compound for formula (II) with a compound of formula (III) according to an esterification reaction,

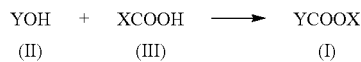

YOH + XCOOH → YCOOX
(II)   (III)      (I)

the functional groups optionally present being protected by protecting groups when appropriate;
removing, when present, said protecting groups in the obtained protected compound of formula (I); and
optionally recovering the obtained compound of formula (I).

6. The method of claim 5, wherein the compound of formula (II) has the formula (IIa) and is prepared from a compound of formula (IVa) and a compound of formula (IVb):

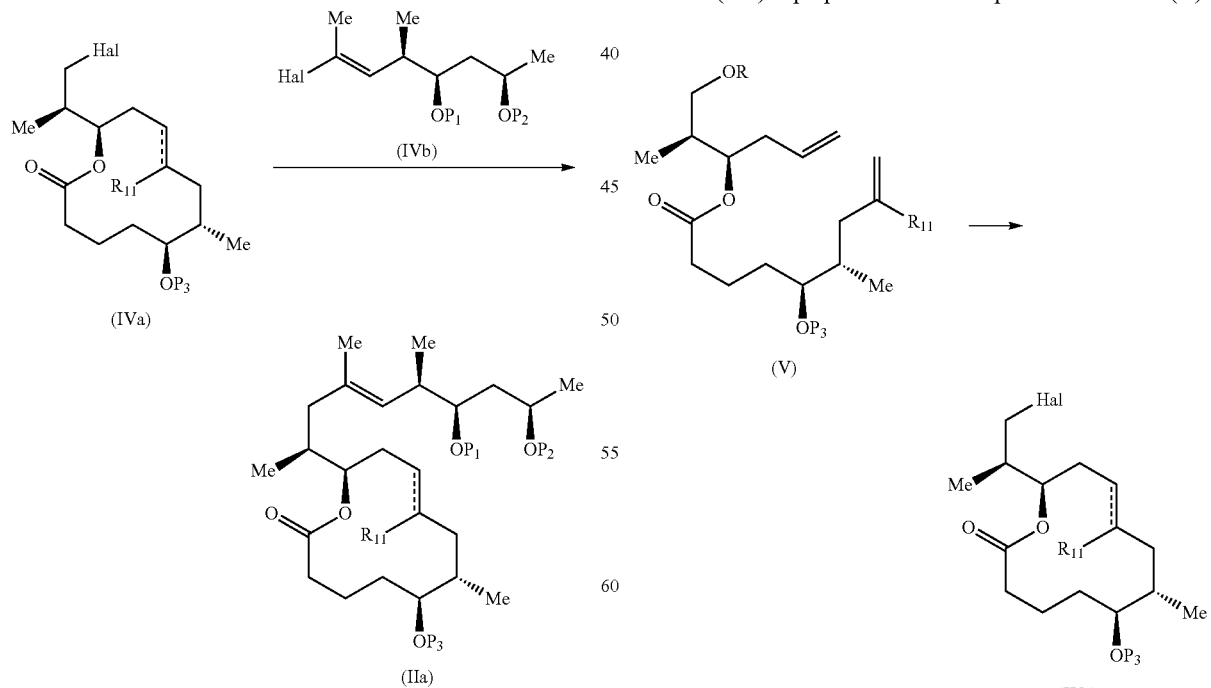

wherein,
$P_1$, $P_2$ and $P_3$ are protecting groups and Hal is halogen.

7. The method of claim 5, wherein the compound of formula (IVa) is prepared from a compound of formula (V):

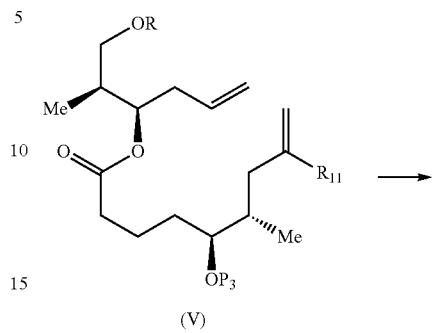

wherein R is Ms or Ts.

8. The method of claim 6, wherein the compound of formula (IVa) is prepared from a compound of formula (V):

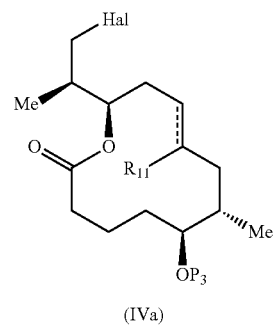

wherein R is Ms or Ts.

9. A compound selected from:

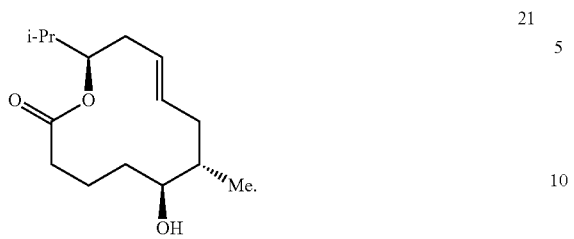

10. A method for treating inflammation, autoimmune disease, allergy, graft rejection, or graft versus host disease, comprising administering to a subject in need thereof an effective amount of the pharmaceutical composition of claim 4.

11. A method for treating pain, comprising administering to a subject in need thereof an effective amount of a compound of claim 1 with the provision that when W is H, and $R^{11}$ is H, then one of $R^{14}$, $R^{15}$ cannot be $C_1$-$C_6$ alkyl.

* * * * *